US012595495B2

(12) United States Patent
Schirmer et al.

(10) Patent No.: US 12,595,495 B2
(45) Date of Patent: *Apr. 7, 2026

(54) METHODS OF PRODUCING OMEGA-HYDROXYLATED FATTY ACID DERIVATIVES

(71) Applicant: Genomatica, Inc., San Diego, CA (US)

(72) Inventors: Andreas W. Schirmer, San Diego, CA (US); Haibo Wang, San Diego, CA (US); Stephen B. Del Cardayre, San Diego, CA (US); Zhihao Hu, San Diego, CA (US); Louis G. Hom, San Diego, CA (US); Baolong Zhu, San Diego, CA (US); Cindy Chang, San Diego, CA (US); Emanuela E. Popova, San Diego, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/595,947

(22) Filed: Mar. 5, 2024

(65) Prior Publication Data

US 2025/0019731 A1     Jan. 16, 2025

Related U.S. Application Data

(63) Continuation of application No. 16/915,454, filed on Jun. 29, 2020, now Pat. No. 11,981,952, which is a continuation of application No. 14/897,285, filed as application No. PCT/US2014/042594 on Jun. 16, 2014, now Pat. No. 10,711,288.

(60) Provisional application No. 61/835,464, filed on Jun. 14, 2013.

(51) Int. Cl.
| | |
|---|---|
| *C12P 7/6409* | (2022.01) |
| *C12N 9/02* | (2006.01) |
| *C12N 9/04* | (2006.01) |
| *C12N 15/52* | (2006.01) |
| *C12N 15/62* | (2006.01) |
| *C12P 7/18* | (2006.01) |
| *C12P 7/42* | (2006.01) |
| *C12P 7/6436* | (2022.01) |

(52) U.S. Cl.
CPC .......... *C12P 7/6409* (2013.01); *C12N 9/0006* (2013.01); *C12N 9/0008* (2013.01); *C12N 9/0071* (2013.01); *C12N 9/0077* (2013.01); *C12N 15/52* (2013.01); *C12N 15/62* (2013.01); *C12P 7/18* (2013.01); *C12P 7/42* (2013.01); *C12P 7/6436* (2013.01); *C12Y 114/14001* (2013.01); *C12Y 114/15003* (2013.01); *C07K 2319/00* (2013.01); *C12Y 101/00* (2013.01); *C12Y 102/01042* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 5,000,000 | A | 3/1991 | Ingram et al. |
| 5,028,539 | A | 7/1991 | Ingram et al. |
| 5,059,532 | A | 10/1991 | Kimura et al. |
| 5,424,202 | A | 6/1995 | Ingram et al. |
| 5,482,846 | A | 1/1996 | Ingram et al. |
| 5,602,030 | A | 2/1997 | Ingram et al. |
| 5,939,250 | A | 8/1999 | Short |
| 5,965,408 | A | 10/1999 | Short |
| 7,169,588 | B2 | 1/2007 | Burch et al. |
| 7,745,652 | B2 | 6/2010 | Lysenko et al. |
| 8,071,799 | B2 | 12/2011 | Olson |
| 8,097,439 | B2 | 1/2012 | Alibhai et al. |
| 8,110,093 | B2 | 2/2012 | Friedman et al. |
| 8,110,670 | B2 | 2/2012 | Hu et al. |
| 8,183,028 | B2 | 5/2012 | Alibhai et al. |
| 8,232,924 | B2 | 7/2012 | Bucca et al. |
| 8,237,003 | B2 | 8/2012 | Holtcamp et al. |
| 8,268,599 | B2 | 9/2012 | Schirmer et al. |
| 8,273,694 | B2 | 9/2012 | Brown et al. |
| 8,283,143 | B2 | 10/2012 | Hu et al. |
| 8,299,313 | B2 | 10/2012 | Takai et al. |
| 8,313,934 | B2 | 11/2012 | Bhatia et al. |
| 8,361,769 | B1 | 1/2013 | Koch et al. |
| 8,372,610 | B2 | 2/2013 | Lee et al. |
| 8,420,840 | B2 | 4/2013 | Olson |

(Continued)

FOREIGN PATENT DOCUMENTS

| | | |
|---|---|---|
| EP | 2 639 308 A1 | 9/2013 |
| JP | 2001-519164 A | 10/2001 |

(Continued)

OTHER PUBLICATIONS

Office Action issued in corresponding MX Application No. MX/a/2020/000981 dated Oct. 12, 2020.

(Continued)

*Primary Examiner* — Todd M Epstein
(74) *Attorney, Agent, or Firm* — Harness Dickey & Pierce P.L.C.

(57) ABSTRACT

The disclosure relates to omega-hydroxylated fatty acid derivatives and methods of producing them. Herein, the disclosure encompasses a novel and environmentally friendly production method that provides omega-hydroxylated fatty acid derivatives at high purity and yield. Further encompassed are recombinant microorganisms that produce omega-hydroxylated fatty acid derivatives through selective fermentation.

21 Claims, 47 Drawing Sheets

Specification includes a Sequence Listing.

(56) References Cited

U.S. PATENT DOCUMENTS

| | | | |
|---|---|---|---|
| 8,530,221 | B2 | 9/2013 | Hu et al. |
| 8,569,560 | B2 | 10/2013 | Schrodi et al. |
| 8,592,188 | B2 | 11/2013 | Franklin et al. |
| 10,711,288 | B2 | 7/2020 | Schirmer et al. |
| 10,787,648 | B2 | 9/2020 | Schirmer et al. |
| 11,384,341 | B2 | 7/2022 | Schirmer et al. |
| 11,421,206 | B2 | 8/2022 | Schirmer et al. |
| 11,441,130 | B2 | 9/2022 | Schirmer et al. |
| 2008/0220419 | A1 | 9/2008 | Kubota et al. |
| 2008/0293060 | A1 | 11/2008 | Schirmer et al. |
| 2009/0140696 | A1 | 6/2009 | Okuto |
| 2009/0264672 | A1 | 10/2009 | Abraham et al. |
| 2010/0071259 | A1 | 3/2010 | Hu et al. |
| 2010/0105955 | A1 | 4/2010 | Alibhai et al. |
| 2010/0105963 | A1 | 4/2010 | Hu |
| 2010/0127318 | A1 | 5/2010 | Noort et al. |
| 2010/0145086 | A1 | 6/2010 | Schrodi et al. |
| 2010/0170826 | A1 | 7/2010 | Friedman et al. |
| 2010/0199548 | A1 | 8/2010 | del Cardayre et al. |
| 2010/0216198 | A1 | 8/2010 | Dubois |
| 2010/0221798 | A1 | 9/2010 | Schirmer et al. |
| 2010/0235934 | A1 | 9/2010 | Friedman et al. |
| 2010/0242345 | A1 | 9/2010 | Keasling et al. |
| 2010/0249470 | A1 | 9/2010 | Schirmer et al. |
| 2010/0251601 | A1 | 10/2010 | Hu et al. |
| 2010/0257777 | A1 | 10/2010 | Sanchez-Riera et al. |
| 2010/0257778 | A1 | 10/2010 | Gaertner et al. |
| 2010/0274033 | A1 | 10/2010 | Sanchez-Riera et al. |
| 2011/0072714 | A1 | 3/2011 | Gaertner |
| 2012/0070868 | A1 | 3/2012 | Lee et al. |
| 2012/0277452 | A1 | 11/2012 | Franklin et al. |
| 2012/0289729 | A1 | 11/2012 | Holtcamp et al. |
| 2013/0130336 | A1 | 5/2013 | Olson |
| 2014/0228586 | A1 | 8/2014 | Beardslee et al. |
| 2015/0111253 | A1 | 4/2015 | Schaffer et al. |
| 2017/0145390 | A1* | 5/2017 | Zhu ..................... C12N 9/0077 |
| 2021/0071212 | A1 | 3/2021 | Schirmer et al. |
| 2023/0159901 | A1 | 5/2023 | Schirmer et al. |
| 2023/0167419 | A1 | 6/2023 | Schirmer et al. |

FOREIGN PATENT DOCUMENTS

| | | | | |
|---|---|---|---|---|
| JP | 2004-357707 | A | 12/2004 | |
| JP | 2009-005687 | A | 1/2009 | |
| JP | 2009-221482 | A | 10/2009 | |
| JP | 2010-229407 | A | 10/2010 | |
| JP | 2011520455 | A | 7/2011 | |
| JP | 2016-519714 | A | 7/2016 | |
| WO | 91/16427 | A1 | 10/1991 | |
| WO | 2006/051729 | A1 | 5/2006 | |
| WO | 2007/136762 | A2 | 11/2007 | |
| WO | 2008/119082 | A2 | 10/2008 | |
| WO | 2008147781 | A2 | 12/2008 | |
| WO | 2009/140696 | A2 | 11/2009 | |
| WO | 2010022090 | A1 | 2/2010 | |
| WO | 2010/062480 | A2 | 6/2010 | |
| WO | 2010075483 | A2 | 7/2010 | |
| WO | 2010118409 | A1 | 10/2010 | |
| WO | 2010/127318 | A2 | 11/2010 | |
| WO | 2011038132 | A1 | 3/2011 | |
| WO | 2011038134 | A1 | 3/2011 | |
| WO | 2011/062987 | A2 | 5/2011 | |
| WO | WO-2012071439 | A1 * | 5/2012 | ............... C12N 1/20 |
| WO | 2011127409 | A3 | 6/2012 | |
| WO | 2013/024114 | A2 | 2/2013 | |
| WO | 2013/135650 | A1 | 9/2013 | |
| WO | 2014201474 | A1 | 12/2014 | |
| WO | 2015/195697 | A1 | 12/2015 | |

OTHER PUBLICATIONS

Extended European Search Report from corresponding European Patent Application No. 20168885.0 dated Oct. 30, 2020.

Examination Report from corresponding Indian Patent Application No. 11837/DELNP/2015 dated Jul. 24, 2020.

Office Action from corresponding Korean Patent Application No. 10-2016-7000963 dated Nov. 19, 2020.

Notice of Reasons for Refusal issued in corresponding Japanese Application No. 2019-183765 dated Jan. 6, 2021.

Fujii, T., et al., "Production of a,w-Alkanediols Using *Escherichia coli* Expressing a Cytochrome P450 from *Acinetobacter* sp OC4," Biosci. Biotechnol. Biochem., 70(6): 1379-1385 (2006).

Schwartz, G.P., et al., "A superactive insulin: [B10-Aspartic acid]insulin(human)," Proc. Natl. Acad. Sci. USA, 84: 6408-6411 (1987).

Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111: 2129-2138 (1990).

Office Action from corresponding Canadian Application No. 2915229 dated Jul. 5, 2021.

Ba, L., et al., "Semi-Rational Engineering of Cytochrome P450sca-2 in a Hybrid System for Enhanced Catalytic Activity: Insights Into the Important Role of Electron Transfer," Biotechnology and Bioengineering, 110(11): 2815-2825 (2013).

Office Action from corresponding Japanese Application No. 2019-183765 dated Dec. 27, 2021.

Nodate et al: "Functional expression system for cytochrome P450 genes using the reductase domain of self-sufficient P450RhF from *Rhodococcus* sp. NCIMB 9784", Applied Microbiology and Biotechnology, 71(4), 455-462 (2006).

Kubota et al: "Isolation and Functional Analysis of Cytochrome P450 CYP153A Genes from Various Environments", Bioscience, Biotechnology, and Biochemistry, 69(12), 2421-2430 (2005).

Bordeaux et al: "A Regioselective Biocatalyst for Alkane Activation under Mild Conditions", Angewandte Chemie International Edition, 50(9), 2075-2079 (2011).

Bordeaux et al: "Catalytic, Mild, and Selective Oxyfunctionalization of Linear Alkanes: Current Challenges", Angewandte Chemie International Edition, 51(43), 10712-10723 (2012).

Office Action issued in corresponding MY Application No. PI2020000977 dated Oct. 25, 2022.

Office Action issued in corresponding ID Application No. P00202001448 dated Oct. 11, 2022.

Office Action from corresponding JP Application No. 2021129428 dated Oct. 3, 2022.

Office Action from corresponding CN Application No. 2014800337028 dated Jul. 19, 2023.

Honda et al., (2012). Bacterial CYP153A monooxygenases for the synthesis of omega-hydroxylated fatty acids.Chem. Commun., 48:5115-17.

Gen Bank, Accession No. ABM17701 (2011).

Correspond, thefreedictionary.com, accessed Feb. 23, 2023. (2023).

Office Action from corresponding U.S. Appl. No. 16/915,454 dated Nov. 10, 2021.

Office Action from corresponding U.S. Appl. No. 16/915,454 dated May 23, 2022.

Office Action from corresponding U.S. Appl. No. 16/915,454 dated Mar. 1, 2023.

Altschul et al., "Basic Local Alignment Search Tool," Journal of Molecular Biology, May 15, 1990, vol. 215, pp. 403-410.

Altschul et al., "Protein database searches using compositionally adjusted substitution matrices," FEBS J, Aug. 4, 2005, vol. 272, pp. 5101-5109.

Amann et al., "Tightly regulated tac promoter vectors useful for the expression of unfused and fused proteins in *Escherichia coli*," Gene., Jun. 15, 1988, vol. 69, pp. 301-315.

Arkin et al., "An algorithm for protein engineering: Simulations of recursive ensemble mutagenesis," Proc. Natl. Acad. Sci., Aug. 1992, vol. 89, pp. 7811-7815.

Arnold, "Protein engineering for unusual environments," Curr. Opin. Biotech., Aug. 1993, vol. 4, pp. 450-455.

(56) References Cited

OTHER PUBLICATIONS

Baldari et al., "A novel leader peptide which allows efficient secretion of a fragment of human interleukin 1 beta in *Saccharomyces cerevisiae*", EMBO J., Jan. 1, 1987, vol. 6, No. 1, pp. 229-234.

Bieniek et al., "Advanced Fine-Tuning of Grubs/Hoveyda Olefin Metathesis Catalysts: A Further Step toward an Optimum Balance between Antinomic Properties," J. Am. Chem. Soc., vol. 128, Oct. 4, 2006, oaaes 13652-13653.

Bowie et al., "Deciphering the Message in Protein Sequences: Tolerance to Amino Acid Substitutions," Science, Mar. 16, 1990, vol. 247, pp. 1306-1310.

Braun, "Minireviews—FhuA (TonA), the Career of a Protein," J. Bacteriol, Jun. 2009, (published ahead of print on Mar. 27, 2009), vol. 191, No. 11, pp. 3431-3436.

Cadwell et al., "Randomization of Genes by PCR Mutagenesis," PCR Methods Applic., Jun. 8, 1992, vol. 2, pp. 28-33.

Gaviglia et al., "Rat Long Chain Acyl-CoA Synthetase 5, but Not 1, 2, 3, or 4, Complements *Escherichia coli* fadD," J. Biol. Chem, Mar. 19, 2004, vol. 279, No. 12, pp. 11163-11169.

Clark, "Regulation of Fatty Acid Degration in *Escherichia coli*: Analysis by Operon Fusion," J Bacteriol, Nov. 1, 1981, vol. 148, No. 2, pp. 521-526.

Communication pursuant to Article 94(3) EPC in EP Patent Application No. 14738962.1 mailed Feb. 16, 2017 (5 pages).

Communication pursuant to Article 94(3) EPC in EP Patent Application No. 14738962.1 mailed Mar. 6, 2018 (4 pages).

Communication pursuant to Article 94(3) EPC in EP Patent Application No. 14 738962.1 mailed Sep. 27, 2018 (4 pages).

Communication pursuant to Article 94(3) EPC in EP Patent Application No. 15732504.4 mailed Feb. 17, 2017 (4 pages).

Communication pursuant to Article 94(3) EPC in EP Patent Application No. 15732504.4 mailed Jul. 31, 2019 (3 pages).

Communication pursuant to Article 94(3) EPC in EP Patent Application No. 15732504.4 mailed Sep. 14, 2018 (3 pages).

Cronan et al., "FadR, transcriptional co-ordination of metabolic expediency," Mole. Microbial, vol. 29, No. 4, Apr. 9, 1998, pp. 937-943.

Currie., "Source Apportionment of Atmospheric particles," Characterization of Environmental Particles, IUPAC Environmental Analytical Chemistry Series, vol. 1, Mar. 17, 1992, pp. 3-75.

De Mot et al., "A novel class of self-sufficient cytochrome P450 monooxygenases in prokaryotes," Trends Microbial, vol. 10, No. 11, Nov. 2002, pp. 502-508.

Decision of Rejection in JP Patent Application No. 2016-519714 mailed Jun. 6, 2019 (29 pages).

Delegrave et al., "Searching Sequence Space to Engineer Proteins: Exponential Ensemble Mutagenesis," Biotech. Res, vol. 11, Dec. 1993, pp. 1548-1552.

Dietrich et al., "Cloning, expression and characterisation of CYP102A7, a self-sufficient P450 monooxygenase from Bacillus licheniformis," Appl. Microbial. Biotechnol, vol. 79, Issue 6, Jul. 2008 (first online May 16, 2008), pp. 931-940 (abstract only).

Enzyme entry EC 2.3.1.75 (last viewed on Dec. 17, 2014), 2 pages.

Erijman et al., "Transfer-PCR (TPCR): A highway for DNA cloning and protein engineering," J. Structural Bio, vol. 175, Apr. 15, 2011, pp. 171-177.

Examination Report No. 1 in AU Patent Application No. 2015277261 dated Feb. 11, 2020 (3 pages).

Fasan, R., "Tuning P450 Enzymes as Oxidation Catalysts," ACS Catal., vol. 2, Feb. 22, 2012, pp. 647-666.

Final Office Action in U.S. Appl. No. 14/897,285 mailed Jan. 19, 2018 (17 pages).

Final Office Action in U.S. Appl. No. 15/319,272 mailed Apr. 24, 2019 (7 pages).

First Examination Report in AU Patent Application No. 2014277874 mailed Nov. 19, 2019, 3 pages.

First Office Action in CN Patent Application No. 201480033702.8 mailed Aug. 2, 2018 (with English translation) (16 pages).

Forman et al., "Metathesis of renewable unsaturated fatty acid esters catalyzed by a phobanindenylidene ruthenium catalyst," J. Org. Chem, Jun. 23, 2006, vol. 691, pp. 5513-5516.

Fujita et al., "Comparison of Two Vectors for Functional Expression of a Bacterial Cytochrome P450 Gene in *Escherichia coli* Using CYP153 Genes," Biosci. Biotechnol. Biochem, vol. 73, No. 8, Aug. 7, 2009, pp. 1825-1830.

Funhoff et al., "CYP153A6, a Soluble P450 Oxygenase Catalyzing Terminal-Alkane Hydroxylation," J. Bacteriol., vol. 188, No. 14, Jul. 2006, pp. 5220-5227.

Funhoff, E.G. et al., "Hydroxylation and epoxidation reactions catalyzed by CYP153 enzymes" Enzyme Microb. Technol, vol. 40, Mar. 5, 2007, pp. 806-812.

Galan et al., "A Rapid and Simple Cleanup Procedure for Metathesis Reactions," Org. Letters, Feb. 28, 2007, vol. 9, No. 7, Feb. 28, 2007, pp. 1203-1206.

Genbank, accession No. ABM17701, Aug. 25, 2017, www.ncbi. nlm.nih.gov, 1 page.

Genbank, Accession No. WP_026137860.1, Oct. 17, 2019, www. ncbi.nlm.nih.gov, 2 pages.

Goeddel., "Gene Expression Technology: Methods in Enzymology," Academic Press, vol. 185, Jun. 11, 1990, pp. 3-7.

Grela et al., "A Highly Efficient Ruthenium Catalyst for Metathesis Reactions," Angew. Chem. Int. Ed, vol. 41, No. 21, Jul. 19, 2002, pp. 4038-4040.

Grosjean et al., "Preferential codon usage in prokaryotic genes: the optimal codon-anticodon interaction energy and the selective codon usage in efficiently expressed genes," Gene, vol. 18, Apr. 29, 1982, pp. 199-209.

Guo et al., "Protein tolerance to random amino acid change," Jun. 22, 2004, Natl. Acad. Sci., vol. 101, No. 25, pp. 9205-9210.

Hill et al., "Functional Analysis of Conserved Histidines in ADP-Glucose Pyrophosphorylase from *Escherichia coli*," Biochem. Biophys. Res. Comm., vol. 244, No. 2, Feb. 11, 1998, pp. 573-577.

Hong et al., "Prevention of Undesirable Isomerization during Olefin Metathesis," J. Am. Chem Soc. Dec. 14, 2005, vol. 127, No. 49, pp. 17160-17161.

Hunter et al., "Analysis of the domain properties of the novel cytochrome P450 RhF," FEBS Lett., vol. 579, Mar. 19, 2005, pp. 2215-2220.

International Preliminary Report on Patentability in International Patent Application No. PCT/US2014/042594 mailed Dec. 15, 2015 (9 pages).

International Preliminary Report on Patentability in International Patent Application No. PCT/US2015/036078 mailed Jun. 1, 2016 (15 pages).

International Preliminary Report on Patentability in International Patent Application No. PCT/US2016/066405, mailed Jun. 19, 2018 (6 pages).

International Preliminary Report on Patentability on PCT/EP2015/079832, mailed May 4, 2018, 18 pages.

International Search Report and Written Opinion in International Patent Application No. PCT/EP2015/079832 mailed Sep. 27, 2016 (11 pages).

International Search Report and Written Opinion in International Patent Application No. PCT/US2014/042594 mailed Oct. 16, 2014 (14 pages).

International Search Report and Written Opinion on PCT/US2015/036078, mailed Jan. 11, 2016, 11 pages.

International Search Report and Written Opinion on PCT/US2016/066405, mailed Apr. 28, 2017, 11 pages.

Knothe., "Dependence of biodiesel fuel properties on the structure of fatty acid alkyl esters," Fuel Processing Technology, vol. 86, Jun. 2005, pp. 1059-1070.

Kubota et al., "Isolation and Functional Analysis of Cytochrome P450 CYP153A Genes from Various Environments," Biosci Biotechnol. Biochem., vol. 69, No. 12, Aug. 20, 2005, pp. 2421-.

Kurjan et al., "Structure of a Yeast Pheromone Gene (MFa): A Putative a-Factor Precursor Contains Four Tandem Copies of Mature a-Factor," Cell, Oct. 1982, vol. 30, pp. 933-943.

Lazar et al., "Transforming Growth Factor alpha: Mutation of Aspartic Acid 4 7 and Leucine 48 Results in Different Biological Activity," Mol. Cell. Biol., vol. 8, No. 3, Mar. 1988, pp. 1247-1252.

(56) References Cited

OTHER PUBLICATIONS

Lentz et al., "Altering the regioselectivity of cytochrome P450 CYP102A3 of Bacillus subtilis by using a new versatile assay system," Chem Bio., vol. 7, 2006, pp. 345-350.

Lentz et al., "Substrate specificity of native and mutated cytochrome P450 (CYP102A3) from Bacillus subtilis," J. Biotechnol., vol. 108, Issue 1, Feb. 19, 2004, pp. 41-49 (abstract only), 1 page.

Leung et al., "A Journal of Methods in Cell and Molecular Biology," Technique, vol. 1, Aug. 1989, pp. 11-15.

Luckow et al., "High Level Expression of Nonfused Foreign Genes with Autographa californica Nuclear Polyhedrosis Virus Expression Vectors," Virology, May 1989, vol. 170, pp. 31-39.

Malca et al., "Bacterial CYP153A monooxygenases for the synthesis of omega-hydroxylated fatty acids," Chem. Commun., vol. 48, Mar. 23, 2012, pp. 5115-5117.

Malca, S.H., "Substrate characterization and protein engineering of bacterial cytochrome P450 monooxygenases for the bio-based synthesis of omega-hydroxy aliphatic compounds," Institute of Technical Biochemistry at the University of Stuggart, Mar. 14, 2013, pp. 1-147.

Maniatis et al., "Regulation of Inducible and Tissue-Specific Gene Expression", Science, Jun. 5, 1987, vol. 236, pp. 1237-1245.

Marvey et al., "The metathesis of polyunsaturated fatty esters using the homogeneous(O-2,6-C6H3X2)2Cl4/Me4Sn catalytic," J. Mol. Cat. A. Chem., Apr. 13, 2004, vol. 213, pp. 151-157.

Marvey., "Sunflower-based Feedstocks in Nonfood Applications; perspectives from Olefin Metathesis," International Journal of Molecular Sciences, Aug. 13, 2008, vol. 9, pp. 1393-1406.

Needleman et al., "A General Method Applicable to the Search for Similarities in the Amino Acid Sequence of Two Proteins", Mar. 28, 1970, J. Mol. Biol., vol. 48, pp. 443-453.

Nestl et al., "Recent progress in industrial biocatalysis," Curr. Opin. Chem. Bio., vol. 15, Apr. 2011, pp. 187-193 (abstract only), 1 page.

Ngo et al., "The Protein Folding Problem and Tertiary Structure Prediction," Birkhauser, date unknown, pp. 433 and 492-495.

Nicolaides et al., "Metathesis of Fatty Esters Derived from South African Sunflower Oil," JAOCS, vol. 67, No. 6, Jun. 1990, pp. 362-363.

Nodate, et al., "Functional expression system for cytochrome P450 genes using the reductase domain of self-sufficient P450RhF gtom Rhodococcus sp. NCIMB 9784," Appl. Microbial. Biotech., vol. 71, Aug. 2006, pp. 455-462.

Non-Final Office Action in U.S. Appl. No. 13/444,579, mailed Dec. 16, 2013 (7 pages).

Non-Final Office Action in U.S. Appl. No. 14/007,829 mailed Oct. 27, 2015 (24 pages).

Non-Final Office Action in U.S. Appl. No. 14/897,285 mailed May 18, 2017 (20 pages).

Non-Final Office Action in U.S. Appl. No. 14/897,285 mailed Oct. 23, 2018 (22 pages).

Non-Final Office Action in U.S. Appl. No. 15/319,272 mailed Aug. 10, 2018 (10 pages).

Non-Final Office Action in U.S. Appl. No. 15/319,272 dated Feb. 25, 2020.

Non-Final Office Action in U.S. Appl. No. 16/063,198 mailed Oct. 31, 2019, (10 pages).

Notice of Allowance in U.S. Appl. No. 13/444,579 mailed Jun. 22, 2015 (7 pages).

Notice of Allowance in U.S. Appl. No. 14/897,285 mailed Aug. 13, 2019 (10 pages).

Notice of Reasons for Rejection in JP Patent Application No. 2016-519714 mailed Jun. 11, 2018 (with English translation) (28 pages).

Notice of Reasons for Rejection in JP Patent Application No. 2016-573541 dated Apr. 16, 2020 (with English translation) (6 pages).

Notice of Reasons for Rejection in JP Patent Application No. 2016-573541 dated Apr. 20, 2020 (with English translation) (6 pages).

Notice of Reasons for Rejection in JP Patent Application No. 2016-573541 mailed May 16. 2019 (with English translation) (1 O pages).

Office Action in CO Patent Application No. 15293885 dated Jan. 21, 2016 (with English translation) (8 pages).

Office Action in CO Patent Application No. 15293885 mailed Aug. 10, 2017 (with English translation) (21 pages).

Office Action in CO Patent Application No. NC2016/0005882 dated Aug. 31, 2018 (no English translation available) (8 pages).

Office Action in MX Patent Application No. MX/a/2015/016947 mailed Aug. 28, 2019 (with English translation) (9 pages).

Office Action in MX Patent Application No. MX/a/2016/016565 dated Aug. 6, 2019 (with English translation) (8 pages).

Office Action on CO NC2016/0005882, mailed Jan. 13, 2017, 2 pages, Counsel analysis, no translation.

Oliver et al., "A Single Mutation in Cytochrome P450 BM3 Changes Substrate Orientation in a Catalytic Intermediate and the Regiospecificity of Hydroxylation," Biochem., vol. 36, Feb. 18, 1997, p. 1567(abstract only).

Partial Search Report in EP Patent Application No. 20160184.6 dated May 7, 2020, (14 pages).

Pre-Appeal Examination Report in JP Patent Application No. 2016-519714 dated Jan. 22, 2020 (with English translation) (9 pages).

Preliminary Office Action in BR Patent Appliation No. 112015031233-0 mailed Oct. 23, 2019 (with English translation) (7 pages).

Preliminary Office Action in BR Patent Application No. 112016029235.9, mailed Dec. 10, 2019 (with English Translation) (6 pages).

Reidhaar-Olson et al., "Combinatorial Cassette Mutagenesis as a Probe of the Informational Content of Protein Sequences," Science, Jul. 1, 1988, vol. 241, pp. 53-57.

Rejection Decision in CN Patent Application No. 201480033702.8 dated Apr. 2, 2020 (with English translation) (19 pages).

Roberts et al., "A Self-sufficient Cytochrome P450 with a Primary Structural Organization That Includes a Flavin Domain and a [2Fe—2S] Redox Center," J. Biol. Chem., vol. 278, No. 49, Dec. 5, 2003, pp. 48914-48920.

Rosenberg, "Multiple Sequence Alignment Accuracy and Evolutionary Distance Estimation," BMC Bioinformatics, Nov. 23, 2005, vol. 6, No. 278, pp. 1-10.

Rude et al., "Terminal Olefin (1-Alkene) Biosynthesis by a Novel P450 Fatty Acid Decarboxylase from Jeotgalicoccus Species", Appl. Environ. Microbial., Mar. 2011, vol. 77, No. 5, pp. 1718-1727.

Sambrook et al., "Molecular Cloning: A Laboratory Manual," 2nd Ed., Cold Spring Harbor Laboratory Press, Dec. 1989, pp. 16.30-16.37.

Scheps et al., "Regioselective omega-hydroxylation of medium-chain n-alkanes and primary alcohols by CYP153 enzymes from Mycobacterium marinum and Polaromonas sp. strain JS666," Org. Biomol. Chem, vol. 9, Jun. 24, 2011, pp. 6727-6733.

Scheps et al., "Synthesis of [omega]-hydroxyl dodecanoic acid based on an engineered CYP153A fusion construct," Microbial Biotechnology, vol. 6 , Jun. 8, 2013, pp. 2-15.

Schultz et al., "Expression and secretion in yeast of a 400-kDa envelope glycoprotein derived from Epstein-Barr virus," Gene, Mar. 2, 1987, vol. 54, pp. 113-123.

Second Office Action in CN Patent Application No. 201480033702.8 mailed Jul. 1, 2019 (with English translation) (14 pages).

Smith et al., "Single-step purification of polypeptides expressed in Escherichia coli as fusions with glutathione S-transferase," Gene, Mar. 16, 1988, vol. 67, pp. 31-40.

Smith et al., "Production of Human Beta Interferon in Insect Cells Infected with a Baculovirus Expression Vector," Molecular and Cellular Biology, vol. 3, No. 12, Dec. 1983, pp. 2156-2165.

Soydan et al., "The Evaluation of the Role of Beta-Hydroxy Fatty Acids on Chronic Inflammation and Insulin Resistance," Mediators of Inflammation, vol. 2006, Aug. 7, 2006, pp. 1-6.

Steen et al., "Microbial production of fatty-acid derived fuels and chemicals from plant biomass," Nature Letters, vol. 463, No. 28, Jan. 28, 2010, pp. 559-563.

Stemmer, "DNA shuffling by random fragmentation and reassembly: In vitro recombination for molecular evolution," Proc. Natl. Acad. Sci., Oct. 1994, vol. 91, pp. 10747-10751.

(56)  References Cited

OTHER PUBLICATIONS

Studier et al., "Use of T7 RNA Polymerase to Direct Expression of Cloned Genes," Methods in Enzymology, Jun. 11, 1990, vol. 185, pp. 60-89.

Stuver et al., "Discussion: Reporting 14C Data," Radiocarbon, vol. 19, No. 3, 1988, pp. 355-363.

Substantive Examination Adverse Report in MY Patent Application No. PI2015002915, mailed Nov. 27, 2019, 5 pages.

Substantive Examination Report Stage I in ID Patent Application No. P00201600007 mailed Aug. 21, 2019 (with English translation) (5 pages).

Van Beilen., "Cytochrome P450 Alkane Hydroxylases of the CYP153 Family Are Common in Alkane-Degrading Eubacteria Lacking Integral Membrane Alkane Hydroxylases," Appl. Environ. Microbial., vol. 72, No. 1, Jan. 2006, pp. 59-65.

Van Bogaert et al., "The Role of cytochrome P450 monoxygenases in microbial fatty acid metabolism," FEBS Journal, vol. 278, 2011, pp. 206-221.

Wacey et al., "Disentangling the perturbational effects of amino acid substitutions in the DNA binding domain of p53.", Hum Genet, Feb. 1999, vol. 104, pp. 15-22.

Whitehouse et al., "P450BM3 (CYP102A1): connecting the dots," Chem. Soc. Rev. vol. 41, 2012, pp. 1218-1260, 43 pages.

Yang et al., "Efficient Method for the Synthesis of Chiral Pyrrolidine Derivatives via Ring-Closing Enyne Metathesis Reaction," Org. Letters, Feb. 6, 2007, vol. 9, No. 5, pp. 769-771.

Notice of Allowance in U.S. Appl. No. 16/063,198 dated May 14, 2020.

Second Substantive Examination Adverse Report on MY PI2015002915, dated May 29, 2020 (2 pages).

First Office Action in CA Patent Application No. 2915229, dated Jun. 8, 2020 (7 pages).

Non-Final Office Acton in U.S. Appl. No. 17/001,015, dated Aug. 24, 2020.

Non-Final Office Action in U.S. Appl. No. 17/834,681, dated Jan. 29, 2024.

* cited by examiner

METHODS OF PRODUCING OMEGA-HYDROXYLATED FATTY ACID DERIVATIVES

CROSS-REFERENCE TO RELATED APPLICATIONS

This application is a continuation of U.S. patent application Ser. No. 16/915,454, filed Jun. 29, 2020, which is a continuation of U.S. patent application Ser. No. 14/897,285, now U.S. Pat. No. 10,711,288, filed Dec. 10, 2015, which is U.S. National Stage Application under 35 U.S.C. § 371 of International Application No. PCT/US2014/042594, filed Jun. 16, 2014, which claims the benefit of U.S. Provisional Application No. 61/835,464, filed Jun. 14, 2013, the entire disclosures of which are hereby incorporated by reference.

SEQUENCE LISTING

This application contains references to amino acid sequences and/or nucleic acid sequences which have been submitted concurrently herewith as the sequence listing .xml file entitled "ST26_SL_Conversion_4_March_2024.xml", file size 187,000 Bytes, created on 4 Mar. 2024. The aforementioned sequence listing is hereby incorporated by reference in its entirety.

FIELD

The disclosure relates to omega-hydroxylated fatty acid derivatives and methods of producing them. Herein, the disclosure encompasses a novel and environmentally friendly production method that provides omega-hydroxylated fatty acid derivatives at high purity and yield. Further encompassed are recombinant microorganisms that produce omega-hydroxylated fatty acid derivatives through selective fermentation.

BACKGROUND

Omega-hydroxylated (ω-hydroxy) fatty acid derivatives have many commercial uses as components of industrial agents. The industry recognizes various types of ω-hydroxy fatty acid derivatives including ω-hydroxy fatty acids; ω-hydroxy fatty acid methyl esters; ω-oxo fatty acids; ω-amino fatty acids; ω-amino fatty acid methyl esters; alpha-, omega-diacids (α,ω-diacids); omega-carboxy fatty acid methyl esters (ω-carboxy fatty acid methyl ester); alpha-, omega-diesters (α,ω-diesters); alpha-, omega-diols (α,ω-diols); and the like. These molecules are also important as precursors to various other compounds. For example, α,ω-dicarboxylic acids, and other α,ω-bifunctional molecules are important chemicals with industrial applications in polymer resins, metal working fluids, adhesives, corrosion inhibitors, capacitor electrolytes, diester synthetic lubricants, fibers, powder coating curatives, plasticizers, polyester coatings, epoxy resins, polyamide resins, flavors, fragrances, surfactants, detergents, additives, and more. Today, ω-hydroxy fatty acid derivatives are still mostly made from petroleum-based materials or through the bioconversion of paraffin and fatty acids. The chemical methods for producing these compounds require the use of hazardous reagents and are energy intensive and environmentally costly. Conversely, emerging fermentation routes, while considered green processes, are still too expensive and are limited in the types of products that can be made. Thus, a process for the direct production of ω-hydroxy fatty acid derivatives of various types and functionalities from renewable feedstocks would not only be safer for the environment but also considerably more cost effective. The disclosure addresses this need.

SUMMARY

One aspect of the disclosure provides a recombinant microorganism for producing an omega-hydroxylated (ω-hydroxy) fatty acid derivative in vivo when grown in a fermentation broth in the presence of a carbon source from a renewable feedstock. The microorganism includes a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase of EC 1.14.15.3. The modified ω-hydroxylase has a modified cytochrome P450 monooxygenase (P450) enzymatic activity and efficiently catalyzes the ω-position of hydrocarbon chains in vivo. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V. Herein, the ω-hydroxylase hybrid fusion protein variant has at least one mutation at amino acid position 27, 82, 141, 178, 231, 309, 407, 415, 516, 666 and/or 796. The recombinant microorganism produces ω-hydroxy fatty acid derivatives, including but not limited to, ω-hydroxy fatty acids and ω-hydroxy fatty acid methyl esters.

Another aspect of the disclosure provides a recombinant microorganism for producing an ω-hydroxy fatty acid derivative in vivo when grown in a fermentation broth in the presence of a carbon source from a renewable feedstock. The microorganism includes a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase of EC 1.14.15.3. The modified ω-hydroxylase has a modified cytochrome P450 monooxygenase (P450) enzymatic activity and efficiently catalyzes the ω-position of hydrocarbon chains in vivo. In one aspect, the recombinant microorganism is engineered to further express a nucleic acid sequence encoding a polypeptide including an alcohol dehydrogenase of EC 1.1.1.1/2 or an alcohol oxidase of EC 1.1.3.13 or EC 1.1.3.20. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V. The recombinant microorganism produces ω-hydroxy fatty acid derivatives, including but not limited to, ω-oxo fatty acids and ω-oxo fatty acid methyl esters.

Another aspect of the disclosure provides a recombinant microorganism for producing an ω-hydroxy fatty acid derivative in vivo when grown in a fermentation broth in the presence of a carbon source from a renewable feedstock. The microorganism includes a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase (cytochrome P450 monooxygenase) of EC 1.14.15.3. In one aspect, the recombinant microorganism is engineered to further express a nucleic acid sequence encoding a polypeptide including an alcohol dehydrogenase of EC 1.1.1.1/2 or an alcohol oxidase of EC 1.1.3.13 or EC 1.1.3.20. In another aspect, the recombinant microorganism is engineered to still further express a nucleic acid sequence encoding a polypeptide including an aldehyde dehydrogenase of EC 1.2.1.3/4/5 or an aldehyde oxidase of EC 1.2.3.1. The modified ω-hydroxylase has a modified cytochrome P450 monooxygenase (P450) enzymatic activity and efficiently catalyzes the ω-position of hydrocarbon chains in vivo. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V. The recombinant microorganism produces ω-hydroxy fatty acid derivatives, including but not limited to, ω-hydroxy fatty acid derivatives that are α,ω-diacids or ω-carboxy fatty acid methyl esters.

Still, another aspect of the disclosure provides a recombinant microorganism for producing an ω-hydroxy fatty acid derivative in vivo when grown in a fermentation broth in the presence of a carbon source from a renewable feedstock. The microorganism includes a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase of EC 1.14.15.3. In one aspect, the recombinant microorganism is engineered to further express a nucleic acid sequence encoding a polypeptide including an alcohol dehydrogenase of EC 1.1.1.1/2 or an alcohol oxidase of EC 1.1.3.13 or EC 1.1.3.20. In another aspect, the recombinant microorganism is engineered to still further express a nucleic acid sequence encoding a polypeptide including an aldehyde dehydrogenase of EC 1.2.1.3/4/5 or an aldehyde oxidase of EC 1.2.3.1. In yet another aspect, the recombinant microorganism is engineered to further express a nucleic acid sequence encoding a polypeptide including an acyl-CoA ligase of EC 6.2.1.3 or an acyl-CoA transferase of EC 2.8.3.6. The modified ω-hydroxylase has a modified cytochrome P450 monooxygenase (P450) enzymatic activity and efficiently catalyzes the ω-position of hydrocarbon chains in vivo. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V. The recombinant microorganism produces ω-hydroxy fatty acid derivatives, including but not limited to, ω-hydroxy fatty acid derivatives that are α,ω-diesters.

The disclosure further encompasses a recombinant microorganism for producing an ω-hydroxy fatty acid derivative in vivo when grown in a fermentation broth in the presence of a carbon source from a renewable feedstock. The microorganism includes a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase of EC 1.14.15.3. In one aspect, the recombinant microorganism is engineered to further express a nucleic acid sequence encoding a polypeptide including an alcohol dehydrogenase of EC 1.1.1.1/2 or an alcohol oxidase of EC 1.1.3.13 or EC 1.1.3.20. In another aspect, the recombinant microorganism is engineered to further express a nucleic acid sequence encoding a polypeptide including an amino transferase of EC 2.6.1 or an amine dehydrogenases of EC 1.4.9, EC 1.4.98 or EC 1.4.99. The ω-hydroxylase has a modified cytochrome P450 monooxygenase (P450) enzymatic activity and efficiently catalyzes the ω-position of hydrocarbon chains in vivo. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V. The recombinant microorganism produces ω-hydroxy fatty acid derivatives, including but not limited to, ω-amino fatty acids and ω-amino fatty acid methyl esters.

Another aspect of the disclosure provides a recombinant microorganism for producing an ω-hydroxy fatty acid derivative in vivo when grown in a fermentation broth in the presence of a carbon source from a renewable feedstock. The microorganism includes a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase of EC 1.14.15.3. In one aspect, the recombinant microorganism is engineered to further express a nucleic acid sequence encoding a polypeptide comprising an alcohol dehydrogenase of EC 1.1.-.- and a carboxylic acid reductase of 1.2.99. The ω-hydroxylase has a modified cytochrome P450 monooxygenase (P450) enzymatic activity and efficiently catalyzes the ω-position of hydrocarbon chains in vivo. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V. The recombinant microorganism produces ω-hydroxy fatty acid derivatives, including but not limited to, ω-hydroxy fatty acid derivatives that are α,ω-diols.

The disclosure further contemplates a cell culture comprising the microorganism (supra), wherein the cell culture produces ω-hydroxy fatty acid derivatives including, but not limited to, ω-hydroxy fatty acids including ω-hydroxy free fatty acids; ω-hydroxy fatty acid methyl esters; ω-oxo fatty acids; ω-oxo fatty acid methyl esters; α,ω-diacids; α,ω-diols; α,ω-diesters; ω-carboxy fatty acid methyl esters; ω-amino fatty acids; and ω-amino fatty acid methyl esters.

Another aspect of the disclosure provides a method of producing an ω-hydroxy fatty acid derivative including providing a recombinant microorganism in a fermentation broth, the microorganism having a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase of EC 1.14.15.3. The method further includes adding a renewable feedstock containing a carbon source to the fermentation broth, and isolating a ω-hydroxy fatty acid derivative from the fermentation broth. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V. In one aspect, the produced ω-hydroxy fatty acid derivative is an ω-hydroxy free fatty acid or an ω-hydroxy fatty acid methyl ester.

Another aspect of the disclosure provides a method of producing an ω-hydroxy fatty acid derivative including providing a recombinant microorganism in a fermentation broth, the microorganism having a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and an ω-hydroxylase (cytochrome P450 monooxygenase) of EC 1.14.15.3. In one particular aspect, the recombinant microorganism is engineered to further express a nucleic acid sequence encoding a polypeptide including an alcohol dehydrogenase of EC 1.1.1.1/2 or an alcohol oxidase of EC 1.1.3.13 or EC 1.1.3.20. The method further includes adding a renewable feedstock containing a carbon source to the fermentation broth, and isolating a ω-hydroxy fatty acid derivative from the fermentation broth. In one aspect, the produced ω-hydroxy fatty acid derivative is an ω-oxo fatty acid or ω-oxo fatty acid methyl ester.

Another aspect of the disclosure provides a method of producing an ω-hydroxy fatty acid derivative including providing a recombinant microorganism in a fermentation broth, the microorganism having a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase of EC 1.14.15.3. In one particular aspect, the recombinant microorganism is engineered to further express a nucleic acid sequence encoding a polypeptide including an alcohol dehydrogenase of EC 1.1.1.1/2 or an alcohol oxidase of EC 1.1.3.13 or EC 1.1.3.20. In another specific aspect, the recombinant microorganism is engineered to further express a nucleic acid sequence encoding a polypeptide including an aldehyde dehydrogenase of EC 1.2.1.3/4/5 or an aldehyde oxidase of EC 1.2.3.1. The method further includes adding a renewable feedstock containing a carbon source to the fermentation broth, and isolating a ω-hydroxy fatty acid derivative from the fermentation broth. In one aspect, the produced ω-hydroxy fatty acid derivative is an α,ω-diacid or an α,ω-fatty acid di-methyl ester. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V.

Another aspect of the disclosure provides a method of producing an ω-hydroxy fatty acid derivative including providing a recombinant microorganism in a fermentation broth, the microorganism having a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase of EC 1.14.15.3. In one particular aspect, the recombinant microorganism is engineered to further express a nucleic acid sequence encoding a polypeptide including an alcohol dehydrogenase of EC 1.1.1.1/2 or an alcohol oxidase of EC 1.1.3.13 or EC 1.1.3.20. In another specific aspect, the recombinant microorganism is engineered to further express a nucleic acid sequence encoding a polypeptide including an amino transferase of EC 2.6.1 or an amine dehydrogenases of EC 1.4.9, EC 1.4.98 or EC 1.4.99. The method further includes adding a renewable feedstock containing a carbon source to the fermentation broth, and isolating a ω-hydroxy fatty acid derivative from the fermentation broth. In one aspect, the produced ω-hydroxy fatty acid derivative is an ω-amino fatty acid or ω-amino fatty acid methyl ester. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V.

The disclosure further contemplates a method of producing an ω-hydroxy fatty acid derivative including providing a recombinant microorganism in a fermentation broth, the microorganism having a pathway engineered to express at least two nucleic acid sequences encoding a polypeptide including a thioesterase of EC 3.1.2.-, 3.1.1.5, or 3.1.2.14; or an ester synthase of EC 2.3.1.75 or EC 2.3.1.20; and a modified ω-hydroxylase of EC 1.14.15.3. In one particular aspect, the recombinant microorganism is engineered to further express a nucleic acid encoding a polypeptide including a carboxylic acid reductase of EC 1.2.99.6 or and an alcohol dehydrogenase of EC 1.1.-.-. The method further includes adding a renewable feedstock containing a carbon source to the fermentation broth, and isolating a ω-hydroxy fatty acid derivative from the fermentation broth. In one aspect, the produced ω-hydroxy fatty acid derivative is an α,ω-diol. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V.

Another aspect of the present disclosure provides a method (supra), wherein the renewable feedstock is carbon based, including but not limited to, corn, sugar cane, sorghum, beet, switch grass, ensilage, straw, lumber, pulp, sewage, garbage, cellulosic urban waste, flu-gas, syn-gas, and carbon dioxide. In one aspect, the carbon source is selected from glucose, fructose, mannose, galactose, xylose, arabinose, fructo-oligosaccharide, galacto-oligosaccharide, starch, cellulose, pectin, xylan, sucrose, maltose, cellobiose, turanose, hemicellulose, methyl cellulose, sodium carboxymethyl cellulose, succinate, lactate, acetate, ethanol, methanol, glycerol, and mixtures thereof.

The disclosure further contemplates a polymer composition produced by the methods disclosed herein (supra), wherein the polymer composition includes, but is not limited to, polyurethane, polyester polyol, polyester resin, alkyl coating resin, fiberglass resin, gel coating resin, and polyester thermoplastic.

Another aspect of the disclosure provides a recombinant microorganism for producing an ω-hydroxy fatty acid derivative in vivo when grown in a fermentation broth in the presence of a carbon source from a renewable feedstock, the microorganism comprising a pathway engineered to express at least three nucleic acid sequences encoding a polypeptide including an acyl-ACP reductase of EC 1.2.1.42, an alcohol dehydrogenase of EC 1.1.-.-, and a modified ω-hydroxylase of EC 1.14.15.3. The ω-hydroxylase has a modified cytochrome P450 monooxygenase (P450) enzymatic activity and efficiently catalyzes the ω-position of hydrocarbon chains in vivo. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N407A, V415R, T516V, P666A, P666D and/or A796V. The produced ω-hydroxy fatty acid derivative is an α,ω-diol. In one aspect, a cell culture including the microorganisms disclosed herein (supra) is also provided.

Yet, another aspect of the disclosure provides a method of producing a ω-hydroxy fatty acid derivative including providing a recombinant microorganism in a fermentation broth, the microorganism having a pathway engineered to express at least three nucleic acid sequences encoding a polypeptide including an acyl-ACP reductase of EC 1.2.1.42, an alcohol dehydrogenase of EC 1.1.-.-, and a modified ω-hydroxylase of EC 1.14.15.3. The method further includes adding a renewable feedstock containing a carbon source to the fermentation broth, and isolating an ω-hydroxy fatty acid derivative from the fermentation broth. In one embodiment, the modified ω-hydroxylase is a ω-hydroxylase hybrid fusion protein variant of EC 1.14.15.3. In another embodiment, the modified ω-hydroxylase is a CYP153A-reductase hybrid fusion polypeptide. In another embodiment, the CYP153A-reductase hybrid fusion polypeptide is a self-sufficient CYP153A-RedRhF hybrid fusion protein. In still another embodiment, the modified ω-hydroxylase that is a ω-hydroxylase hybrid fusion protein variant has at least 90% sequence identity to SEQ ID NO: 6 and has one or more mutations including V141I, V141T, V141Q, V141G, V141M, V141L, R27L, R82D, R178N, A231T, N309R, N407A, V415R, T516V, P666A, P666D and/or A796V. Herein, the ω-hydroxy fatty acid derivative is an α,ω-diol. In one aspect, the renewable feedstock is carbon based and includes corn, sugar cane, sorghum, beet, switch grass, ensilage, straw, lumber, pulp, sewage, garbage, cellulosic urban waste, flu-gas, syn-gas, and carbon dioxide. In another aspect, the carbon source is selected from glucose, fructose, mannose, galactose, xylose, arabinose, fructo-oligosaccharide, galacto-oligosaccharide, starch, cellulose, pectin, xylan, sucrose, maltose, cellobiose, turanose, hemicellulose, methyl cellulose, sodium carboxymethyl cellulose, succinate, lactate, acetate, ethanol, methanol, glycerol, and mixtures thereof. Still further included is a polymer composition produced by the method, wherein the polymer composition includes, but is not limited to, polyurethane, polyester polyol, polyester resin, alkyl coating resin, fiberglass resin, gel coating resin, and polyester thermoplastic.

The disclosure further contemplates a fragrance chemical composition produced by the methods described herein (supra), wherein the fragrance chemical composition is a C9 to C16 saturated or unsaturated macrolide. The fragrance chemical composition includes chemical entities selected from ambrettolide, dihydro ambrettolide, macrolactone of 15-hydroxy pentadecanoic acid, and macrolactone of 15-hydroxy pentadecenoic acid and/or others.

BRIEF DESCRIPTION OF THE DRAWINGS

The present disclosure is best understood when read in conjunction with the accompanying figures, which serve to illustrate the preferred embodiments. It is understood, however, that the disclosure is not limited to the specific embodiments disclosed in the figures.

DETAILED DESCRIPTION

General Overview

Figure 1:
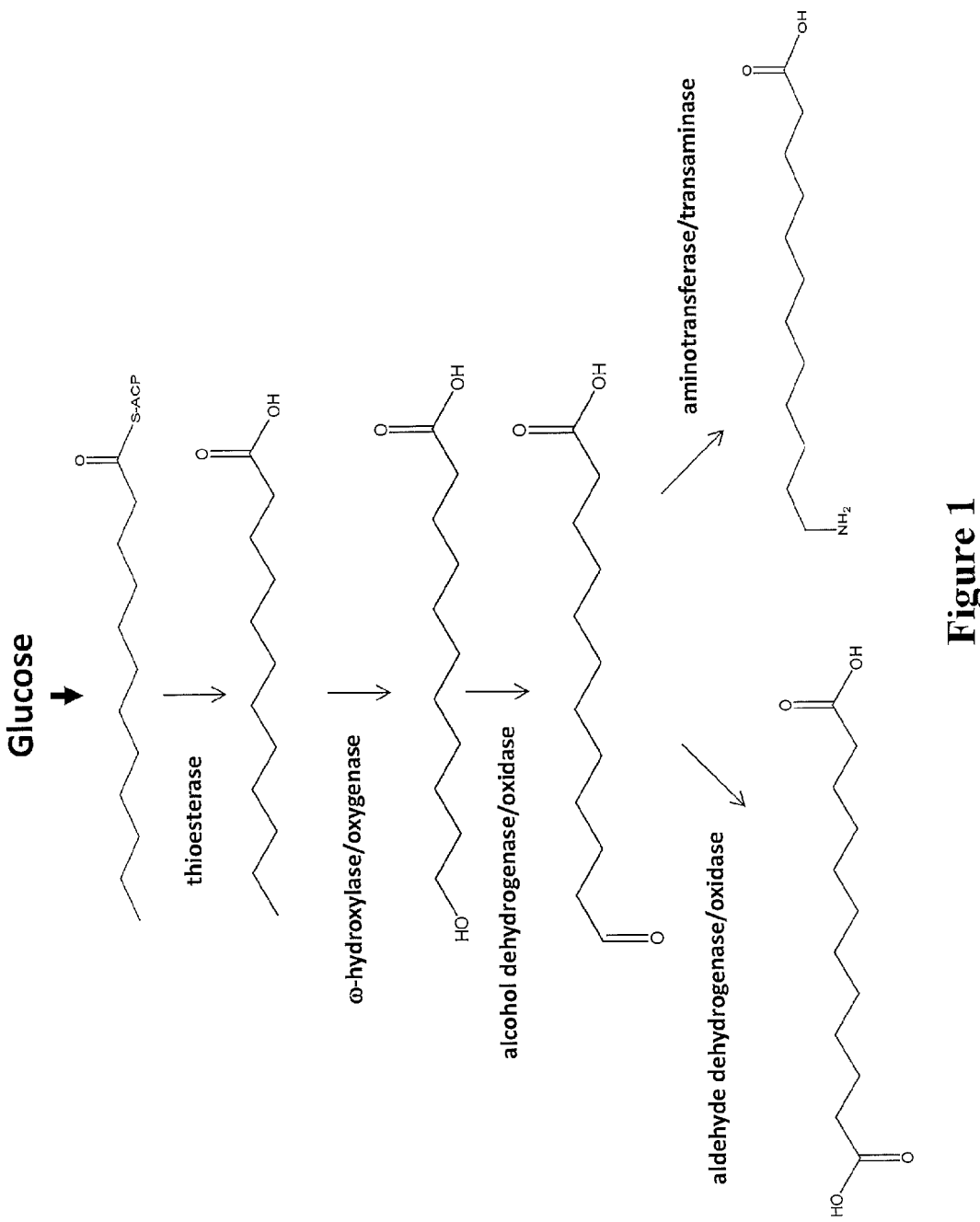
FIG. 1 depicts pathways for making ω-hydroxy-carboxylic acids, ω-oxo-carboxylic acids, ω-amino-carboxylic acids and α,ω-diacids. A fatty acid derivative with 12 carbon atoms is depicted as an example.

The development of a new and environmentally friendly method for the production of ω-hydroxy fatty acid derivatives denotes a significant improvement to the industry. The method allows these compounds to be produced efficiently from a simple carbon source derived from a renewable feedstock. Particularly, the method provides for the production of ω-hydroxy fatty acid derivatives from renewable materials such as carbohydrates from corn, cane, or lignocellulosic biomass; or waste products such as glycerol, flu-gas, syn-gas; or the reformation of organic materials such as biomass or natural gas or carbon dioxide.

More specifically, the present disclosure provides novel recombinant microorganisms that have been engineered to convert renewable feedstocks, such as carbohydrates, to specific ω-hydroxy fatty acid derivatives including ω-hydroxy fatty acids; ω-hydroxy-fatty acid methyl esters; ω-carboxy-fatty acid methyl esters; ω-oxo fatty acids, ω-amino fatty acids, ω-amino fatty acid methyl esters, α,ω-diacids; α,ω-di esters; α,ω-diols and the like. As such, bifunctional molecules include, but are not limited to, ω-hydroxy fatty acids; α,ω-hydroxy fatty alcohols; α,ω-hydroxy-fatty acid methyl esters; α,ω-hydroxy amines; α,ω-diacids; α,ω-di-fatty acid methyl esters, α,ω-diols and the like. The recombinant microorganisms allow for cost-effective fermentation processes for the production of these compounds. The disclosure encompasses a microbial fatty acid metabolism and the conversion of its intermediates to specific chemicals.

The advantages of the present disclosure are numerous. The disclosure provides for a simpler production method, i.e., employing a simple fermentation procedure rather than multiple chemical and/or biocatalytic processes, which is faster, less costly, and environmentally friendlier because fewer waste products are generated. The use of renewable feedstock (sustainable raw materials) and/or industrial waste products (e.g., glycerol) as source materials adds another cost benefit and protects the environment. The disclosure provides for the selective manufacture of specific target products, i.e., compositions that include chemical entities with selective chain lengths and chemistries. The access to diverse chemical functionalities allows for new target market applications.

Definitions

As used herein, the terms "omega-hydroxylated fatty acid derivative" and "ω-hydroxylated fatty acid derivative" and "ω-hydroxy fatty acid derivative" and "ω-hydroxyl fatty acid derivative" and "ω-OH fatty acid derivative" are used interchangeably herein and refer to a chemical entity that originated from fatty acid metabolism and that has at least one OH group at the omega position or is derived from an intermediate that has at least one OH group at the omega position. Herein, the "omega position" refers to the terminal carbon atom of a fatty acid derivative at the opposite end in regard to its primary functional group. Such ω-hydroxy fatty acid derivatives include, but are not limited to, ω-hydroxy fatty acids; ω-hydroxy-fatty acid methyl esters; ω-carboxy-fatty acid methyl esters; ω-oxo fatty acids; ω-amino fatty acids; ω-amino fatty acid methyl esters; as well as α,ω-diacids; α,ω-diesters; and α,ω-diols. The term "ω-hydroxy fatty acid derivative" includes "α,ω-bifunctional fatty acid derivatives".

An "ω-hydroxy fatty acid derivative composition" as referred to herein is produced by a recombinant host cell and typically comprises a mixture of certain types of ω-hydroxy fatty acid derivatives with various chain lengths and/or saturation and/or branching characteristics (e.g., α,ω-diacids of various chain length and/or saturation and/or branching characteristics; or α,ω-diesters of various chain length and/or saturation and/or branching characteristics; or α,ω-diols of various chain length and/or saturation and/or branching characteristics; and the like). In some cases, the ω-hydroxy fatty acid derivative composition includes mostly one type of ω-hydroxy fatty acid derivative such as, for example, 1,12-dodecenediol, or 1,14-tetradecaneiol, or 16-hydroxy hexadecanoic acid methyl ester, or 16-hydroxy-hexadecenoic acid, or 15-hydroxy-pentadecanoic acid, or 15-hydroxypentadecenoic acid, or 18-hydroxy octacecenoic acid, or the methyl esters of any of these fatty acid derivatives, or others. In still other cases, the ω-hydroxy fatty acid derivative composition comprises a mixture of more than one type of ω-hydroxy fatty acid derivative in order to provide a specifically designed composition (e.g., about 20% 1,12-docecenediol and about 80% 1,16-hexadecanediol in the same composition would provide such an example).

The term "subterminally" hydroxylated fatty acid derivative refers to a chemical entity that has at least one OH group (or is derived from an intermediate that has at least one OH group) at the omega-1 position, and/or omega-2 position, and/or omega-3 position, and/or omega-4 position, etc. (e.g., ω-1, ω-2 and/or ω-3; etc.). Exemplary species are an ω-1, ω-2, and/or ω-3-hydroxy fatty acid; or an ω-1-hydroxy fatty acid methyl ester; or an ω-1, ω-2, ω-3, ω-4, and/or ω-5-hydroxy dodecanoic acid; etc.

The term "enzyme classification (EC) number" refers to a number that denotes a specific enzymatic activity. EC numbers classify enzymes according to the reaction they catalyze under a system of enzyme nomenclature. EC numbers specify enzyme-catalyzed reactions. For example, if different enzymes from different organisms catalyze the same reaction, then they have the same EC number. In addition, different protein folds can catalyze an identical reaction and therefore would be assigned an identical EC number (e.g., non-homologous isofunctional enzymes, or NISE). EC numbers are established by the nomenclature committee of the international union of biochemistry and molecular biology (IUBMB), a description of which is available on the IUBMB enzyme nomenclature website on the world wide web. For example, the cytochrome P450 monooxygenase (P450) enzymatic activity, including the ω-hydroxylase or ω-oxygenase enzymatic activity is classified under EC 1.14.15.3 (also known as long-chain acyl-[acyl-carrier-protein]reductase). The functionality of enzymes that fall under the P450 enzyme family is conserved in most prokaryotes from one species to the next. Thus, different microbial species can carry out the same enzymatic activity that is classified under EC 1.14.15.3. An example of an enzymatic activity that is characterized by EC 1.14.15.3 is the enzymatic activity of a CYP153A-reductase hybrid fusion polypeptide or variant thereof as discussed herein (supra).

The term "modified ω-hydroxylase of EC 1.14.15.3" and "modified ω-hydroxylase" are used interchangeably herein and refer to a cytochrome P450 monooxygenase enzymatic activity that efficiently catalyzes the ω position of hydrocarbon chains in vivo (e.g., in a microorganism).

The terms "ω-hydroxylase hybrid fusion protein variant of EC 1.14.15.3" and "ω-hydroxylase hybrid fusion protein variant" are used interchangeably herein and refer to a modified ω-hydroxylase hybrid fusion polypeptide that has at least one mutation in its amino acid sequence so that the expression of the ω-hydroxylase hybrid fusion protein variant in recombinant host cells results in improved titer, yield and/or productivity of ω-OH fatty acids and/or ω-OH fatty acid derivative compositions when compared to the expression of a natural P450 fusion protein in a corresponding host cell. For example, when a cell has been transformed with an ω-hydroxylase hybrid fusion protein variant it is a cell that expresses the ω-hydroxylase hybrid fusion protein variant (e.g., a recombinant cell). In one embodiment, the titer and/or yield of an ω-OH fatty acid produced by a cell that expresses the ω-hydroxylase hybrid fusion protein variant is at least twice that of a corresponding cell that expresses a natural P450 fusion protein. In another embodiment, the titer and/or yield of an ω-OH fatty acid or derivative thereof produced by a cell that expresses the ω-hydroxylase hybrid fusion protein variant is at least about 1 times, at least about 2 times, at least about 3 times, at least about 4 times, at least about 5 times, at least about 6 times, at least about 7 times, at least about 8 times, at least about 9 times, or at least about 10 times greater than that of a corresponding cell that expresses the natural P450 fusion protein. In one embodiment, the titer and/or yield of an ω-OH fatty acid or derivative thereof produced by a cell expressing the ω-hydroxylase hybrid fusion protein variant is at least about 1 percent, at least about 2 percent, at least about 3 percent, at least about 4 percent, at least about 5 percent, at least about 6 percent, at least about 7 percent, at least about 8 percent, at least about 9 percent, or about 10 percent greater than that of a corresponding cell that expresses the natural P450 fusion protein. In another embodiment, the titer and/or yield of an ω-OH fatty acid or derivative thereof produced in a recombinant cell due to the expression of the ω-hydroxylase hybrid fusion protein variant is at least about 20 percent to at least about 80 percent greater than that of a corresponding cell that expresses the natural P450 fusion protein. In some embodiments, the titer and/or yield of an ω-OH fatty acid produced by a cell is at least about 20 percent, at least about 25 percent, at least about 30 percent, at least about 35 percent, at least about 40 percent, at least about 45 percent at least about 50 percent, at least about 55 percent, at least about 60 percent, at least about 65 percent, at least about 70 percent, at least about 75 percent, at least about 80 percent, at least about 85 percent, at least about 90 percent, at least about 95 percent, at least about 97 percent, at least about 98 percent, or at least about 100 percent greater than that of the corresponding cell that expresses the natural P450 fusion protein.

The term "CYP153A-reductase hybrid fusion polypeptide" refers to a polypeptide sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 6. The CYP153A-reductase hybrid fusion polypeptide is self-sufficient and possesses ω-hydroxylase enzymatic activity that catalyzes the reaction of a fatty acid to an ω-OH fatty acid. An example of a CYP153A-reductase hybrid fusion polypeptide is a hybrid cyp153A-RedRhF-type fusion polypeptide.

The term "accession number" or "NCBI accession number" or "GenBank accession number" refers to a number that denotes a specific nucleic acid sequence. Sequence accession numbers that are discussed in this description were obtained from databases provided by the NCBI (National Center for Biotechnology Information) maintained by the National Institutes of Health, U.S.A., and from the UniProt Knowledgebase (UniProtKB) and Swiss-Prot databases provided by the Swiss Institute of Bioinformatics (also referred to as UniProtKB accession number).

As used herein, the term "nucleotide" refers to a monomeric unit of a polynucleotide that consists of a heterocyclic base, a sugar, and one or more phosphate groups. The naturally occurring bases (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids or polynucleotides, though many other linkages are known in the art (e.g., phosphorothioates, boranophosphates, and the like).

As used herein, the term "polynucleotide" refers to a polymer of ribonucleotides (RNA) or deoxyribonucleotides (DNA), which can be single-stranded or double-stranded and which can contain non-natural or altered nucleotides. The terms "polynucleotide," "nucleic acid sequence," and "nucleotide sequence" are used interchangeably herein to refer to a polymeric form of nucleotides of any length, either RNA or DNA. These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides. The polynucleotide can be in any form, including but not limited to, plasmid, viral, chromosomal, EST, cDNA, mRNA, and rRNA.

As used herein, the terms "polypeptide" and "protein" are used interchangeably to refer to a polymer of amino acid residues. The term "recombinant polypeptide" refers to a polypeptide that is produced by recombinant techniques, wherein generally DNA or RNA encoding the expressed protein is inserted into a suitable expression vector that is in turn used to transform a host cell to produce the polypeptide.

As used herein, the terms "homolog," and "homologous" refer to a polynucleotide or a polypeptide comprising a sequence that is at least about 50% identical to the corresponding polynucleotide or polypeptide sequence. Preferably homologous polynucleotides or polypeptides have polynucleotide sequences or amino acid sequences that have at least about 80%, 81%, 82%, 83%, 84%, 85%, 86%, 87%, 88%, 89%, 90%, 91%, 92%, 93%, 94%, 95%, 96%, 97%, 98% or at least about 99% homology to the corresponding amino acid sequence or polynucleotide sequence. As used herein the terms sequence "homology" and sequence "identity" are used interchangeably. One of ordinary skill in the art is well aware of methods to determine homology between two or more sequences. Briefly, calculations of "homology" between two sequences can be performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a first sequence that is aligned for comparison purposes is at least about 30%, preferably at least about 40%, more preferably at least about 50%, even more preferably at least about 60%, and even more preferably at least about 70%, at least about 75%, at least about 80%, at least about 85%, at least about 90%, at least about 95%, or about 100% of the length of a second sequence. The amino acid residues or nucleotides at corresponding amino acid positions or nucleotide positions of the first and second sequences are then compared. When a position in the first sequence is occupied by the same amino acid residue or nucleotide as the corresponding position in the second sequence, then the molecules are identical at that position. The percent homology between the two sequences is a function of the number of identical positions shared by the sequences, taking into account the number of gaps and the length of each gap, that need to be introduced for optimal alignment of the two sequences. The comparison of sequences and determination of percent homology between two sequences can be accomplished using a mathematical algorithm, such as BLAST (Altschul et al. (1990) *J. Mol. Biol.* 215(3): 403-410). The percent homology between two amino acid sequences also can be determined using the Needleman and Wunsch algorithm that has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6 (Needleman and Wunsch, (1970) *J. Mol. Biol.* 48:444-453). The percent homology between two nucleotide sequences also can be determined using the GAP program in the GCG software package, using a NWSgapdna.CMP matrix and a gap weight of 40, 50, 60, 70, or 80 and a length weight of 1, 2, 3, 4, 5, or 6. One of ordinary skill in the art can perform initial homology calculations and adjust the algorithm parameters accordingly. A preferred set of parameters (and the one that should be used if a practitioner is uncertain about which parameters should be applied to determine if a molecule is within a homology limitation of the claims) are a Blossum 62 scoring matrix with a gap penalty of 12, a gap extend penalty of 4, and a frameshift gap penalty of 5. Additional methods of sequence alignment are known in the biotechnology arts (see, e.g., Rosenberg (2005) *BMC Bioinformatics* 6:278); Altschul et al. (2005) *FEBS J.* 272(20): 5101-5109).

An "endogenous" polypeptide refers to a polypeptide encoded by the genome of the host cell (e.g., parental microbial cell) from which the recombinant cell is engineered or derived.

An "exogenous" polypeptide refers to a polypeptide which is not encoded by the genome of the parental microbial cell. A variant (i.e., mutant) polypeptide is an example of an exogenous polypeptide.

The term "heterologous" generally means derived from a different species or derived from a different organism. As used herein it refers to a nucleotide sequence or a polypeptide sequence that is not naturally present in a particular organism. Heterologous expression means that a protein or polypeptide is experimentally added to a cell that does not normally express that protein. As such, heterologous refers to the fact that a transferred protein was initially derived from a different cell type or a different species then the recipient. For example, a polynucleotide sequence endogenous to a plant cell can be introduced into a bacterial host cell by recombinant methods, and the plant polynucleotide is then a heterologous polynucleotide in a recombinant bacterial host cell.

As used herein, the term "fragment" of a polypeptide refers to a shorter portion of a full-length polypeptide or protein ranging in size from four amino acid residues to the entire amino acid sequence minus one amino acid residue. In certain embodiments of the disclosure, a fragment refers to the entire amino acid sequence of a domain of a polypeptide or protein (e.g., a substrate binding domain or a catalytic domain).

As used herein, the term "mutagenesis" refers to a process by which the genetic information of an organism is changed in a stable manner. Mutagenesis of a protein coding nucleic acid sequence produces a mutant protein. Mutagenesis also refers to changes in non-coding nucleic acid sequences that result in modified protein activity.

As used herein, the term "gene" refers to nucleic acid sequences encoding either an RNA product or a protein product, as well as operably-linked nucleic acid sequences affecting the expression of the RNA or protein (e.g., such sequences include but are not limited to promoter or enhancer sequences) or operably-linked nucleic acid sequences encoding sequences that affect the expression of the RNA or protein (e.g., such sequences include but are not limited to ribosome binding sites or translational control sequences).

Expression control sequences are known in the art and include, for example, promoters, enhancers, polyadenylation signals, transcription terminators, internal ribosome entry sites (IRES), and the like, that provide for the expression of the polynucleotide sequence in a host cell. Expression control sequences interact specifically with cellular proteins involved in transcription (Maniatis et al. (1987) *Science* 236:1237-1245). Exemplary expression control sequences are described in, for example, Goeddel, Gene Expression Technology: Methods in Enzymology, Vol. 185, Academic Press, San Diego, Calif. (1990).

In the methods of the disclosure, an expression control sequence is operably linked to a polynucleotide sequence. By "operably linked" is meant that a polynucleotide sequence and an expression control sequence(s) are connected in such a way as to permit gene expression when the appropriate molecules (e.g., transcriptional activator proteins) are bound to the expression control sequence(s). Operably linked promoters are located upstream of the selected polynucleotide sequence in terms of the direction of transcription and translation. Operably linked enhancers can be located upstream, within, or downstream of the selected polynucleotide.

As used herein, the term "vector" refers to a nucleic acid molecule capable of transporting another nucleic acid, i.e., a polynucleotide sequence, to which it has been linked. One type of useful vector is an episome (i.e., a nucleic acid capable of extra-chromosomal replication). Useful vectors are those capable of autonomous replication and/or expression of nucleic acids to which they are linked. Vectors capable of directing the expression of genes to which they are operatively linked are referred to herein as "expression vectors." In general, expression vectors of utility in recombinant DNA techniques are often in the form of "plasmids," which refer generally to circular double stranded DNA loops that, in their vector form, are not bound to the chromosome. The terms "plasmid" and "vector" are used interchangeably herein, in as much as a plasmid is the most commonly used form of vector. However, also included are such other forms of expression vectors that serve equivalent functions and that become known in the art subsequently hereto. In some embodiments, a recombinant vector further comprises a promoter operably linked to the polynucleotide sequence. In some embodiments, the promoter is a developmentally-regulated, an organelle-specific, a tissue-specific, an inducible, a constitutive, or a cell-specific promoter. The recombinant vector typically comprises at least one sequence including (a) an expression control sequence operatively coupled to the polynucleotide sequence; (b) a selection marker operatively coupled to the polynucleotide sequence; (c) a marker sequence operatively coupled to the polynucleotide sequence; (d) a purification moiety operatively coupled to the polynucleotide sequence; (e) a secretion sequence operatively coupled to the polynucleotide sequence; and (f) a targeting sequence operatively coupled to the polynucleotide sequence. In certain embodiments, the nucleotide sequence is stably incorporated into the genomic DNA of the host cell, and the expression of the nucleotide sequence is under the control of a regulated promoter region. The expression vectors described herein include a polynucleotide sequence described herein in a form suitable for expression of the polynucleotide sequence in a host cell. It will be appreciated by those skilled in the art that the design of the expression vector can depend on such factors as the choice of the host cell to be transformed, the level of expression of polypeptide desired, etc. The expression vectors described herein can be introduced into host cells to produce polypeptides, including fusion polypeptides, encoded by the polynucleotide sequences as described herein. Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombinant polypeptide. Such fusion vectors typically serve one or more of the following three purposes: (1) to increase expression of the recombinant polypeptide; (2) to increase the solubility of the recombinant polypeptide; and (3) to aid in the purification of the recombinant polypeptide by acting as a ligand in affinity purification. Often, in fusion expression vectors, a proteolytic cleavage site is introduced at the junction of the fusion moiety and the recombinant polypeptide. This enables separation of the recombinant polypeptide from the fusion moiety after purification of the fusion polypeptide. In certain embodiments, a polynucleotide sequence of the disclosure is operably linked to a promoter derived from bacteriophage T5. In certain embodiments, the host cell is a yeast cell, and the expression vector is a yeast expression vector. Examples of vectors for expression in yeast *S. cerevisiae* include pYepSec1 (Baldari et al. (1987) *EMBO J.* 6:229-234), pMFa (Kurjan et al. (1982) *Cell* 30: 933-943), pJRY88 (Schultz et al. (1987) *Gene* 54: 113-123), pYES2 (Invitrogen Corp., San Diego, CA), and picZ (Invitrogen Corp., San Diego, CA). In other embodiments, the host cell is an insect cell, and the expression vector is a baculovirus expression vector. Baculovirus vectors available for expression of proteins in cultured insect cells (e.g., Sf9 cells) include, for example, the pAc series (Smith et al. (1983) *Mol. Cell Biol.* 3:2156-2165) and the pVL series (Lucklow et al. (1989) *Virology* 170:31-39). In yet another embodiment, the polynucleotide sequences described herein can be expressed in mammalian cells using a mammalian expression vector. Other suitable expression systems for both prokaryotic and eukaryotic cells are well known in the art; see, e.g., Sambrook et al., "Molecular Cloning: A Laboratory Manual," second edition, Cold Spring Harbor Laboratory, (1989).

As used herein "acyl-CoA" refers to an acyl thioester formed between the carbonyl carbon of alkyl chain and the sulfhydryl group of the 4'-phosphopantethionyl moiety of coenzyme A (CoA), which has the formula R—C(O)S-CoA, where R is any alkyl group having at least 4 carbon atoms.

As used herein "acyl-ACP" refers to an acyl thioester formed between the carbonyl carbon of alkyl chain and the sulfhydryl group of the phosphopantetheinyl moiety of an acyl carrier protein (ACP). The phosphopantetheinyl moiety is post-translationally attached to a conserved serine residue on the ACP by the action of holo-acyl carrier protein synthase (ACPS), a phosphopantetheinyl transferase. In some embodiments an acyl-ACP is an intermediate in the synthesis of fully saturated acyl-ACPs. In other embodiments an acyl-ACP is an intermediate in the synthesis of unsaturated acyl-ACPs. In some embodiments, the carbon chain will have about 5, 6, 7, 8, 9, 10, 11, 12, 13, 14, 15, 16, 17, 18, 19, 20, 21, 22, 23, 24, 25, or 26 carbons. Each of these acyl-ACPs are substrates for enzymes that convert them to fatty acid derivatives.

As used herein, the term "fatty acid biosynthetic pathway" means a biosynthetic pathway that produces fatty acids and derivatives thereof including ω-hydroxylated fatty acid derivatives. The fatty acid biosynthetic pathway may include additional enzymes or polypeptides with enzymatic activities besides the ones discussed herein to produce fatty acid derivatives such as ω-hydroxylated fatty acid derivatives having the desired characteristics.

As used herein, the term "clone" typically refers to a cell or group of cells descended from and essentially genetically identical to a single common ancestor, for example, the bacteria of a cloned bacterial colony arose from a single bacterial cell.

As used herein, the term "culture" typical refers to a liquid media comprising viable cells. In one embodiment, a culture comprises cells reproducing in a predetermined culture media under controlled conditions, for example, a culture of recombinant host cells grown in liquid media comprising a selected carbon source and nitrogen. "Culturing" or "cultivation" refers to growing a population of recombinant host cells under suitable conditions in a liquid or solid medium. In particular embodiments, culturing refers to the fermentative bioconversion of a substrate to an end-product. Culturing media are well known and individual components of such culture media are available from commercial sources, e.g., under the Difco™ and BBL™ trademarks. In one non-limiting example, the aqueous nutrient medium is a "rich medium" comprising complex sources of nitrogen, salts, and carbon, such as YP medium, comprising 10 g/L of peptone and 10 g/L yeast extract of such a medium. The host cell of a culture can be additionally engineered to assimilate carbon efficiently and use cellulosic materials as carbon sources according to methods described in U.S. Pat. Nos. 5,000,000; 5,028,539; 5,424,202; 5,482,846; 5,602,030; WO 2010127318. In addition, in some embodiments the host cell is engineered to express an invertase so that sucrose can be used as a carbon source.

As used herein, the term "under conditions effective to express a genetically engineered polynucleotide sequence" means any condition that allows a host cell to produce a desired ω-hydroxy fatty acid derivative. Suitable conditions include, for example, fermentation conditions.

The term "recombinant microorganism" refers to a host cell that has been genetically modified such that certain enzymatic activities within the host cell have been altered, added and/or deleted relative to the parent cell or native host cell. A genetically modified host cell is an example of a recombinant microorganism. As such, a "modified or altered level of activity of a protein", for example an enzyme, in a recombinant host cell refers to a difference in one or more characteristics in the activity determined relative to the parent or native host cell in which that same modification is absent. Typically differences in activity are determined between a recombinant host cell, having modified activity, and the corresponding wild-type host cell (e.g., comparison of a culture of a recombinant host cell relative to the corresponding wild-type host cell), not having that modified activity. Modified activities can be the result of, for example, modified amounts of protein expressed by a recombinant host cell (e.g., as the result of increased or decreased number of copies of DNA sequences encoding the protein, increased or decreased number of mRNA transcripts encoding the protein, and/or increased or decreased amounts of protein translation of the protein from mRNA); changes in the structure of the protein (e.g., changes to the primary structure, such as, changes to the protein's coding sequence that result in changes in substrate specificity, changes in observed kinetic parameters); and changes in protein stability (e.g., increased or decreased degradation of the protein). In some embodiments, the polypeptide is a mutant or a variant of any of the polypeptides described herein. In certain instances, the coding sequences for the polypeptides described herein are codon optimized for expression in a particular host cell. For example, for expression in *E. coli*, one or more codons can be optimized (as described in, e.g., Grosjean et al. (1982) *Gene* 18:199-209).

The term "regulatory sequences" as used herein typically refers to a sequence of bases in DNA, operably-linked to DNA sequences encoding a protein that ultimately controls the expression of the protein. Examples of regulatory sequences include, but are not limited to, RNA promoter sequences, transcription factor binding sequences, transcription termination sequences, modulators of transcription (such as enhancer elements), nucleotide sequences that affect RNA stability, and translational regulatory sequences (such as, ribosome binding sites (e.g., Shine-Dalgarno sequences in prokaryotes or Kozak sequences in eukaryotes), initiation codons, termination codons).

The terms "altered level of expression" and "modified level of expression" are used interchangeably and mean that a polynucleotide, polypeptide, metabolite, or product (such as an ω-hydroxy fatty acid derivative) is present in a different concentration in an engineered host cell as compared to its concentration in a corresponding wild-type cell under the same conditions.

As used herein, the term "titer" refers to the quantity of ω-fatty acid derivative produced per unit volume of host cell culture. The titer may refer to a particular ω-fatty acid derivative or a combination of ω-fatty acid derivatives produced by a given recombinant host cell culture.

As used herein, the "yield of ω-hydroxy fatty acid derivative produced by a host cell" refers to the efficiency by which an input carbon source is converted to a product (e.g., ω-hydroxy fatty acid, α,ω-diacid, etc.) in a host cell. The yield may refer to a particular ω-hydroxy fatty acid derivative or a combination of ω-hydroxy fatty acid derivatives produced by a given recombinant host cell culture. The ω-hydroxy fatty acid derivatives include, but are not limited to, ω-hydroxy fatty acids including ω-hydroxy free fatty acids; ω-hydroxy fatty acid methyl esters; ω-oxo fatty acids; ω-oxo fatty acid methyl esters; bifunctional compounds such as α,ω-diacids; α,ω-diols; α,ω-diesters; ω-carboxy fatty acid methyl esters; ω-amino fatty acids; and ω-amino fatty acid methyl esters.

As used herein, the term "productivity" refers to the quantity of a ω-hydroxy fatty acid derivative or derivatives produced per unit volume of host cell culture per unit time. The productivity may refer to a particular ω-hydroxy fatty acid derivative or a combination of fatty acid derivatives produced by a given recombinant host cell culture.

As used herein, the term "glucose utilization rate" means the amount of glucose used by the culture per unit time, reported as grams/liter/hour (g/L/hr).

As used herein, the term "carbon source" refers to a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, and gases (e.g., CO and $CO_2$). Exemplary carbon sources include, but are not limited to, monosaccharides, such as glucose, fructose, mannose, galactose, xylose, and arabinose; oligosaccharides, such as fructo-oligosaccharide and galacto-oligosaccharide; polysaccharides such as starch, cellulose, pectin, and xylan; disaccharides, such as sucrose, maltose, cellobiose, and turanose; cellulosic material and variants such as hemicelluloses, methyl cellulose and sodium carboxymethyl cellulose; succinate, lactate, and acetate; alcohols, such as ethanol, methanol, and glycerol, or mixtures thereof. The carbon source can also be a product of photosynthesis, such as glucose. In certain embodiments, the carbon source is biomass. In other embodiments, the carbon source is glucose. In other embodiments the carbon source is sucrose.

The term "carbon source from a renewable feedstock" when used alone or in reference to a feed source includes any biological material (including renewable feedstocks and/or biomass and/or waste products) from which carbon is derived except oleochemicals (i.e., refined oils from plants and animals such as fatty acids, fatty acid esters, TAGs, hydroxy fatty acids, and the like) and petrochemicals (i.e., chemicals derived from petroleum such as alkanes, alkenes, and the like). Thus, the term "carbon source from a renewable feedstock", as used herein, excludes carbon derived from oleochemicals and petrochemicals. In some embodiments, the carbon source includes sugars or carbohydrates (e.g., monosaccharides, disaccharides, or polysaccharides). In some embodiments, the carbon source is glucose and/or sucrose. In other embodiments, the carbon source is derived from a renewable feedstock such as carbohydrates from corn, sugar cane, or lignocellulosic biomass; or waste products such as glycerol, flu-gas, syn-gas; or the reformation of organic materials such as biomass or natural gas; or is carbon dioxide that is fixed photosynthetically. In other embodiments, a biomass is processed into a carbon source, which is suitable for bioconversion. In still other embodiments, the biomass does not require further processing into a carbon source but can be used directly as carbon source. An exemplary source of such biomass is plant matter or vegetation, such as switchgrass. Another exemplary carbon source includes metabolic waste products, such as animal matter (e.g., cow manure). Further exemplary sources of carbon include algae and other marine plants. Another carbon source (including biomass) includes waste products from industry, agriculture, forestry, and households, including, but not limited to, fermentation waste, fermentation biomass, glycerol/glycerine, ensilage, straw, lumber, sewage, garbage, maniple solid waste, cellulosic urban waste, and food leftovers.

As used herein, the term "isolated," with respect to products (such as ω-hydroxy fatty acid derivatives) refers to products that are separated from cellular components, cell culture media, or chemical or synthetic precursors. The ω-hydroxy fatty acid derivatives and ω-hydroxy fatty acid derivative compositions produced by the methods described herein can be relatively immiscible in the fermentation broth, as well as in the cytoplasm. Therefore, the ω-hydroxy fatty acid derivatives and ω-hydroxy fatty acid derivative compositions can collect in an organic phase either intracellularly or extracellularly. In one preferred method, the ω-hydroxy fatty acid derivatives and ω-hydroxy fatty acid derivative compositions collect extracellularly.

As used herein, the terms "purify," "purified," or "purification" mean the removal or isolation of a molecule from its environment by, for example, isolation or separation. "Substantially purified" molecules are at least about 60% free (e.g., at least about 70% free, at least about 75% free, at least about 85% free, at least about 90% free, at least about 95% free, at least about 97% free, at least about 99% free) from other components with which they are associated. As used herein, these terms also refer to the removal of contaminants from a sample. For example, the removal of contaminants can result in an increase in the percentage of fatty acid derivatives in a sample. For example, when an ω-hydroxy fatty acid derivative is produced in a recombinant host cell, the ω-hydroxy fatty acid derivative can be purified by the removal of host cell proteins. After purification, the percentage of ω-hydroxy fatty acid derivative in the sample is increased. The terms "purify," "purified," and "purification" are relative terms which do not require absolute purity. Thus, for example, when an ω-hydroxy fatty acid derivative is produced in recombinant host cells, a purified ω-hydroxy fatty acid derivative is an ω-hydroxy fatty acid derivative that is substantially separated from other cellular components (e.g., nucleic acids, polypeptides, lipids, carbohydrates, or other hydrocarbons).

The term "producing an ω-hydroxy fatty acid derivative in vivo", as used for the purpose of the specification and claims, means producing an ω-hydroxy fatty acid derivative in viable and/or genetically modified host cells from a renewable feedstock such as a carbohydrate or others, wherein the renewable feedstock is added to a fermentation broth as a carbon source so that the host cells can take up and metabolize the carbon source during fermentation. This differs from methods where ω-hydroxy fatty acid derivatives are produced in vitro, wherein purified enzymes or cell lysates are being used and the direct substrate for the enzymatic conversion, e.g., a fatty acid or fatty acid derivative, is being added to the purified enzyme or to the cell lysate solutions. This also differs from methods where ω-hydroxy fatty acid derivatives are produced in biotransformations, wherein resting cells are being used and the direct substrate for the enzymatic conversion, e.g., a fatty acid or fatty acid derivative, is being exogenously added to the resting cells.

Pathway Engineering and Enzymatic Activities

Fatty acid synthesis is one of the most conserved systems of the bacterial biosynthetic machinery. The fatty acid synthase (FAS) multi-enzyme complex is present in all bacteria and eukaryotes. Most of the FAS related genes are indispensable for cell growth and survival. Eukaryotic and bacterial FAS drive essentially the same type of biochemical transformation. In eukaryotes, FAS is referred to as FAS I and most of its catalytic domains are encoded by one polypeptide chain (non-dissociable). In prokaryotes such as bacteria, FAS is referred to as FASII and its individual enzymes and carrier proteins are encoded by separate genes coding for discrete (dissociable) proteins. As such, FASII is a complex system with significant variations and distinct peculiarities.

The acyl carrier protein (ACP) along with the enzymes in a FAS pathway control the length, degree of saturation and branching of the fatty acids produced in a native organism. The steps in this pathway are catalyzed by enzymes of the fatty acid biosynthesis (FAB) and acetyl-CoA carboxylase (ACC) gene families. For example, enzymes that can be included in a FAS pathway include AccABCD, FabD, FabH, FabG, FabA, FabZ, FabI, FabK, FabL, FabM, FabB, and FabF. Depending upon the desired product one or more of these genes can be attenuated or over-expressed. As such, prokaryotes have been engineered to increase production of fatty acid derivatives from renewable feedstock such as glucose or other carbon sources. Herein the major goal is to increase the activity of key control enzymes that regulate the production of fatty acid derivatives in order to convert the bacterial strain into a microbial factory for fatty acid derivative production, including fatty acid methyl esters (FAMEs), fatty acid ethyl esters (FAEEs), and fatty alcohols (FALC) (see, e.g., U.S. Pat. No. 8,283,143, incorporated by reference herein).

The present disclosure identifies polynucleotides that encode polypeptides of enzymatic function in order to modify enzymatic pathways for the production of desirable compounds such as ω-hydroxy fatty acid derivatives. These polypeptides, which are identified herein by Enzyme Accession Numbers (EC Numbers), are useful for engineering fatty acid pathways that lead to production of bi-functional molecules such as ω-hydroxy fatty acid derivatives. FIGS. 1-4 depict pathways that have been engineered to produce these compounds. FIG. 5 depicts a pathway that leads to lactams and polymers such as nylon.

In one embodiment, pathways are depicted in FIGS. 1 through 4 that use a renewable feedstock such as glucose to produce ω-hydroxy fatty acid derivatives. Glucose is converted to an acyl-ACP by the native organism (see step 1 in Figures through 4). Polynucleotides that code for polypeptides with fatty acid degradation enzyme activity can be optionally attenuated depending on the desired product (see Examples, infra). Non-limiting examples of such polypeptides are acyl-CoA synthetase (FadD) and acyl-CoA dehydrogenase (FadE). Table 1 provides a comprehensive list of enzymatic activity (infra) within the metabolic pathway, including various fatty acid degradation enzymes that can be optionally attenuated according to methods known in the art (see, e.g., U.S. Pat. No. 8,283,143, supra).

For example, FadR (see Table 1, infra) is a key regulatory factor involved in fatty acid degradation and fatty acid biosynthetic pathways (Cronan et al., *Mol. Microbiol.*, 29(4): 937-943 (1998)). The *E. coli* enzyme FadD (see Table 1, infra) and the fatty acid transport protein FadL are components of a fatty acid uptake system. FadL mediates transport of fatty acids into the bacterial cell, and FadD mediates formation of acyl-CoA esters. When no other carbon source is available, exogenous fatty acids are taken up by bacteria and converted to acyl-CoA esters, which can bind to the transcription factor FadR and depress the expression of the fad genes that encode proteins responsible for fatty acid transport (FadL), activation (FadD), and β-oxidation (FadA, FadB, and FadE). When alternative sources of carbon are available, bacteria synthesize fatty acids as acyl-ACPs, which are used for phospholipid synthesis, but are not substrates for β-oxidation. Thus, acyl-CoA and acyl-ACP are both independent sources of fatty acids that can result in different end-products (Caviglia et al., *J. Biol. Chem.*, 279(12): 1163-1169 (2004)).

TABLE 1

| | | Enzymatic Activities | | | |
|---|---|---|---|---|---|
| Gene Designation | Source Organism | Enzyme Name | Accession # | EC Number | Exemplary Use |
| | | Fatty Acid Production Increase | | | |
| accA | E. coli, Lactococci | Acetyl-CoA carboxylase, subunit A (carboxyltransferase alpha) | AAC73296, NP_414727 | 6.4.1.2 | increase Malonyl-CoA production |

TABLE 1-continued

Enzymatic Activities

| Gene Designation | Source Organism | Enzyme Name | Accession # | EC Number | Exemplary Use |
|---|---|---|---|---|---|
| accB | *E. coli*, *Lactococci* | Acetyl-CoA carboxylase, subunit B (BCCP: biotin carboxyl carrier protein) | NP_417721 | 6.4.1.2 | increase Malonyl-CoA production |
| accC | *E. coli*, *Lactococci* | Acetyl-CoA carboxylase, subunit C (biotin carboxylase) | NP_417722 | 6.4.1.2, 6.3.4.14 | increase Malonyl-CoA production |
| accD | *E. coli*, *Lactococci* | Acetyl-CoA carboxylase, subunit D (carboxyltransferase beta) | NP_416819 | 6.4.1.2 | increase Malonyl-CoA production |
| fadD | *E. coli* W3110 | acyl-CoA synthase | AP_002424 | 2.3.1.86, 6.2.1.3 | increase Fatty acid production |
| fabA | *E. coli* K12 | β-hydroxydecanoyl thioester dehydratase/isomerase | NP_415474 | 4.2.1.60 | increase fatty acyl-ACP/CoA production |
| fabB | *E. coli* | 3-oxoacyl-[acyl-carrier-protein] synthase I | BAA16180 | 2.3.1.41 | increase fatty acyl-ACP/CoA production |
| fabD | *E. coli* K12 | [acyl-carrier-protein] S-malonyltransferase | AAC74176 | 2.3.1.39 | increase fatty acyl-ACP/CoA production |
| fabF | *E. coli* K12 | 3-oxoacyl-[acyl-carrier-protein] synthase II | AAC74179 | 2.3.1.179 | increase fatty acyl-ACP/CoA production |
| fabG | *E. coli* K12 | 3-oxoacyl-[acyl-carrier protein] reductase | AAC74177 | 1.1.1.100 | increase fatty acyl-ACP/CoA production |
| fabH | *E. coli* K12 | 3-oxoacyl-[acyl-carrier-protein] synthase III | AAC74175 | 2.3.1.180 | increase fatty acyl-ACP/CoA production |
| fabI | *E. coli* K12 | enoyl-[acyl-carrier-protein] reductase | NP_415804 | 1.3.1.9 | increase fatty acyl-ACP/CoA production |
| fabR | *E. coli* K12 | Transcriptional Repressor | NP_418398 | none | modulate unsaturated fatty acid production |
| fabV | *Vibrio cholerae* | enoyl-[acyl-carrier-protein] reductase | YP_001217283 | 1.3.1.9 | increase fatty acyl-ACP/CoA production |
| fabZ | *E. coli* K12 | (3R)-hydroxymyristol acyl carrier protein dehydratase | NP_414722 | 4.2.1.— | increase fatty acyl-ACP/CoA production |
| fadE | *E. coli* K13 | acyl-CoA dehydrogenase | AAC73325 | 1.3.99.3, 1.3.99.— | reduce fatty acid degradation |
| fadD | *E. coli* K12 | acyl-CoA synthetase | NP_416319 | 6.2.1.3 | reduce fatty acid degradation |
| fadA | *E. coli* K12 | 3-ketoacyl-CoA thiolase | YP_02627 | 2.3.1.16 | reduce fatty acid degradation |
| fadB | *E. coli* K12 | enoyl-CoA hydratase, 3-OH acyl-CoA epimerase/dehydrogenase | NP_418288 | 4.2.1.17, 5.1.2.3, 1.1.1.35 | reduce fatty acid degradation |
| fadR | *E. coli* | transcriptional regulatory protein | NP_415705 | none | Block or reverse fatty acid degradation |

Chain Length Control

| tesA (with or without leader sequence) | *E. coli* | thioesterase - leader sequence is amino acids 1-26 | P0ADA1 | 3.1.2.—, 3.1.1.5 | C18 Chain Length |
| tesA (without leader sequence) | *E. coli* | thioesterase | AAC73596, NP_415027 | 3.1.2.—, 3.1.1.5 | C18:1 Chain Length |
| tesA (mutant of *E. coli* thioesterase I complexed with octanoic acid) | *E. coli* | thioesterase | L109P | 3.1.2.—, 3.1.1.5 | <C18 Chain Length |
| fatB1 | *Umbellularia californica* | thioesterase | Q41635 | 3.1.2.14 | C12:0 Chain Length |
| fatB2 | *Cuphea hookeriana* | thioesterase | AAC49269 | 3.1.2.14 | C8:0-C10:0 Chain Length |
| fatB3 | *Cuphea hookeriana* | thioesterase | AAC72881 | 3.1.2.14 | C14:0-C16:0 Chain Length |

TABLE 1-continued

Enzymatic Activities

| Gene Designation | Source Organism | Enzyme Name | Accession # | EC Number | Exemplary Use |
|---|---|---|---|---|---|
| fatB | *Cinnamomumcamphora* | thioesterase | Q39473 | 3.1.2.14 | C14:0 Chain Length |
| fatB | *Arabidopsis thaliana* | thioesterase | CAA85388 | 3.1.2.14 | C16:1 Chain Length |
| fatB1 | *Umbellularia californica* | thioesterase | Q41635 | 3.1.2.14 | C12:0 Chain Length |
| fatA1 | *Helianthus annuus* | thioesterase | AAL79361 | 3.1.2.14 | C18:1 Chain Length |
| fatA | *Arabidopsis thaliana* | thioesterase | NP_189147, NP_193041 | 3.1.2.14 | C18:1 Chain Length |
| fatA | *Brassica juncea* | thioesterase | CAC39106 | 3.1.2.14 | C18:1 Chain Length |
| fatA | *Cuphea hookeriana* | thioesterase | AAC72883 | 3.1.2.14 | C18:1 Chain Length |
| tes | *Photbacterium profundum* | thioesterase | YP_130990 | 3.1.2.14 | Chain Length |
| tesB | *E. coli* | thioesterase | NP_414986 | 3.1.2.14 | Chain Length |
| fadM | *E. coli* | thioesterase | NP_414977 | 3.1.2.14 | Chain Length |
| yciA | *E. coli* | thioesterase | NP_415769 | 3.1.2.14 | Chain Length |
| ybgC | *E. coli* | thioesterase | NP_415264 | 3.1.2.14 | Chain Length |
| | | Saturation Level Control | | | |
| Sfa | *E. coli* | Suppressor of fabA | AAN79592, AAC44390 | none | increase monounsaturated fatty acids |
| fabA | *E. coli* K12 | β-hydroxydecanoyl thioester dehydratase/isomerase | NP_415474 | 4.2.1.60 | produce unsaturated fatty acids |
| GnsA | *E. coli* | suppressors of the secG null mutation | ABD18647.1 | none | increase unsaturated fatty acid esters |
| GnsB | *E. coli* | suppressors of the secG null mutation | AAC74076.1 | none | increase unsaturated fatty acid esters |
| fabB | *E. coli* | 3-oxoacyl-[acyl-carrier-protein] synthase I | BAA16180 | 2.3.1.41 | modulate unsaturated fatty acid production |
| des | *Bacillus subtilis* | D5 fatty acyl desaturase | O34653 | 1.14.19 | modulate unsaturated fatty acid production |
| | | Ester Production | | | |
| AT3G51970 | *Arabidopsis thaliana* | long-chain-alcohol O-fatty-acyltransferase | NP_190765 | 2.3.1.26 | ester production |
| ELO1 | *Pichia angusta* | Fatty acid elongase | BAD98251 | 2.3.1.— | produce very long chain length fatty acids |
| plsC | *Saccharomyces cerevisiae* | acyltransferase | AAA16514 | 2.3.1.51 | ester production |
| DAGAT/DGAT | *Arabidopsis thaliana* | diacylglycerol acyltransferase | AAF19262 | 2.3.1.20 | ester production |
| hWS | *Homo sapiens* | acyl-CoA wax alcohol acyltransferase | AAX48018 | 2.3.1.20 | ester production |
| aft1 | *Acinetobacter* sp. ADP1 | bifunctional wax ester synthase/acyl-CoA:diacylglycerol acyltransferase | AAO17391 | 2.3.1.20 | ester production |
| ES9 | *Marinobacter hydrocarbonoclasticus* | wax ester synthase | ABO21021 | 2.3.1.20 | ester production |
| mWS | *Simmondsia chinensis* | wax ester synthase | AAD38041 | 2.3.1.— | ester production |
| | | Fatty Alcohol Output | | | |
| | | thioesterases (see above) | | | increase fatty acid/fatty alcohol production |
| BmFAR | *Bombyxmori* | FAR (fatty alcohol forming acyl-CoA reductase) | BAC79425 | 1.1.1.— | convert acyl-CoA to fatty alcohol |
| acr1 | *Acinetobacter* sp. ADP1 | acyl-CoA reductase | YP_047869 | 1.2.1.42 | reduce fatty acyl-CoA to fatty aldehydes |
| yqhD | *E. coli* W3110 | alcohol dehydrogenase | AP_003562 | 1.1.—.— | reduce fatty aldehydes to fatty alcohols; increase fatty alcohol production |
| alrA | *Acinetobacter* sp. ADP1 | alcohol dehydrogenase | CAG70252 | 1.1.—.— | reduce fatty aldehydes to fatty alcohols |
| BmFAR | *Bombyxmori* | FAR (fatty alcohol forming acyl-CoA reductase) | BAC79425 | 1.1.1.— | reduce fatty acyl-CoA to fatty alcohol |
| GTNG_1865 | *Geobacillus-thermodenitrificans* NG80-2 | Long-chain aldehyde dehydrogenase | YP-001125970 | 1.2.1.3 | reduce fatty aldehydes to fatty alcohols |

TABLE 1-continued

Enzymatic Activities

| Gene Designation | Source Organism | Enzyme Name | Accession # | EC Number | Exemplary Use |
|---|---|---|---|---|---|
| AAR | *Synechococcus elongatus* | Acyl-ACP reductase | YP_400611 | 1.2.1.42 | reduce fatty acyl-ACP/CoA to fatty aldehydes |
| carB | *Mycobacterium smegmatis* | carboxylic acid reductase protein | YP_889972 | 6.2.1.3, 1.2.1.42 | reduce fatty acids to fatty aldehyde |
| FadD | *E. coli* K12 | acyl-CoA synthetase | NP_416319 | 6.2.1.3 | activates fatty acids to fatty acyl-CoAs |
| atoB | *Erwiniacarotovora* | acetyl-CoA acetyltransferase | YP_049388 | 2.3.1.9 | production of butanol |
| hbd | *Butyrivibriofibrisolvens* | Beta-hydroxybutyryl-CoA dehydrogenase | BAD51424 | 1.1.1.157 | production of butanol |
| CPE0095 | *Clostridium perfringens* | crotonasebutyryl-CoA dehydryogenase | BAB79801 | 4.2.1.55 | production of butanol |
| bcd | *Clostridium beijerinckii* | butyryl-CoA dehydryogenase | AAM14583 | 1.3.99.2 | production of butanol |
| ALDH | *Clostridium beijerinckii* | coenzyme A-acylating aldehyde dehydrogenase | AAT66436 | 1.2.1.3 | production of butanol |
| AdhE | *E. coli* CFT073 | aldehyde-alcohol dehydrogenase | AAN80172 | 1.1.1.1 1.2.1.10 | production of butanol |

Fatty Alcohol Acetyl Ester Output

| Gene Designation | Source Organism | Enzyme Name | Accession # | EC Number | Exemplary Use |
|---|---|---|---|---|---|
| | | thioesterases (see above) | | | modify output |
| acr1 | *Acinetobacter* sp. ADP1 | acyl-CoA reductase | YP_047869 | 1.2.1.42 | modify output |
| yqhD | *E. Coli* K12 | alcohol dehydrogenase | AP_003562 | 1.1.—.— | modify output |
| AAT | *Fragaria* × *ananassa* | alcohol O-acetyltransferase | AAG13130 | 2.3.1.84 | modify output |

Terminal Olefin Output

| Gene Designation | Source Organism | Enzyme Name | Accession # | EC Number | Exemplary Use |
|---|---|---|---|---|---|
| OleT | *Jeotgalicoccus* sp. | Fatty acid decarboxylase | HQ709266 | 1.11.2.4 | decarboxylate fatty acids |

Product Export

| Gene Designation | Source Organism | Enzyme Name | Accession # | EC Number | Exemplary Use |
|---|---|---|---|---|---|
| AtMRP5 | *Arabidopsis thaliana* | *Arabidopsis thaliana* multidrug resistance-associated | NP_171908 | none | modify product export amount |
| AmiS2 | *Rhodococcus* sp. | ABC transporter AmiS2 | JC5491 | none | modify product export amount |
| AtPGP1 | *Arabidopsis thaliana* | *Arabidopsis thaliana* p glycoprotein 1 | NP_181228 | none | modify product export amount |
| AcrA | *CandidatusProtochlamydiaamoebophila* UWE25 | putative multidrug-efflux transport protein acrA | CAF23274 | none | modify product export amount |
| AcrB | *CandidatusProtochlamydiaamoebophila* UWE25 | probable multidrug-efflux transport protein, acrB | CAF23275 | none | modify product export amount |
| TolC | *Francisellatularensis* subsp. *novicida* | Outer membrane protein [Cell envelope biogenesis, transmembrane protein affects septum formation and cell membrane permeability | ABD59001 | none | modify product export amount |
| AcrE | *Shigellasonnei* Ss046 | | YP_312213 | none | modify product export amount |
| AcrF | *E. coli* | Acriflavine resistance protein F | P24181 | none | modify product export amount |
| tll1619 | *Thermosynechococcus elongatus* [BP-1] | multidrug efflux transporter | NP_682409.1 | none | modify product export amount |
| tll0139 | *Thermosynechocaccus elongatus* [BP-1] | multidrug efflux transporter | NP_680930.1 | none | modify product export amount |

Fermentation

| Gene Designation | Source Organism | Enzyme Name | Accession # | EC Number | Exemplary Use |
|---|---|---|---|---|---|
| replication checkpoint genes | | | | | increase output efficiency |
| umuD | *Shigellasonnei* Ss046 | DNA polymerase V, subunit | YP_310132 | 3.4.21.— | increase output efficiency |
| umuC | *E. coli* | DNA polymerase V, subunit | ABC42261 | 2.7.7.7 | increase output efficiency |

TABLE 1-continued

| | | Enzymatic Activities | | | |
|---|---|---|---|---|---|
| Gene Designation | Source Organism | Enzyme Name | Accession # | EC Number | Exemplary Use |
| pntA, pntB | *Shigella flexneri* | NADH:NADPH transhydrogenase (alpha and beta subunits) | P07001, P0AB70 | 1.6.1.2 | increase output efficiency |
| | | Other | | | |
| fabK | *Streptococcus pneumoniae* | trans-2-enoyl-ACP reductase II | AAF98273 | 1.3.1.9 | Contributes to fatty acid biosynthesis |
| fabL | *Bacillus licheniformis* DSM13 | enoyl-(acyl carrier protein) reductase | AAU39821 | 1.3.1.9 | Contributes to fatty acid biosynthesis |
| fabM | *Streptococcus mutans* | trans-2, cis-3-decenoyl-ACP isomerase | DAA05501 | 4.2.1.17 | Contributes to fatty acid biosynthesis |

TABLE 2A

Examples of ω-Hydroxylase/ω-Oxygenase (EC 1.14.15.3)

| Gene Designation | Source Organism | Accession No. | Redox System | Hydroxylation Position |
|---|---|---|---|---|
| cyp153A (aciA) | *Acinetobacter* sp. OC4 | BAE78452 | operon with ferredoxin and ferredoxin reductase | ω-hydroxylase |
| cyp153A16 | *Mycobacterium marinum* M | YP_001851443 | operon with ferredoxin and ferredoxin reductase | ω-hydroxylase |
| cyp153A6 | *Mycobacterium* sp. HXN-1500 | AJ833989 | operon with ferredoxin and ferredoxin reductase | ω-hydroxylase |
| cyp153A | *Marinobacter aquaeolei* VT8 | YP_957888 | operon with ferredoxin and ferredoxin reductase | ω -hydroxylase |
| alkB | *Pseudomonas putida* GPo1 | CAB54050 | requires rubredoxin and rubredoxin reductase | ω-hydroxylase |
| alkB | *Pseudomonas fluorescens* CHA0 | CAB51045 | requires rubredoxin and rubredoxin reductase | ω-hydroxylase |
| alkM | *Acinetobacter baylyi* | YP_046098 | requires rubredoxin and rubredoxin reductase | ω-hydroxylase |
| alkB | *Gordonia* sp. SoGc | ADT82701 | requires rubredoxin and rubredoxin reductase | ω-hydroxylase |
| alkW1 | *Dietzia* sp. DQ12-45-1b | IIQ850582 | c-terminal rubredoxin fusion, requires rubredoxin reductase | ω-hydroxylase |
| alkB | *Pseudomonas putida* GPo1 | CAB54050 | requires rubredoxin and rubredoxin reductase | ω-hydroxylase |
| alkB | *Pseudomonas fluorescens* CHA0 | CAB51045 | requires rubredoxin and rubredoxin reductase | ω-hydroxylase |

TABLE 2B

Examples of Redox Partners for ω-Hydroxylase/ω-Oxygenase (EC 1.14.15.3)

| Designation/Name | Organism | Accession # |
|---|---|---|
| ferredoxin, ferredoxin reductase | *Acinetobacter* sp. OC4 | BAE78451, BAE78453 |
| ferredoxin, ferredoxin reductase | *Mycobacterium marinum* M | YP_001851444, YP_001851442 |
| ferredoxin, ferredoxin reductase | *Marinobacter aquaeoli* VT8 | YP_957887, YP_957889 |
| alkG, alkT | *Pseudomonas putida* GPo1 | CAB54052, CAB54063 |
| rubA, rubB | *Acinetobacter baylyi* ADP1 | CAA86925, CAA86926 |

TABLE 2C

Examples of Self-Sufficient ω-1, ω-2, ω-3-Hydroxylase/Oxygenase
(EC 1.14.14.1) Fusion Proteins

| Gene Designation | Source Organism | Accession No. | Redox System | Hydroxylation Position |
|---|---|---|---|---|
| P450-BM3 (cyp102A1) | *Bacillus megaterium* | AAA87602 | fusion protein with reductase domain | ω-1,-2,-3 hydroxylation |
| yrhJ (cyp102A3) | *Bacillus subtilis* | NP_390594 | fusion protein with reductase domain | ω-1,-2,-3 hydroxylation |
| yrhJ (cyp102A7) | *Bacillus licheniformis* | AAU41718 | fusion protein with reductase domain | ω-1,-2,-3 hydroxylation |

TABLE 2D

Examples of Self-Sufficient Class-I
P450-Fused PFOR Fusion Proteins

| Designation/Name | Organism | Accession # |
|---|---|---|
| P450RhF | *Rhodococcus* sp. NCIMB 9784 | AAM67416 |
| REQ_44300 | *Rhodococcus equi* 103S | YP_004009071 |
| HMPREF0018_01193 | *Acinetobacter radioresistens* SH164 | ZP_06072406 |
| BMAA1669 | *Burkholderia mallei* ATCC 23344 | YP_106239 |
| Rmet_4932 | *Cupriavidus metallidurans* CH34 | YP_587063 |
| H16_B1279 | *Ralstonia eutropha* H16 | YP_840799 |

TABLE 3A

Examples of Alcohol Dehydrogenase (EC 1.1.1.1/2)
or Alcohol Oxidase (EC 1.1.3.13, EC 1.1.3.20)

| Designation/Name | Organism | Accession # |
|---|---|---|
| alkJ | *Pseudomonas putida* GPo1 | CAB54054 |
| alkJ | *Alcanivorax borkumensis* AP1 | CAC38030 |
| cddC | *Rhodococcus ruber* SC1 | AAL14237 |

TABLE 3B

Examples of Aldehyde Dehydrogenase (EC 1.2.1.3/4/5/)
or Aldehyde Oxidase (EC 1.2.3.1)

| Designation/Name | Organism | Accession # |
|---|---|---|
| alkH | *Pseudomonas putida* GPo1 | CAB51050 |
| alkH | *Alcanivorax borkumensis* AP1 | CAC38029 |
| cddD | *Rhodococcus ruber* SC1 | AAL14238 |

TABLE 4

Examples of Amino Transferase/Transaminase (EC 2.6.1) and
Amine Dehydrogenases (EC 1.4.9, EC 1.4.98, EC 1.4.99)

| Designation/Name | Function | Organism | Accession # |
|---|---|---|---|
| beta alanine-pyruvate transaminase | Beta-alanine:pyruvate transaminase | *Pseudomonas aeruginosa* PA7 | YP_001345604 |
| ygjG | Putrescine aminotransferase | *Escherichia coli* MG1655 | NP_417544 |
| gabT | 5-aminovalerate transaminase | *Pseuodomonas aeruginosa* PA01 | AAG03655 |
| Lat | L-lysine 6-transaminase | *Mycobacterium tuberculosis* H37Rv | NP_217807 |
| GABA-T | 4-aminobutyrate transaminase | *Sus scrofa* | NP_999428 |
| Ald | Alanine dehydrogenase | *Bacillus subtilis* subsp. *natto* BEST195 | BAI86717 |
| gdhA | Glutamate dehydrogenase (NADPH) | *Escherichia coli* MG1655 | NP_416275 |
| Gdh | Glutamate dehydrogenase (NADH) | *Peptoniphilus asaccharolyticus* | AAA25611 |
| L-lysine 6-dehydrogenase | L-lysine 6-dehydrogenase | *Achromobacter denitrificans* | AAZ94428 |
| mauRFBEDACJGMN | Methylamine dehydrogenase | *Paracoccus denitrificans* | P52685.1 P29897.2 P29894.1 P29896.2 P29895.2 P22619.2 P22364.1 P22566.2 ABL72797.1 ABL72798.1 AAA86469.1 |

TABLE 5

Examples of Esterase (EC 3.1.1.1) and Lipase (EC 3.1.1.3)

| Designation/Name | Organism | Accession # |
|---|---|---|
| lipA | *Pseudomonas fluorescens* B52 | AAF80996 |
| phaZ | *Pseudomonas fluorescens* GK13 | AAA64538 |

TABLE 6

Examples of Hydrolase (EC 3.5.2.12)

| Designation/Name | Organism | Accession # |
|---|---|---|
| ω-laurolactam hydrolase | *Acidovorax* sp. T31 | BAH09870 |
| ω-laurolactam hydrolase | *Cupriavidus* sp. U124 | BAH09871 |

TABLE 7

Examples of acyl-CoA Synthase/acyl-CoA Ligase (EC 6.2.1.3)/Transferase (EC 2.8.3.6)

| Designation/Name | Organism | Accession # |
|---|---|---|
| fadD | *Escherichia coli* MG 1655 | NP_416319 |
| fadK | *Escherichia coli* MG 1655 | NP_416216 |
| pimA | *Rhodopseudomonas palustris* | NP_949053 |
| dcaI/dcaJ | *Acinetobacter baylyi* ADP1 | YP_046360/ YP_046361 |

TABLE 8

Examples of Amide Synthase

| Designation/Name | Organism | Accession # |
|---|---|---|
| palmitoylputrescine synthase (PPS) | Uncultured *bacterium* | AAV33349 |
| N-(4-amino-2-hydroxybutyl) tetradecanamide synthase (AhtS) | Uncultured *bacterium* | ACX33975 |

TABLE 9

Examples of Ester Synthase (EC 2.3.1.75 or EC 2.3.1.20)

| Designation/Name | Organism | Accession # |
|---|---|---|
| AtfA | *Acinetobacter* sp. ADP1 | Q8GGG1 |
| AtfA1 | *Alcanivorax borkumensis*SK2 | YP_694462 |
| AtfA2 | *Alcanivorax borkumensis*SK2 | YP_693524 |
| WS/DGAT | *Marinobacter alginolyticus* | WP_007153340 |
| WS/DGAT | *Limnobacter* sp. MED105 | WP_008251579 |
| ES9 | *Marinobacter hydrocarbonoclasticus* | ABO21021 |

Figure 2A:
FIG. 2A depicts pathways for making ω-hydroxy-carboxylic acids, ω-amino-carboxylic acids and α,ω-diacids via methyl ester intermediates. A fatty acid derivative with 12 carbon atoms is depicted as an example.
Figure 2B:
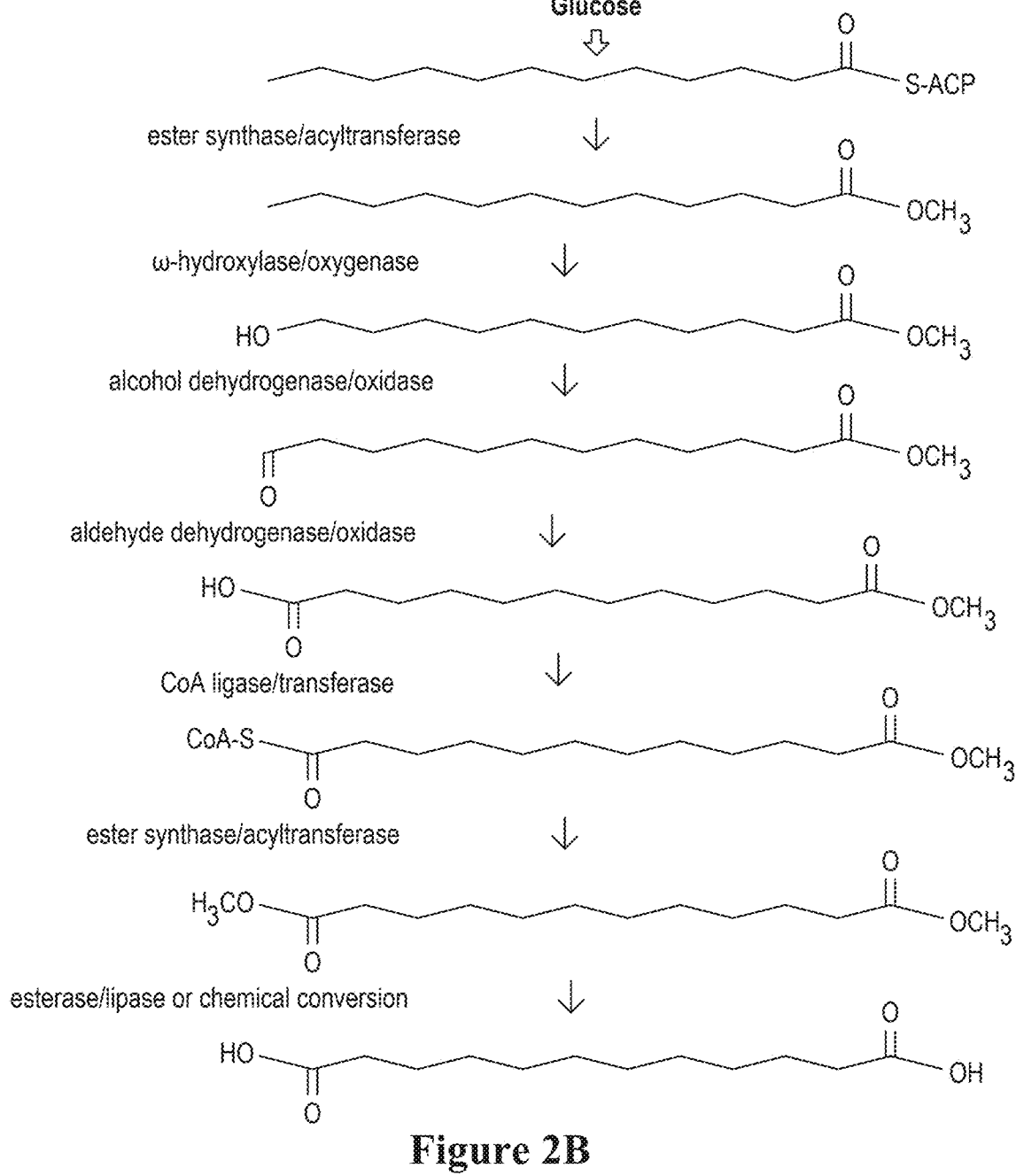
FIG. 2B depicts a pathway for making α,ω-diacids via dimethyl ester intermediates. A fatty acid derivative with 12 carbon atoms is depicted as an example.

FIGS. 1 and 2 show pathways where an acyl-ACP can be converted to an α,ω-diacid via two similar pathways, employing a C12 free fatty acid (FFA) as a precursor intermediate (see FIG. 1) or C12 fatty acid methyl ester (FAME) as a intermediate (see FIGS. 2A and 2B), respectively.

In one embodiment, FIG. 1 shows the production of various chemical compounds, including ω-hydroxy fatty acids, ω-oxo fatty acids, α,ω-diacids and ω-amino fatty acids. In step 2 of FIG. 1, a thioesterase is employed to covert an acyl-ACP to a FFA. In certain embodiments, the gene encoding a thioesterase is tesA, 'tesA, tesB, fatB1, fatB2, fatB3, fatA1, or fatA. (See also Table 1 that shows polypeptides that have the enzymatic activity of a thioesterase that can be used to catalyze this step, supra). In step 3, an ω-hydroxylase also referred to as ω-oxygenase is used to generate ω-hydroxy fatty acids. As can be seen in FIG. 1, the omega position of the fatty acid is hydroxy.

CYP153A-Reductase Hybrid Fusion Polypeptides Expressed in Recombinant Host Cells Examples for suitable ω-hydroxylases/ω-oxygenases (EC 1.14.15.3) and their redox partners are listed in Tables 2A and 2B (supra). These are certain non-heme di-iron oxygenases (e.g., alkB from *Pseudomonas putida* GPo1) or certain heme-type P450 oxygenases (e.g., cyp153A from *Marinobacter aquaeolei*) also known as cytochrome P450s. Cytochromes P450s are ubiquitously distributed enzymes, which possess high complexity and display a broad field of activity. They are proteins encoded by a superfamily of genes that convert a broad variety of substrates and catalyze a variety of chemical reactions. Cyp153A is a sub-family of soluble bacterial cytochrome P450s that hydroxylate hydrocarbon chains with high selectivity for the ω-position (van Beilen et al. (2006) *Appl. Environ. Microbiol.* 72:59-65). Members of the cyp153A family have been shown in vitro to selectively hydroxylate the ω-position of alkanes, fatty acids or fatty alcohols, for example cyp153A6 from *Mycobacterium* sp. HXN-1500 (Funhoff et al. (2006) *J. Bacteriol.* 188:5220-5227), cyp153A16 from *Mycobacterium marinum* and cyp153A from *Polaromonas* sp. JS666 (Scheps et al. (2011) *Org. Biomol. Chem.* 9:6727-6733) as well as cyp153A from *Marinobacter aquaeoli* (Honda-Malca et al. (2012) *Chem. Commun.* 48:5115-5117).

As with all cytochrome P450s, Cyp153A ω-hydroxylases require electrons for their catalytic activity, which are provided via specific redox proteins such as ferredoxin and ferredoxin reductase. These are discrete proteins interacting with cyp153A. A self-sufficient hybrid (chimeric) cyp153A oxygenase (i.e., an oxygenase that does not require discrete ferredoxin and ferredoxin reductase proteins for activity) has previously been created by fusing cyp153A from *Alcanivorax borkumensis* SK2 (Kubota et al. (2005) *Biosci. Biotechnol. Biochem.* 69:2421-2430; Fujita et al. (2009) *Biosci. Biotechnol. Biochem.* 73:1825-1830) with the reductase domain from P450RhF, which includes flavin mononucleotide (FMN) and NADPH-binding sites and a [2FeS] ferredoxin center (Hunter et al. (2005) *FEBS Lett.* 579:2215-2220). P450RhF belongs to the class-I P450-fused PFOR (DeMot and Parret (2003) *Trends Microbiol.* 10: 502). This hybrid cyp153A-RedRhF fusion protein was shown in in vitro biotransformations to hydroxylate octane in the ω-position and also hydroxylate other compounds such as cyclohexane or butylbenzene. Examples of natural P450-Reductase fusion proteins are shown in Tables 2C and 2D (supra).

Given their high selectivity towards the ω-position of hydrocarbon chains, the cyp153A family oxygenases appeared to be good examples of suitable candidates to produce α,ω-bifunctional fatty acid derivatives from a renewable carbon source. This would allow for the development of commercially feasible processes to produce these valuable compounds. Yet, as with other cytochrome P450s, the cyp153A family proteins have so far mostly been applied to in vitro experiments with purified enzymes or crude cell lysates or in resting cell biotransformations to which fatty acid derivatives or hydrocarbons are added exogenously (Kubota et al., Fujita et al., Honda-Malca et al., supra). However, the hybrid fusion-employing in vitro procedures or resting cell biotransformations are not conducive to large scale and cost-efficient production of ω-hydroxy fatty acid derivatives. The widely accepted knowledge in the art is that many cytochrome P450s as well as alkB-type ω-hydroxy-lases are not easy to express functionally in recombinant microorganisms because the enzymes are often inactive and their chemistry has been difficult to elucidate. In fact, the only in vivo work using a renewable carbon source other than fatty acid-derivatives that has so far been attempted employed alkB ω-hydroxylase and achieved only low titer of ω-hydroxy fatty acid derivatives in a high cell density fermentation (WO2013/024114A2).

The Applicants have created CYP153A-reductase hybrid fusion proteins and variants thereof that are capable of efficiently producing ω-hydroxy fatty acid derivatives in vivo from a renewable carbon source. More specifically, a gene from *Marinobacter aquaeoli* coding for a hybrid fusion protein of the CYP153A (G307A) P450 catalytic domain, where a glycine (G) was substituted for an alanine (A) at position 307, was fused with a gene coding for the c-termi-nal FMN- and Fe/S-containing reductase domain of P450RhF from *Rhodococcus* sp. NCIMB9784 (see Example 6, infra). The resulting polypeptide is a CYP153A-RedRhF hybrid fusion polypeptide (SEQ ID NO: 6) with a corre-sponding nucleic acid sequence (SEQ ID NO: 5). When this CYP153A-reductase hybrid fusion protein was expressed in *E. coli* cells with a simple carbon source such as glucose fatty acid derivatives were efficiently converted to ω-hy-droxy fatty acid derivatives (see Examples, infra). Other examples for suitable ω-hydroxylases (EC 1.14.15.3) and their redox partners that can be used to generate similar CYP153A-reductase hybrid fusion polypeptides are listed in Tables 2A and 2B (supra).

The present disclosure provides microorganisms that can efficiently and selectively produce ω-hydroxy fatty acid derivatives including α,ω-bifunctional fatty acid derivatives in vivo. In one embodiment, the CYP153A-RedRhF hybrid fusion protein was engineered to be expressed in a micro-organism such that it could efficiently convert compounds such as dodecanoic acid or dodecanoic acid methyl ester to 12-hydroxy dodecanoic acid or 12-hydroxy dodecanoic acid methyl ester in vivo from a carbon source such as glucose. Any renewable feedstock instead of glucose could be used as carbon source. Thus, it was shown for the first time that an engineered hybrid fusion protein (i.e., illustrated via the CYP153A-RedRhF hybrid fusion protein) that possesses P450 enzymatic activity can efficiently convert fatty acids in vivo to specific desirable ω-hydroxylated compounds (e.g., ω-hydroxy fatty acids; ω-hydroxy fatty acid methyl esters; α,ω-hydroxy diacids; α,ω-hydroxy diesters; and α,ω-diols) when the hybrid fusion protein is ω-expressed with a thio-esterase in a host cell (e.g., *E. coli*) and feed a carbon source from a renewable feedstock (see Example 6 as well as FIGS. 25 and 26). By following the present disclosure, other hybrid fusion proteins can be engineered by linking a P450 gene such as a gene coding for a cyp153A protein to a reductase gene, e.g., coding for a c-terminal reductase domain of a class-I P450-fused PFOR protein or other reductase domain. Tables 2A and 2D (supra) give examples for cyp153A and class-I P450-fused PFOR proteins, respectively. Following these instructions, similar fusion proteins can be created from other types of ω-hydroxylases/w-oxygenases.

The route to α,ω-diacids or ω-amino fatty acids as shown in FIG. 2A through a ω-hydroxy fatty acid methyl ester, or a route to α,ω-diacids as shown in FIG. 2B through a α,ω-fatty acid dimethyl ester can be advantageous, because the methyl esters are not charged which provides advantages for large scale production and recovery. Furthermore, the route through ω-hydroxy fatty acid methyl ester allows direct enzymatic lactamization via catalysis by certain hydrolases. In step 3 of FIG. 1 or FIGS. 2A and 2B, an alcohol dehydrogenase or oxidase can further convert the ω-hydroxy fatty acid to an ω-oxo fatty acid (e.g., Table 3A shows polypeptides that have the enzymatic activity of an alcohol dehydrogenase or oxidase that can be used to catalyze this step, supra). For example, suitable enzymes that can oxidize 12-hydroxy dodecanoic acid or 12-hydroxy dodecanoic acid methyl ester to 12-oxo dodecanoic acid or 12-oxo dodecanoic acid methyl ester are alcohol oxidases (flavoproteins, e.g., alkJ from *Pseudomonas putida*) (EC 1.1.3.13, EC 1.1.3.20) (see SEQ ID NO: 67) or NAD(P)-dependent alcohol dehydrogenases (e.g., cddC from *Rhodo-coccus ruber* (EC 1.1.1.1) (see Table 3A, supra). At this point, the pathway can follow two different alternative pathways from here on, i.e., convert the ω-oxo fatty acid to an α,ω-diacid via aldehyde dehydrogenase or oxidase (e.g., Table 3B shows polypeptides that have the enzymatic activ-ity of an aldehyde dehydrogenase or oxidase that can be used to catalyze this step, supra), or convert the ω-oxo fatty acid to an ω-amino fatty acid via an aminotransferase or transaminase or amino acid dehydrogenase (e.g., Table 4 shows polypeptides that have the enzymatic activity of an aminotransferase or transaminase or amino acid dehydroge-nase that can be used to catalyze this step, supra). For example, suitable transaminases to convert 12-oxo lauric acid or 12-oxo lauric acid methyl ester to 12-amino lauric acid or 12-amino methyl ester are shown in Table 4 (supra). These enzymes transfer the amine group from a suitable donor to the ω-oxo acid or ester to generate the correspond-ing terminal amine. The availability of amine donors (e.g., alanine or glutamate) can be improved in vivo through the coexpression of the respective amino acid dehydrogenase (e.g., alanine dehydrogenase, glutamate dehydrogenase, see Table 4, supra). Furthermore, overexpression of homologs or other variants of glutamate dehydrogenase that can utilize NADH instead of NADPH can provide additional improve-ments to production. Examples of other classes of enzymes, such as methylamine dehydrogenase or lysine 6-dehydro-genase, that are suitable for converting 12-oxo lauric acid or 12-oxo lauric acid methyl ester to 12-amino lauric acid or 12-amino methyl ester are also listed in Table 4.

In another embodiment, FIGS. 2A and 2B show the production of various chemical compounds, including α,ω-diacids and ω-amino fatty acids via methyl esters as inter-mediates. Step 6 of FIG. 2B shows the production of α,ω-diesters (using an acyl-CoA ligase/transferase). In step 2 of FIGS. 2A and 2B, an ester synthase is employed to covert an acyl-ACP to a fatty acid methyl ester (FAME). In certain embodiments, a gene encoding an ester synthase is one encoding an enzyme of enzyme classification EC 2.3.1.75 or EC 2.3.1.20, one encoding wax/dgat, a bifunc-tional ester synthase/acyl-CoA:diacylglycerl acyltransferase from *Simmondsia chinensis, Acinetobacter* sp. ADP1, *Alca-nivorax borkumensis, Pseudomonas aeruginosa, Fundi-bacter jadensis, Arabidopsis thaliana*, or *Alkaligenes eutro-phus*, or one encoding AtfA1, AtfA2, ES9, or ES8, or a variant thereof (see also Table 9, which shows polypeptides that have the enzymatic activity of an ester synthase that can be used to catalyze this step, supra). In step 3, an ω-hy-droxylase (or ω-oxygenase) is used to generate ω-hydroxy fatty acid methyl esters (e.g., Table 2A shows polypeptides that have the enzymatic activity that can be used to catalyze this step, supra). As can be seen in FIG. 2A, the omega position of the fatty acid methyl ester is hydroxy. In step 3 of FIG. 2A, an alcohol dehydrogenase or oxidase can further convert the ω-hydroxy fatty acid methyl ester to an ω-oxo fatty acid methyl ester (e.g., Table 3A shows polypeptides that have the enzymatic activity of an alcohol dehydrogenase or oxidase that can be used to catalyze this step, supra). Similarly, the pathway can follow two different alternative pathways from here on, i.e., one pathway converts the ω-oxo fatty acid methyl ester to an α,ω-diacid via aldehyde dehydrogenase or oxidase (see Table 3B, supra), and finally an esterase or lipase (see Table 5, supra) or by chemical conversion; while another pathway converts the ω-oxo fatty acid methyl ester to an ω-amino fatty acid via an aminotransferase or transaminase or amino acid dehydrogenase (see Table 4, supra), and finally an esterase or lipase (see Table 5, supra). The final step (i.e., wherein an esterase or lipase catalyzes the conversion of an α,ω-fatty acid methyl ester or an ω-amino fatty acid methyl ester into the final product as shown), can be the result of an enzymatic as well as a chemical conversion step. For example, suitable enzymes that can hydrolyze this step are listed in Table 5. The lipases (EC 3.1.1.3) or esterases (EC 3.1.1.1) chosen are located in the periplasm or are secreted into the supernatant. Suitable secretion signals or anchoring sequences can be engineered according to methods known in the art. In another embodiment, FIG. 2B shows the production of α,ω-diacids via α,ω-fatty acid dimethyl ester. This pathway is similar to the left branch in FIG. 2A, but it uses an additional acyl-CoA synthase/acyl-CoA ligase or transferase (see Table 7 for suitable candidates, supra). The ester synthase/acyltransferase catalyzing the first step can also catalyze the penultimate step.

Figure 3:
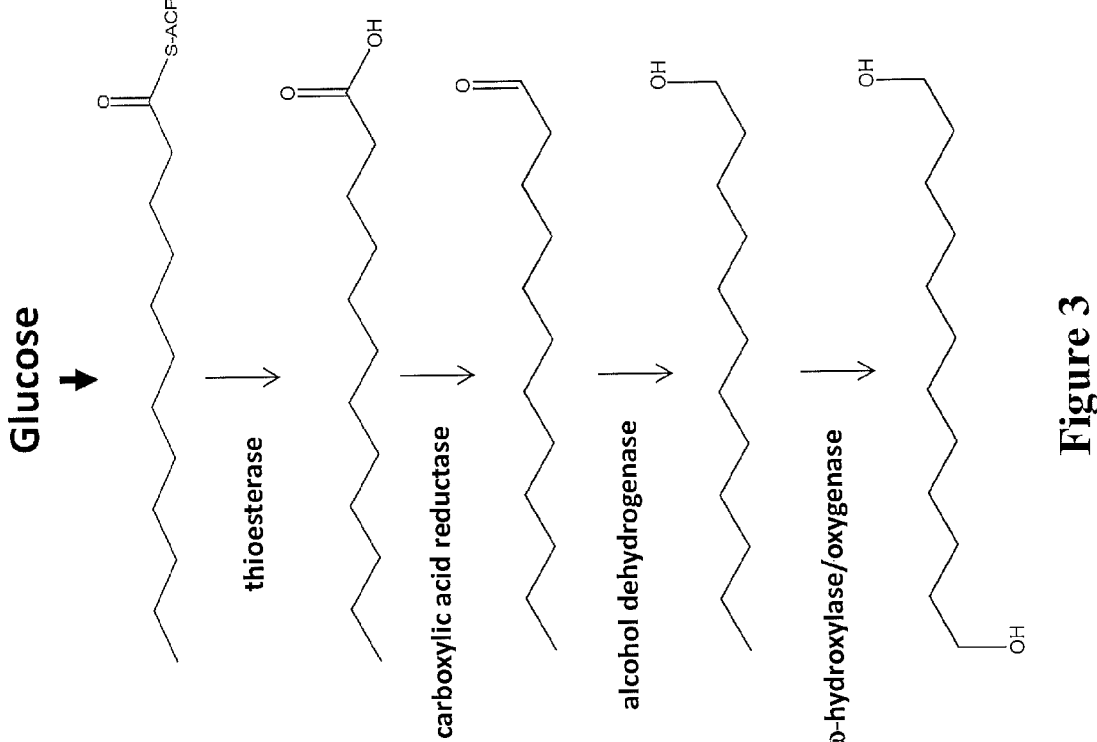
FIG. 3 depicts a pathway for making α,ω-diols using a thioesterase and a carboxyl acid reductase. A fatty acid derivative with 12 carbon atoms is depicted as an example.
Figure 4:
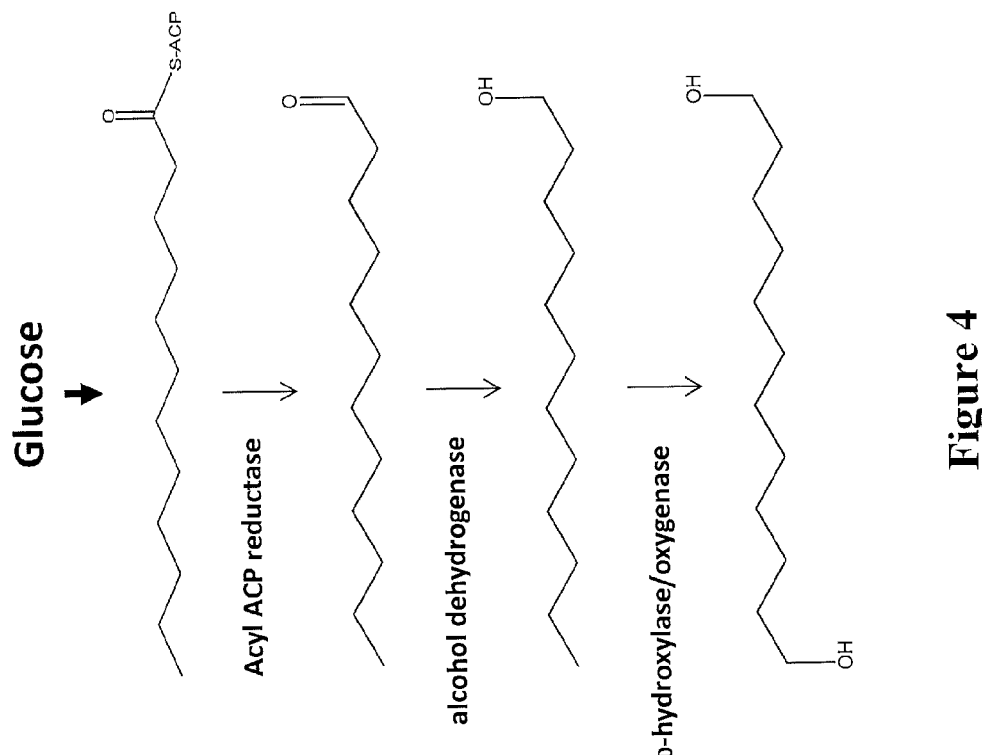
FIG. 4 depicts a pathway for making α,ω-diols using an acyl-ACP reductase reductase. A fatty acid derivative with 12 carbon atoms is depicted as an example.
Figure 5:
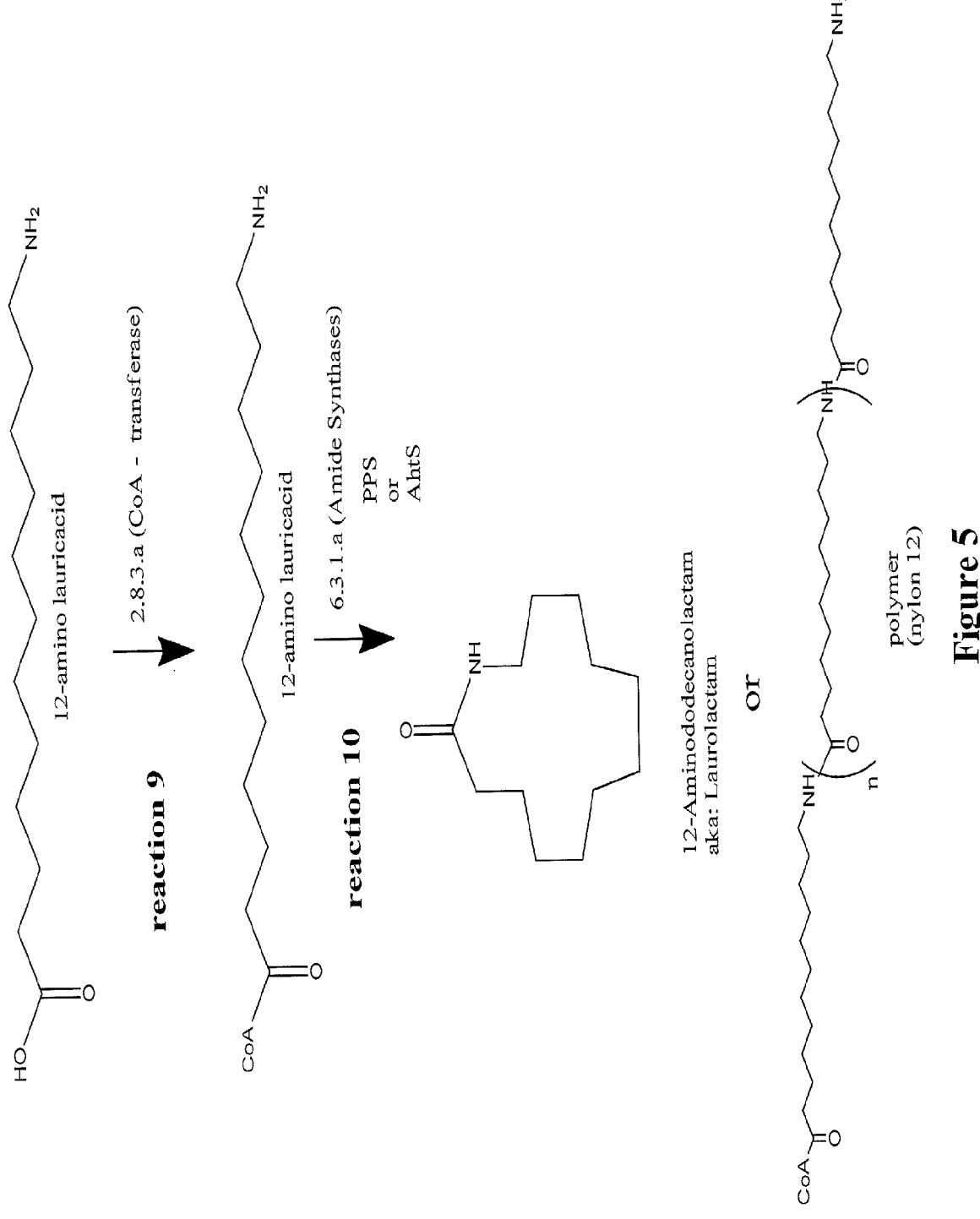
FIG. 5 illustrates a pathway that converts an ω-amino carboxylic acid to a lactam. A fatty acid derivative with 12 carbon atoms is depicted as an example.

In another embodiment, pathways are depicted in FIGS. 3 and 4 that can use a carbon source from a renewable feedstock (e.g., glucose) to produce α,ω-diols from fatty alcohols (FALC) produced in the cell. In one embodiment, FIG. 3 illustrates a pathway wherein α,ω-diols are made by employing thioesterase and carboxylic acid reductase activity (see Table 1, supra, for polypeptides that can catalyze these steps). Herein, a thioesterase can convert an acyl-ACP to a free fatty acid (FFA) in step 2. A carboxylic acid reductase can convert the resulting FFA to a fatty aldehyde in step 3. In step 4, an alcohol dehydrogenase (see Table 1, supra) can convert the fatty aldehyde to a fatty alcohol (FALC). Finally, in step 5, an ω-hydroxylase or ω-oxygenase (see Table 2A, supra) can convert a FALC to an α,ω-diol. Alternatively, acyl-ACP can be directly converted to fatty aldehyde by an acyl-ACP reductase as illustrated in FIG. 4. (Table 1 shows polypeptides that have the enzymatic activity of a thioesterase, carboxylic acid reductase, acyl-ACP reductase or alcohol dehydrogenase in order to catalyze these steps, supra.)

In yet another embodiment, a pathway is shown that produces lactams, which can be chemically converted to polymers. This is illustrated in FIG. 5 via an example of an ω-amino fatty acid such as 12-amino lauric acid that can be converted to a lactam through an acyl-CoA-transferase (see Table 7, supra) and amide synthase (see Table 8, supra). In this particular example, the resulting lactam is a 12-aminododecanolactam or laurolactam. An example of a polymer derived thereof is nylon 12 as shown in FIG. 5. Suitable enzymes to directly lactamize 12-amino lauric acid methyl ester to the corresponding lactam are certain hydrolases (see Table 6, supra) that can be used in combination with the other enzymes in the same biocatalyst to direct production of laurolactam; or may be used in a separate biotransformation of 12-amino lauric acid methyl ester. A lipase or esterase (see Table 5, supra) may also directly lactamize 12-amino lauric acid methyl ester to the corresponding lactam.

The disclosure identifies polynucleotides that code for polypeptides with enzymatic activity that are useful in the recombinant host cells and methods of production. The polypeptides with enzymatic activity contribute to the production of compositions including the compounds. It will be generally recognized that absolute sequence identity to such polynucleotides is not necessary. For example, changes in a particular polynucleotide sequence (e.g., a polynucleotide encoding a polypeptide with enzymatic function) can be made and the encoded polypeptide screened for activity. Such changes typically comprise conservative mutations and silent mutations (e.g., codon optimization). Genetically engineered or modified polynucleotides and encoded variant polypeptides can be screened for a desired function, including but not limited to, increased catalytic activity, increased stability, or decreased inhibition (e.g., decreased feedback inhibition), using methods known in the art.

In addition, the disclosure identifies enzymatic activities involved in various steps (i.e., reactions) of engineered pathways involved in ω-hydroxylated fatty acid derivative production as described herein (supra) according to Enzyme Classification (EC) number, and provides exemplary polypeptides (e.g., enzymes) categorized by such EC numbers, and exemplary polynucleotides encoding such polypeptides. Such exemplary polypeptides and polynucleotides, which are identified herein by Accession Numbers and/or Sequence Identifier Numbers (SEQ ID NOs), are useful for engineering fatty acid pathways that lead to production of ω-hydroxy fatty acid derivatives including other bi-functional molecules such as α,ω-diacids in parental host cells to obtain the genetically modified host cells described herein. The polypeptides and polynucleotides described herein are exemplary and non-limiting. The sequences of homologues of exemplary polypeptides described herein are available to those of skill in the art through various databases (e.g., the Entrez databases provided by the National Center for Biotechnology Information (NCBI), the ExPasy databases provided by the Swiss Institute of Bioinformatics, the BRENDA database provided by the Technical University of Braunschweig, and the KEGG database provided by the Bioinformatics Center of Kyoto University and University of Tokyo, all which are available on the world wide web).

In one embodiment, recombinant microorganisms as described herein (supra) produce ω-hydroxy fatty acid derivatives with an even carbon chain. In another embodiment, recombinant microorganisms can be engineered to produce ω-hydroxy fatty acid derivatives with an odd carbon chain. For example, ω-hydroxylase pathways can be expressed in recombinant cells (e.g., *E. coli*) that overproduce odd-chain fatty acid derivatives (overproduction of odd-chain fatty acid derivatives via certain bacterial strains is described in U.S. Patent Application Publication US2012/0070868, which is incorporated by reference herein). This allows for the production of odd-chain ω-hydroxylated fatty acid derivatives. In one embodiment, a recombinant strain that overproduces odd-chain fatty acids when combined with expression of an ω-hydroxylase (e.g., a CYP153A-RedRhF hybrid fusion protein) and a fatty acid decarboxylase such as oleT (e.g., see Rude et al. (2011) Appl. Environ. Microbiol. 77:1718) produces even-chain fatty alcohols with a terminal double bond, such as, e.g., 9-decene-1-ol, 11-dodecene-1-ol, 13-tetradecene-1-ol and 15-hexadecene-1-ol.

In another embodiment, subterminally hydroxylated fatty acid derivatives are provided. These are compounds that have at least one OH group at the omega-1 position, and/or omega-2 position, and/or omega-3 position, and/or omega-4 position, etc. (e.g., ω-1, ω-2 and/or ω-3; etc.). Examples 8 and 9 show the production of these compounds in genetically modified host cells by employing cytochrome P450 oxygenases from the cyp102A family (Whitehouse et al. (2012) *Chem. Soc. Rev.* 41: 1218). The cytochrome P450 oxygenases of the cyp102A family are suitable to produce subterminally hydroxylated fatty acid derivatives. However, these enzymes are not suitable to efficiently produce ω-hydroxylated fatty acid derivatives in recombinant hosts unless their substrate specificity is altered such that they predominantly hydroxylate fatty acid derivatives in the ω-position, which so far has only been partially successful (Lentz et al. (2006) *ChemBioChem.* 7: 345).

CYP153A-Reductase Hybrid Fusion Polypeptide Variants Expressed in Recombinant Host Cells The present disclosure identifies CYP153A-reductase hybrid fusion polypeptide variants that result in high titer, yield and/or productivity of ω-hydroxylated fatty acid derivative compositions when expressed in recombinant host cells. In non-limiting examples of the present disclosure the CYP153A(G307A)-RedRhF hybrid fusion polypeptide (see Example 6, infra) was used as a template to efficiently engineer CYP153A-reductase hybrid fusion polypeptide variants (see Examples 14-10, infra) to produce increased amounts of ω-OH fatty acids and ω-OH fatty acid derivatives. For example, a CYP153A-reductase hybrid fusion polypeptide variant when expressed in a host cell can efficiently convert compounds such as dodecanoic acid to 12-hydroxy dodecanoic acid in vivo from a simple carbon source such as glucose. Any simple carbon source, e.g., as derived from a renewable feedstock is suitable. It was shown that an engineered CYP153A-reductase hybrid fusion polypeptide variant (i.e., illustrated via an engineered CYP153A-RedRhF hybrid fusion polypeptide variant) can efficiently convert fatty acids in vivo to specific desirable compounds (including ω-OH fatty acids) when ω-expressed with a thioesterase in a host cell (e.g., *E. coli*) by using a carbon source (e.g., glucose) from a renewable feedstock (see Examples, infra). By following the present disclosure, other hybrid fusion polypeptide variants can be engineered by linking a mutated gene such as a gene coding for a CYP153A protein to a mutated gene coding for a c-terminal reductase domain (see Tables 2A through 2D, supra). Variations are encompassed herein, for example, mutating both genes (the P5450 and reductase domain) or mutating one gene (the P450 or reductase domain). Following these instructions, similar fusion protein variants can be created from other types of ω-hydroxylases and expressed in recombinant host cells to produce ω-OH fatty acid derivatives.

Thus, the present disclosure relates to recombinant host cells that express CYP153A-reductase hybrid fusion polypeptide variants that result in high titer, yield and/or productivity of ω-hydroxylated fatty acid derivative compositions when cultured with a carbon source (e.g., glucose, sucrose or any other carbon source derived from a renewable feedstock). The CYP153A-reductase hybrid fusion polypeptide variant has one or more mutations in the CYP153A domain or reductase domain or both. In one embodiment, the present disclosure provides a CYP153A-reductase hybrid fusion polypeptide variant having at least about 90%, 91%, 92%, 93%, 94%, 95%, 96%, 97%, 98% or 99% sequence identity to SEQ ID NO: 6 and having one or more mutation at an amino acid position including position 27, 82, 141, 178, 231, 309, 407, 415, 516, 666 and/or 796, wherein the CYP153A-reductase hybrid fusion polypeptide variant catalyzes the conversion of a fatty acid to an ω-OH fatty acid in vivo. More specifically, the CYP153A-reductase hybrid fusion polypeptide variant has one or more of the following mutations, including R27L where arginine (R) is substituted for lysine (L); position R82D where arginine (R) is substituted for aspartic acid (D); position V141I where valine is substituted for isoleucine (I); position V141Q where valine (V) is substituted for glutamine (Q); position V141G where valine (V) is substituted for glycine (G); position V141M where valine (V) is substituted for methionine (M); position V141L where valine (V) is substituted for leucine (L); position V141T where valine (V) substituted for threonine (T); position R178N where arginine (R) is substituted for asparagine (N); position A231T where alanine (A) is substituted for threonine (T); position N309R where asparagine (N) is substituted for arginine (R); position N407A where asparagine (N) is substituted for alanine (A); position V415R where valine (V) is substituted for arginine (R); position T516V where threonine (T) is substituted for valine (V); position P666A where proline (P) is substituted for alanine (A); position P666D where proline (P) is substituted for aspartic acid (D); and position A796V where alanine (A) is substituted for valine (V). Examples of CYP153A-reductase hybrid fusion polypeptide variants include SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28 or SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 and SEQ ID NO: 46. In one embodiment, the CYP153A-reductase hybrid fusion polypeptide variant is a hybrid cyp153A-RedRhF-type fusion protein variant. In another embodiment, the CYP153A-reductase hybrid fusion polypeptide variant in a recombinant host cell results in a higher titer of an ω-OH fatty acid derivative composition as compared to the titer of an ω-OH fatty acid composition produced by expression of a CYP153A-reductase hybrid fusion polypeptide in a corresponding host cell. In another embodiment, the CYP153A-reductase hybrid fusion polypeptide variant in a recombinant host cell results in a higher titer of an ω-OH fatty acid derivative composition including, but not limited to, ω-OH $C_{12}$, ω-OH $C_{14}$, ω-OH $C_{16}$, ω-OH $C_{18}$, ω-OH $C_{12:1}$, ω-OH $C_{14:1}$, ω-OH $C_{16:1}$, and ω-OH $C_{18:1}$ fatty acid derivative composition.

In another embodiment, the CYP153A-reductase hybrid fusion polypeptide variant has a mutation at amino acid position 141, including V141I and/or V141T. Herein, the expression of the CYP153A-reductase hybrid fusion polypeptide variant with mutations V141I or V141T in a recombinant host cell results in a higher titer of an ω-OH $C_{12}$, or $C_{16}$ fatty acid composition, respectively, as compared to a titer of an ω-OH $C_{12}$ or $C_{16}$ fatty acid composition produced by expression of a CYP153A-reductase hybrid fusion polypeptide. In one embodiment, the CYP153A-reductase hybrid fusion polypeptide variant has mutations V141I and A231T (SEQ ID NO: 32) and produces increased amounts of ω-OH $C_{12}$ fatty acids when expressed in a host cell with an enzymatic function of thioesterase. In another embodiment, the CYP153A-reductase hybrid fusion polypeptide variant has mutations R27L, R82D, V141M, R178N and N407A (SEQ ID NO: 34) and produces increased amounts of ω-OH $C_{12}$ fatty acids when expressed in a host cell with an enzymatic function of thioesterase. In another embodiment, the CYP153A-reductase hybrid fusion polypeptide variant has mutation P666A (SEQ ID NO: 36) and produces increased amounts of ω-OH $C_{12}$ fatty acids when expressed in a host cell with an enzymatic function of thioesterase. In another embodiment, the CYP153A-reductase hybrid fusion polypeptide variant has mutation A796V (SEQ ID NO: 38) and produces increased amounts of ω-OH $C_{12}$ fatty acids when expressed in a host cell with an enzymatic function of thioesterase. In another embodiment, the CYP153A-reductase hybrid fusion polypeptide variant has mutations A796V, P666D and T516V (SEQ ID NO: 40) and produces increased amounts of ω-OH $C_{12}$ fatty acids when expressed in a host cell with an enzymatic function of thioesterase. In another embodiment, the CYP153A-reductase hybrid fusion polypeptide variant has mutations V141I, A231T and A796V (SEQ ID NO: 42) and produces increased amounts of ω-OH $C_{12}$ and $C_{16}$ fatty acids when expressed in a host cell with an enzymatic function of thioesterase. In another embodiment, the CYP153A-reductase hybrid fusion polypeptide variant has mutations R27L, R82D, V141M, R178N, N407A and A796V (SEQ ID NO: 44) and produces increased amounts of ω-OH $C_{12}$ fatty acids when expressed in a host cell with an enzymatic function of thioesterase. In another embodiment, the CYP153A-reductase hybrid fusion polypeptide variant has mutations V141T, A231T and A796V (SEQ ID NO: 46) and produces increased amounts of ω-OH $C_{16}$ fatty acids when expressed in a host cell with an enzymatic function of thioesterase.

The disclosure identifies CYP153A-reductase hybrid fusion-related polynucleotide and polypeptide variants. The CYP153A-reductase hybrid fusion polypeptide variants include SEQ ID NOS: 8, 10, 12, 14, 16, 18, 20, 22, 24, 26, 28, 30, 32, 34, 36, 38, 40, 42, 44 and 46. The CYP153A-reductase hybrid fusion nucleic acid variants (DNA sequences) include SEQ ID NOS: 7, 9, 11, 13, 15, 17, 19, 21, 23, 25, 27, 29, 31, 33, 35, 37, 39, 41, 43, 45 and 47. However, it will be recognized that absolute sequence identity to CYP153A-reductase hybrid fusion polynucleotide variants is not necessary. For example, changes in a particular polynucleotide sequence can be made and the encoded polypeptide screened for activity. Such changes typically include conservative mutations and silent mutations such as, for example, through codon optimization. Modified or mutated (i.e., mutant) polynucleotides and encoded variant polypeptides can be screened for a desired function, such as, an improved function compared to the wild type or template polypeptide, including but not limited to increased catalytic activity, increased stability, or decreased inhibition (e.g., decreased feedback inhibition), using methods known in the art. The disclosure identifies enzymatic activities involved in various steps (i.e., reactions) of the fatty acid biosynthetic pathways described herein according to Enzyme Classification (EC) number, and provides exemplary polypeptides (e.g., that function as specific enzymes and display specific enzyme activity) categorized by such EC numbers, and exemplary polynucleotides encoding such polypeptides. Such exemplary polypeptides and polynucleotides, which are identified herein by Sequence Identifier Numbers (SEQ ID NOs; supra), are useful for engineering fatty acid pathways in host cells such as the one shown in FIG. 1. It is to be understood, however, that polypeptides and polynucleotides described herein are exemplary and, thus, non-limiting. The sequences of homologues of exemplary polypeptides described herein are available to those of skill in the art using databases such as, for example, the Entrez databases provided by the National Center for Biotechnology Information (NCBI), the ExPasy databases provided by the Swiss Institute of Bioinformatics, the BRENDA database provided by the Technical University of Braunschweig, and the KEGG database provided by the Bioinformatics Center of Kyoto University and University of Tokyo, all which are available on the World Wide Web.

In one embodiment, a CYP153A-reductase hybrid fusion polypeptide variant for use in practicing the disclosure has at least about 90%, 91%, 92%, 93%, 94%, 95%, 96%, 97%, 98%, 99% or 100% sequence identity to SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28 or SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 and SEQ ID NO: 46. In some embodiments the CYP153A-reductase hybrid fusion polypeptide variant is derived from a CYP153A (G307A) polypeptide from *Marinobacter aquaeolei* where a glycine (G) is substituted for an alanine (A), and fused with a reductase domain of P450RhF from *Rhodococcus* sp. NCIMB9784. Cytochrome P450RhF is self-sufficient, displays a high degree of substrate promiscuity and catalyzes a wide range of functional groups. In other embodiments, a CYP153A-reductase hybrid fusion polypeptide variant for use in practicing the disclosure has at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% sequence identity to SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28 or SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 or SEQ ID NO: 46, and may also include one or more substitutions which results in useful characteristics and/or properties as described herein. In other embodiments, a CYP153A-reductase hybrid fusion polypeptide variant for use in practicing the disclosure has 100%, 99%, 98%, 97%, 96%, 95%, 94%, 93%, 92%, 91% or 90% sequence identity to SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28 or SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44 or SEQ ID NO: 46. In still other embodiments, the P450 catalytic domain of the CYP153A-reductase hybrid fusion polypeptide variant is derived from a species other than *Marinobacter aquaeolei*. Such other species include, but are not limited to, *Acinetobacter* sp., *Mycobacterium marinum*, *Polaromonas* sp., *Alcanivorax borkumensis*, *Burkholderia fungorum*, *Caulobacter crescentus*, *Hyphomonas neptunium*, *Rhodopseudomonas palustris*, *Sphingomonas* sp., *Mycobacterium* sp. In still other embodiments, the reductase domain of the CYP153A-reductase hybrid fusion polypeptide variant is derived from a species other than *Rhodococcus* sp. Such other species include, but are not limited to, *Rhodococcus equi*, *Acinetobacter radioresistens*, *Burkholderia mallei*, *Burkholderia mallei*, *Ralstonia eutropha*, *Cupriavidus metallidurans*.

In a related embodiment, the disclosure includes a CYP153A-reductase hybrid fusion polynucleotide variant that has at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or at least 99% sequence identity to SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45 or SEQ ID NO: 47. In some embodiments the nucleic acid sequence encodes a CYP153A-reductase hybrid fusion polypeptide variant with one or more substitutions which results in improved characteristics and/or properties as described herein. In yet another related embodiment, a CYP153A-reductase hybrid fusion polypeptide variant for use in practicing the disclosure is encoded by a nucleotide sequence having 100%, 99%, 98%, 97%, 96%, 95%, 94%, 93%, 92%, 91% or 90% sequence identity to SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45 or SEQ ID NO: 47. In another aspect, the disclosure relates to CYP153A-reductase hybrid fusion polypeptide variants that encompass an amino acid sequence encoded by a nucleic acid sequence that hybridizes under stringent conditions over substantially the entire length of a nucleic acid sequence corresponding to SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45 or SEQ ID NO: 47. In some embodiments the CYP153A-reductase hybrid fusion polypeptide variant is derived from a *Marinobacter aquaeolei* species. In other embodiments, the P450 hybrid fusion polypeptide is derived from *Acinetobacter* sp., *Mycobacterium marinum, Polaromonas* sp., *Alcanivorax borkumensis., Burkholderia fungorum, Caulobacter crescentus, Hyphomonas neptunium, Rhodopseudomonas palustris, Sphingomonas* sp., and *Mycobacterium* sp.

Variations and Mutations

A variant polypeptide as used herein refers to a polypeptide having an amino acid sequence that differs from a wild-type or template polypeptide by at least one amino acid. For example, the variant (e.g., mutant) can have one or more of the following conservative amino acid substitutions, including but not limited to, replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue. In some embodiments, the variant polypeptide has about 1, 2, 3, 4, 5, 6, 7, 8, 9, 10, 15, 20, 30, 40, 50, 60, 70, 80, 90, 100, or more amino acid substitutions, additions, insertions, or deletions. Some preferred fragments of a polypeptide that function as a variant or mutant retain some or all of the biological function (e.g., enzymatic activity) of the corresponding wild-type polypeptide. In some embodiments, the fragment retains at least 75%, at least 80%, at least 90%, at least 95%, or at least 98% or more of the biological function of the corresponding wild-type polypeptide. In other embodiments, the fragment or mutant retains about 100% of the biological function of the corresponding wild-type polypeptide. In other embodiments, some fragments exhibit increased biological function as compared to the corresponding wild-type polypeptide. Guidance in determining which amino acid residues may be substituted, inserted, or deleted without affecting biological activity may be found using computer programs well known in the art, for example, LASERGENE software (DNASTAR, Inc., Madison, WI). In some embodiments, a fragment exhibits increased biological function as compared to a corresponding wild-type polypeptide or template polypeptide. For example, a fragment may display at least a 10%, at least a 25%, at least a 50%, at least a 75%, or at least a 90% improvement in enzymatic activity as compared to the corresponding wild-type polypeptide or template polypeptide. In other embodiments, the fragment displays at least 100%, at least 200%, or at least 500% improvement in enzymatic activity as compared to the corresponding wild-type polypeptide or template polypeptide.

It is understood that the polypeptides described herein may have additional conservative or non-essential amino acid substitutions which do not have a substantial effect on the polypeptide function. Whether or not a particular substitution will be tolerated (i.e., will not adversely affect the desired biological function, such as ω-hydroxylase enzymatic activity), can be determined as known in the art (see Bowie et al. (1990) Science, 247:1306-1310). A conservative amino acid substitution is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Variants can be naturally occurring or created in vitro. In particular, such variants can be created using genetic engineering techniques, such as site directed mutagenesis, random chemical mutagenesis, Exonuclease III deletion procedures, or standard cloning techniques. Alternatively, such variants, mutants, fragments, analogs, or derivatives can be created using chemical synthesis or modification procedures. Methods of making variants are well known in the art. For example, variants can be prepared by using random and site-directed mutagenesis. Random and site-directed mutagenesis is generally known in the art (see, for example, Arnold (1993) *Curr. Opin. Biotech.* 4:450-455). Random mutagenesis can be achieved using error prone PCR (see, for example, Leung et al. (1989) *Technique* 1:11-15; and Caldwell et al. (1992) *PCR Methods Applic.* 2: 28-33). In error prone PCR, the actual PCR is performed under conditions where the copying fidelity of the DNA polymerase is low, such that a high rate of point mutations is obtained along the entire length of the PCR product. Briefly, in such procedures, nucleic acids to be mutagenized (e.g., a polynucleotide sequence encoding a P450 protein or P450 hybrid fusion polypeptide) are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mMKCl, 10 mM Tris HCl (pH 8.3), 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated by those in the art that these parameters can be varied as appropriate. The mutagenized nucleic acids are then cloned into an appropriate vector, and the activities of the polypeptides encoded by the mutagenized nucleic acids are evaluated. Site-directed mutagenesis can be achieved using oligonucleotide-directed mutagenesis to generate site-specific mutations in any cloned DNA of interest. Oligonucleotide mutagenesis is described in the art (see, for example, Reidhaar-Olson et al. (1988) *Science* 241:53-57). Briefly, in such procedures a plurality of double stranded oligonucleotides bearing one or more mutations to be introduced into the cloned DNA are synthesized and inserted into the cloned DNA to be muta- genized (e.g., a polynucleotide sequence encoding a P450 polypeptide or P450 hybrid fusion polypeptide). Clones containing the mutagenized DNA are recovered, and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction (see U.S. Pat. No. 5,965,408). Still another method of generating variants is sexual PCR mutagenesis. In sexual PCR mutagenesis, forced homologous recombination occurs between DNA molecules of different, but highly related, DNA sequences in vitro as a result of random fragmentation of the DNA molecule based on sequence homology. This is followed by fixation of the crossover by primer extension in a PCR reaction. Sexual PCR mutagen- esis is described publications known in the art (see, for example, Stemmer (1994) *Proc. Natl. Acad. Sci. U.S.A.* 91:10747-10751). Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair path- ways. Such mutator strains have a higher random mutation rate than that of a wild-type strain. Propagating a DNA sequence (e.g., a polynucleotide sequence encoding an P450 hybrid fusion polypeptide) in one of these strains will eventually generate random mutations within the DNA. Mutator strains suitable for use for in vivo mutagenesis are described in publication in the art (see, for example, Inter- national Patent Application Publication No. WO1991/ 016427). Variants can also be generated using cassette mutagenesis. In cassette mutagenesis, a small region of a double-stranded DNA molecule is replaced with a synthetic oligonucleotide cassette that differs from the native sequence. The oligonucleotide often contains a completely and/or partially randomized native sequence. Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of com- binatorial cassette mutagenesis (see, for example, Arkin et al. (1992) *Proc. Natl. Acad. Sci., U.S.A.* 89:7811-7815). In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins (see, for example, Delegrave et al. (1993) *Biotech. Res.* 11:1548-1552). In some embodiments, vari- ants are created using shuffling procedures wherein portions of a plurality of nucleic acids that encode distinct polypep- tides are fused together to create chimeric nucleic acid sequences that encode chimeric polypeptides (as described in, for example, U.S. Pat. Nos. 5,965,408 and 5,939,250).
Expression Vectors In some embodiments, a polynucleotide (or gene) sequence is provided to the host cell by way of a recombi- nant vector, which includes a promoter operably linked to the polynucleotide sequence. In certain embodiments, the promoter is a developmentally-regulated, an organelle-spe- cific, a tissue-specific, an inducible, a constitutive, or a cell-specific promoter. In some embodiments, the recombi- nant vector includes at least one sequence selected from an expression control sequence operatively coupled to the polynucleotide sequence; a selection marker operatively coupled to the polynucleotide sequence; a marker sequence operatively coupled to the polynucleotide sequence; a puri- fication moiety operatively coupled to the polynucleotide sequence; a secretion sequence operatively coupled to the polynucleotide sequence; and a targeting sequence opera- tively coupled to the polynucleotide sequence. The expres- sion vectors described herein include a polynucleotide sequence in a form suitable for expression of the polynucle- otide sequence in a host cell. It will be appreciated by those skilled in the art that the design of the expression vector can depend on such factors as the choice of the host cell to be transformed, the level of expression of polypeptide desired, and the like. The expression vectors described herein can be introduced into host cells to produce polypeptides, including fusion polypeptides, encoded by the polynucleotide sequences as described above (supra). Expression of genes encoding polypeptides in prokaryotes, for example, *E. coli*, is most often carried out with vectors containing constitutive or inducible promoters directing the expression of either fusion or non-fusion polypeptides. Fusion vectors add a number of amino acids to a polypeptide encoded therein, usually to the amino- or carboxy-terminus of the recombi- nant polypeptide. Such fusion vectors typically serve one or more of the following three purposes including increasing expression of the recombinant polypeptide; increasing the solubility of the recombinant polypeptide; and aiding in the purification of the recombinant polypeptide by acting as a ligand in affinity purification. Often, in fusion expression vectors, a proteolytic cleavage site is introduced at the junction of the fusion moiety and the recombinant polypep- tide. This allows separation of the recombinant polypeptide from the fusion moiety after purification of the fusion polypeptide. Examples of such enzymes, and their cognate recognition sequences, include Factor Xa, thrombin, and enterokinase. Exemplary fusion expression vectors include pGEX vector (Pharmacia Biotech, Inc., Piscataway, NJ; Smith et al. (1988) Gene 67:31-40), pMAL vector (New England Biolabs, Beverly, MA), and pRITS vector (Phar- macia Biotech, Inc., Piscataway, N.J.), which fuse gluta- thione S-transferase (GST), maltose E binding protein, or protein A, respectively, to the target recombinant polypep- tide.

Examples of inducible, non-fusion *E. coli* expression vectors include pTrc vector (Amann et al. (1988) Gene 69:301-315) and pET 11d vector (Studier et al., Gene Expression Technology: Methods in Enzymology 185, Aca- demic Press, San Diego, Calif. (1990) 60-89). Target gene expression from the pTrc vector relies on host RNA poly- merase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains such as BL21(DE3) or HMS174(DE3) from a resident λ prophage harboring a T7 gnl gene under the transcriptional control of the lacUV 5 promoter. Suitable expression systems for both prokaryotic and eukaryotic cells are well known in the art (see, e.g., Sambrook et al. (1989) Molecular Cloning: A Laboratory Manual, second edition, Cold Spring Harbor Laboratory). Examples of inducible, non-fusion *E. coli* expression vectors include pTrc vector (Amann et al. (1988) *Gene* 69:301-315) and PET 11d vector (Studier et al. (1990) Gene Expression Technology: Methods in Enzymology 185, Academic Press, San Diego, CA, pp. 60-89). In certain embodiments, a polynucleotide sequence of the disclosure is operably linked to a promoter derived from bacteriophage T5. In one embodiment, the host cell is a yeast cell. In this embodiment, the expression vector is a yeast expression vector. Vectors can be introduced into prokaryotic or eukaryotic cells via a variety of art-recognized techniques for introducing foreign nucleic acid (e.g., DNA) into a host cell. Suitable methods for transforming or transfecting host cells can be found in, for example, Sambrook et al. (supra). For stable transformation of bacterial cells, it is known that (depending upon the expression vector and transformation technique used) a certain fraction of cells will take-up and replicate the expression vector. In order to identify and select these transformants, a gene that encodes a selectable marker (e.g., resistance to an antibiotic) can be introduced into the host cells along with the gene of interest. Selectable markers include those that confer resistance to drugs such as, but not limited to, ampicillin, kanamycin, chloramphenicol, or tetracycline. Nucleic acids encoding a selectable marker can be introduced into a host cell on the same vector as that encoding a polypeptide described herein or can be introduced on a separate vector.

Optional Pathway Engineering

The host cells or microorganisms of the disclosure include host strains or host cells that are genetically engineered or modified to contain alterations in order to test the efficiency of specific mutations on enzymatic activities (i.e., recombinant cells or microorganisms). Various optional genetic manipulations and alterations can be used interchangeably from one host cell to another, depending on what native enzymatic pathways are present in the original host cell. In one embodiment, a host strain can be used for testing the expression of a CYP153A-reductase hybrid fusion polypeptide or variant thereof in combination with other biosynthetic polypeptides (e.g., enzymes). A host strain may encompasses a number of genetic alterations in order to test specific variables, including but not limited to, culture conditions including fermentation components, carbon source (e.g., feedstock), temperature, pressure, reduced culture contamination conditions, and oxygen levels.

In one embodiment, a host strain encompasses an optional fadE and fhuA deletion. Acyl-CoA dehydrogenase (FadE) is an enzyme that is important for metabolizing fatty acids. It catalyzes the second step in fatty acid utilization (beta-oxidation), which is the process of breaking long chains of fatty acids (acyl-CoAs) into acetyl-CoA molecules. More specifically, the second step of the β-oxidation cycle of fatty acid degradation in bacteria is the oxidation of acyl-CoA to 2-enoyl-CoA, which is catalyzed by FadE. When *E. coli* lacks FadE, it cannot grow on fatty acids as a carbon source but it can grow on acetate. The inability to utilize fatty acids of any chain length is consistent with the reported phenotype of fadE strains, i.e., fadE mutant strains where FadE function is disrupted. The fadE gene can be optionally knocked out or attenuated to assure that acyl-CoAs, which may be intermediates in a fatty acid derivative pathway, can accumulate in the cell such that all acyl-CoAs can be efficiently converted to fatty acid derivatives. However, fadE attenuation is optional when sugar is used as a carbon source since under such condition expression of FadE is likely repressed and FadE therefore may only be present in small amounts and not able to efficiently compete with ester synthase or other enzymes for acyl-CoA substrates. FadE is repressed due to catabolite repression. *E. coli* and many other microbes prefer to consume sugar over fatty acids, so when both sources are available sugar is consumed first by repressing the fad regulon (see D. Clark, *J Bacteriol.* (1981) 148(2):521-6)). Moreover, the absence of sugars and the presence of fatty acids induces FadE expression. Acyl-CoA intermediates could be lost to the beta oxidation pathway since the proteins expressed by the fad regulon (including FadE) are upregulated and will efficiently compete for acyl-CoAs. Thus, it can be beneficial to have the fadE gene knocked out or attenuated. Since most carbon sources are mainly sugar based, it is optional to attenuate FadE. The gene fhuA codes for the TonA protein, which is an energy-coupled transporter and receptor in the outer membrane of *E. coli* (V. Braun (2009) *J Bacteriol.* 191(11):3431-3436). Its deletion is optional. The fhuA deletion allows the cell to become more resistant to phage attack which can be beneficial in certain fermentation conditions. Thus, it may be desirable to delete fhuA in a host cell that is likely subject to potential contamination during fermentation runs.

In another embodiment, the host strain (supra) also encompasses optional overexpression of one or more of the following genes including fadR, fabA, fabD, fabG, fabH, fabV, and/or fabF. Examples of such genes are fadR from *Escherichia coli*, fabA from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156). The overexpression of one or more of these genes, which code for enzymes and regulators in fatty acid biosynthesis, can serve to increase the titer of fatty-acid derivative compounds including ω-OH fatty acids and derivatives thereof under various culture conditions.

In another embodiment, *E. coli* strains are used as host cells for the production of ω-OH fatty acids and derivatives thereof. Similarly, these host cells provide optional overexpression of one or more biosynthesis genes (i.e., genes coding for enzymes and regulators of fatty acid biosynthesis) that can further increase or enhance the titer of fatty-acid derivative compounds such as fatty acid derivatives (e.g., ω-OH fatty acids and α,ω-diacids, etc.) under various culture conditions including, but not limited to, fadR, fabA, fabD, fabG, fabH, fabV and/or fabF. Examples of genetic alterations include fadR from *Escherichia coli, fabA* from *Salmonella typhimurium* (NP_460041), fabD from *Salmonella typhimurium* (NP_460164), fabG from *Salmonella typhimurium* (NP_460165), fabH from *Salmonella typhimurium* (NP_460163), fabV from *Vibrio cholera* (YP_001217283), and fabF from *Clostridium acetobutylicum* (NP_350156). In some embodiments, synthetic operons that carry these biosynthetic genes can be engineered and expressed in cells in order to test P450 expression under various culture conditions and/or further enhance ω-OH fatty acid and α,ω-diacid production. Such synthetic operons contain one or more biosynthetic gene. The ifab138 operon, for example, is an engineered operon that contains optional fatty acid biosynthetic genes, including fabV from *Vibrio cholera*, fabH from *Salmonella typhimurium*, fabD from *S. typhimurium*, fabG from *S. typhimurium, fabA* from

*S. typhimurium* and/or fabF from *Clostridium acetobutyli-cum* that can be used to facilitate overexpression of fatty acid derivatives in order to test specific culture conditions. One advantage of such synthetic operons is that the rate of ω-OH fatty acid derivative production can be further increased or enhanced.

In some embodiments, the host cells or microorganisms that are used to express ACP and biosynthetic enzymes (e.g., ω-hydroxylase, thioesterase, etc.) will further express genes that encompass certain enzymatic activities that can increase the production to one or more particular fatty acid derivative(s) such as ω-OH fatty acids, ω-OH fatty acid derivatives, α,ω-diacids and the like. In one embodiment, the host cell has thioesterase activity (E.C. 3.1.2.* or E.C. 3.1.2.14 or E.C. 3.1.1.5) for the production of fatty acids which can be increased by overexpressing the gene. In another embodiment, the host cell has ester synthase activity (E.C. 2.3.1.75) for the production of fatty esters. In another embodiment, the host cell has acyl-ACP reductase (AAR) (E.C. 1.2.1.80) activity and/or alcohol dehydrogenase activity (E.C. 1.1.1.1.) and/or fatty alcohol acyl-CoA reductase (FAR) (E.C. 1.1.1.*) activity and/or carboxylic acid reductase (CAR) (EC 1.2.99.6) activity for the production of fatty alcohols. In another embodiment, the host cell has acyl-ACP reductase (AAR) (E.C. 1.2.1.80) activity for the production of fatty aldehydes. In another embodiment, the host cell has acyl-ACP reductase (AAR) (E.C. 1.2.1.80) activity and decarbonylase (ADC) activity for the production of alkanes and alkenes. In another embodiment, the host cell has acyl-CoA reductase (E.C. 1.2.1.50) activity, acyl-CoA synthase (FadD) (E.C. 2.3.1.86) activity, and thioesterase (E.C. 3.1.2.* or E.C. 3.1.2.14 or E.C. 3.1.1.5) activity for the production of fatty alcohols. In another embodiment, the host cell has ester synthase activity (E.C. 2.3.1.75), acyl-CoA synthase (FadD) (E.C. 2.3.1.86) activity, and thioesterase (E.C. 3.1.2.* or E.C. 3.1.2.14 or E.C. 3.1.1.5) activity for the production of fatty esters. In another embodiment, the host cell has OleA activity for the production of ketones. In another embodiment, the host cell has OleBCD activity for the production of internal olefins. In another embodiment, the host cell has acyl-ACP reductase (AAR) (E.C. 1.2.1.80) activity and alcohol dehydrogenase activity (E.C. 1.1.1.1.) for the production of fatty alcohols. In another embodiment, the host cell has thioesterase (E.C. 3.1.2.* or E.C. 3.1.2.14 or E.C. 3.1.1.5) activity and decarboxylase activity for making terminal olefins. The expression of enzymatic activities in microorganisms and microbial cells is taught by U.S. Pat. Nos. 8,097,439; 8,110,093; 8,110,670; 8,183,028; 8,268,599; 8,283,143; 8,232,924; 8,372,610; and 8,530,221, which are incorporated herein by reference. In other embodiments, the host cells or microorganisms that are used to express ACP and other biosynthetic enzymes will include certain native enzyme activities that are upregulated or overexpressed in order to produce one or more particular fatty acid derivative(s) such as ω-OH fatty acids, ω-OH fatty acid derivatives, and α,ω-diacids. In one embodiment, the host cell has a native thioesterase (E.C. 3.1.2.* or E.C. 3.1.2.14 or E.C. 3.1.1.5) activity for the production of fatty acids which can be increased by overexpressing the thioesterase gene.

The present disclosure includes host strains or microorganisms that express genes that code for CYP153A-reductase hybrid fusion polypeptides and variants thereof and other biosynthetic enzymes (supra). The recombinant host cells produce fatty acid derivatives including ω-hydroxy fatty acid derivatives (e.g., ω-hydroxy fatty acids including ω-hydroxy free fatty acids; ω-hydroxy fatty acid methyl esters; ω-oxo fatty acids; ω-oxo fatty acid methyl esters; α,ω-diacids; α,ω-diols; α,ω-diesters; ω-carboxy fatty acid methyl esters; ω-amino fatty acids; and ω-amino fatty acid methyl esters) and compositions and blends thereof. The fatty acid derivatives are typically recovered from the culture medium and/or are isolated from the host cells. In one embodiment, the fatty acid derivatives are recovered from the culture medium (extracellular). In another embodiment, the fatty acid derivatives are isolated from the host cells (intracellular). In another embodiment, the fatty acid derivatives are recovered from the culture medium and isolated from the host cells. The fatty acid derivatives composition produced by a host cell can be analyzed using methods known in the art, for example, GC-FID, in order to determine the distribution of particular fatty acid derivatives as well as chain lengths and degree of saturation of the components of the fatty acid derivative compositions such as ω-hydroxy fatty acids including ω-hydroxy free fatty acids; ω-hydroxy fatty acid methyl esters; ω-oxo fatty acids; ω-oxo fatty acid methyl esters; bifunctional compounds such as α,ω-diacids; α,ω-diols; α,ω-diesters; ω-carboxy fatty acid methyl esters; ω-amino fatty acids; ω-amino fatty acid methyl esters; and the like.

In other embodiments, the host cells or microorganisms that are used to express ACP and other biosynthetic enzymes will include certain native enzyme activities that are upregulated or overexpressed in order to produce one or more particular fatty acid derivative including ω-hydroxy fatty acid derivatives (e.g., ω-hydroxy fatty acids including ω-hydroxy free fatty acids; ω-hydroxy fatty acid methyl esters; ω-oxo fatty acids; ω-oxo fatty acid methyl esters; bifunctional compounds such as α,ω-diacids; α,ω-diols; α,ω-diesters; ω-carboxy fatty acid methyl esters; ω-amino fatty acids; and ω-amino fatty acid methyl esters). In one embodiment, the host cell has a native thioesterase (E.C. 3.1.2.* or E.C. 3.1.2.14 or E.C. 3.1.1.5) activity for the production of fatty acids which can be increased by overexpressing the thioesterase gene.

Recombinant Host Cells and Fermentation

In order to produce ω-hydroxy fatty acid derivatives, a number of modifications were made to production host cells (supra). Thus, the disclosure provides recombinant host cells which have been engineered to provide an ω-fatty acid biosynthesis pathway relative to non-engineered or native host cells (e.g., wild type host cells that function as control cells), which is accomplished, for example, through specific strain improvements. The production host organisms of the present disclosure include plant, animal, or microbial cells. Microorganisms or microbial cells such as bacteria, cyanobacteria, yeast, algae, or filamentous fungi can be used as production hosts. Non-limiting examples of microorganisms that may be used as production hosts include *E. coli, S. cerevisiae*, and others (infra). Microbial strains efficiently convert glucose or other carbon sources from a renewable feedstock into fatty acids or fatty acid esters, such as fatty acid methyl esters (FAMEs), fatty acid ethyl esters (FAEEs), and fatty alcohols (FALC). In order to achieve that, the strains have been carefully engineered to express key enzymes including thioesterases (e.g., TesA from *E. coli*) for the production of fatty acids, or ester synthases (e.g., ES9 from *M. hydrocarbonoclasticus*) for the production of FAME. Protocols and procedures for high density fermentations for the production of various compounds have been established (see U.S. Pat. Nos. 8,372,610; 8,323,924; 8,313, 934; 8,283,143; 8,268,599; 8,183,028; 8,110,670; 8,110, 093; and 8,097,439, incorporated herein by reference).

The enzymatic steps discussed herein can be added to these microorganisms that function as biocatalysts using genetic engineering techniques to create novel microorganisms with the ability to produce bi-functional fatty acid derivatives such α,ω-diacids as shown in FIGS. 1 and 2 as well as α,ω-diols as shown in FIGS. 3 and 4. The products are expected to be secreted outside of the cells, allowing for easy harvesting via centrifugation. Certain recombinant enzymatic steps can be combined in one microorganism for the direct production of specific compounds such as 12-amino lauric acid or 12-aminolauric acid methyl ester as illustrated in FIGS. 1 and 2. Alternatively, biotransformations using intermediates produced from renewable resources can be applied in the fermentation methods of the present disclosure. For example, lauric acid methyl ester obtained from a recombinant microorganism expressing enzymes such as a thioesterase or ester synthase can be fed to a recombinant microorganism expressing enzymes such as alcohol dehydrogenase or oxidase; amino transferase or transaminase; and/or esterase or lipase. As such, a chemical entity that was obtained from one recombinant microorganism expressing certain enzymes that catalyze certain steps can be fed to yet another recombinant microorganism expressing enzymes catalyzing other steps. Thus, the host cells provide a system of production where intermediates are interchangeable and fermentation procedures can be applied to all host cells in order to generate the desired ω-hydroxy fatty acid derivatives. Notably, methods to directly and efficiently produce ω-hydroxy fatty acid derivatives such as, for example, α,ω-diacids; α,ω-diols; or ω-amino fatty acids from glucose or other renewable feedstocks other than exogenous fatty acids or paraffins did not exist until now. Yet, these bifunctional fatty acid derivatives are important precursors for polymer synthesis. The fermentation based method for the production of ω-hydroxy fatty acid derivatives as presented herein provides a fast and environmentally friendly alternative to chemical methods employed in the art.

The present method provides for the direct production of ω-hydroxy fatty acid derivatives from a carbon source derived from renewable feedstocks (e.g., carbohydrates from corn, cane, or lignocellulosic biomass; or waste products such as glycerol, flu-gas, syn-gas; or the reformation of organic materials such as biomass). In one embodiment, the method relies cost effective and renewable alternative sources for the production of these important chemicals. The method includes producing ω-hydroxy fatty acid derivatives by providing a recombinant microorganism (e.g., host cell) in a fermentation broth; adding a renewable feedstock to a fermentation broth; and isolating the ω-hydroxy fatty acid derivative from the fermentation broth. The host cell of a particular microorganism includes a pathway that was engineered to express at least two nucleic acid sequences encoding a polypeptide including a thioesterase or an ester synthase and an ω-hydroxylase.

As used herein, the term fermentation broadly refers to the conversion of organic materials into target substances by host cells, for example, the conversion of a carbon source derived from a renewable feedstock by recombinant host cells into ω-OH fatty acid derivatives and compositions thereof by propagating a culture of the recombinant host cells in a media comprising the carbon source. The conditions permissive for the production refer to any conditions that allow a host cell to produce a desired product, such as ω-OH fatty acid derivatives. Similarly, the condition or conditions in which the polynucleotide sequence of a vector is expressed means any conditions that allow a host cell to synthesize a polypeptide. Suitable conditions include, for example, fermentation conditions. Fermentation conditions can include many parameters including, but not limited to, temperature ranges, levels of aeration, feed rates and media composition. Each of these conditions, individually and in combination, allows the host cell to grow. Fermentation can be aerobic, anaerobic, or variations thereof (such as micro-aerobic). Exemplary culture media include broths or gels. Generally, the medium includes a carbon source that can be metabolized by a host cell directly. In addition, enzymes can be used in the medium to facilitate the mobilization (e.g., the depolymerization of starch or cellulose to fermentable sugars) and subsequent metabolism of the carbon source.

For small scale production, the engineered host cells can be grown in batches of, for example, about 100 μL, 200 μL, 300 μL, 400 μL, 500 μL, 1 mL, 5 mL, 10 mL, 15 mL, 25 mL, 50 mL, 75 mL, 100 mL, 500 mL, 1 L, 2 L, 5 L, or 10 L; fermented; and induced to express a desired polynucleotide sequence, such as a polynucleotide sequence encoding a CYP153A-reductase hybrid fusion polypeptide alone or in combination with other enzymatic functionalities. For large scale production, the engineered host cells can be grown in batches of about 10 L, 100 L, 1000 L, 10,000 L, 100,000 L, and 1,000,000 L or larger; fermented; and induced to express a desired polynucleotide sequence. Alternatively, large scale fed-batch fermentation may be carried out. The ω-OH fatty acids derivative compositions described herein are found in the extracellular environment of the recombinant host cell culture and can be readily isolated from the culture medium. An ω-OH fatty acid or derivative thereof may be secreted by the recombinant host cell, transported into the extracellular environment or passively transferred into the extracellular environment of the recombinant host cell culture. The ω-OH fatty acid derivative thereof is isolated from a recombinant host cell culture using routine methods known in the art.

In some embodiments, the host cell is cultured in a culture medium comprising an initial concentration of a carbon source such as a renewable feedstock of about 2 g/L to about 100 g/L. In other embodiments, the culture medium comprises an initial concentration of about 2 g/L to about 10 g/L of a carbon source, of about 10 g/L to about 20 g/L of a carbon source, of about 20 g/L to about 30 g/L of a carbon source, of about 30 g/L to about 40 g/L of a carbon source, or of about 40 g/L to about 50 g/L of a carbon source. In some embodiments, the fermentation can be monitored for the level of carbon source in the culture medium. In some embodiments, the method further includes adding a supplemental carbon source to the culture medium when the level of the carbon source in the medium is less than about 0.5 g/L. In some embodiments, supplemental carbon source is added to the culture medium when the level of the carbon source in the medium is less than about 0.4 g/L, less than about 0.3 g/L, less than about 0.2 g/L, or less than about 0.1 g/L. In some embodiments, the supplemental carbon source is added to maintain a carbon source level of about 1 g/L to about 25 g/L. In some embodiments, the supplemental carbon source is added to maintain a carbon source level of about 2 g/L or more (e.g., about 2 g/L or more, about 3 g/L or more, about 4 g/L or more). In certain embodiments, the supplemental carbon source is added to maintain a carbon source level of about 5 g/L or less (e.g., about 5 g/L or less, about 4 g/L or less, about 3 g/L or less). In some embodiments, the supplemental carbon source is added to maintain a carbon source level of about 2 g/L to about 5 g/L, of about 5 g/L to about 10 g/L, or of about 10 g/L to about 25 g/L. In some embodiments, the carbon source is glucose or another type of renewable feedstock such as glycerol.

In some embodiments, the ω-hydroxy fatty acid derivative is produced at a concentration of about 1 g/L to about 200 g/L. In some embodiments, the ω-hydroxy fatty acid derivative is produced at a concentration of about 1 g/L or more (e.g., about 1 g/L or more, about 10 g/L or more, about 20 g/L or more, about 50 g/L or more, about 100 g/L or more). In some embodiments, the ω-hydroxy fatty acid derivative is produced at a concentration of about 1 g/L to about 170 g/L, of about 1 g/L to about 10 g/L, of about 40 g/L to about 170 g/L, of about 100 g/L to about 170 g/L, of about 10 g/L to about 100 g/L, of about 1 g/L to about 40 g/L, of about 40 g/L to about 100 g/L, or of about 1 g/L to about 100 g/L.

In some embodiments, the ω-hydroxy fatty acid derivative is produced at a titer of about 25 mg/L, about 50 mg/L, about 75 mg/L, about 100 mg/L, about 125 mg/L, about 150 mg/L, about 175 mg/L, about 200 mg/L, about 225 mg/L, about 250 mg/L, about 275 mg/L, about 300 mg/L, about 325 mg/L, about 350 mg/L, about 375 mg/L, about 400 mg/L, about 425 mg/L, about 450 mg/L, about 475 mg/L, about 500 mg/L, about 525 mg/L, about 550 mg/L, about 575 mg/L, about 600 mg/L, about 625 mg/L, about 650 mg/L, about 675 mg/L, about 700 mg/L, about 725 mg/L, about 750 mg/L, about 775 mg/L, about 800 mg/L, about 825 mg/L, about 850 mg/L, about 875 mg/L, about 900 mg/L, about 925 mg/L, about 950 mg/L, about 975 mg/L, about 1000 mg/L, about 1050 mg/L, about 1075 mg/L, about 1100 mg/L, about 1125 mg/L, about 1150 mg/L, about 1175 mg/L, about 1200 mg/L, about 1225 mg/L, about 1250 mg/L, about 1275 mg/L, about 1300 mg/L, about 1325 mg/L, about 1350 mg/L, about 1375 mg/L, about 1400 mg/L, about 1425 mg/L, about 1450 mg/L, about 1475 mg/L, about 1500 mg/L, about 1525 mg/L, about 1550 mg/L, about 1575 mg/L, about 1600 mg/L, about 1625 mg/L, about 1650 mg/L, about 1675 mg/L, about 1700 mg/L, about 1725 mg/L, about 1750 mg/L, about 1775 mg/L, about 1800 mg/L, about 1825 mg/L, about 1850 mg/L, about 1875 mg/L, about 1900 mg/L, about 1925 mg/L, about 1950 mg/L, about 1975 mg/L, about 2000 mg/L (2 g/L), 3 g/L, 5 g/L, 10 g/L, 20 g/L, 30 g/L, 40 g/L, 50 g/L, 60 g/L, 70 g/L, 80 g/L, 90 g/L, 100 g/L or a range bounded by any two of the foregoing values. In other embodiments, an ω-fatty acid derivative is produced at a titer of more than 100 g/L, more than 200 g/L, more than 300 g/L, or higher, such as 500 g/L, 700 g/L, 1000 g/L, 1200 g/L, 1500 g/L, or 2000 g/L. The preferred titer of ω-hydroxy fatty acid derivative produced by a recombinant host cell according to the methods of the disclosure is from 5 g/L to 200 g/L, 10 g/L to 150 g/L, 20 g/L to 120 g/L and 30 g/L to 100 g/L. In one embodiment, the titer of ω-fatty acid derivative produced by a recombinant host cell according to the methods of the disclosure is about 1 g/L to about 250 g/L and more particularly, 90 g/L to about 120 g/L. The titer may refer to a particular ω-fatty acid derivative or a combination of ω-fatty acid derivatives produced by a given recombinant host cell culture.

In other embodiments, the host cells engineered to produce ω-hydroxy fatty acid derivatives according to the methods of the disclosure have a yield of at least 1%, at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, or at least 30%, or at least 40% or a range bounded by any two of the foregoing values. In other embodiments, an ω-hydroxy fatty acid derivative or derivatives is produced at a yield of more than 30%, 40%, 50%, 60%, 70%, 80%, 90% or more. Alternatively, or in addition, the yield is about 30% or less, about 27% or less, about 25% or less, or about 22% or less. Thus, the yield can be bounded by any two of the above endpoints. For example, the yield of an ω-hydroxy fatty acid derivative or derivatives produced by the recombinant host cell according to the methods of the disclosure can be 5% to 15%, 10% to 25%, 10% to 22%, 15% to 27%, 18% to 22%, 20% to 28%, or 20% to 30%. In a particular embodiment, the yield of an ω-hydroxy fatty acid derivative or derivatives produced by the recombinant host cell is about 10% to about 40%. In another particular embodiment, the yield of an ω-hydroxy fatty acid derivative or derivatives produced by the recombinant host cell is about 25% to about 30%. The yield may refer to a particular ω-hydroxy fatty acid derivative or a combination of ω-hydroxy fatty acid derivatives produced by a given recombinant host cell culture. In addition, the yield will also be dependent on the feedstock used.

In some embodiments, the productivity of an ω-hydroxy fatty acid derivative or derivatives produced by a recombinant host cell is at least 100 mg/L/hour, at least 200 mg/L/hour, at least 300 mg/L/hour, at least 400 mg/L/hour, at least 500 mg/L/hour, at least 600 mg/L/hour, at least 700 mg/L/hour, at least 800 mg/L/hour, at least 900 mg/L/hour, at least 1000 mg/L/hour, at least 1100 mg/L/hour, at least 1200 mg/L/hour, at least 1300 mg/L/hour, at least 1400 mg/L/hour, at least 1500 mg/L/hour, at least 1600 mg/L/hour, at least 1700 mg/L/hour, at least 1800 mg/L/hour, at least 1900 mg/L/hour, at least 2000 mg/L/hour, at least 2100 mg/L/hour, at least 2200 mg/L/hour, at least 2300 mg/L/hour, at least 2400 mg/L/hour, or at least 2500 mg/L/hour. For example, the productivity of an ω-hydroxy fatty acid derivative or derivatives produced by a recombinant host cell according to the methods of the disclosure may be from 500 mg/L/hour to 2500 mg/L/hour, or from 700 mg/L/hour to 2000 mg/L/hour. In one particular embodiment, the productivity is about 0.7 mg/L/h to about 3 g/L/h. The productivity may refer to a particular ω-hydroxy fatty acid derivative or a combination of ω-hydroxy fatty acid derivatives produced by a given recombinant host cell culture.

Strategies to increase production of ω-OH fatty acid compositions by recombinant host cells include increased flux through the fatty acid biosynthetic pathway by expressing a CYP153A-reductase hybrid fusion gene and a thioesterase gene in the production host. As used herein, the term recombinant host cell or engineered host cell refers to a host cell whose genetic makeup has been altered relative to the corresponding wild-type host cell, for example, by deliberate introduction of new genetic elements and/or deliberate modification of genetic elements naturally present in the host cell. The offspring of such recombinant host cells also contain these new and/or modified genetic elements. In any of the aspects of the disclosure described herein, the host cell can be selected from a plant cell, insect cell, fungus cell (e.g., a filamentous fungus, such as *Candida* sp., or a budding yeast, such as *Saccharomyces* sp.), an algal cell and a bacterial cell. In one embodiment, recombinant host cells are recombinant microorganisms. Examples of host cells that are microorganisms include, but are not limited to, cells from the genus *Escherichia, Bacillus, Lactobacillus, Zymomonas, Rhodococcus, Pseudomonas, Aspergillus, Trichoderma, Neurospora, Fusarium, Humicola, Rhizomucor, Kluyveromyces, Pichia, Mucor, Myceliophtora, Penicillium, Phanerochaete, Pleurotus, Trametes, Chrysosporium, Saccharomyces, Stenotrophamonas, Schizosaccharomyces,*

*Yarrowia,* or *Streptomyces.* In some embodiments, the host cell is a Gram-positive bacterial cell. In other embodiments, the host cell is a Gram-negative bacterial cell. In some embodiments, the host cell is an *E. coli* cell. In some embodiment, the host cell is an *E. coli* B cell, an *E. coli* C cell, an *E. coli* K cell, or an *E. coli* W cell. In other embodiments, the host cell is a *Bacillus lentus* cell, a *Bacillus brevis* cell, a *Bacillus stearothermophilus* cell, a *Bacillus lichenoformis* cell, a *Bacillus alkalophilus* cell, a *Bacillus coagulans* cell, a *Bacillus circulans* cell, a *Bacillus pumilis* cell, a *Bacillus thuringiensis* cell, a *Bacillus clausii* cell, a *Bacillus megaterium* cell, a *Bacillus subtilis* cell, or a *Bacillus amyloliquefaciens* cell. In other embodiments, the host cell is a *Trichoderma koningii* cell, a *Trichoderma viride* cell, a *Trichoderma reesei* cell, a *Trichoderma longibrachiatum* cell, an *Aspergillus awamori* cell, an *Aspergillus fumigates* cell, an *Aspergillus foetidus* cell, an *Aspergillus nidulans* cell, an *Aspergillus niger* cell, an *Aspergillus oryzae* cell, a *Humicola insolens* cell, a *Humicola lanuginose* cell, a *Rhodococcusopacus* cell, a *Rhizomucormiehei* cell, or a *Mucormichei* cell. In yet other embodiments, the host cell is a *Streptomyces lividans* cell or a *Streptomyces murinus* cell. In yet other embodiments, the host cell is an Actinomycetes cell. In some embodiments, the host cell is a *Saccharomyces cerevisiae* cell.

In other embodiments, the host cell is a eukaryotic plant cell, an alga cell, a cyanobacterium cell, a green-sulfur bacterium cell, a green non-sulfur bacterium cell, a purple sulfur bacterium cell, a purple non-sulfur bacterium cell, an extremophile cell, a yeast cell, a fungus cell, an engineered cell of any of species described herein, or a synthetic organism. In some embodiments, the host cell is light-dependent or fixes carbon. In some embodiments, the host cell has autotrophic activity. In some embodiments, the host cell has photoautotrophic activity, such as in the presence of light. In some embodiments, the host cell is heterotrophic or mixotrophic in the absence of light. In certain embodiments, the host cell is a cell from *Arabidopsis thaliana, Panicum virgatum, Miscanthus giganteus, Zea mays, Botryococcuse braunii, Chlamydomonas reinhardtii, Dunaliela salina,* Synechococcus Sp. PCC 7002, Synechococcus Sp. PCC 7942, *Synechocystis* Sp. PCC 6803, *Thermosynechococcus elongates* BP-1, *Chlorobium tepidum, Chlorojlexus auranticus, Chromatiumm vinosum, Rhodospirillum rubrum, Rhodobacter capsulatus, Rhodopseudomonas palusris, Clostridium ljungdahlii, Clostridium thermocellum, Penicillium chrysogenum, Pichiapastoris, Saccharomyces cerevisiae, Schizosaccharomyces pombe, Pseudomonas fluorescens,* or *Zymomonas mobilis.* In one embodiment, the microbial cell is from a cyanobacteria including, but not limited to, Prochlorococcus, Synechococcus, *Synechocystis,* Cyanothece, and *Nostoc punctiforme.* In another embodiment, the microbial cell is from a specific cyanobacterial species including, but not limited to, Synechococcus *elongatus* PCC7942, *Synechocystis* sp. PCC6803, and Synechococcus sp. PCC7001.

Products Derived From Recombinant Microorganisms

As used herein, the fraction of modem carbon or fM has the same meaning as defined by National Institute of Standards and Technology (NIST) Standard Reference Materials (SRMs4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), fM is approximately 1.1. Bioproducts (e.g., the fatty acid derivatives including ω-OH fatty acids and derivatives produced in accordance with the present disclosure) include biologically produced organic compounds. In particular, the fatty acid derivatives (e.g., ω-OH fatty acids and derivatives thereof) produced using the fatty acid biosynthetic pathway herein, have not been produced from renewable sources and, as such, are new compositions of matter. These new bioproducts can be distinguished from organic compounds derived from petrochemical carbon on the basis of dual carbon-isotopic fingerprinting or $^{14}C$ dating. Additionally, the specific source of biosourced carbon (e.g., glucose vs. glycerol) can be determined by dual carbon-isotopic fingerprinting (see, e.g., U.S. Pat. No. 7,169,588). The ability to distinguish bioproducts from petroleum based organic compounds is beneficial in tracking these materials in commerce. For example, organic compounds or chemicals including both biologically based and petroleum based carbon isotope profiles may be distinguished from organic compounds and chemicals made only of petroleum based materials. Hence, the bioproducts herein can be followed or tracked in commerce on the basis of their unique carbon isotope profile. Bioproducts can be distinguished from petroleum based organic compounds by comparing the stable carbon isotope ratio ($^{13}C/^{12}C$) in each sample. The $^{13}C/^{12}C$ ratio in a given bioproduct is a consequence of the $^{13}C/^{12}C$ ratio in atmospheric carbon dioxide at the time the carbon dioxide is fixed. It also reflects the precise metabolic pathway. Regional variations also occur. Petroleum, C3 plants (the broadleaf), C4 plants (the grasses), and marine carbonates all show significant differences in $^{13}C/^{12}C$ and the corresponding $\delta^{13}C$ values. Furthermore, lipid matter of C3 and C4 plants analyze differently than materials derived from the carbohydrate components of the same plants as a consequence of the metabolic pathway. Within the precision of measurement, $^{13}C$ shows large variations due to isotopic fractionation effects, the most significant of which for bioproducts is the photosynthetic mechanism. The major cause of differences in the carbon isotope ratio in plants is closely associated with differences in the pathway of photosynthetic carbon metabolism in the plants, particularly the reaction occurring during the primary carboxylation (i.e., the initial fixation of atmospheric $CO_2$). Two large classes of vegetation are those that incorporate the C3 (or Calvin-Benson) photosynthetic cycle and those that incorporate the C4 (or Hatch-Slack) photosynthetic cycle. In C3 plants, the primary $CO_2$ fixation or carboxylation reaction involves the enzyme ribulose-1,5-diphosphate carboxylase, and the first stable product is a 3-carbon compound. C3 plants, such as hardwoods and conifers, are dominant in the temperate climate zones. In C4 plants, an additional carboxylation reaction involving another enzyme, phosphoenol-pyruvate carboxylase, is the primary carboxylation reaction. The first stable carbon compound is a 4-carbon acid that is subsequently decarboxylated. The $CO_2$ thus released is refixed by the C3 cycle. Examples of C4 plants are tropical grasses, corn, and sugar cane. Both C4 and C3 plants exhibit a range of $^{13}C/^{12}C$ isotopic ratios, but typical values are about −7 to about −13 per mil for C4 plants and about −19 to about −27 per mil for C3 plants (see, e.g., Stuiver et al. (1977) *Radiocarbon* 19:355). Coal and petroleum fall generally in this latter range. The $^{13}C$ measurement scale was originally defined by a zero set by Pee Dee Belemnite (PDB) limestone, where values are given in parts per thousand deviations from this material. The $\delta$13C values are expressed in parts per thousand (per mil), abbreviated, ‰, and are calculated as follows:

$$\delta^{13}C\ (‰)=[(^{13}C/^{12}C)\ sample-(^{13}C/^{12}C)\ standard]/(^{13}C/^{12}C)\ standard\times1000$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45, and 46. The compositions described herein include bioproducts produced by any of the methods described herein, including, for example, fatty acid derivative products. Specifically, the bioproduct can have a $\delta^{13}C$ of about −28 or greater, about −27 or greater, −20 or greater, −18 or greater, −15 or greater, −13 or greater, −10 or greater, or −8 or greater. For example, the bioproduct can have a $\delta^{13}C$ of about −30 to about −15, about −27 to about −19, about −25 to about −21, about −15 to about −5, about −13 to about −7, or about −13 to about −10. In other instances, the bioproduct can have a $\delta^{13}C$ of about −10, −11, −12, or −12.3. Bioproducts produced in accordance with the disclosure herein, can also be distinguished from petroleum based organic compounds by comparing the amount of $^{14}C$ in each compound. Because $^{14}C$ has a nuclear half-life of 5730 years, petroleum based fuels containing older carbon can be distinguished from bioproducts which contain newer carbon (see, e.g., Currie, Source Apportionment of Atmospheric Particles, Characterization of Environmental Particles, J. Buffle and H. P. van Leeuwen, Eds., 1 of Vol. I of the IUPAC Environmental Analytical Chemistry Series (Lewis Publishers, Inc.) 3-74, (1992)). The basic assumption in radiocarbon dating is that the constancy of $^{14}C$ concentration in the atmosphere leads to the constancy of $^{14}C$ in living organisms. However, because of atmospheric nuclear testing since 1950 and the burning of fossil fuel since 1850, $^{14}C$ has acquired a second, geochemical time characteristic. Its concentration in atmospheric $CO_2$, and hence in the living biosphere, approximately doubled at the peak of nuclear testing, in the mid-1960s. It has since been gradually returning to the steady-state cosmogenic (atmospheric) baseline isotope rate ($^{14}C/^{12}C$) of about $1.2\times10^{-12}$, with an approximate relaxation "half-life" of 7-10 years. This latter half-life must not be taken literally; rather, one must use the detailed atmospheric nuclear input/decay function to trace the variation of atmospheric and biospheric $^{14}C$ since the onset of the nuclear age. It is this latter biospheric $^{14}C$ time characteristic that holds out the promise of annual dating of recent biospheric carbon. $^{14}C$ can be measured by accelerator mass spectrometry (AMS), with results given in units of fraction of modern carbon (fM). fM is defined by National Institute of Standards and Technology (NIST) Standard Reference Materials (SRMs) 4990B and 4990C. As used herein, fraction of modern carbon or fM has the same meaning as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), fM is approximately 1.1. The compositions described herein include bioproducts that can have an $fM^{14}C$ of at least about 1. For example, the bioproduct of the disclosure can have an $fM^{14}C$ of at least about 1.01, an $fM^{14}C$ of about 1 to about 1.5, an $fM^{14}C$ of about 1.04 to about 1.18, or an $fM^{14}C$ of about 1.111 to about 1.124.

Another measurement of $^{14}C$ is known as the percent of modern carbon (pMC). For an archaeologist or geologist using $^{14}C$ dates, AD 1950 equals zero years old. This also represents 100 pMC. Bomb carbon in the atmosphere reached almost twice the normal level in 1963 at the peak of thermo-nuclear weapons. Its distribution within the atmosphere has been approximated since its appearance, showing values that are greater than 100 pMC for plants and animals living since AD 1950. It has gradually decreased over time with today's value being near 107.5 pMC. This means that a fresh biomass material, such as corn, would give a $^{14}C$ signature near 107.5 pMC. Petroleum based compounds will have a pMC value of zero. Combining fossil carbon with present day carbon will result in a dilution of the present day pMC content. By presuming 107.5 pMC represents the $^{14}C$ content of present day biomass materials and 0 pMC represents the $^{14}C$ content of petroleum based products, the measured pMC value for that material will reflect the proportions of the two component types. For example, a material derived 100% from present day soybeans would give a radiocarbon signature near 107.5 pMC. If that material was diluted 50% with petroleum based products, it would give a radiocarbon signature of approximately 54 pMC. A biologically based carbon content is derived by assigning 100% equal to 107.5 pMC and 0% equal to 0 pMC. For example, a sample measuring 99 pMC will give an equivalent biologically based carbon content of 93%. This value is referred to as the mean biologically based carbon result and assumes all the components within the analyzed material originated either from present day biological material or petroleum based material. A bioproduct comprising one or more fatty acid derivatives as described herein can have a pMC of at least about 50, 60, 70, 75, 80, 85, 90, 95, 96, 97, 98, 99, or 100. In other instances, a fatty acid derivative described herein can have a pMC of between about 50 and about 100; about 60 and about 100; about 70 and about 100; about 80 and about 100; about 85 and about 100; about 87 and about 98; or about 90 and about 95. In yet other instances, a fatty acid derivative described herein can have a pMC of about 90, 91, 92, 93, 94, or 94.2.

ω-Hydroxy Fatty Acid Derivatives and Formulations

Compounds such as ω-hydroxyl fatty acid derivatives are molecules that are valuable and desirable in many industrial applications. The present disclosure produces such compounds through recombinant microorganisms in vivo and thereby generates a range of useful products. Such products include ω-hydroxy fatty acid derivatives. The ω-hydroxy fatty acid derivatives include, but are not limited to, ω-hydroxy fatty acids; ω-hydroxy-fatty acid methyl esters; ω-amino fatty acids; ω-oxo fatty acids, ω-amino fatty acid methyl esters; ω-oxo fatty acid methyl esters; α,ω-diacids; α,ω-diesters; and α,ω-diols as well as compositions thereof. While mostly even chain ω-hydroxy-fatty acid derivatives are described herein, odd chain ω-hydroxy-fatty acid derivatives are also included, such as those having 7, 9, 11, 13, 15, 19, etc., carbons.

Examples of ω-hydroxy fatty acids include, but are not limited to, 8-hydroxy octanoic acid, 10-hydroxy decenoic acid, 10-hydroxy decanoic acid, 12-hydroxy dodecenoic acid, 12-hydroxy dodecanoic acid, 14-hydroxy tetradecenoic acid, 14-hydroxy tetradecanoic acid, 16-hydroxy hexadecenoic acid, 16-hydroxy hexadecanoic acid, 18-hydroxy octadecenoic acid, and 18-hydroxy octadecenoic acid.

Examples of ω-hydroxy-fatty acid methyl esters include, but are not limited to, 8-hydroxy octanoic acid methyl ester, 10-hydroxy decenoic acid methyl ester, 10-hydroxy decanoic acid methyl ester, 12-hydroxy dodecenoic acid methyl ester, 12-hydroxy dodecanoic acid methyl ester, 14-hydroxy tetradecenoic acid methyl ester, 14-hydroxy tetradecanoic acid methyl ester, 16-hydroxy hexadecenoic acid methyl ester, 16-hydroxy hexadecanoic acid methyl ester, 18-hydroxy octadecenoic acid methyl ester, and 18-hydroxy octadecenoic acid methyl ester.

Examples of ω-amino fatty acids include, but are not limited to, 8-amino octanoic acid, 10-amino decenoic acid, 10-amino decanoic acid, 12-amino dodecenoic acid, 12-amino dodecanoic acid, 14-amino tetradecenoic acid, 14-amino tetradecanoic acid, 16-amino hexadecenoic acid, 16-amino hexadecanoic acid, 18-amino octadecenoic acid, and 18-amino octadecenoic acid.

Examples of ω-amino fatty acid methyl esters include, but are not limited to, 8-amino octanoic acid methyl ester, 10-amino decenoic acid methyl ester, 10-amino decanoic acid methyl ester, 12-amino dodecenoic acid methyl ester, 12-amino dodecanoic acid methyl ester, 14-amino tetradecenoic acid methyl ester, 14-amino tetradecanoic acid methyl ester, 16-amino hexadecenoic acid methyl ester, 16-amino hexadecanoic acid methyl ester, 18-amino octadecenoic acid methyl ester, and 18-amino octadecenoic acid methyl ester.

Examples of ω-oxo fatty acids include, but are not limited to, 8-oxo octanoic acid, 10-oxo decenoic acid, 10-oxo decanoic acid, 12-oxo dodecenoic acid, 12-oxo dodecanoic acid, 14-oxo tetradecenoic acid, 14-oxo tetradecanoic acid, 16-oxohexadecenoic acid, 16-oxo hexadecanoic acid, 18-oxo octadecenoic acid, and 18-oxo octadecenoic acid.

Examples of ω-oxo fatty acid methyl esters include, but are not limited to, 8-oxo octanoic acid methyl ester, 10-oxo decenoic methyl ester, 10-oxo decanoic methyl ester, 12-oxo dodecenoic methyl ester, 12-oxo dodecanoic methyl ester, 14-oxo tetradecenoic methyl ester, 14-oxo tetradecanoic methyl ester, 16-oxohexadecenoic methyl ester, 16-oxo hexadecanoic methyl ester, 18-oxo octadecenoic methyl ester, and 18-oxo octadecenoic methyl ester.

Examples of α,ω-diacids include, but are not limited to, 1,8-octanedoic acid, 1,10-decenedioic acid, 1,10-decanedioic acid, 1,12-dodecenedioic acid, 1,12-dodecanedioic acid, 1,14-tetradecenedioic acid, 1,14-tetradecanedioic acid, 1,16-hexadecenedioic acid, 1,16-hexadecanedioic acid, 1,18-octadecenedioic acid, 1,18-octadecanedioic acid.

Examples of α,ω-diesters include, but are not limited to, 1,8-octanoic dimethylester, 1,10-decenoic dimethylester, 1,10-decanoic dimethylester, 1,12-dodecenoic dimethylester, 1,12-dodecanoic dimethylester, 1,14-tetradecenoic dimethylester, 1,14-tetradecanoic dimethylester, 1,16-hexadecenoic dimethylester, 1,16-hexadecanoic dimethylester, 1,18-octadecenoic dimethylester, 1,18-octadecanoic dimethylester.

Examples of a ω-diols include, but are not limited to, 1,8-octanediol, 1,10-decenediol, 1,10-decanediol, 1,12-dodecenediol, 1,12-dodecanediol, 1,14-tetradecenediol, 1,14-tetradecanediol, 1,16-hexadecenediol, 1,16-hexadecanediol, 1,18-octadecenediol, and 1,18-octadcanediol.

While even chain ω-hydroxy-fatty acid derivatives are described herein, odd chain ω-hydroxy-fatty acid derivatives are also included, such as those having 7, 9, 11, 13, 15, 19, etc., carbons. Examples of odd-chain ω-hydroxy fatty acids include, but are not limited, e.g., 11-hydroxy undecenoic acid, 11-hydroxy undecanoic acid, 13-hydroxy tridecenoic acid, 13-hydroxy tridecanoic acid, 15-hydroxy pentadecenoic acid, 15-hydroxy pentadecanoic acid, 17-hydroxy heptadecenoic acid and 17-hydroxy heptadecanoic acid. Examples of odd-chain α,ω-diacids include, but are not limited, e.g. 1,11-undecenedioc acid, 1,11-undecanedioc acid, 1,13-tridecenedioc acid, 13-tridecanedioc acid, 1,15-pentadecenedioc acid, 1,15-pentadecanedioc acid, 1,17-heptadecenedioc acid and 1,17-heptadecanedioc acid. Examples of odd-chain α,ω-diols include, but are not limited, e.g. 1,11-undecenediol, 1,11-undecanediol, 1,13-tridecenediol, 13-tridecanediol, 1,15-pentadecenediol, 1,15-pentadecanediol, 1,17-heptadecenedioland 1,17-heptadecanediol The compounds and compositions of the ω-hydroxy fatty acid derivatives of the present disclosure can be formulated such that desirable products can be made including flavors, fragrances, lubricants, gels, various polymers, resins, industrial fluids, adhesives, corrosion inhibitors, capacitor electrolytes, fibers, powder coating curatives, plasticizers, polyester coatings, epoxy resins, polyamide resins, surfactants, detergents, additives, and more.

EXAMPLES

The following examples further illustrate the disclosure but should not be construed as in any way limiting its scope.

Example 1: Cultivating Recombinant *E. coli* Strains for the Production of ω-Hydroxy Fatty Acid Derivatives The strains were grown over night in Luria-Bertani (LB) media. The cultures were diluted 1:10 into fresh LB media, grown for 2-3 hours (h) at 32° C., and then again diluted 1:10 into defined FA2 media (see table 10, infra). In some experiments, the media were supplemented with 0.5 mM δ-aminolevulinic acid and a trace vitamin solution. Antibiotics such as spectimocycin (100 μg/ml) or kanamycin (50 μg/ml) were added when strains contain plasmids with the respective antibiotic resistance markers. After growth for 4-5h at 32° C., the cultures were induced with 1 mM IPTG and cultivated for another 16-18h at the same temperature. In some experiments dodecanoic acid, dodecanol or dodecanoic acid methyl ester were added at a final concentration of 1 g/L at the time of induction. Cultures that aimed at producing derivatives of fatty acid methyl esters were supplemented with methanol (2%, v/v) at the time of induction.

TABLE 10

| FA2 Media Composition | |
| --- | --- |
| Media component | Final concentration |
| 5× M9 Salt Solution | 1× |
| 100 g/LNH4Cl | 1 g/L |
| 10 mg/mL Thiamine | 1 μg/L |
| 1M MgSO4 | 1 mM |
| 1M CaCl2 | 1 mM |
| 500 g/L glucose | 30 g/L |
| 1000× Trace Mineral Solution (TM2) | 1× |
| 10 g/L Fe Citrate | 10 mg/L |
| 2M BisTris (pH 7.0) | 100 mM |
| 10% Triton X-100 | 0.25% |

Example 2: Analysis of ω-Hydroxylated Fatty Acid Derivatives

Cultures that produced ω-hydroxy fatty acid derivatives were harvested and extracted with butyl acetate using a vortexer (DVX-2500 multi-tube vortexer, VWR) at 2500 rpm for 30 minutes. Extract was centrifuged in an Eppendorf centrifuge (centrifuge 5424) at 15000 rpm for 15 minutes at room temperature. Supernatant (100 μL) was pipetted to a GC vial with insert, derivatized by adding 100 μL of N,O-bis(trimethylsilyl) trifluoroacetamide (BSTFA) and 1% trimethylchlorosilane (TMCS) and mixed using a vortexer for 30 seconds. Supernatants with and without derivatization were both injected on GC-MS separately to generate chromatograms and mass spectra for compound identification. The GC-MS parameters were as follows:

GC Parameters:

Analytical Column: DB-1HT, 15m×250 μm×0.1 μm, available from Agilent with cat #J&W 122-1111E Oven temperature: initial at 50° C., hold for 5 minutes, increase to 300° C. at 25° C./min, and hold for 5.24 minutes for a total run time of 24 minutes Column flow: 1.2 mL/minute Inlet temperature: 300° C.

Sample size: 1 μL

Split ratio: 20:1

Software: ChemStation E.02.01.1177

MS Parameters

Transfer line temperature: 300° C.

MS source: 230° C.

MS Quad: 150° C.

Autosampler

Combi PAL (CTC analytics) distributed by LEAP Technologies

GC/FID Parameters:

Gas Chromatograph Agilent 7890 equipped with a FID, or equivalent.

Data System ChemStation software B.04.03, or equivalent.

Analytical column: DB-1 (10 m×0.18 mm×0.2 μM), or equivalent.

Autosampler: Combi PAL, CTC analytics (Leap Technologies)

Initial temperature: 60° C., hold for 0.5 minute, increase to 300° C. at 25° C./min, and hold 0.9 minute for total run time of 11 minutes Injector Temperature: 320° C.

Detector: Flame ionization detector (FID)

Detector Temperature: 350° C.

Hydrogen Flow: 40 mL/minute

Air Flow: 450 mL/minute

Make-up Flow: 45 mL/minute ($N_2$)

Split ratio: 50:1

Column flow: 0.8 mL/minute

Sample size: 1 μL

Example 3: Conversion of Dodecanoic Acid to 12(ω)-Hydroxy Dodecanoic Acid by *E. coli* Strains Expressing Two cyp153A P450 Oxygenase Operons This example shows the conversion of exogenously added fatty acid to ω-hydroxy fatty acid by recombinant *E. coli* strains expressing cyp153A P450 oxygenase operons. The purpose of this experiment was to investigate the efficiency of the cyp153A P450 oxygenase operons. The cyp153A P450 oxygenases have so far only be employed in vitro (see, e.g., Honda-Malca et al. (2012) Chem. Commun. 48:5115-5117) and the object of this experiment was to test if these operons could produce an ω-hydroxy fatty acid derivative when being provided with exogenous fatty acids in vivo.

The cyp153A operons from two bacteria, *Marinobacter aquaeoli* (Accession Number YP_957888; SEQ ID NO: 3), and *Mycobacterium marinum* (Accession Number YP_001851443; SEQ ID NO: 59), were PCR amplified from genomic DNA of these organisms. The operons are made of the genes encoding ferredoxin (fd), cyp153A P450 oxygenase and ferredoxin reductase (fdR) (see Tables 2A and 2B, supra). The natural order of the genes and intergenic regions were preserved, but the GTG start codon in cyp153A16 from *M. marinum* was replaced with an ATG start codon by crossover PCR. The PCR amplimers were cloned into a pCL1920-derivative vector (SC101 replicon, spectinomycin resistance marker), such that the transcription of the operons was controlled by the IPTG-inducible Ptrc promoter. The resulting plasmids, pAS.017 (see Table 11, infra) and pAS.018 were transformed into *E. coli* MG1655 in which either the fadE gene (encoding acyl-CoA dehydrogenase) or the fadD gene (encoding acyl-CoA synthetase) were deleted. These strains cannot degrade fatty acids, thus, increasing the availability of fatty acids for an increased conversion to product can be achieved by deleting these genes or genes coding for other fatty acid degradation enzymes such as fadA or fadB. This is, however, optional and can be implemented when free fatty acids are exogenously supplied or are intermediates of a product pathway. (Table 1 (supra) provides a comprehensive list of enzymatic activity within the metabolic pathways, including various fatty acid degradation enzymes that can be attenuated to increase the availability of fatty acids in a host strain.) The four resulting strains are summarized in Table 12 (infra). The strains were analyzed for conversion of dodecanoic acid to 12-hydroxy dodecanoic acid as described in Examples 1 and 2.

Figure 6:
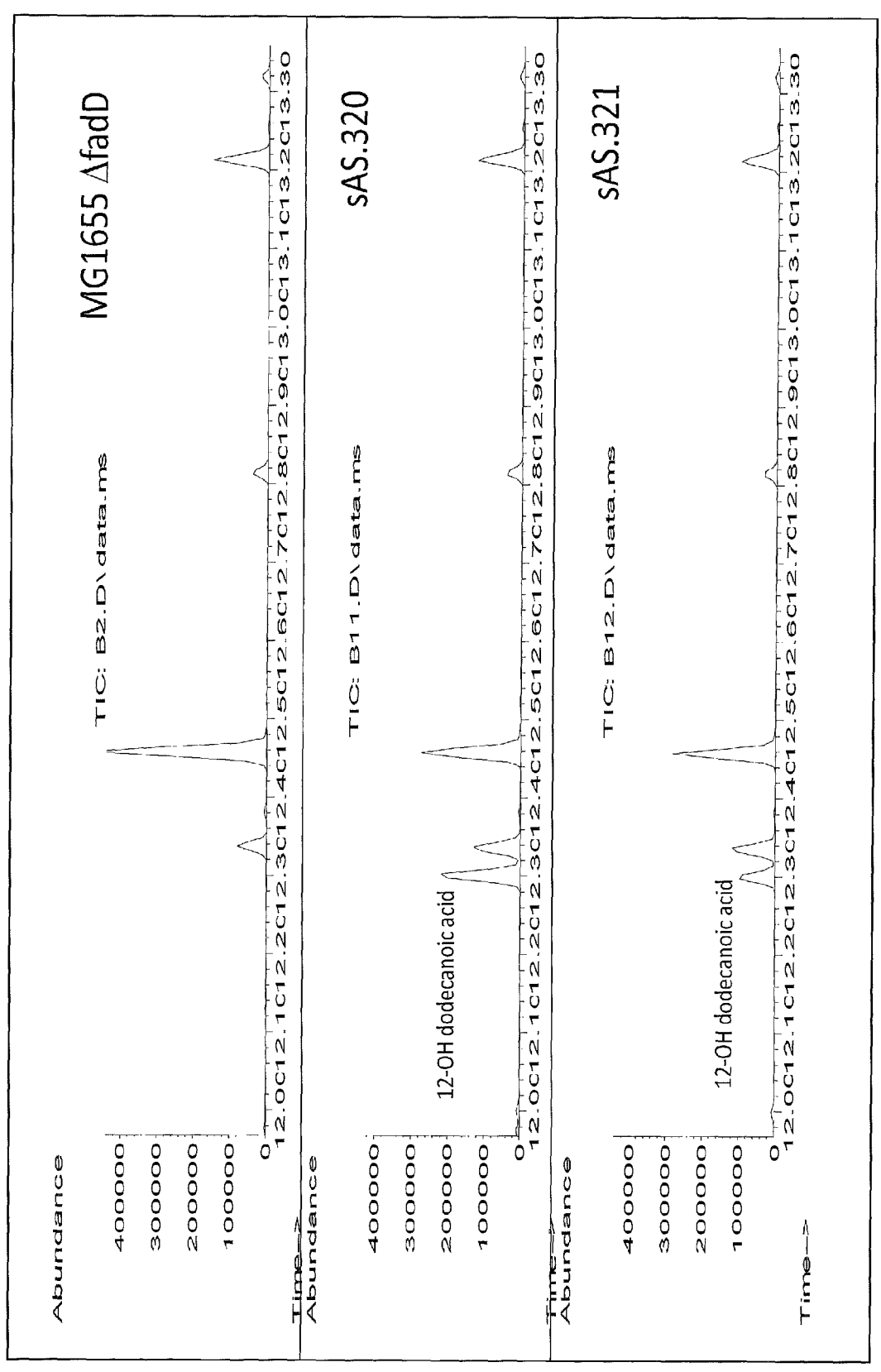
FIG. 6 shows GC/MS chromatographs of extracts from recombinant *E. coli* strains expressing cyp153A operons leading to 12-hydroxy dodecanoic acid formation when fed with dodecanoic acid. A GC/MS chromatograph of an extract from a control strain (MG1655 ΔfadD) is also shown.
Figure 7A:
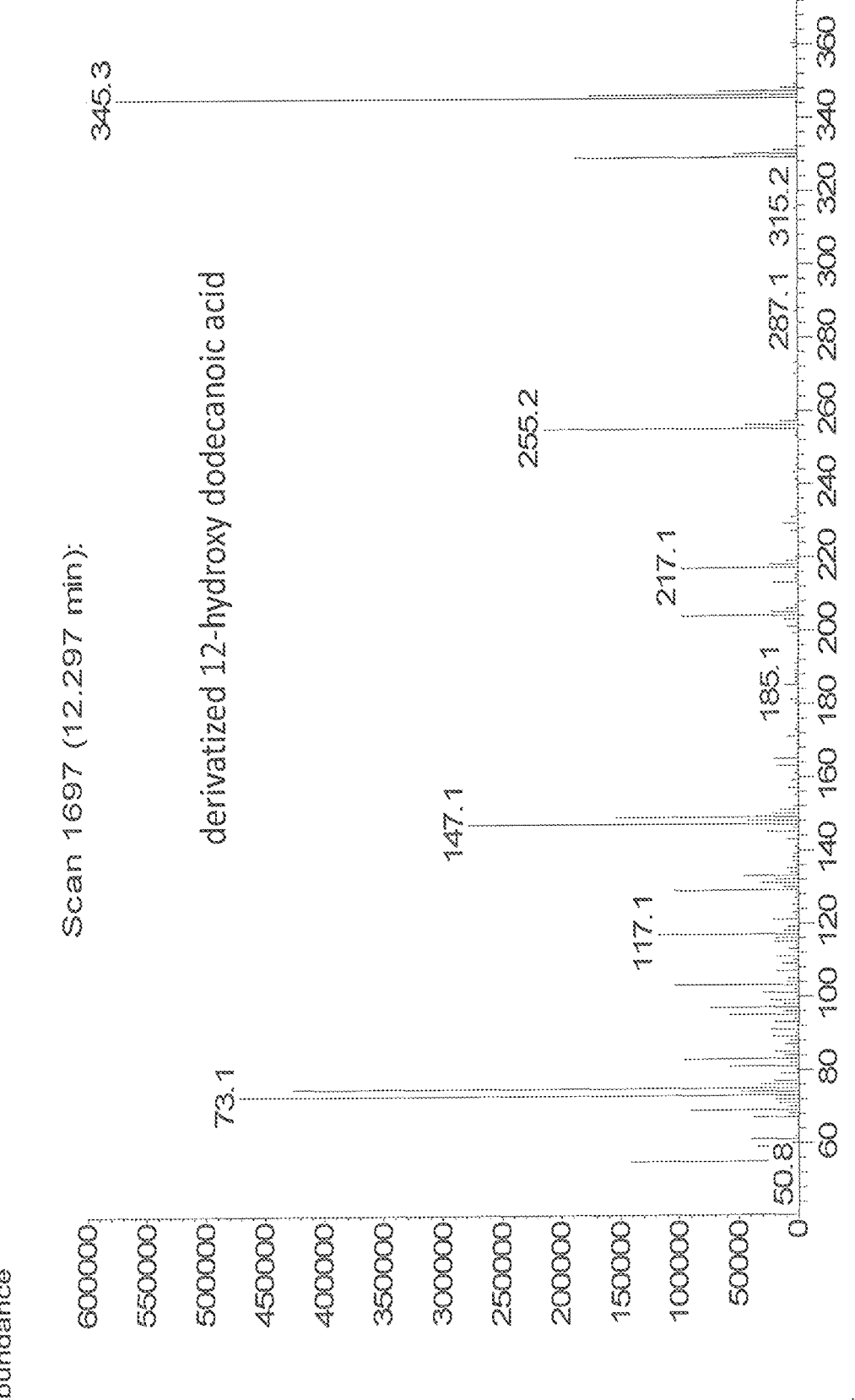
FIGS. 7A through 7C illustrate the mass spectra of derivatized 12-hydroxy dodecanoic acid (peak at 12.297 minutes) (FIG. 7A), derivatized 12-hydroxy dodecanoic acid authentic standard (FIG. 7B), and underivatized 12-hydroxy dodecanoic (peak at 11.393 minutes) (FIG. 7C). Derivatizing agent was BSTFA+1% TMCS. The mass spectra in FIGS. 7A and 7C were from extracts of *E. coli* strain sAS.321.
Figure 7B:
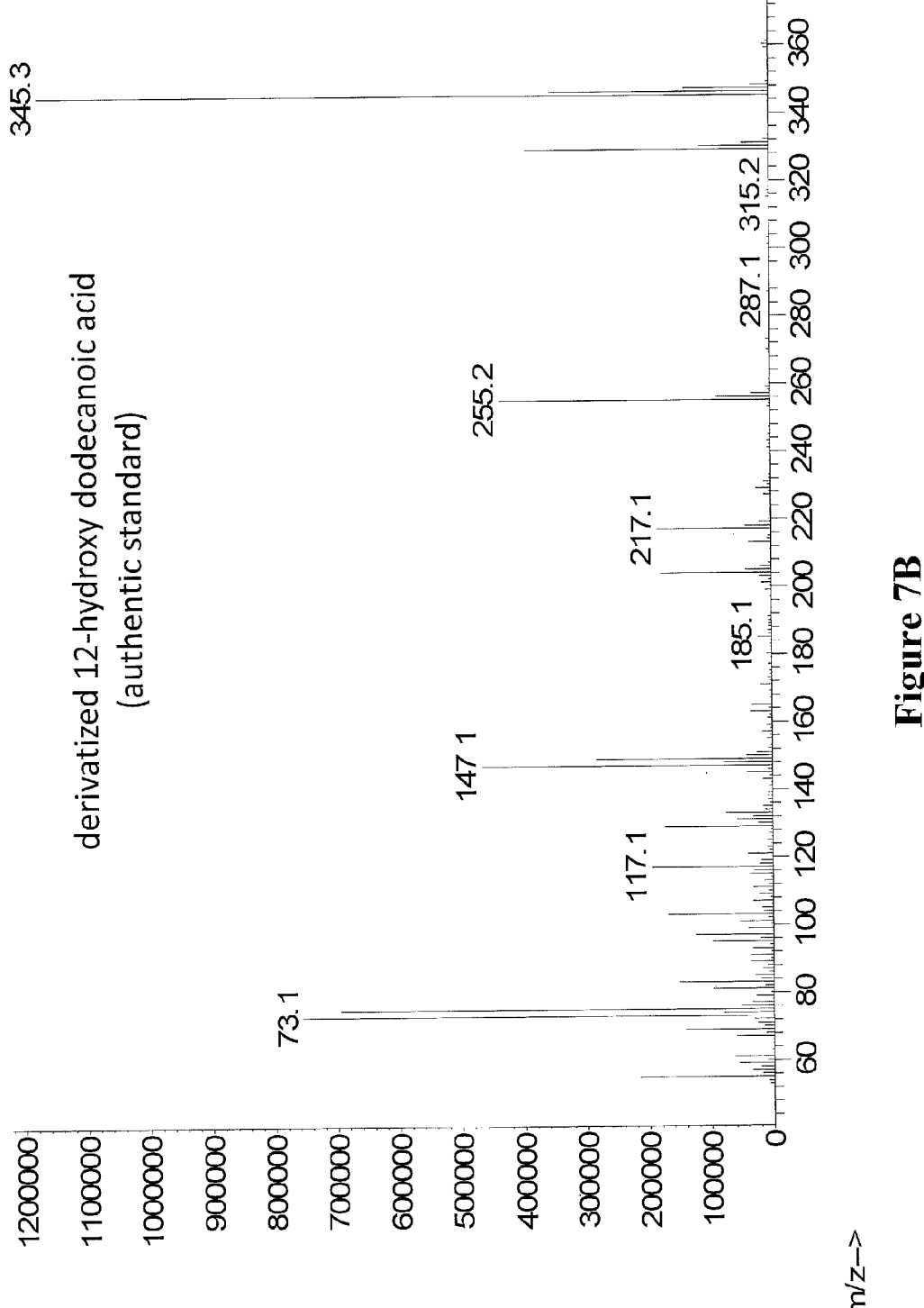
Figure 7C:
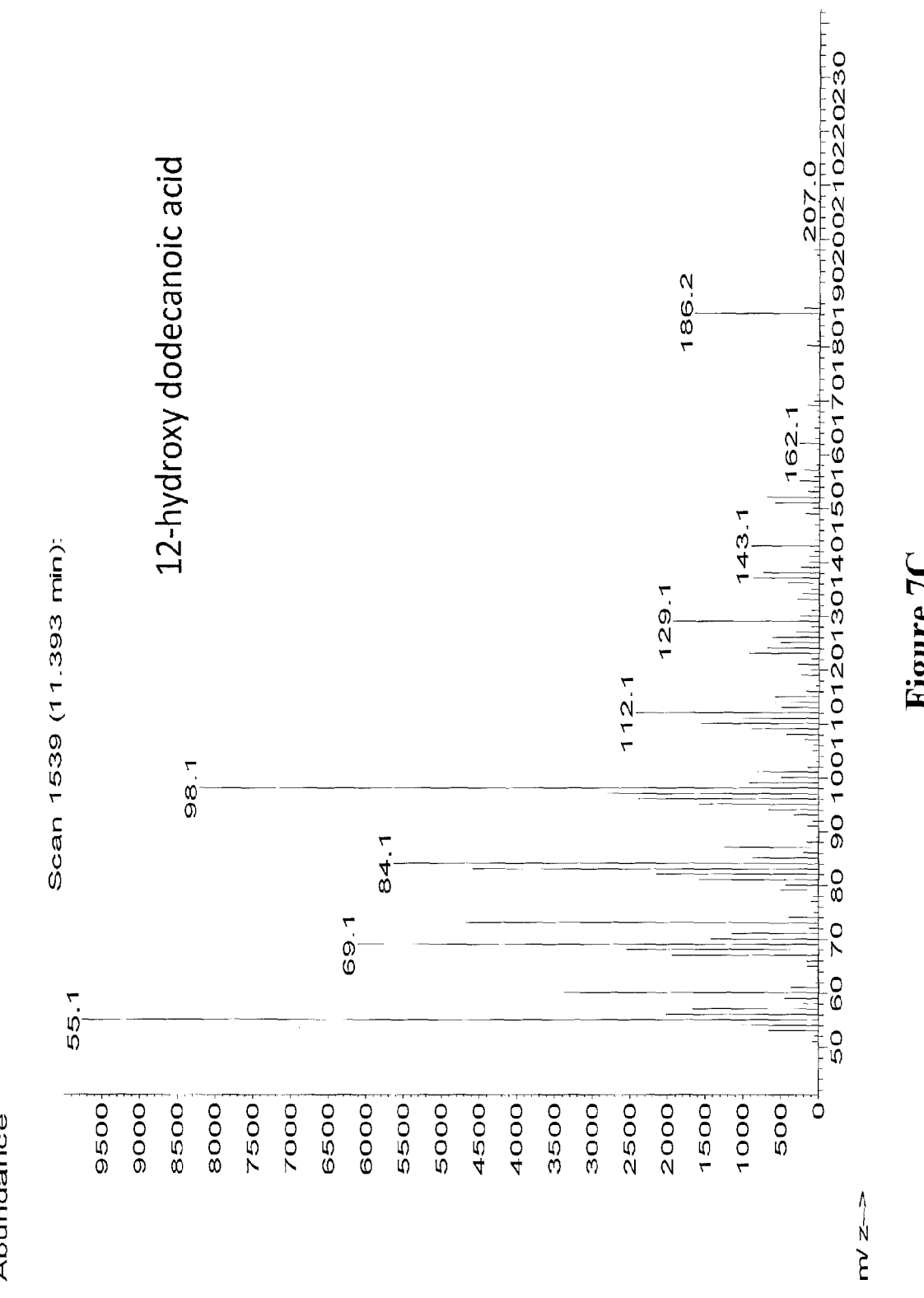
Figure 8A:
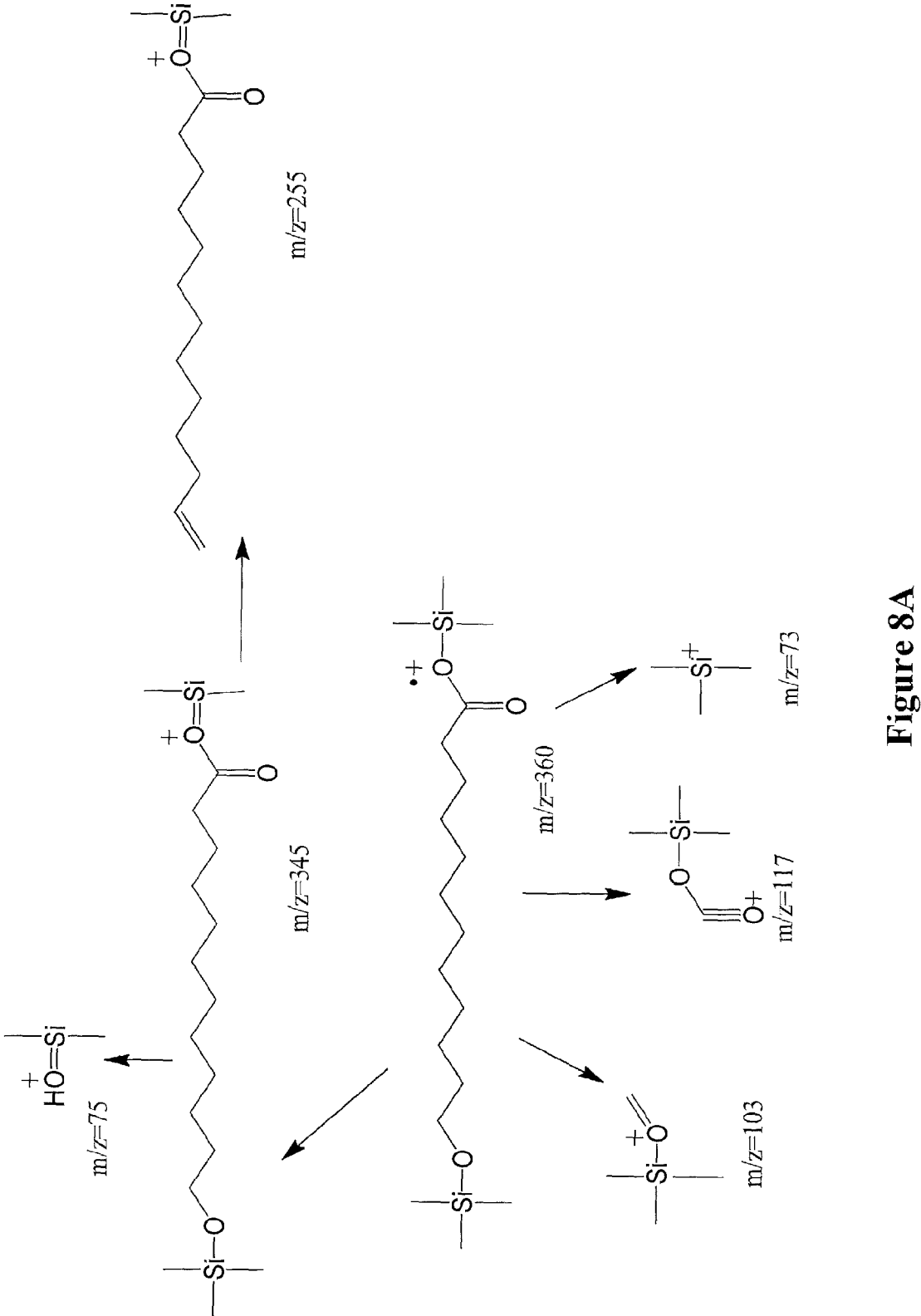
FIGS. 8A through 8B illustrate the ion fragmentation pattern of derivatized 12-hydroxydodecanoic acid (12-trimethylsilyloxydodecanoic acid trimethylsilyl ester) (FIG. 8A) and underivatized 12-hydroxydodecanoic acid (FIG. 8B).
Figure 8B:
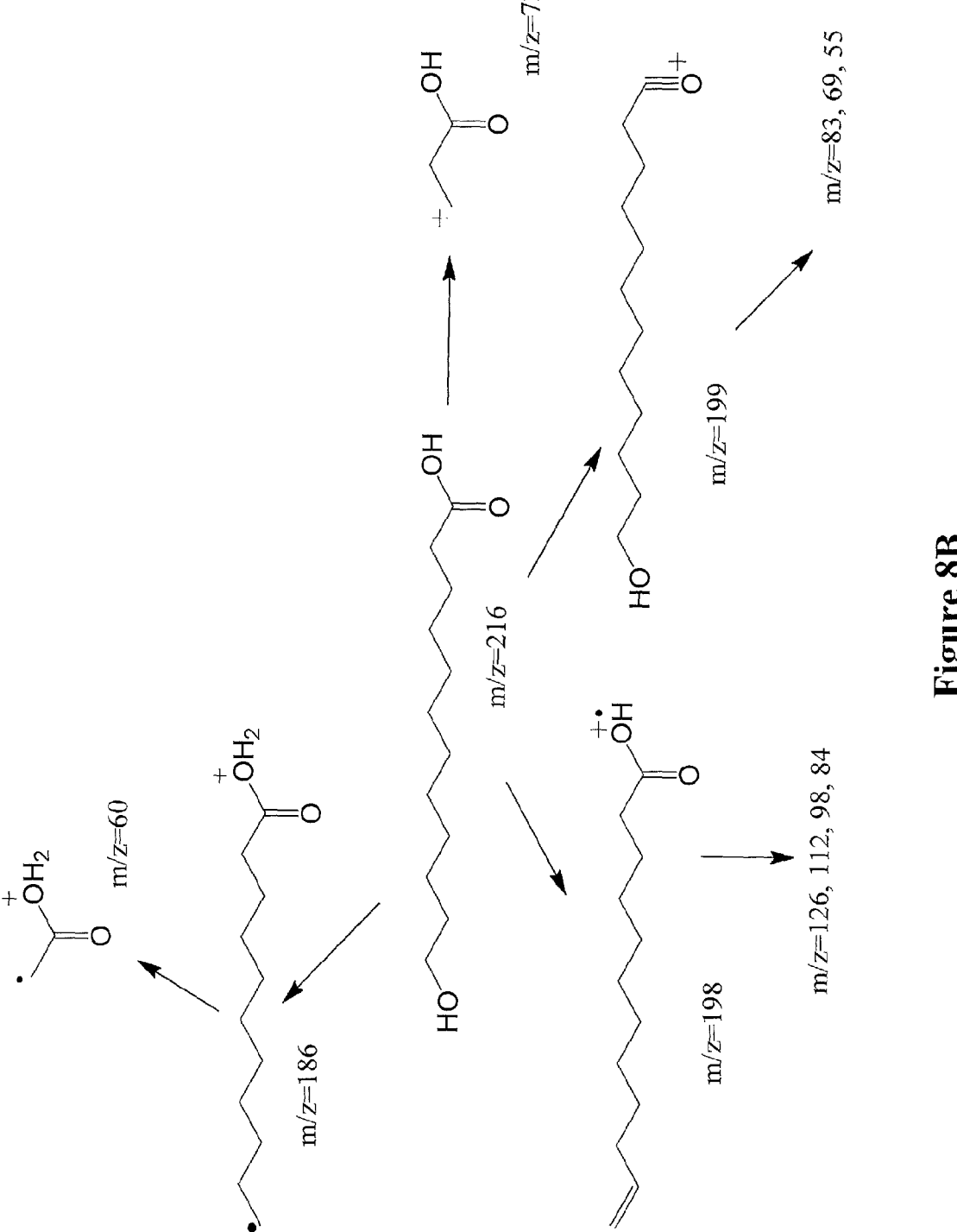

In comparison to the control strain MG1655 ΔfadD, which does not express a cyp153A operon, a new peak at RT 12.303 minutes (after BSTFA derivatization) was detected in the GC-MS chromatograms of all four strains expressing the cyp153A operons (see FIG. 6, only strains sAS.320 and sAS.321 are shown here). The mass spectrum of the peak at RT 12.303 minutes is shown in FIG. 7A. The fragmentation pattern indicated that this peak was 12-trimethylsilyloxy dodecanoic acid trimethylsilyl ester, which is the derivatized form of 12-hydroxy dodecanoic acid. Characteristic ion fragments for 12-trimethylsilyloxy fatty acid trimethylsilyl esters are shown in FIG. 8A. Ions at m/z=129, 147, 204 and 217 (not shown in the Figure but present) are useful diagnostic markers for these compounds. The ion at m/z 255 was used to determine the chain length after loss of $CH_3$ from the carboxyl side (m/z=345) and $(CH_3)_3SiOH$ from the hydroxyl side of this compound (see FIG. 8A). The correct identification of this peak was further confirmed by comparing its retention time and mass spectrum with a 12-trimethylsilyloxy dodecanoic acid trimethyl silyl ester authentic standard as shown in FIG. 7B. The mass spectrum of this compound before derivatization was also recorded and is shown in FIG. 7C. Characteristic ion fragments of the underivatized compound are shown in FIG. 8B. Ions at m/z=98 and 84 (shown) are useful diagnostic markers for ω-hydroxy fatty acids. The ion at m/z 186 is a characteristic fragment of 12-hydroxydodecanoic acid by loss of $CH_2O$ from the hydroxyl side. The molecular ion of the compound can be determined to be 216 by adding $CH_2O$ to fragment ion at m/z 186.

Thus, *E. coli* expressing the cyp153A operons from *Marinobacter aquaeoli* and *Mycobacterium marinum* converted exogenous dodecanoic acid to 12-hydroxy dodecanoic acid in vivo in host cells. As such it was confirmed that the enzyme can indeed produce ω-hydroxy fatty acid derivatives. However, the conversion efficiency of this enzyme was rather low. Thus, the enzymatic activity of the cyp153A operons by themselves is not expected to be ideal for the production of ω-hydroxy fatty acid derivatives and it was determined that further engineering was required to design an enzyme with a higher conversion efficiency.

TABLE 11

Expression Plasmids for the Production
of ω-Hydroxylated Fatty Acid Derivatives

| Plasmid | Description |
| --- | --- |
| pAS.017 | pCL-fd-cyp153A-fdR_Maqu |
| pAS.018 | pCL-fd-cyp153A16-fdR_Mmar |
| pAS.022 | pCL-fd_synIGR_cyp153A(G307A)-fdR_synIGR_Maqu |
| pAS.023 | pCL-cyp153A(G307A)_Maqu-P450-RedRhF_Rhod |
| pEP.125 | pACYC-cyp153A(G307A)_Maqu-P450-RedRhF_Rhod |
| pEP.126 | pACYC-alkJH_Pput |
| pSN.09 | pACYC-cyp102A1(F87A) |
| pSN.12 | pCL-cyp102A1(F87A) |

TABLE 12

Recombinant cyp153A Expressing E. coli Strains
for the Conversion of Fatty Acid Derivatives
to ω-Hydroxylated Fatty Acid Derivatives

| Strain | Strain background | Plasmid |
| --- | --- | --- |
| sAS.314 | MG1655 ΔfadE ΔfhuA | pAS.017 |
| sAS.315 | MG1655 ΔfadE ΔfhuA | pAS.018 |
| sAS.320 | MG1655 ΔfadD | pAS.017 |
| sAS.321 | MG1655 ΔfadD | pAS.018 |
| sAS.335 | MG1655 ΔfadD | pAS.022 |
| sAS.336 | MG1655 ΔfadD | pAS.023 |

Example 4: Conversion of Dodecanoic Acid to 12((ω)-Hydroxy Dodecanoic Acid by an E. coli Strain Expressing a Modified cyp153A P450 Oxygenase Operon This example shows the conversion of exogenously added fatty acid to ω-hydroxy fatty acid by a recombinant E. coli strain expressing a modified cyp153A P450 oxygenase operon. Similarly, the purpose of this experiment was to investigate the capability and efficiency of this modified cyp153A P450 oxygenase operon for the production of ω-hydroxy fatty acid derivatives in vivo.

Figure 9:
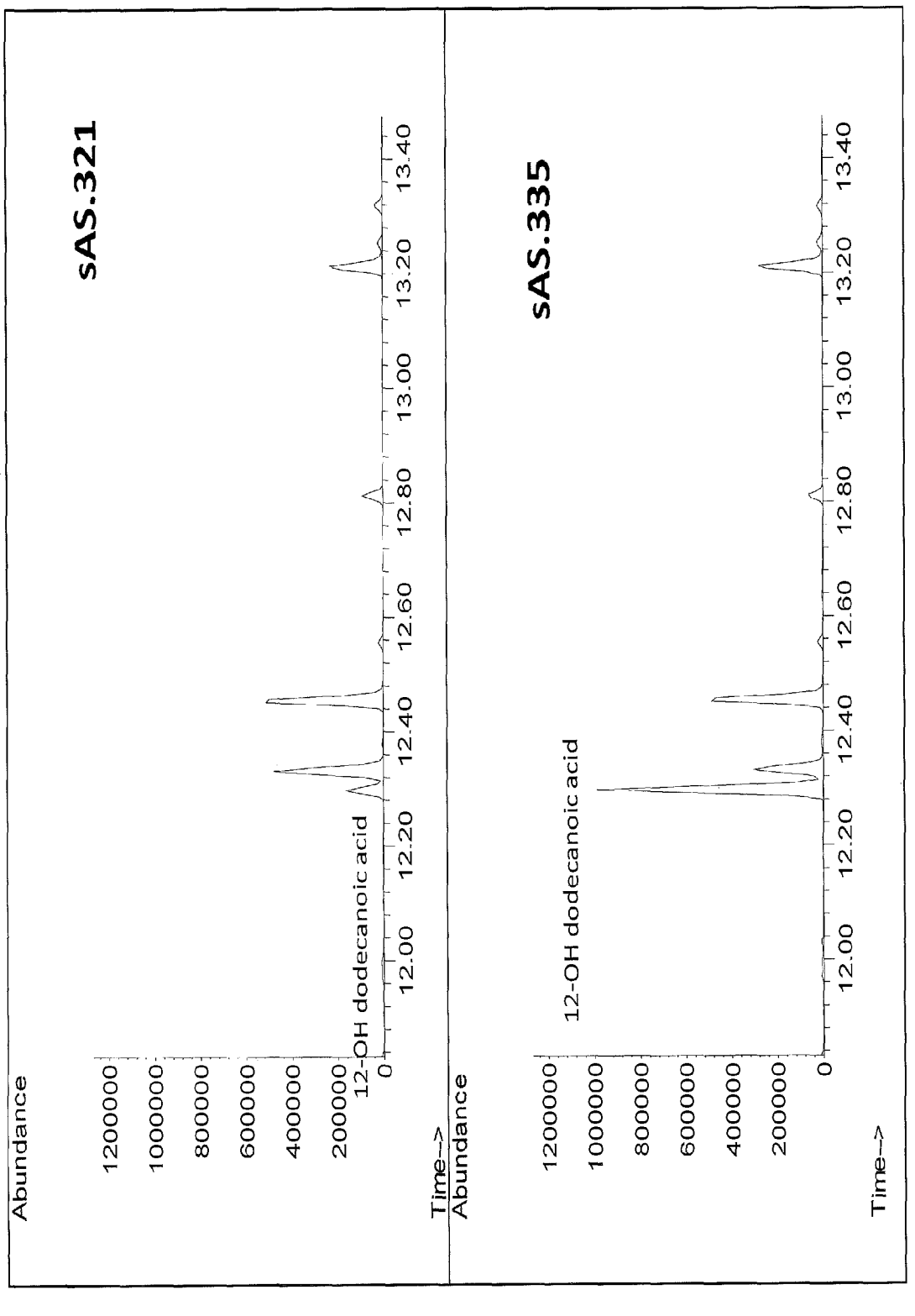
FIG. 9 shows GC/MS chromatographs of extracts from recombinant *E. coli* strains expressing CYP153A operons leading to 12-hydroxy dodecanoic acid formation when fed with dodecanoic acid. Strain sAS.335 expresses an improved CYP153A operon.

A mutant of cyp153A from M. aquaeoli in which glycine 307 was replaced by alanine has previously been described (see Honda Malca et al. (2012) Chem. Commun. 48:5115). Plasmid pAS.017 (see Example 3, supra) was modified in the following way: the codon specifying Gly307 of cyp153_Maqu was changed from GGC to GCC, specifying Ala, and further the two native intergenic regions (IGRs) of the cyp156 operon were replaced with synthetic IGRs (TAAGGAGGAAAACAAA) (SEQ ID NO: 65). The resulting plasmid was named pAS.022 (see Table 11, supra) and was transformed into E. coli MG1655 ΔfadD giving stain sAS.335 (see Table 12, supra). The strain was analyzed for conversion of dodecanoic acid to 12-hydroxy dodecanoic acid as described in Examples 1 and 2 (supra). As can be seen in FIG. 9, sAS.335 converted more dodecanoic acid to 12-hydroxy dodecanoic acid than sAS.320, and the amount of 12-hydroxy dodecanoic acid was quantified as 37.4±0.3 mg/L.

Hence, E. coli expressing a modified cyp153A operons from Marinobacter aquaeoli showed some improved conversion of exogenous dodecanoic acid to 12-hydroxy dodecanoic acid when supplied with exogenous fatty acids in vivo (as compared to Example 3). However, the efficiency conversion of this enzyme was still too low. Thus, the enzymatic activity of the modified cyp153A operons from Marinobacter aquaeoli by themselves are still not expected to be ideal for the production of ω-hydroxy fatty acid derivatives and it was determined that still further engineering is required to design an enzyme with a higher conversion efficiency.

Example 5: Conversion of Fatty Acid Derivatives to ω-Hydroxylated Fatty Acid Derivatives by an E. coli Strain Expressing a Hybrid cyp153A-Red450RhF Fusion Protein This example shows the conversion of exogenously added fatty acids, fatty acid methyl esters or fatty alcohols to ω-hydroxy fatty acids, ω-hydroxy fatty acid methyl esters or α,ω-diols, respectively, by a recombinant E. coli strain expressing a hybrid protein in which a cyp153A P450 oxygenase is fused with a reductase domain. The purpose of this experiment was to create a hybrid fusion protein in which a cyp153A P450 oxygenase is fused with a reductase domain for a significantly improved production of ω-hydroxy fatty acid derivatives.

Self-sufficient cytochrome P450 oxygenases are enzymes in which the reductase partner is fused to the cytochrome P450 catalytic protein. One class of self-sufficient bacterial cytochrome P450 oxygenases is represented by P450RhF from Rhodococcus sp. NCIMB 9784 (Roberts et al. (2003) J. Biol. Chem. 278: 48914; Hunter et al. (2005) FEBS Lett. 579: 2215) and is referred to as "Class-I P450-fused PFOR" (DeMot and Parret (2002) Trends Microbiol. 10: 502).

In this experiment, a gene coding for a hybrid-fusion protein made of the cyp153A(G307A) P450 catalytic protein from Marinobacter aquaeoli and the c-terminal FMN- and Fe/S-containing reductase domain of P450RhF from Rhodococcus sp. NCIMB9784 was created as follows: The cyp165A(G307A)_Maqu gene was amplified from pAS.022 and fused with a codon-optimized synthetic P450RhF reductase domain by cross-over PCR. The resulting fusion gene (SEQ ID NO: 5) was cloned into a pCL1920-derivative (i.e., SC101 replicon, spectinomycin resistance marker) such that its transcription was controlled by the IPTG-inducible Ptrc promoter. The plasmid was named pAS.023 (see Table 11, supra) and was transformed into E. coli MG1655 ΔfadD giving strain sAS.336 (see Table 12, infra).

Figure 10A:
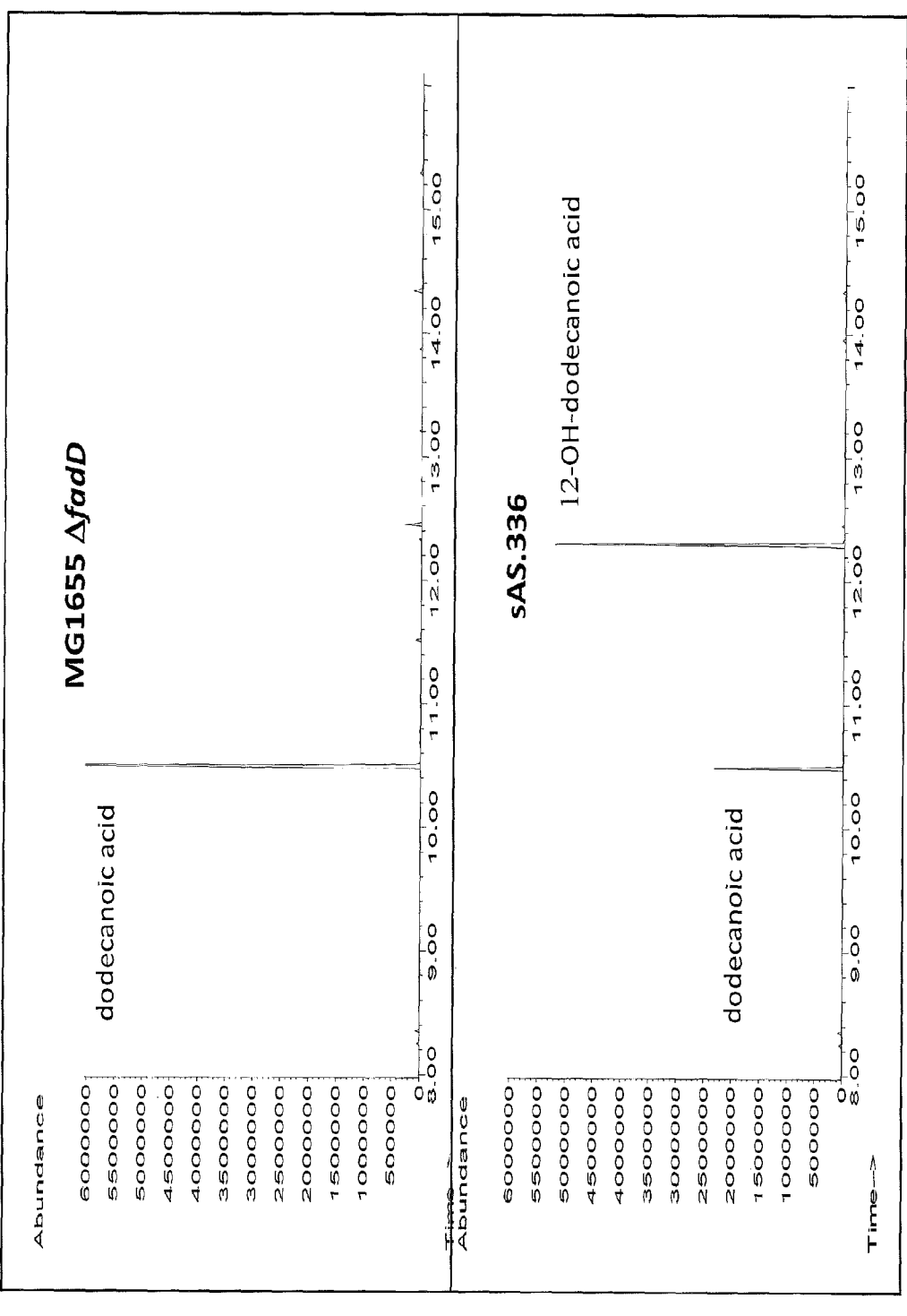
FIGS. 10A through 10C show the GC/MS chromatographs of extracts from an *E. coli* strain expressing CYP153A-RedRhF fusion proteins leading to formation of 12-hydroxy dodecanoic acid from dodecanoic acid (FIG. 10A), 12-hydroxy dodecanoic acid methyl ester from dodecanoic acid methyl ester (FIG. 10B) and 1,12-dodecanediol from dodecanol (FIG. 10C). Extracts of the control strain MG1655 ΔfadD are also shown.
Figure 10B:
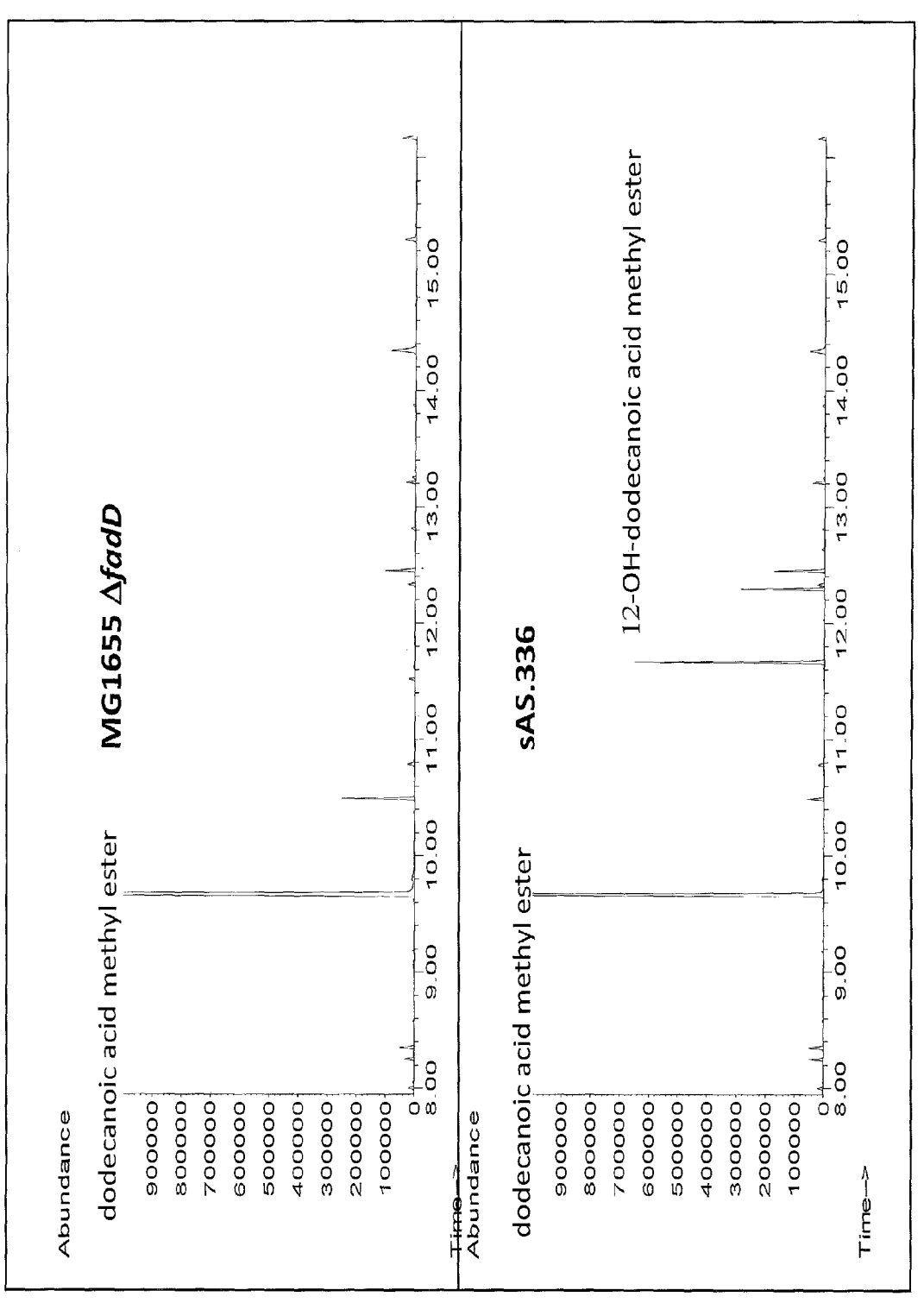
Figure 10C:
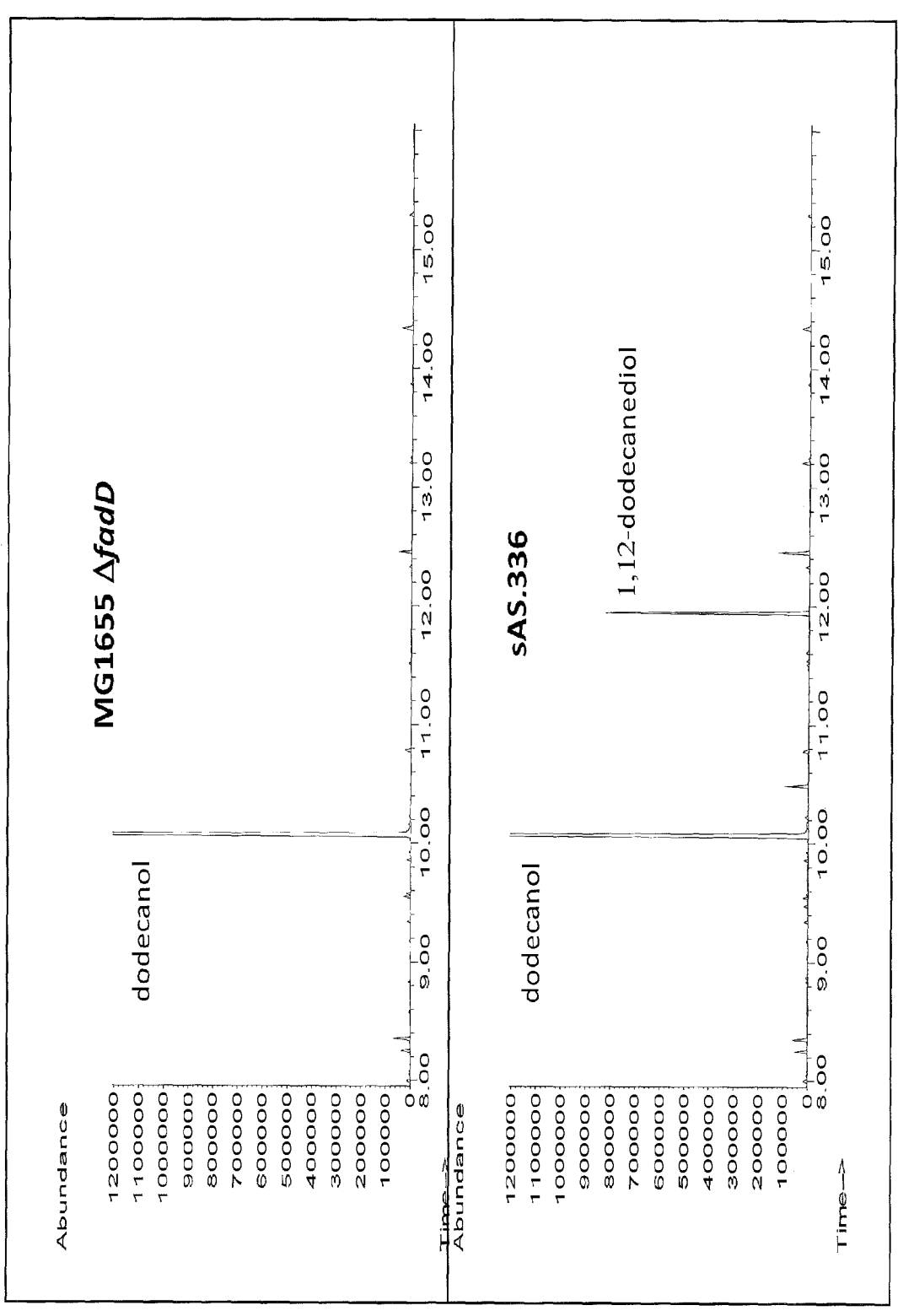

Then, strain sAS.336 was analyzed for conversion of (i) dodecanoic acid to 12-hydroxy dodecanoic acid, (ii) dodecanoic acid methyl ester to 12-hydroxy dodecanoic acid and (iii) dodecanol to 1,12-dodecanediol as described in Examples 1 and 2. In comparison to the control strain MG1655 ΔfadD (supra), new peaks were identified in sAS.336 for all three added compounds in the GC/MS chromatographs (after BSTFA derivatization, see FIGS. 10A through 10C). 12-hydroxy dodecanoic acid was identified as described in Example 3 (supra). The new peaks at RT 11.946 and RT 11.668 minutes (after BSTFA derivatization) were identified as 1,12-dodecanediol and 12-hydroxy dodecanoic acid methyl ester, respectively.

Figure 11A:
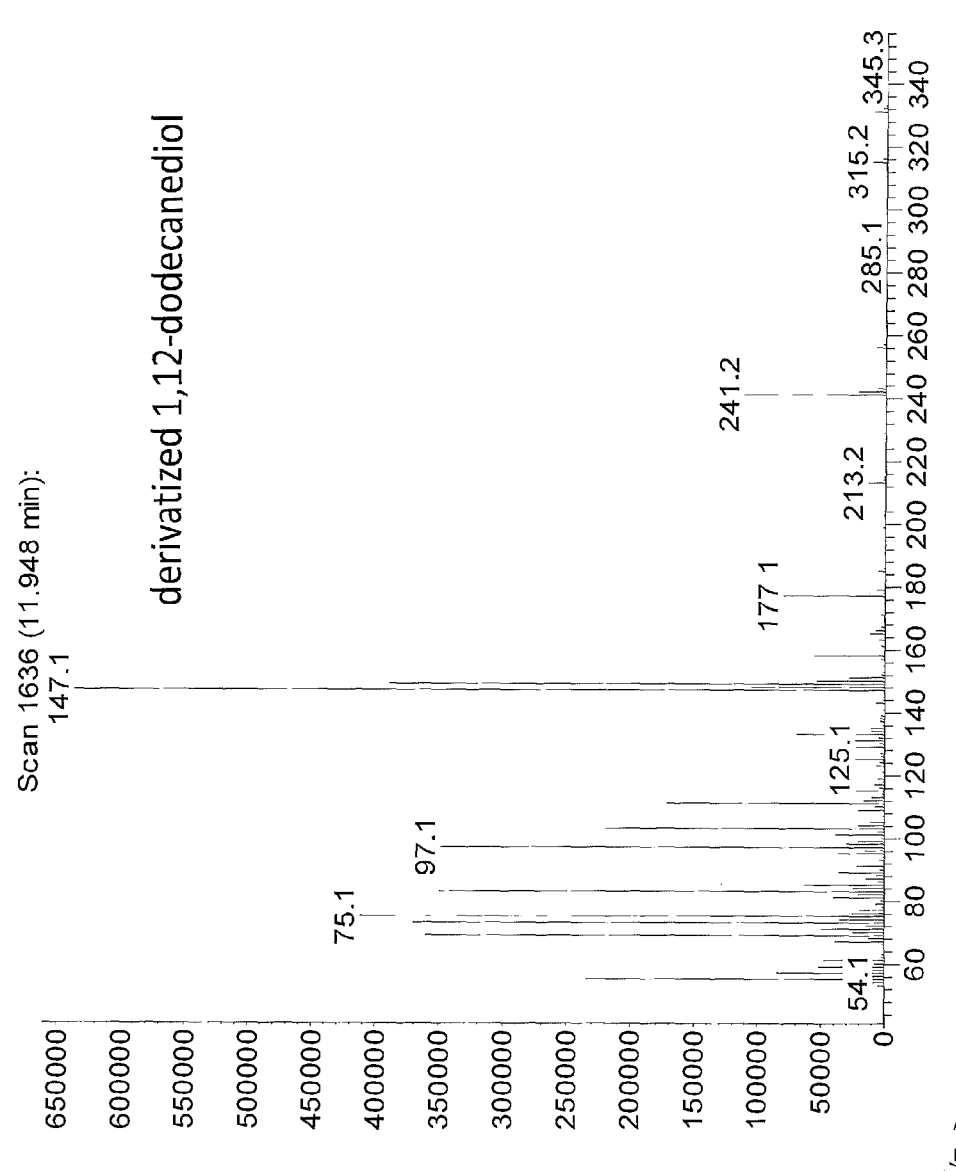
FIGS. 11A through 11B depict the mass spectra of derivatized 1,12-dodecanediol (peak at 11.948 minutes) from an extract of strain sAS.336 (FIG. 11A), and authentic derivatized 1,12-dodecanediol standard (FIG. 11B). Derivatizing agent was BSTFA+1% TMCS.
Figure 11B:
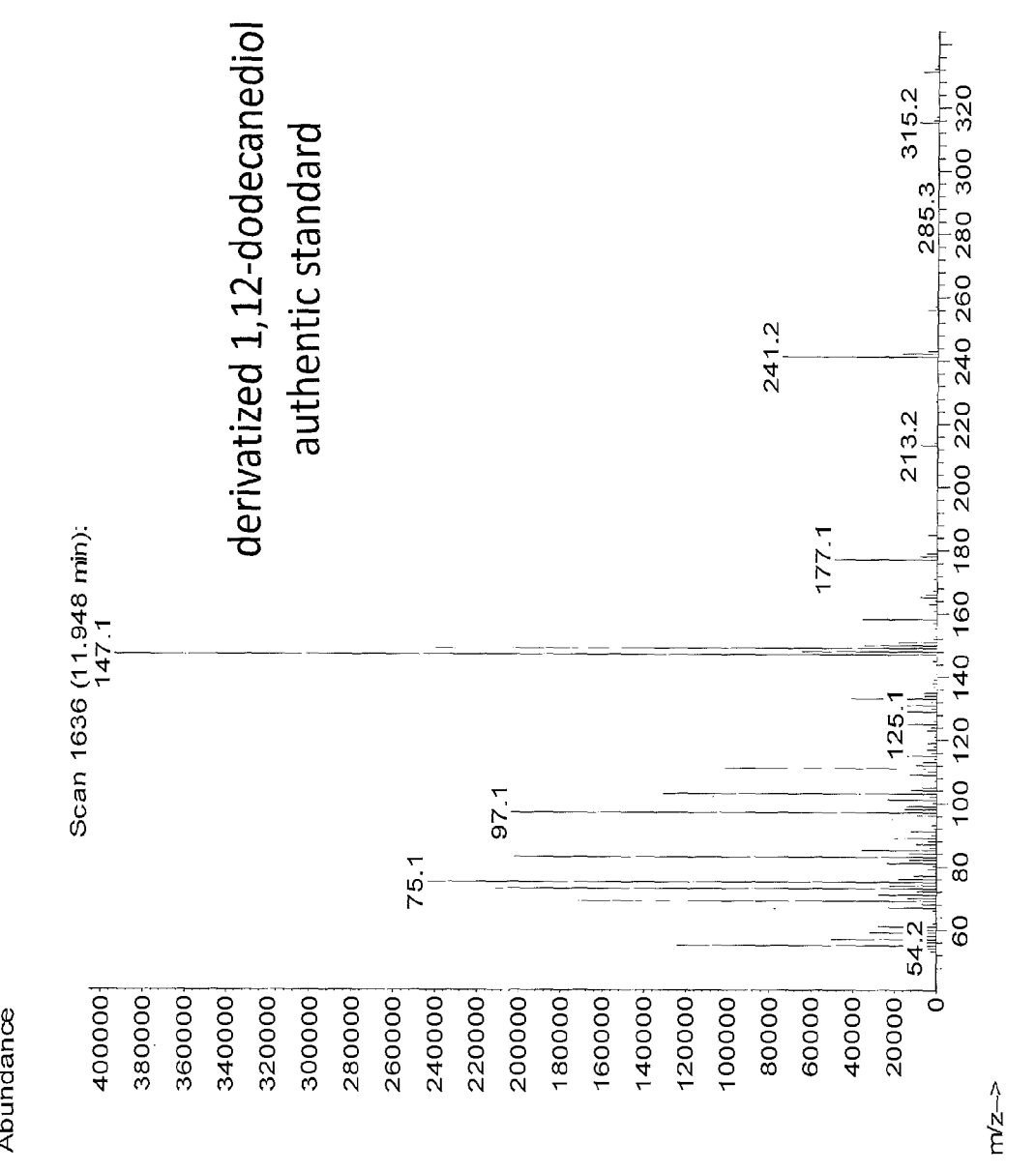
Figure 13A:
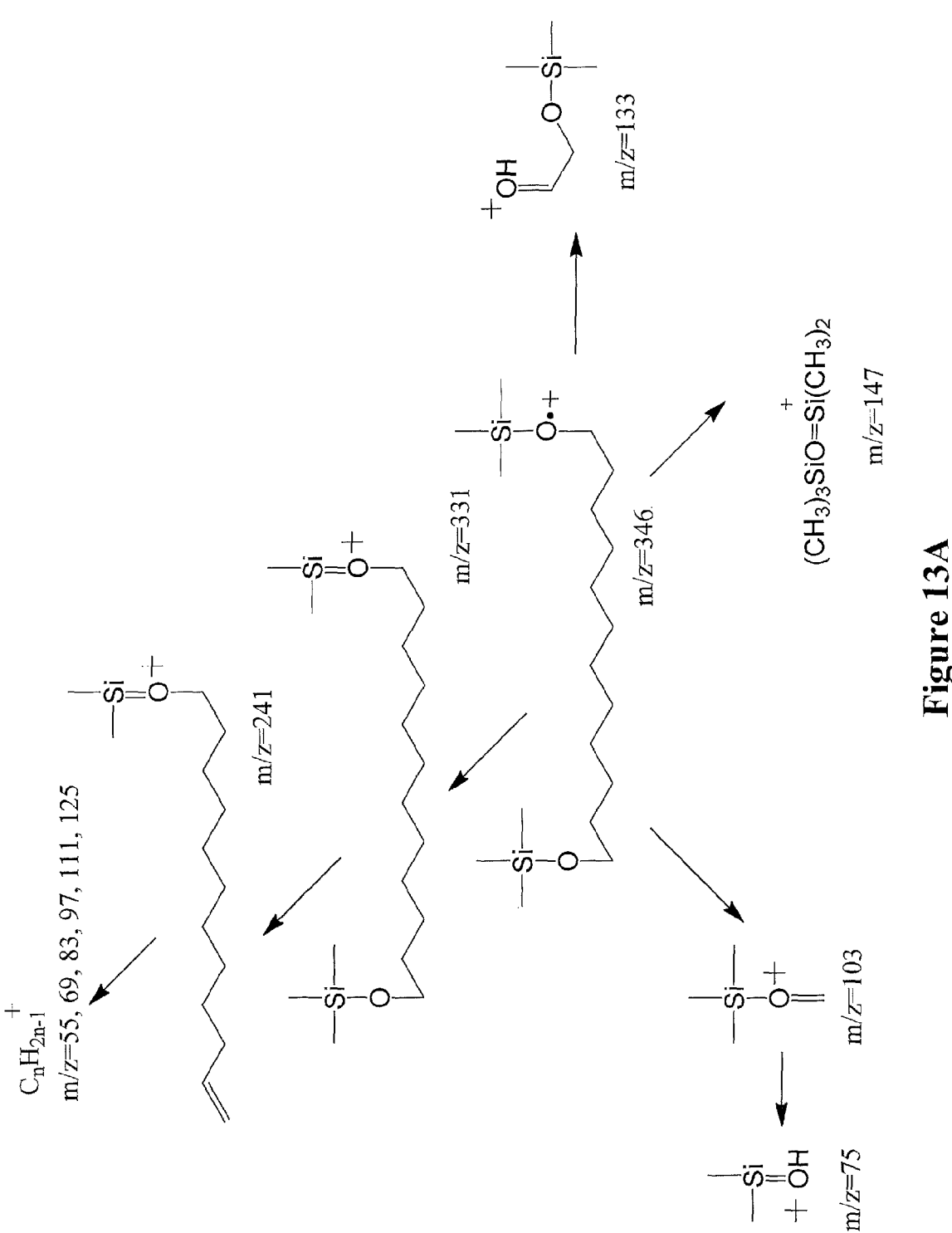
FIGS. 13A through 13B illustrate the ion fragmentation pattern of 1,12-dodecanediol (FIG. 13A) and 12-hydroxydodecanoic acid methyl ester (FIG. 13B) without derivatization.

The mass spectrum of the peak at RT 11.948 minutes is shown in FIG. 11A. The ion fragmentation pattern indicated that this peak was 1,12-bis(trimethylsiloxy) dodecane, which is the derivatized form of 1,12-dodecanediol. The ion fragment pattern for 1,12-bis(trimethylsiloxy) dodecane is shown in FIG. 13A. The Ion at m/z=147 is a characteristic fragment for all diol-related compounds, and ions at m/z=55, 69, 83, 97, 111, and 125 are characteristic allylic cleavage fragments after the loss of the HOSi (CH$_3$)$_3$ moiety. The ion at m/z=241 is a characteristic diagnostic marker to determine the chain length of α,ω-diol compounds as shown in FIG. 13A. The correct identification of this peak was further confirmed by comparing its retention time and mass spectrum with that of an authentic standard of 1,12-dodecanediol derivatized with BSTFA+1% TMCS (FIG. 11B). The chain length of other α,ω-diols can be determined similarly. For example, if a peak has a fragment at m/z 269 and other characteristic ions at m/z 147, 149, 111, 97, 83, 69, and 55, this peak would be 1,14 bis(trimethylsiloxy)tetradecane. For the identification of unsaturated α,ω-diols, similar rules can be applied. Since unsaturated α,ω-diols have two mass units less than their saturated counterpart, the characteristic diagnostic fragment is m/z=239 for 1,12 bis(trimethylsiloxy) dodecene.

Figure 12A:
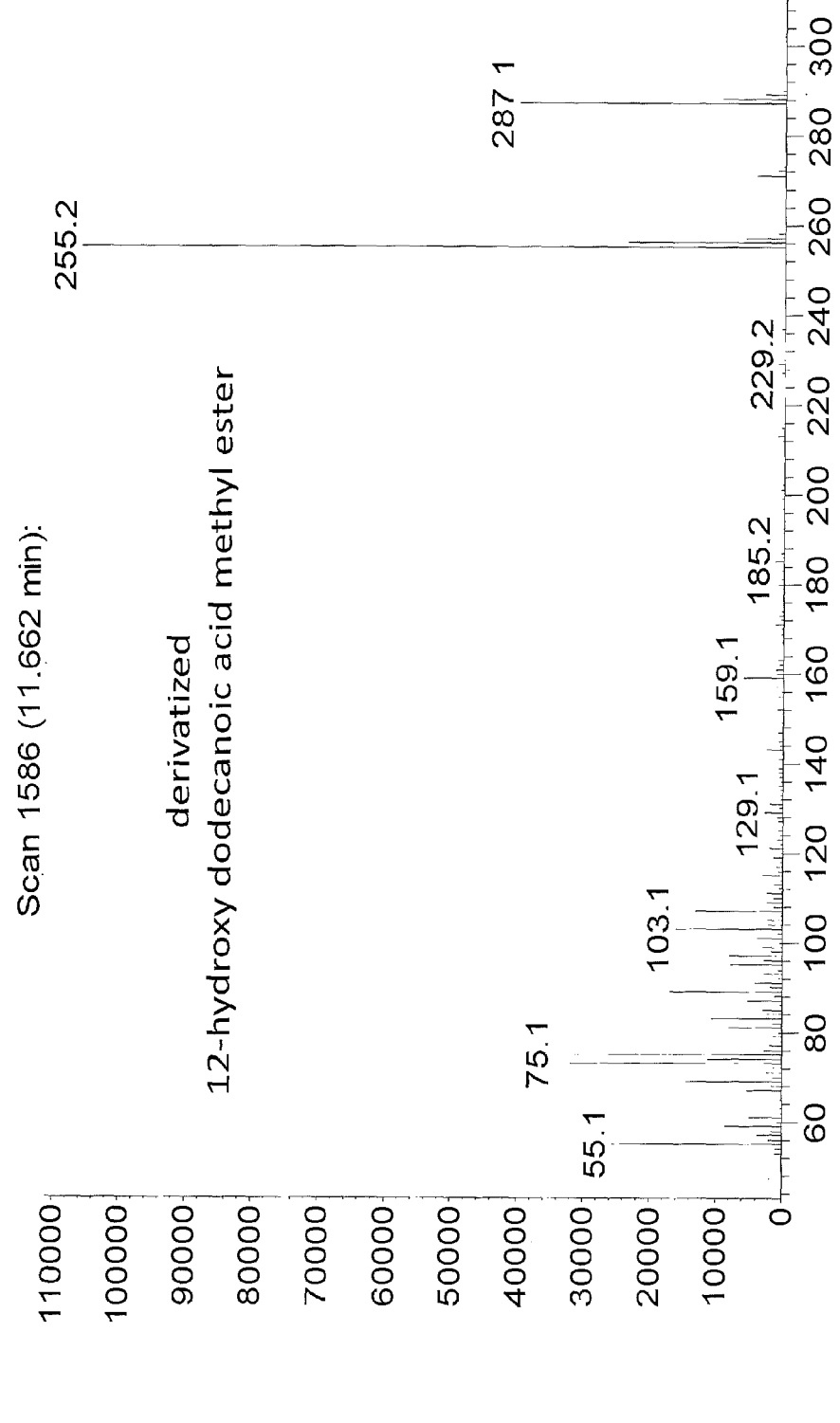
FIGS. 12A through 12B depict the mass spectra of 12-hydroxy dodecanoic acid methyl ester from an extract of strain sAS.336. Underivatized (peak at 11.107 minutes) (FIG. 12A) and derivatized samples are shown (peak at 11.662 minutes) (FIG. 12B). Derivatizing agent was BSTFA+1% TMCS.
Figure 12B:
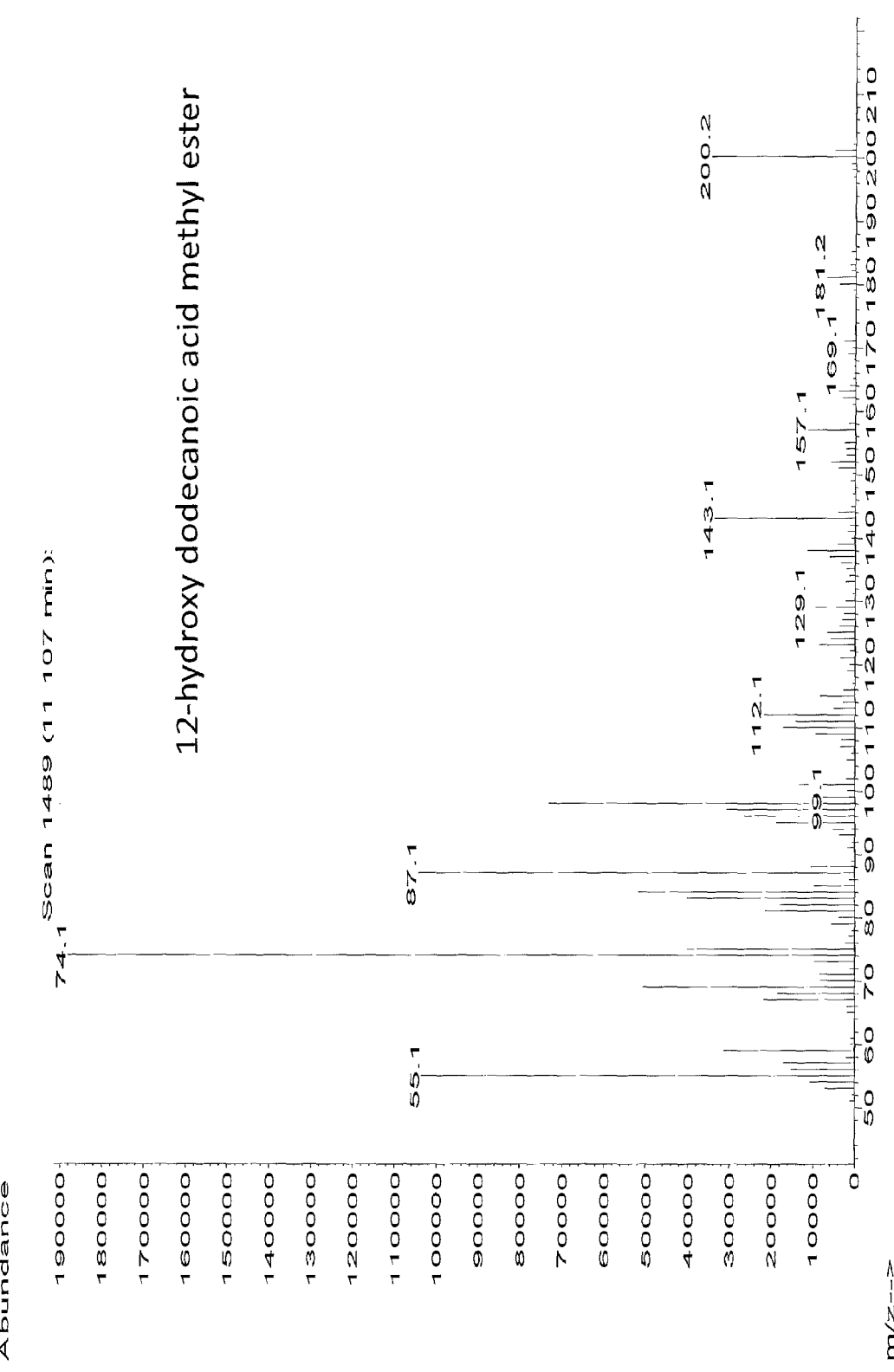
Figure 13B:
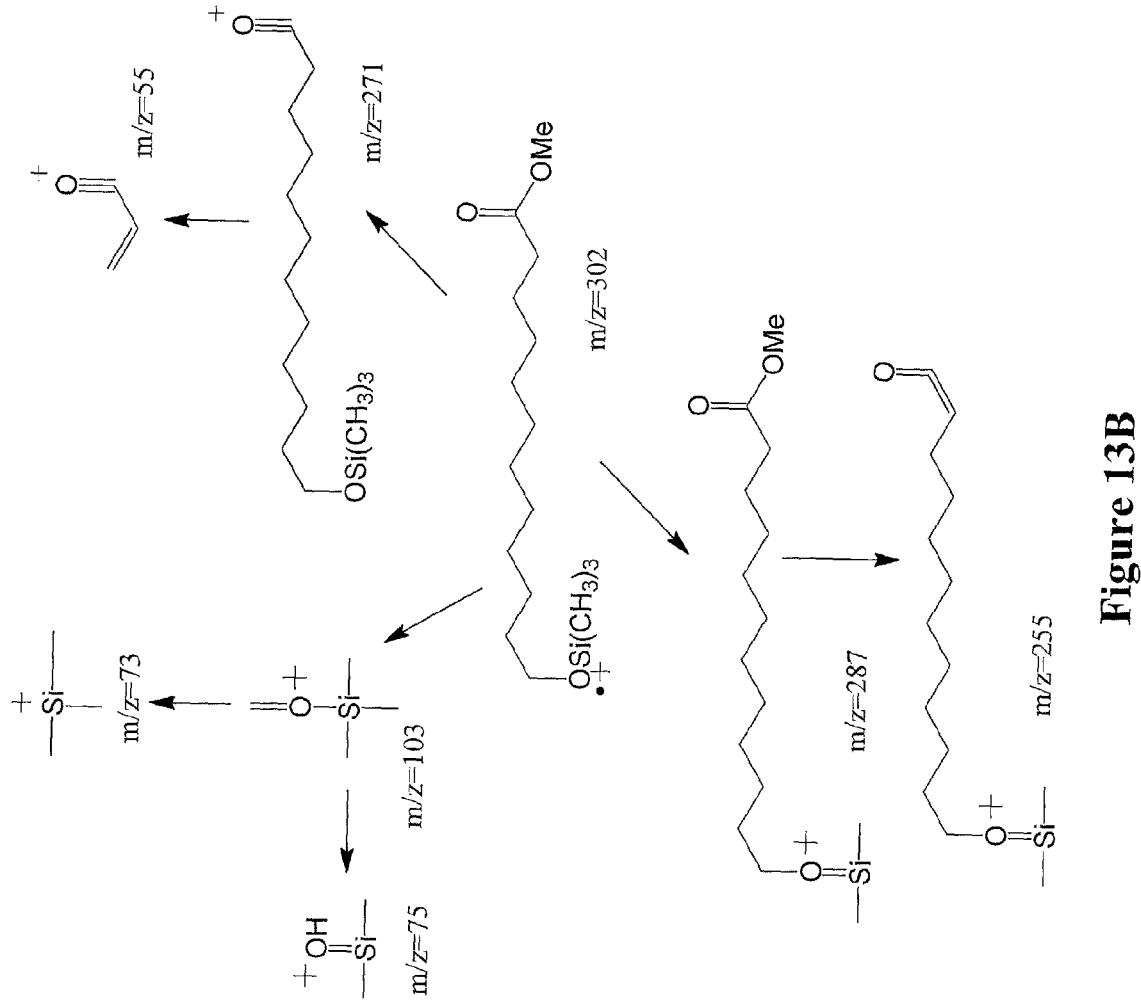

The mass spectrum of the peak at RT 11.668 minutes is shown in FIG. 12A. This peak was identified as 12-trimethylsiloxydodecanoic acid methyl ester based on the ion fragmentation pattern of this compound. As demonstrated in FIG. 13B, the molecule is fragmented to two dominant ions at m/z=287 (M-CH$_3$) and 255 (M-CH$_3$—HOCH$_3$). In addition, the mass spectrum showed a characteristic ion at m/z=271 (M-OCH$_3$), suggesting this molecule has a methyl ester moiety. The ion at m/z=103 suggested that trimethylsiloxy group is in the terminal position. Ions at m/z=287 and 255 are also characteristic ions to determine the chain length of this compound (see FIG. 13B). Accordingly, if a peak has fragmentation ions at m/z=315 and 283 and other ions at m/z 55 and 103, the peak can be identified as 14-trimethylsiloxy tetradecanoic acid methyl ester. This rule was used to identify ω-hydroxy fatty acid methyl esters of different chain length produced by strain stEP677 (see Example 6, infra).

Table 13 (infra) shows the amounts of ω-hydroxylated fatty acid derivatives converted by strain sAS.336 within 18 h at 32° C. As can be seen in Table 13, the hybrid cyp153A-RedRhF fusion protein expressed from pAS.023 converted exogenous fatty acid derivatives efficiently to ω-hydroxylated fatty acid derivatives in comparison to the other enzymes that were tested (supra). Thus, this engineered enzyme was selected for the production of ω-hydroxy fatty acid derivatives in vivo via engineered production hosts through renewable feedstock (see Example 6, infra).

TABLE 13

| ω-Hydroxylated Fatty Acid Derivatives Formed by sAS.336 | | |
| --- | --- | --- |
| fatty acid derivative added (1 g/L) | ω-hydroxylated fatty acid derivative formed (mg/L) * | |
| dodecanoic acid | 12-dodecanoic acid | 814 ± 13 |
| dodecanoic acid methyl ester | 12-hydroxy dodecanoic acid methyl ester | 114 ± 10 |
| dodecanol | 1,12-dodecanediol | 148 ± 2 |

* In triplicate

Example 6: Production ω-Hydroxylated Fatty Acid Derivatives from Glucose by Recombinant *E. coli* Strains Expressing a CYP153A-Red450RhF Hybrid Fusion Protein This example shows the production of ω-hydroxy fatty acid, ω-hydroxy fatty acid methyl ester and α,ω-diols from a renewable carbohydrate feedstock such as glucose, by recombinant *E. coli* strains expressing a chimeric hybrid protein in which a CYP153A P450 oxygenase is fused with a reductase domain.

The gene encoding the CYP153A(G307A)-RedRhF hybrid fusion gene was amplified from pAS.023 and cloned into a pACYC derivative vector (p15a replicon, kanamycin resistance marker), such that the transcription of the fusion gene was controlled by the IPTG-inducible Ptrc promoter. The resulting plasmid was named pEP.125 (see Table 11, supra).

Six recombinant *E. coli* strains that were separately engineered to overproduce fatty acids or fatty acid derivatives from a carbohydrate substrate such as glucose (see Table 14, infra), were either transformed with plasmid pAS.023 or pEP.125 in order to create ω-hydroxylated fatty acid derivative-producing strains (see Table 15, infra). The overproducing fatty acid- or fatty acid derivative strains also served as control strains to readily identify new compounds in the ω-hydroxylated fatty acid derivative-producing strains. These fatty acid- or fatty acid derivative-overproducing strains are briefly described here but should not be construed as limiting. The strain ALcV334 genome was created as follows: the fadE (acyl-CoA dehydrogenase) gene was deleted and a variant of the thioesterase tesA gene was overexpressed. In addition to the genetic manipulations in ALcV334, the genome of strain XL897 contained the following manipulations: a phosphopantetheinyl transferase gene and a synthetic fatty acid biosynthesis operon (including several genes described in table 1) were overexpressed and several operons including a variant of carboxylic acid reductase (carB); a variant of thioesterase (tesA); alcohol dehydrogenase (AlrA); a variant of 3-keto-acyl-ACP synthase (fabB); and a transcriptional regulator (fadR) were integrated. The strain DAM1 genome was manipulated as follows: the acyl-CoA dehydrogenase (fadE) gene was deleted, and the *E. coli* thioesterase (tesA) and acyl-CoA synthase (fadD) genes were overexpressed.

The genomes of strains stNH1293, KASH286 and stNT29 were manipulated as follows: the acyl-CoA dehydrogenase (fadE) gene was deleted and a transcriptional regulator (fadR) and a synthetic fatty acid biosynthesis operon were overexpressed. In addition, strain stNH1293 contained a plasmid expressing a plant thioesterase, an acyl carrier protein (acp) gene and an acetyl-CoA carboxylase (acc) gene complex. Strain KASH286 contained a plasmid expressing a variant of an ester synthase. Strain stNT29 contained a plasmid expressing a variant of an acyl ACP reductase (AAR), an alcohol dehydrogenase (AlrA), an acyl carrier protein (acp) and an acetyl-CoA carboxylase (acc) gene complex.

TABLE 14

| Recombinant *E. coli* Strains Overproducing Fatty Acids or Fatty Acid Derivatives | |
| --- | --- |
| Strain | Phenotype |
| AlcV334 stNH1293 LC972 | Fatty acid producer |
| DAM1 KASH286 XL897 stNT29 XL959 | Fatty acid and fatty acid methyl ester producer Fatty alcohol producer |

The strains engineered to produce ω-hydroxylated fatty acid derivatives (supra) were then analyzed for their ability to produce ω-hydroxylated fatty acid derivatives from a renewable feedstock such as glucose as described in Examples 1 and 2. The ω-hydroxylated fatty acids, fatty acid methyl esters and fatty alcohols were identified as described in Examples 3 and 5.

TABLE 15

Recombinant *E. coli* Strains Expressing cyp153A(G307A)-
RedRhF Fusion Protein for Production of ω-Hydroxylated
Fatty Acid Derivatives from Renewable Carbohydrate Feedstocks

| Strain | Genotype | Phenotype |
|--------|----------|-----------|
| stEP675 | AlcV334/pAS.023 | ω-hydroxylated fatty acid producer |
| stEP682 | stNH1293/pEP.125 | |
| stEP677 | DAM1/pAS.023 | ω-hydroxylated fatty acid and fatty acid methyl ester producer |
| stEP684 | KASH286/pEP.125 | |
| stEP676 | XL897/pAS.023 | α,ω-diol alcohol producer |
| stEP685 | stNT29/pEP.125 | |
| StEP690 | ALKV334/ pAS.023 + pEP.127 | α,ω-diacid producer |

TABLE 16

ω-Hydroxylated Fatty Acid Derivatives Produced
by Recombinant *E. coli* Strains from Glucose

| Strain | ω-hydroxylated fatty acid derivative formed from glucose (mg/L) * | |
|--------|--------------------------------------------------|---|
| stEP675 | ω-hydroxylated fatty acids (C12, C14, C16, C18) | 465 ± 19 |
| stEP682 | ω-hydroxylated fatty acids (C12, C14, C16) | 1177 ± 19 |
| stEP677 | ω-hydroxylated fatty acid methyl esters (C12, C14, C16) | 91 ± 4 |
| | ω-hydroxylated fatty acids (C12, C14, C16) | 56 ± 2 |
| stEP684 | ω-hydroxylated fatty acid methyl esters (C14, C16) | 70 ± 8 |
| | ω-hydroxylated fatty acids (C14, C16) | 14 ± 1 |
| stEP676 | ω-hydroxylated fatty alcohols (C12, C14, C16) | 140 ± 2 |
| stEP685 | ω-hydroxylated fatty alcohols (C14, C16) | 201 ± 32 |
| stEP690 | α,ω-diacid (C12, C14, C16, C18) | 552 ± 28 |

* In triplicate

Figure 14A:
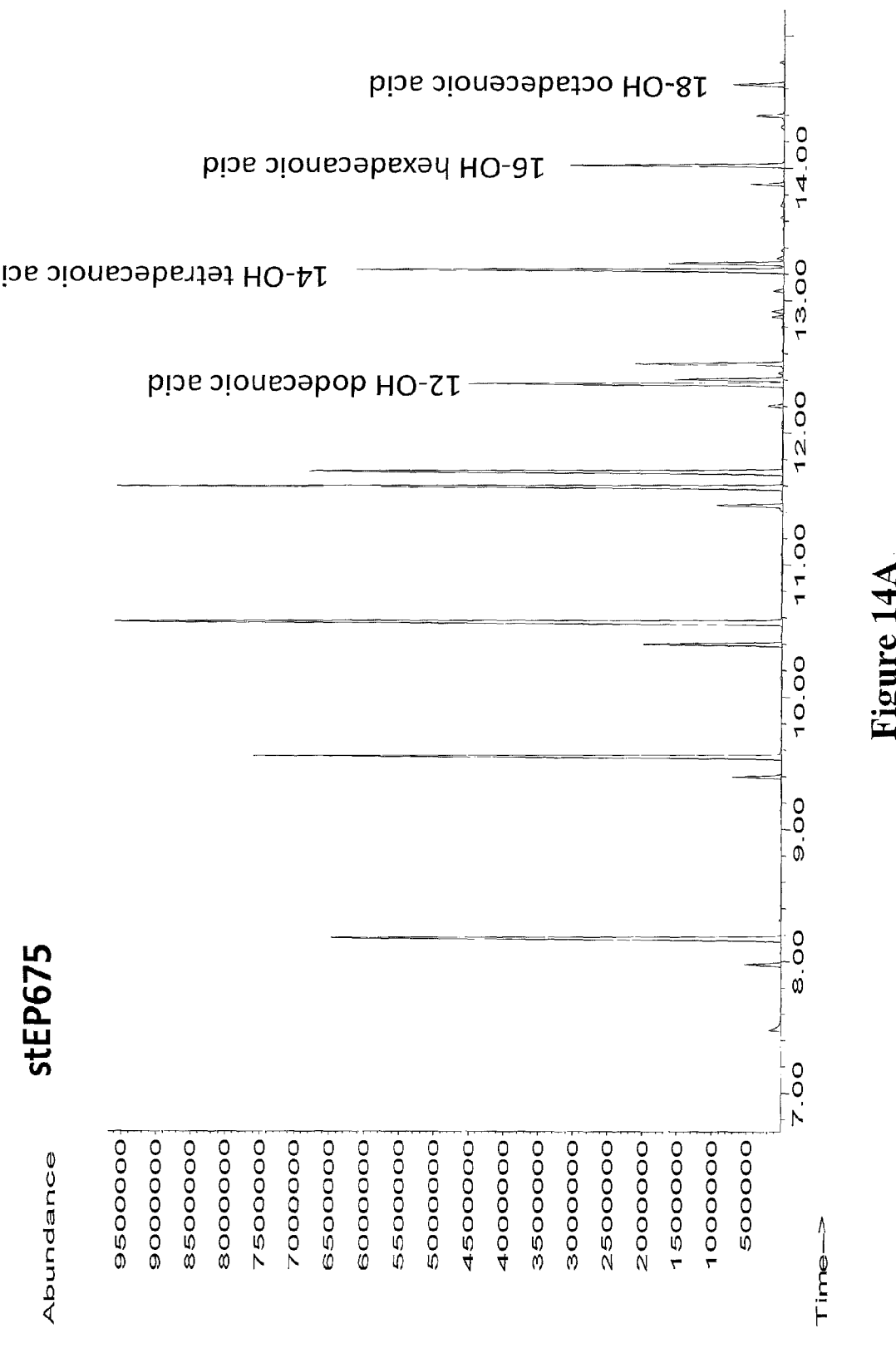
FIGS. 14A through 14C show GC/MS chromatographs of extracts from recombinant *E. coli* strains expressing CYP153A-RedRhF fusion proteins producing ω-OH fatty acids (FIG. 14A), ω-OH fatty acid methyl esters (FIG. 14B) or α,ω-diols (FIG. 14C) from glucose. All samples were derivatized with BSTFA+1% TMCS.
Figure 14B:
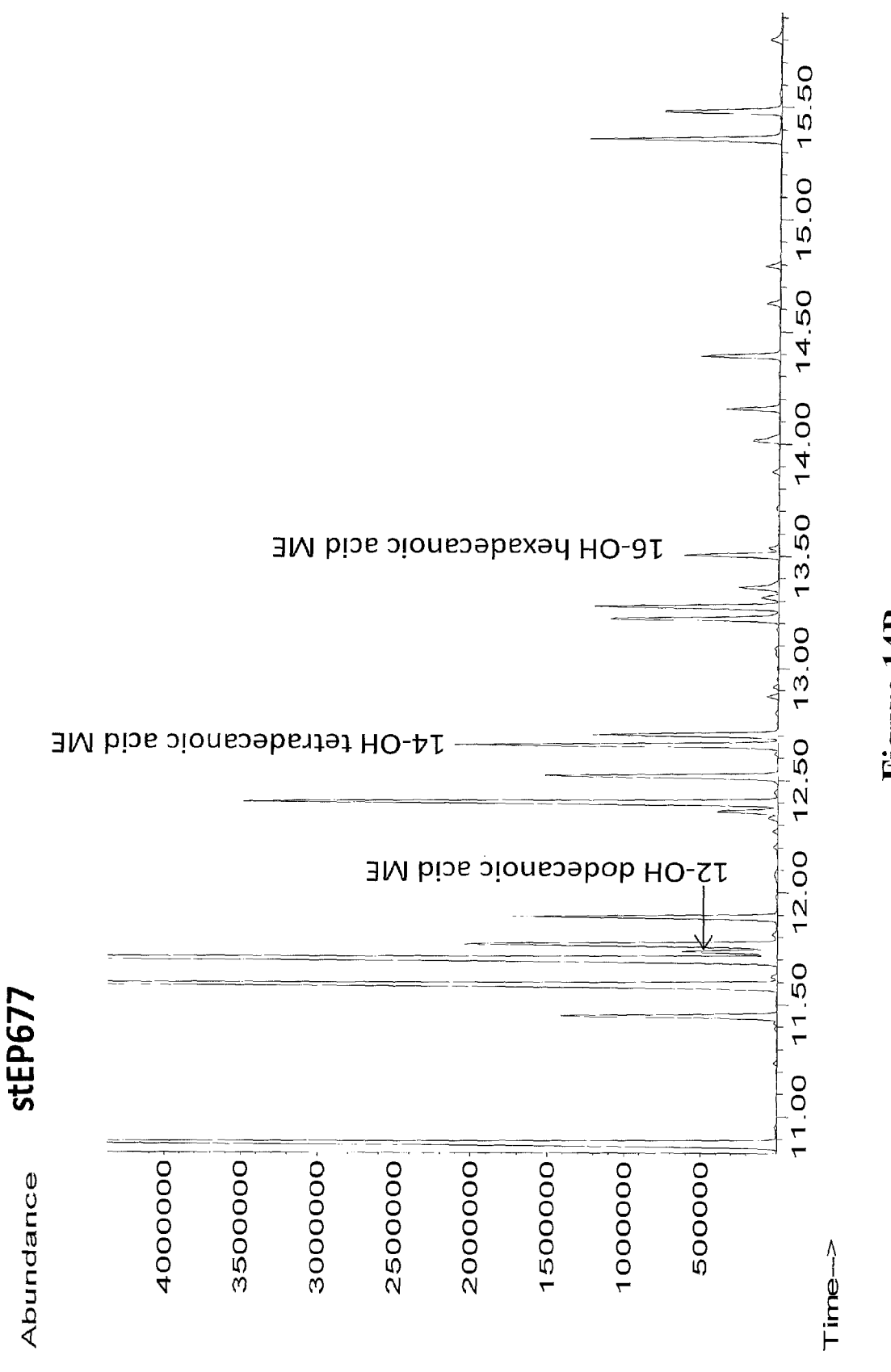
Figure 14C:
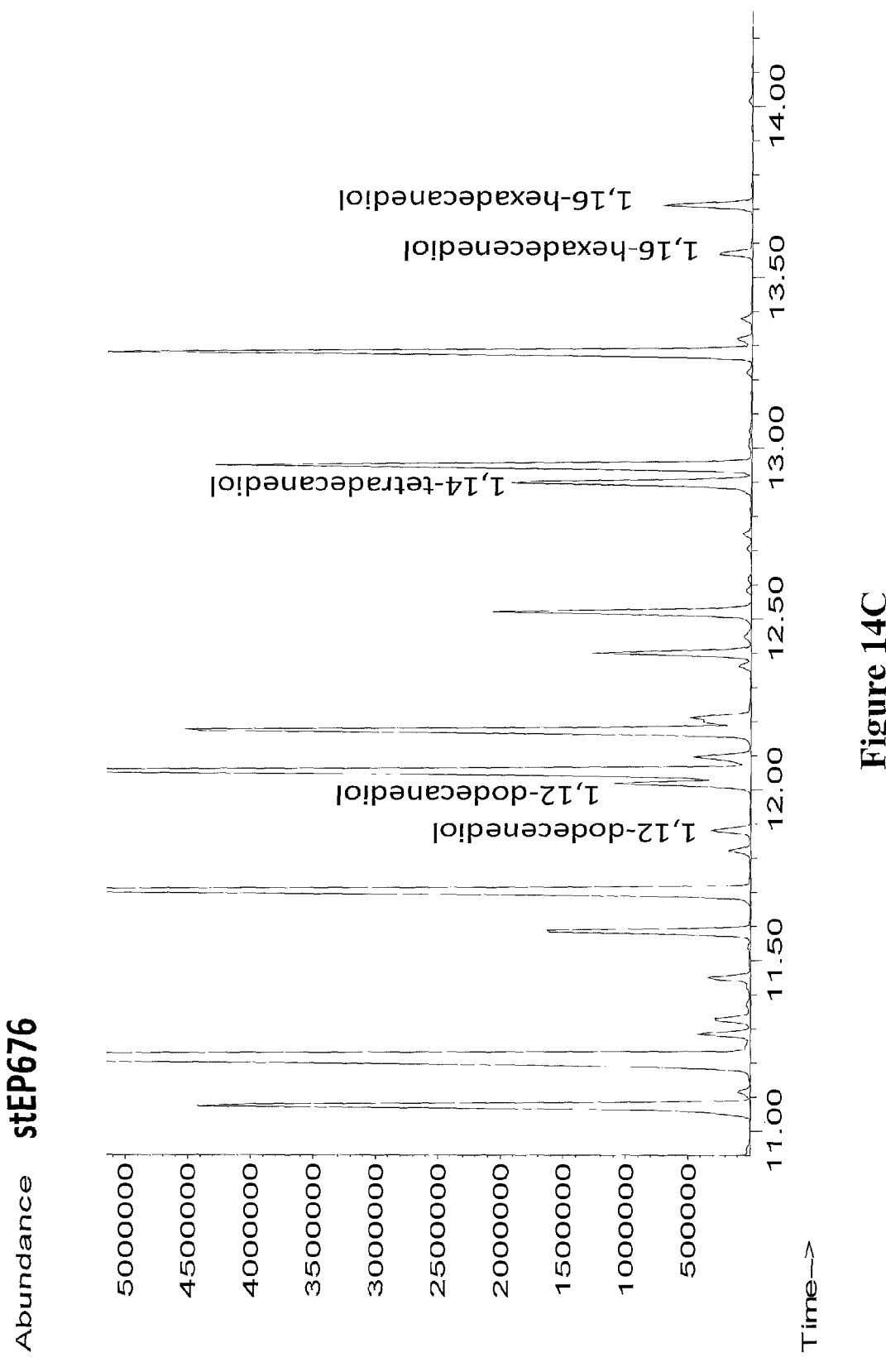
Figure 15:
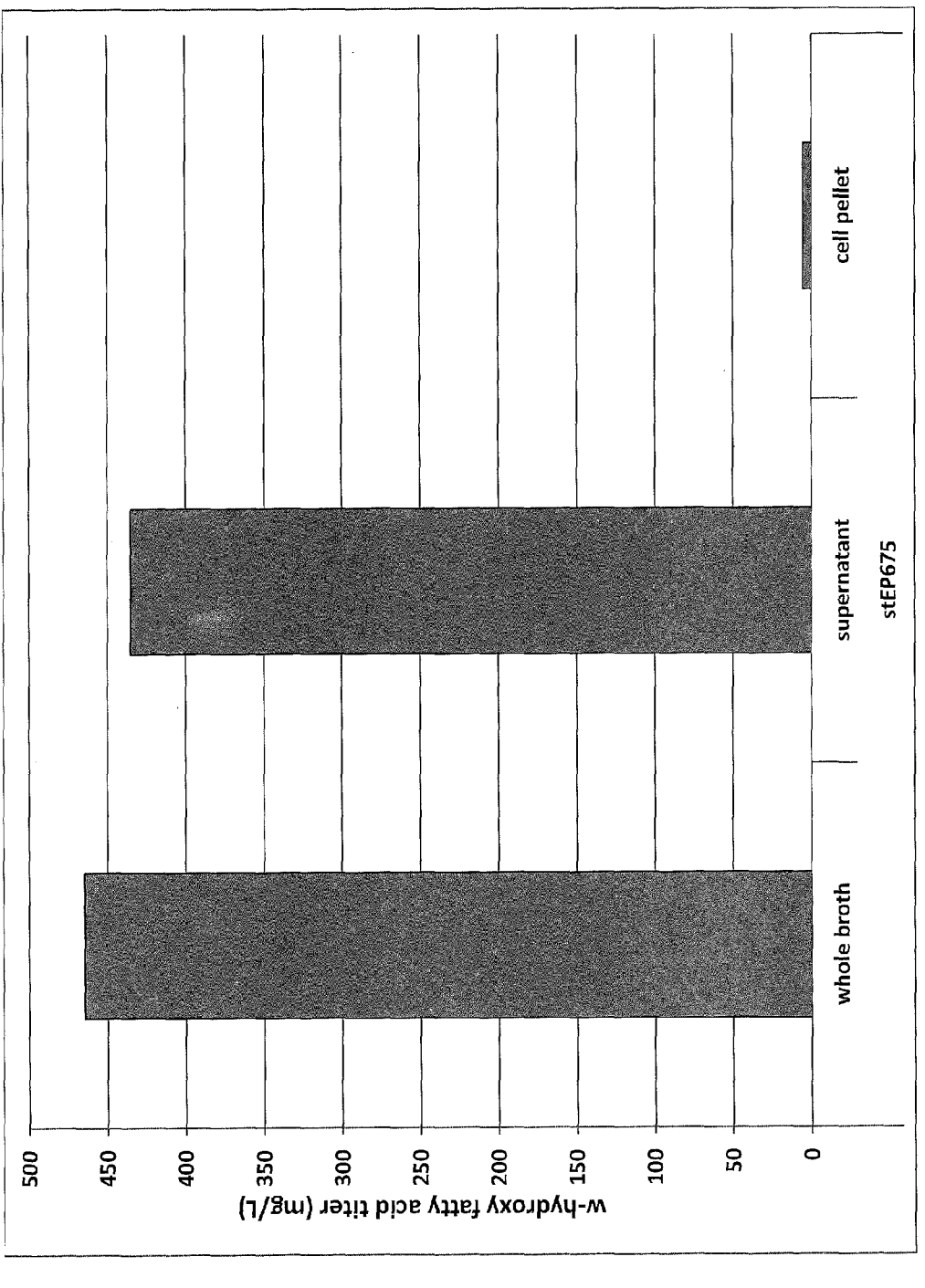
FIG. 15 demonstrates that the ω-hydroxy fatty acids were efficiently secreted from the producing cells.
Figure 16:
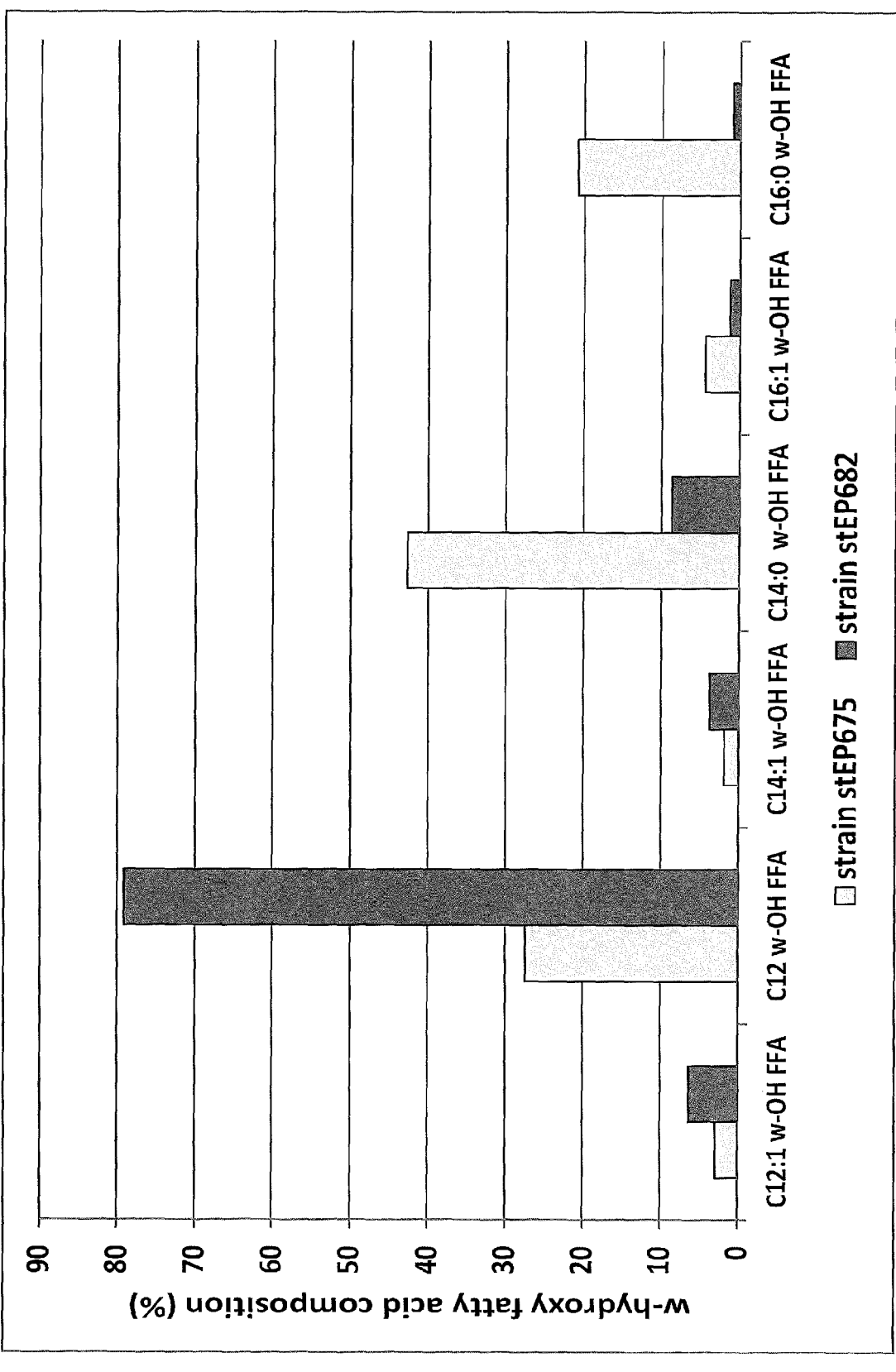
FIG. 16 shows the composition of ω-hydroxy fatty acids produced from two *E. coli* strains when grown on glucose.

In comparison to the control strains (see Table 14, supra), new peaks were identified (as described in Example 5) in all strains expressing cyp153A-RedRhF fusion protein (see Table 15, supra) corresponding to ω-hydroxy fatty acids, ω-hydroxy fatty acid methyl esters and α,ω-diols (see also FIGS. 14A-14C). Table 16 shows the amounts of ω-hydroxy fatty acid derivatives produced by these recombinant strains from glucose within 20h. As can be seen in Table 16, the amount of ω-hydroxy fatty acid derivatives that were made by the recombinant host cells was significant. In particular, ω-hydroxy fatty acid production was found to be very efficient. It is noteworthy that the ω-hydroxy fatty acids produced by strain stEP675 were almost exclusively found in the supernatant (see FIG. 15), which shows that the cells released their product into the supernatant. FIG. 16 shows the composition of ω-hydroxy fatty acids produced by strains stEP675 and stEP682. The most abundant ω-hydroxy fatty acid produced by strain stEP682 was 12-hydroxydodecanoic acid (79%). 14-hydroxytetradecanoic acid (42%) was the most abundant ω-hydroxy fatty acid produced by stEP675.

Overall, strains stEP675 produced the following ω-hydroxy fatty acids: 12-hydroxydodecenoic acid, 12-hydroxydodecanoic acid, 14-hdroxytetradecenoic acid, 14-hydroxytetradecanoic acid, 16-hydroxyhexadecenoic acid, 16-hydroxyhexadecanoic acid and 18-hydroxyoctadecenoic acid (see FIG. 14A). Strains stEP682 produced the following ω-hydroxy fatty acids: 12-hydroxydodecenoic acid, 12-hydroxydodecanoic acid, 14-hydroxytetradecenoic acid, 14-hydroxytetradecanoic acid, 16-hydroxyhexadecenoic acid and 16-hydroxyhexadecanoic acid. Strains stEP677 produced besides ω-hydroxy fatty acids also the following ω-hydroxy fatty acid methyl esters: 12-hydroxydodecanoic acid methyl ester, 14-hydroxytetradecanoic acid methyl ester and 16-hydroxyhexadecanoic acid methyl ester (see FIG. 14B). Strains stEP684 produced besides ω-hydroxy fatty acids also the following ω-hydroxy fatty acid methyl esters: 14-hydroxytetradecanoic acid methyl ester, 16-hydroxyhexadecenoic acid methyl ester and 16-hydroxyhexadecanoic acid methyl ester. Strains stEP676 produced the following α,ω-diols: 1,12-dodecenediol, 1,12-dodecanediol, 1,14-tetradecanediol, 1,16-hexadecenediol and 1,16-hexadecanediol (FIG. 14C). Strains stEP685 produced the following α,ω-diols: 1,14-tetradecanediol, 1,16-hexadecenediol and 1,16-hexadecanediol.

Notably, this example showed that *E. coli* strains engineered for overproducing fatty acid derivatives when combined with the expression of a CYP153A-RedRhF hybrid fusion protein efficiently produced ω-hydroxylated fatty acid derivatives from glucose as sole carbon source. In addition, ω-hydroxylated fatty acids were efficiently secreted into the fermentation broth (i.e., the producing cells or host cells secrete the product into the fermentation broth), which is a desirable characteristic of the present method.

Example 7: Production α,ω-Diacids from Glucose by a Recombinant *E. coli* Strain This example demonstrates the production of α,ω-diacids from a renewable carbohydrate feedstock such as glucose, by a recombinant *E. coli* strain expressing a chimeric hybrid protein in which a cyp153A P450 oxygenase is fused with a reductase domain and an alcohol oxidase and an aldehyde dehydrogenase.

Figure 17:
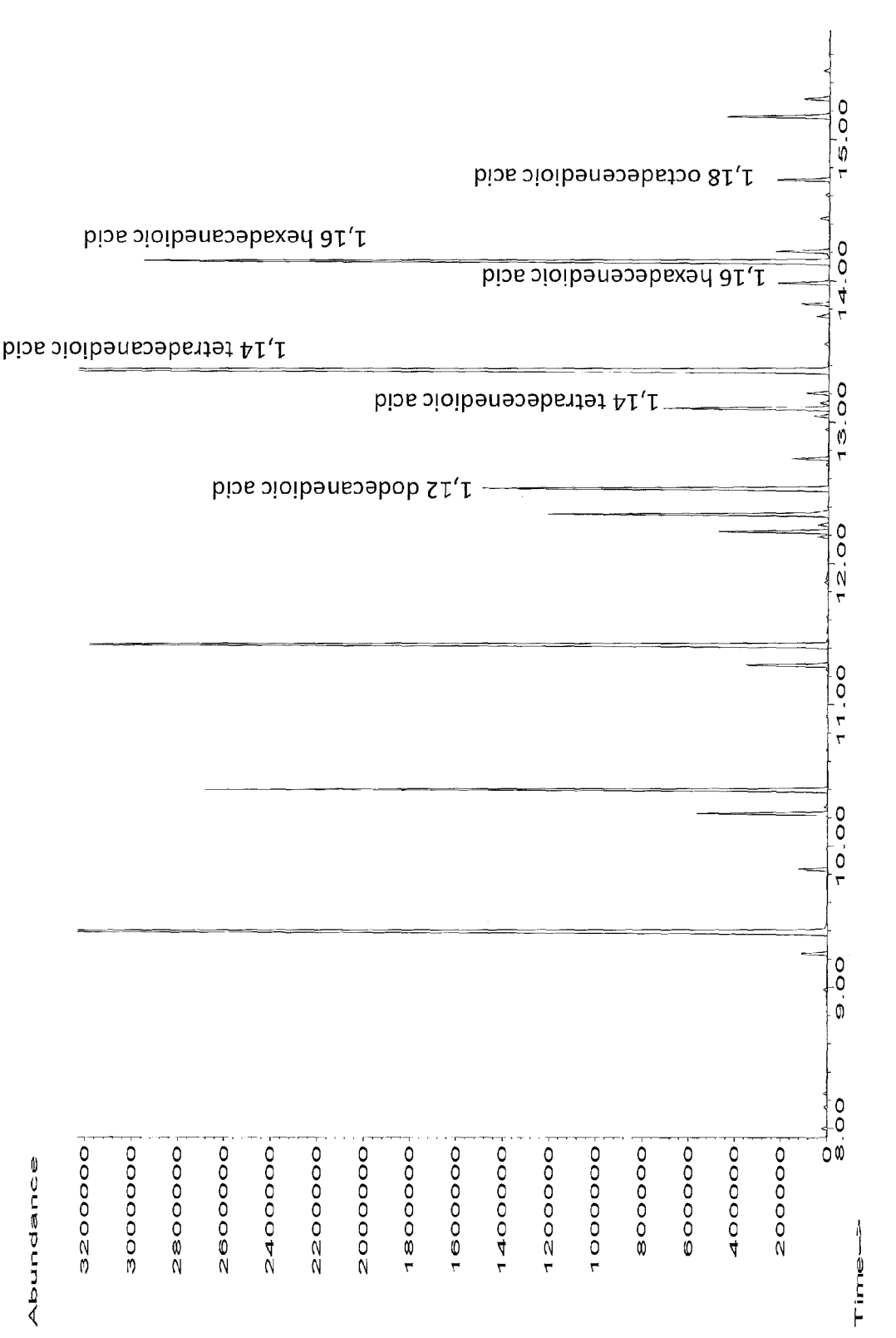
FIG. 17 shows a GC/MS chromatograph of an extract from recombinant *E. coli* strains expressing CYP153A-RedRhF fusion protein, alcohol oxidase and aldehyde dehydrogenase producing α,ω-diacids. All samples were derivatized with BSTFA+1% TMCS.

The genes encoding alcohol oxidase alkJ (accession number CAB54054) (SEQ ID NO: 66) and aldehyde dehydrogenase alkH (accession number CAB51050) (SEQ ID NO: 68) were amplified from genomic DNA of *Pseudomonas putida* ATCC 29347 and cloned into a pACYC derivative vector (p15a replicon, kanamycin resistance marker) such that the two genes form an operon and transcription of the operon is controlled by the IPTG-inducible Ptrc promoter. The resulting plasmid was named pEP.126 (see Table 11, supra). Plasmid pEP126 was cotransformed with plasmid pAS.023 (see Table 11, supra) into the strain AlcV334 (see Table 14, supra) yielding strain sEP690. The strain was analyzed for its ability to produce α,ω-diacids from glucose as described in Examples 1 and 2. In comparison to the control strain AlcV334, several new peaks were identified in sEP690 as can be seen in FIG. 17. These peaks were identified as the derivatized forms of α,ω-diacids and α,ω-bis(trimethylsilyl) fatty acid ester. The ion fragmentation pattern of α,ω-bis(trimethylsilyl) fatty acid esters are very similar to α,ω-bis(trimethylsiloxy) fatty alcohols, the derivatized forms of α,ω-diols (see Example 3), except that α,ω-bis(trimethylsilyl) fatty acid esters do not generate an ion at m/z=103. This ion is therefore an important information to distinguish α,ω-bis(trimethylsiloxy) fatty alcohols from α,ω-bis(trimethylsilyl) fatty acid esters (as well as ω-1, ω-2 and ω-3 trimethylsiloxy fatty alcohols as described below, infra).

Figure 18A:
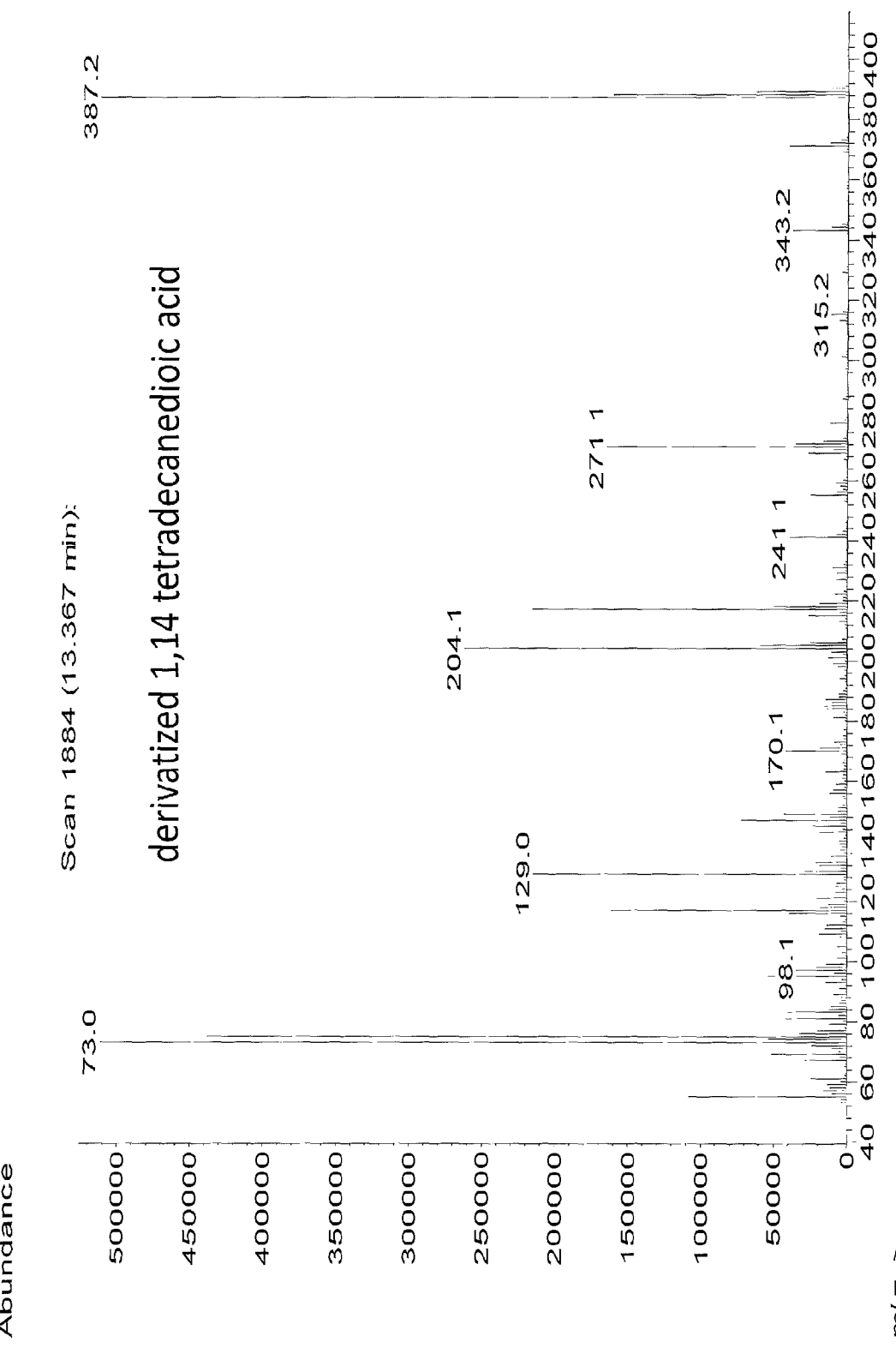
FIGS. 18A through 18B depict the mass spectra of derivatized 1,14-tetradecanedioic acid (peak at 13.367 minutes) from an extract of strain sEP.690 (FIG. 18A), and authentic derivatized 1,14-tetradecanedioic acid standard (FIG. 18B). Derivatizing agent was BSTFA+1% TMCS.
Figure 18B:
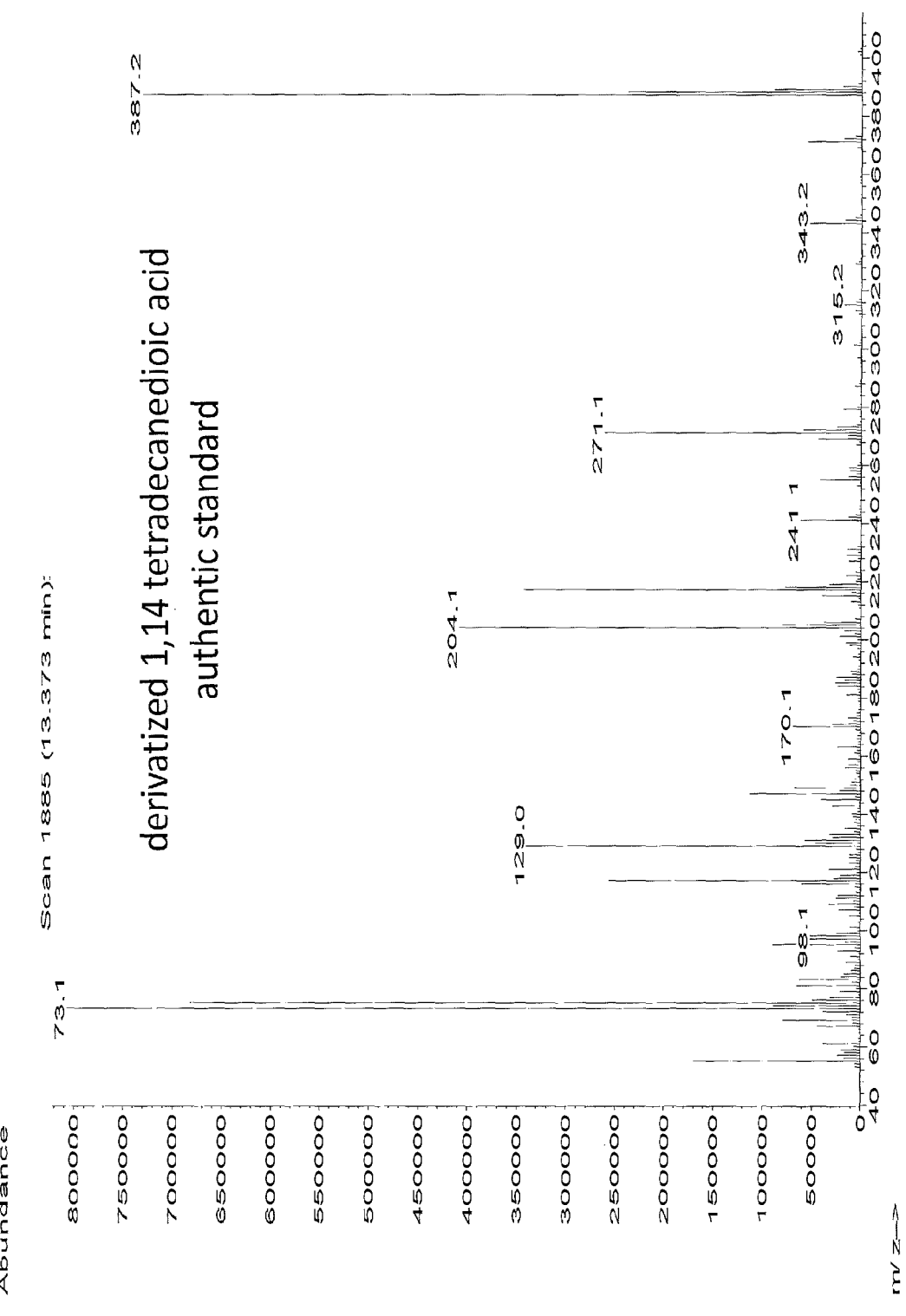
Figure 19:
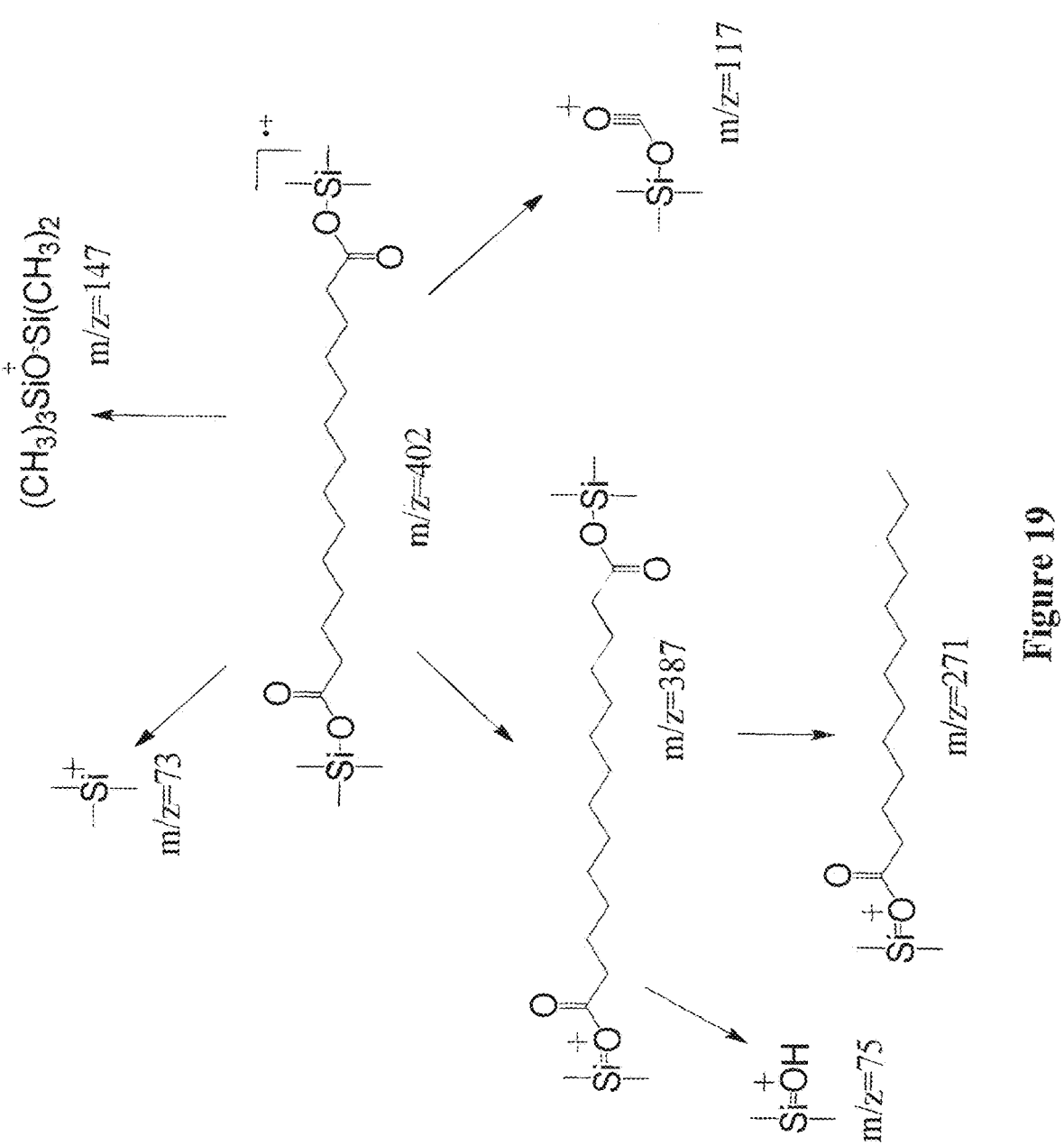
FIG. 19 illustrates the ion fragmentation pattern of derivatized 1,14-tetradecanedioic acid. Derivatizing agent was BSTFA+1% TMCS.

The major compounds produced by strains stEP690 were 1,12-dodecanedioic acid, 1,14-tetradecenedioic acid, 1,14-tetradecanedioic acid, 1,16-hexadecenedioic acid, 1,16-hexadecanedioic acid, 1,18-octadecenedioic acid (see FIG. 17). The most abundant compound produced by this strain was 1,14-tetradecanedioic acid at RT 13.367 minutes. The mass spectrum of this compound after BSTFA derivatization is shown in FIG. 18A. The molecular ion for this compound is m/z=387 (M-CH$_3$) and its fragmentation pattern is shown in FIG. 19. The identification of 1,14-tetradecanedioic acid bis(trimethylsilyl) ester was further confirmed by comparing its mass spectrum and retention time with that of the authentic standard 1,14-tetradecanedioic acid after BSTFA derivatization (FIG. 18B).

Table 16 shows the amounts of α,ω-diacids produced by strain sEP690 from glucose within 20h, which was −550 g/L. This example showed that *E. coli* strains engineered for overproducing fatty acid derivatives when combined with the expression of a CYP153A-RedRhF hybrid fusion protein and combined with expression of an alcohol oxidase (SEQ ID NO: 67) and aldehyde dehydrogenase (SEQ ID NO: 69) efficiently produced α,ω-diacids from glucose as sole carbon source.

Example 8: Production of Subterminally Hydroxylated Fatty Acids by *E. coli* Strains Expressing cyp102A1 from *Bacillus megaterium*

The objective of this experiment was to investigate if it is possible to produce ω-hydroxylated fatty acids or α,ω-diacids in vivo by using genetically modified host strains expressing an F87A variant of cytochrome P450 cyp102A1 (P450-BM3) from *Bacillus megaterium*. It was found that the production of low quantities of subterminally hydroxylated (ω-1, ω-2, ω-3, ω-4, ω-5) fatty acids was possible by using recombinant *E. coli* strains that express this cyp102A1 variant. However, it was not possible to produce ω-hydroxy fatty acids or α,ω-diacids by employing the same *E. coli* strains.

Figure 20:
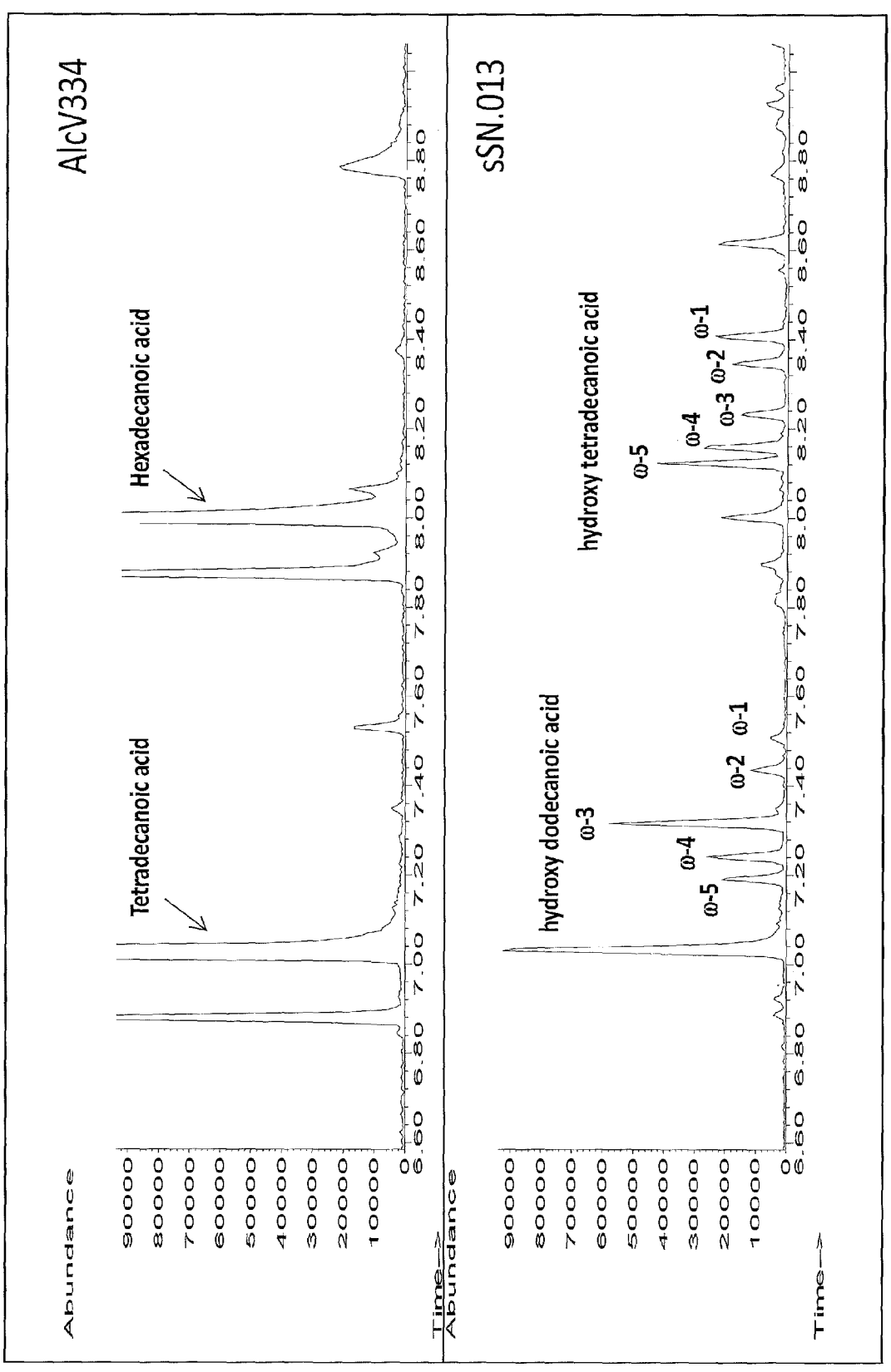
FIG. 20 shows the GC/MS chromatograph of an extract from a recombinant *E. coli* strain expressing cyp102A1 (F87A) producing small amounts of subterminally (e.g., ω-1, ω-2 and/or ω-3) hydroxylated fatty acids. A GC/MS chromatograph of the extract of the control strain AlcV334 is also shown. The samples were derivatized with BSTFA+1% TMCS.
Figure 21A:
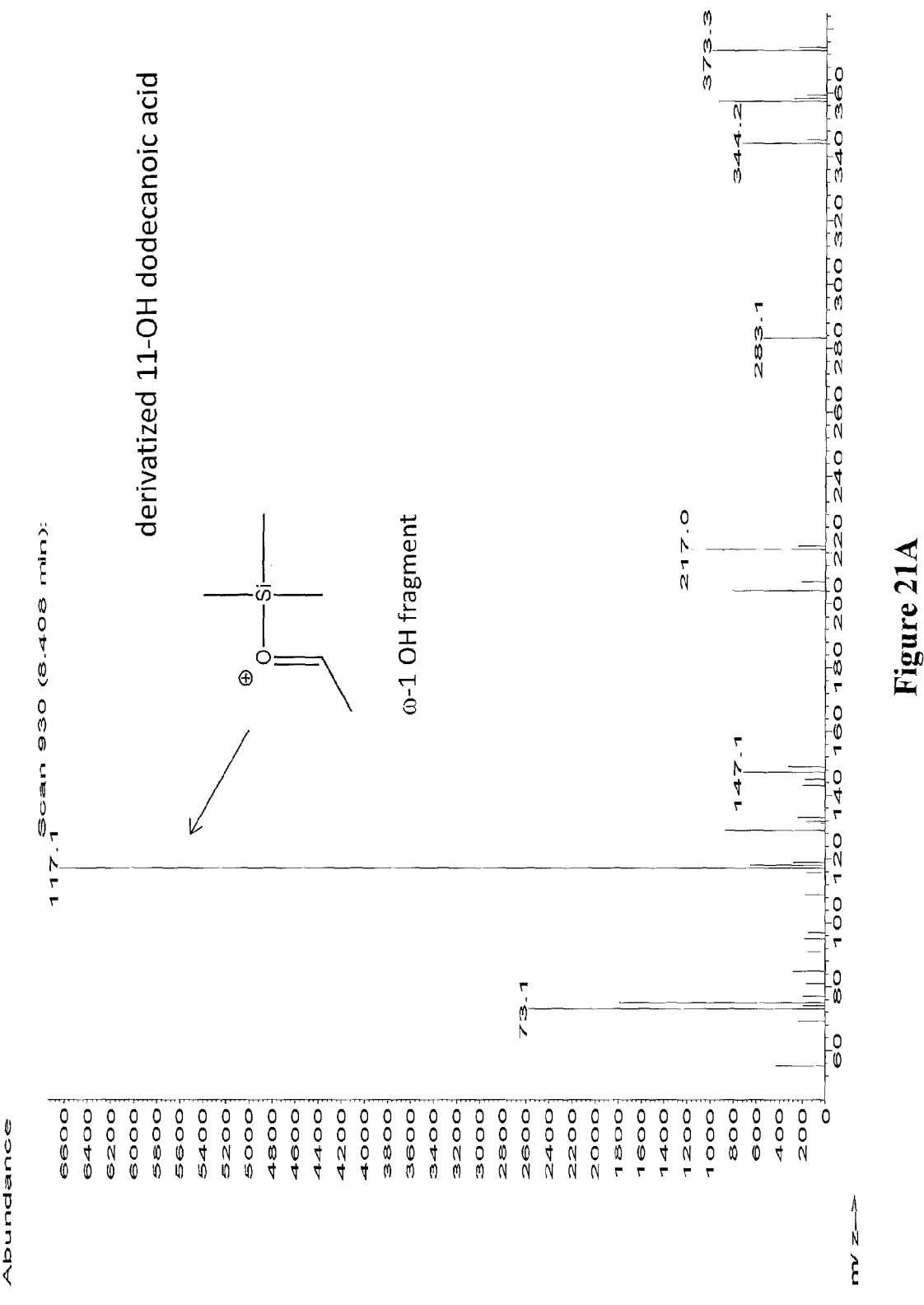
FIGS. 21A through 21E depict the mass spectra of the peaks from RT 7.195 to 7.510 (from FIG. 20) identified as 11-hydroxy dodecanoic acid (FIG. 21A), 10-hydroxy dodecanoic acid (FIG. 21B), 9-hydroxy dodecanoic acid (FIG. 21C), 8-hydroxy dodecanoic acid (FIG. 21D), 7-hydroxy dodecanoic acid (FIG. 21E). The diagnostic ion fragments are depicted for each hydroxylation position. The samples were derivatized with BSTFA+1% TMCS.
Figure 21B:
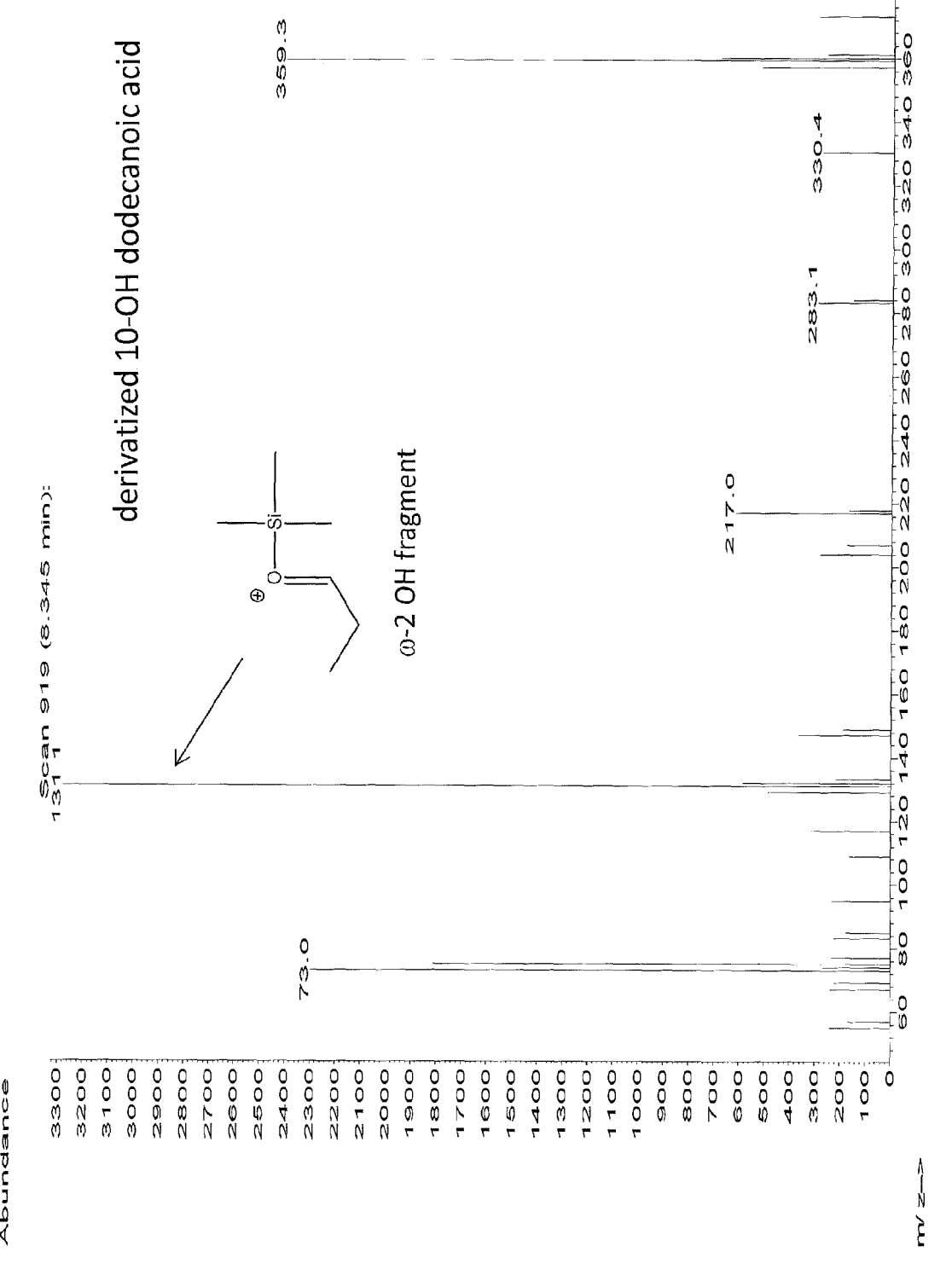
Figure 21C:
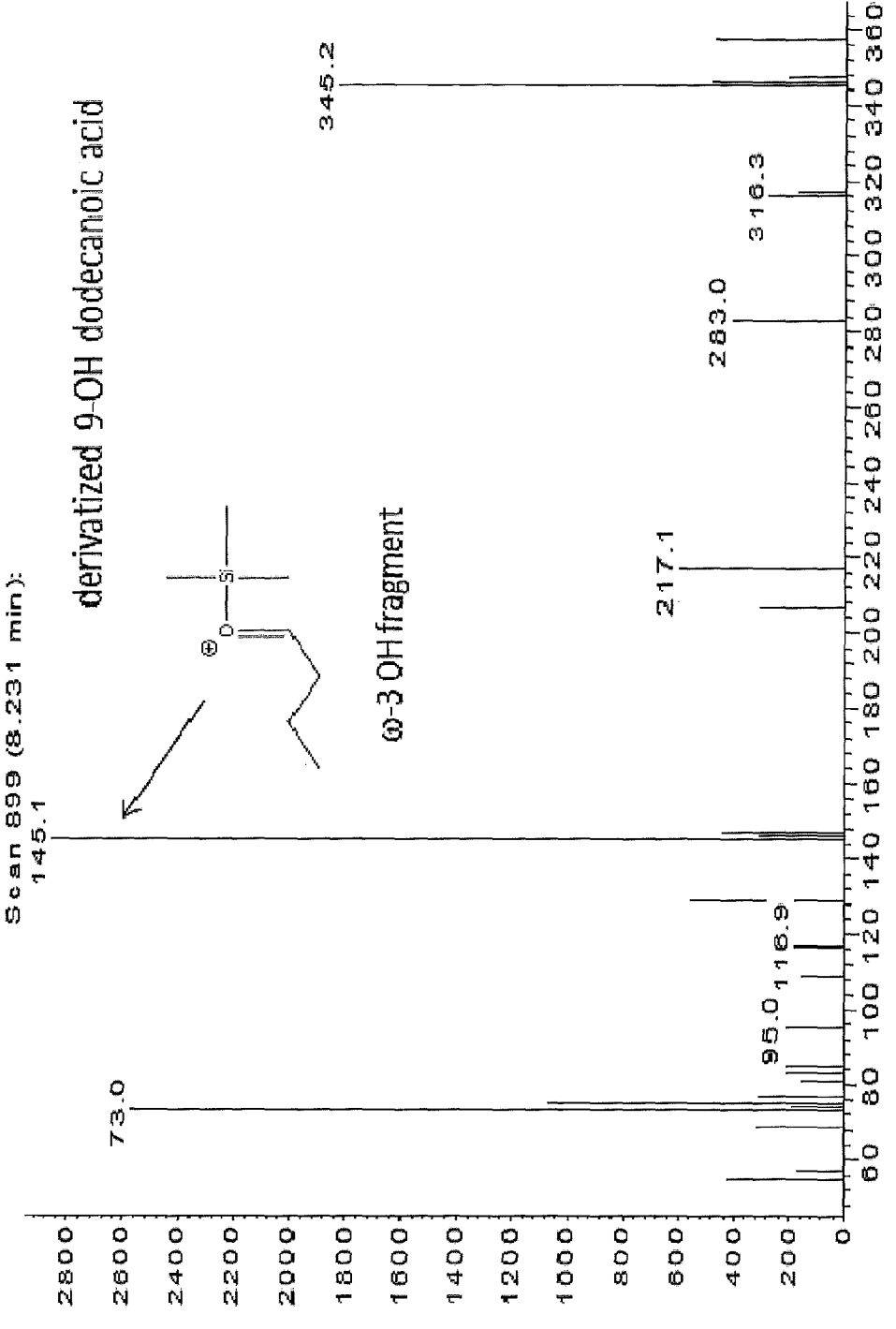
Figure 21D:
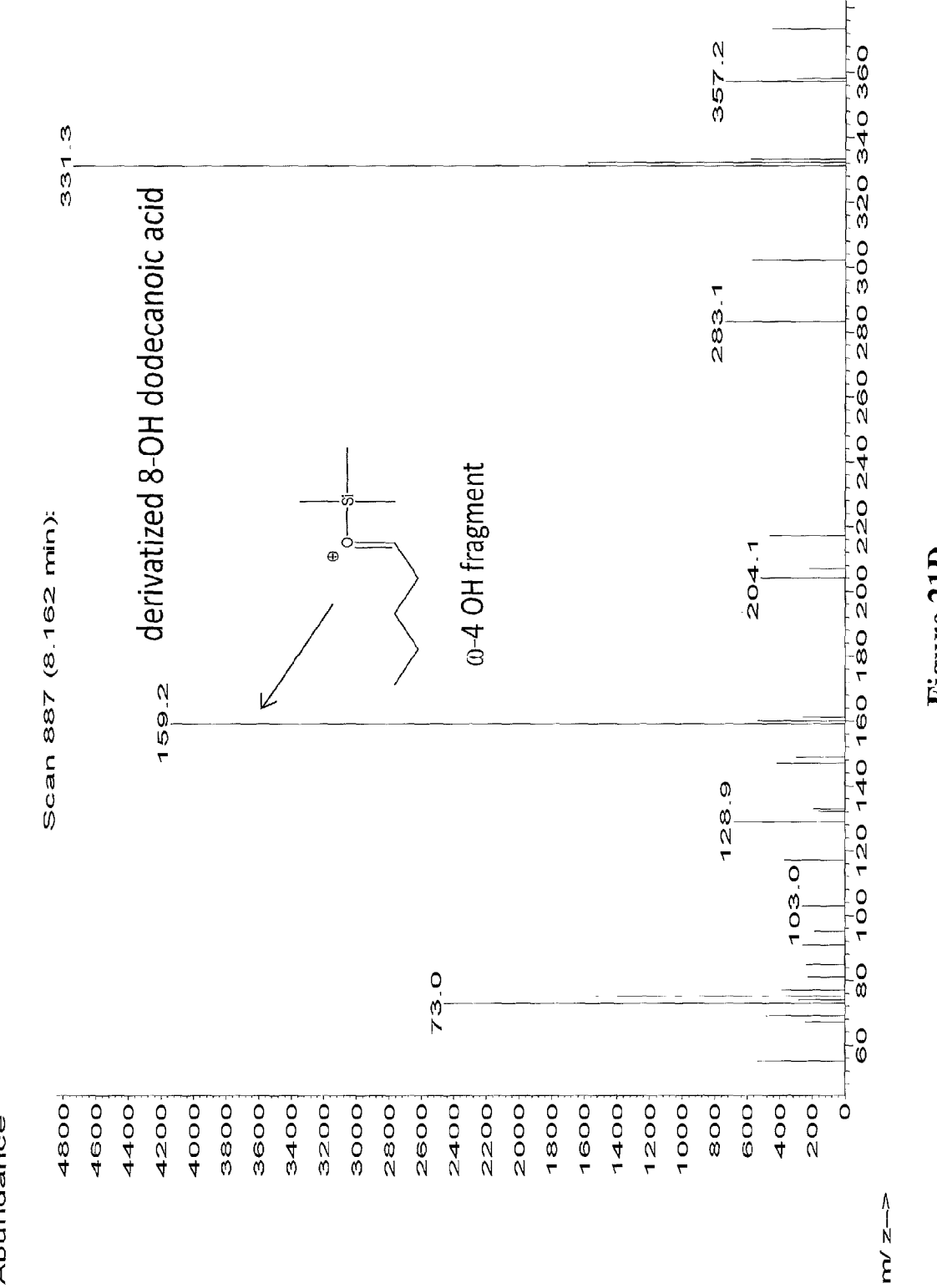
Figure 21E:
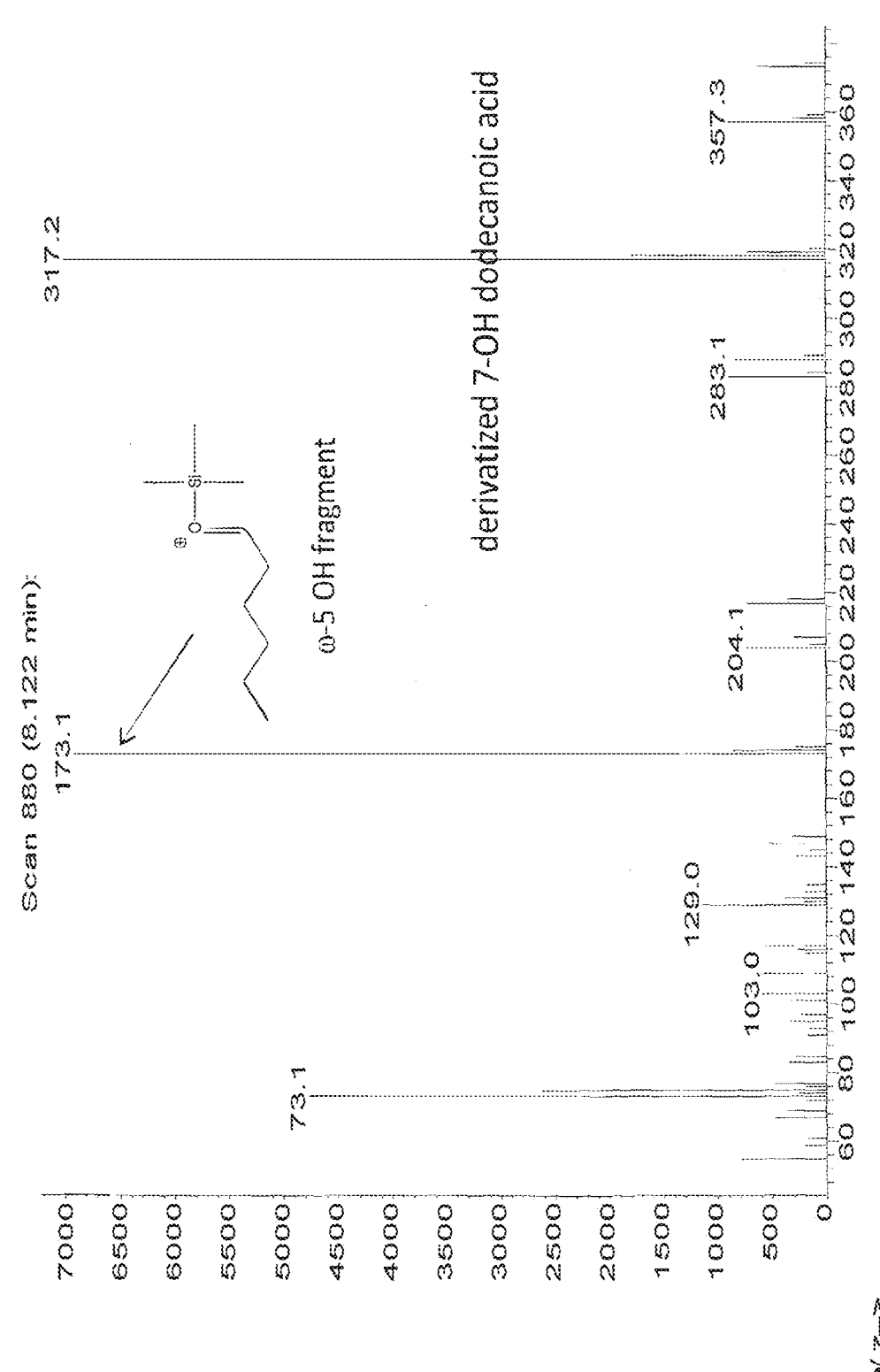

The gene coding for a variant of the cyp102A1 gene from *Bacillus megaterium* (P450-BM3) in which phenylalanine in position 87 is replaced with alanine (F87A) was created by cross-over PCR from *B. megaterium* genomic DNA (Accession Number AAA87602; SEQ ID NO: 61). The amplified DNA was cloned into pCL derivative (SC101 replicon, spectinomycin resistance marker) and pACYC derivative (p15a replicon, kanamycin resistance marker) vectors, such that the transcription of the genes was controlled by the IPTG-inducible Ptrc promoter. The resulting plasmids, pSN.012 and pSN.009 (see Table 17, infra) were transformed into the fatty acid overproducing strain AlcV334 (see Table 14, supra and Example 6, supra) giving strains sSN.012 and sSN.013 (see Table 18, infra). The strains were then analyzed for their ability to produce ω-hydroxylated fatty acids from glucose as described in Examples 1 and 2. In comparison to the control strain AlcV334, small new peaks were identified in both strains (shown for sSN.012 in FIG. 20 after BSTFA derivatization). The fragmentation pattern of the mass spectrum of the new peaks between RT 7.195 to 7.510 and 8.122 to 8.414 did not match ω-hydroxy fatty acids (see Example 3, supra), however they matched the expected fragmentation pattern of fatty acids hydroxylated at the subterminal ω-1, ω-2, ω-3, ω-4, and ω-5 positions. Although subterminally hydroxylated fatty acids show similar ion fragmentation patterns as ω-hydroxy fatty acids (see FIG. 8A for derivatized 12-hydroxy dodecanoic acid), these compounds show additional ion fragments depending on the hydroxylation site of m/z=117 (ω-1), 131 (ω-2), 145 (ω-3), 159 (ω-4) or 173 (ω-5) after derivatization (see FIGS. 21A-21E). As to chain length, the combination of the ions at m/z=117 and 345 are characteristic ions for 11(ω-1)-hydroxydodecanoic acid after derivatization. Similarly, the combination pair of ions at m/z=131 and 331, m/z=145 and 317, m/z=159 and 303, m/z=173 and 289 are the characteristic ions for ω-2, ω-3, ω-4 and ω-5 hydroxydodecanoic acids. Therefore, peaks from RT 7.195 to 7.510 were identified as 7(ω-5)-, 8(ω-4)-, 9(ω-3)-, 10(ω-2)- and 11(ω-1)-hydroxy dodecanioc acid and the peaks from RT 8.122 to 8.414 as 9(ω-5)-, 10(ω-4)-, 11(ω-3)-, 12(ω-2)- and 13(ω-1)-hydroxy tetradecanioc acid. The GC/MS chromatogaphs of strains sSN.012 and sSN.013 were also carefully inspected for the presence of α,ω-diacids, but these bifunctional molecules could not be detected.

In conclusion, this example shows that *E. coli* strains engineered for overproducing fatty acids when combined with the expression of the F87A variant of cyp102A1 from *B. megaterium* do not produce ω-hydroxylated fatty acids, but do produce trace amounts of ω-1, ω-2, ω-3, ω-4, and ω-5 hydroxy fatty acids. It has been reported that the F87A point mutation in cyp102A1 from *B. megaterium* changes the substrate specificity of the enzyme in vitro such that the enzyme almost exclusively hydroxylates dodecanoic acid or tetradecanoic acid at the ω-position (see Oliver et al. (1997) *Biochem.* 36: 1567). It has also been reported that P450-BM3 (cyp102A3) and P450-BM3(F87A) (cyp153(F87A)) from *B. subtilis* produce 14-hydroxy tetradeconoic acid and 1,14, tetradecanedioc acid (see, e.g., WO 2012/071439). However, this could not be confirmed and appears to contradict the present findings. Moreover, recent reports on altering the substrate specificity of cyp102A3 of *Bacillus subtilis*, a close homolog of cyp102A1 support the data presented herein (see Lentz et al. (2004) *J. Biotechnol.* 108:41 and Lentz et al. (2006) *ChemBioChem.* 7:345). As such, a mutation of the equivalent phenylalanine residue in cyp102A3 to valine (F88V) mainly hydroxylated fatty acids in the ω-1, ω-2, ω-3 and ω-4 positions, and no ω-hydroxylated products were observed in vitro with dodecanoic acid or hexadecanoic acid as substrates. Thus, it can be concluded that the variants described above of cyp102A1 from *B. megaterium* and cyp102A3 from *B. subtilis* are not suitable to produce ω-hydroxy fatty acids or α,ω-diacids as the latter require ω-hydroxy fatty acids as intermediates.

TABLE 17

| Expression Plasmids Constructed for the Production of Subterminally Hydroxylated Fatty Acid Derivatives | |
| --- | --- |
| Plasmid | Description |
| pSN.009 | pACYC-cyp102A1(F87A)_*B. megaterium* |
| pSN.012 | pCL-cyp102A1(F87A)_ *B. megaterium* |
| pHM105 | pCL-cyp102A7_*B. licheniformis* |
| pSL170.02 | pCL-cyp102A7_ *B. licheniformis*-tesA*-alrA-fabB*-fadR |

TABLE 18

Recombinant *E. coli* Strains Expressing cyp102A Proteins
for Production of Subterminally Hydroxylated Fatty Acid
Derivatives from Renewable Carbohydrate Feedstocks

| Strain | Genotype | Phenotype |
|--------|----------|-----------|
| sSN.012 | AlcV334/pSN.012 | Produce trace amounts of subterminally |
| sSN.013 | AlcV334/pSN.009 | hydroxylated fatty acids |
| XL960 | LC972/pHM105 | Produce large amounts of subterminally |
| XL961 | LC972/pSL170.02 | hydroxylated fatty acids |
| XL962 | XL959/pHM105 | Produce large amounts of subterminally |
| XL963 | XL959/pSL170.02 | hydroxylated fatty alcohols |

Example 9: Efficient Production ω-1, ω-2 and
ω-3-Hydroxylated Fatty Acids from Glucose by *E.
coli* Strains Expressing cyp102A7 from *Bacillus
licheniformis*

The object of this example was to test *E. coli* strains expressing cytochrome P450-BM3-type oxygenase cyp102A7 from *Bacillus licheniformis* for the production of subterminally hydroxylated fatty acids. The data demonstrated the efficient production of ω-1, ω-2 and ω-3-hydroxy fatty acids and fatty alcohols by recombinant *E. coli* strains expressing the cytochrome P450-BM3-type oxygenase cyp102A7. This was surprising and unexpected.

Figure 22A:
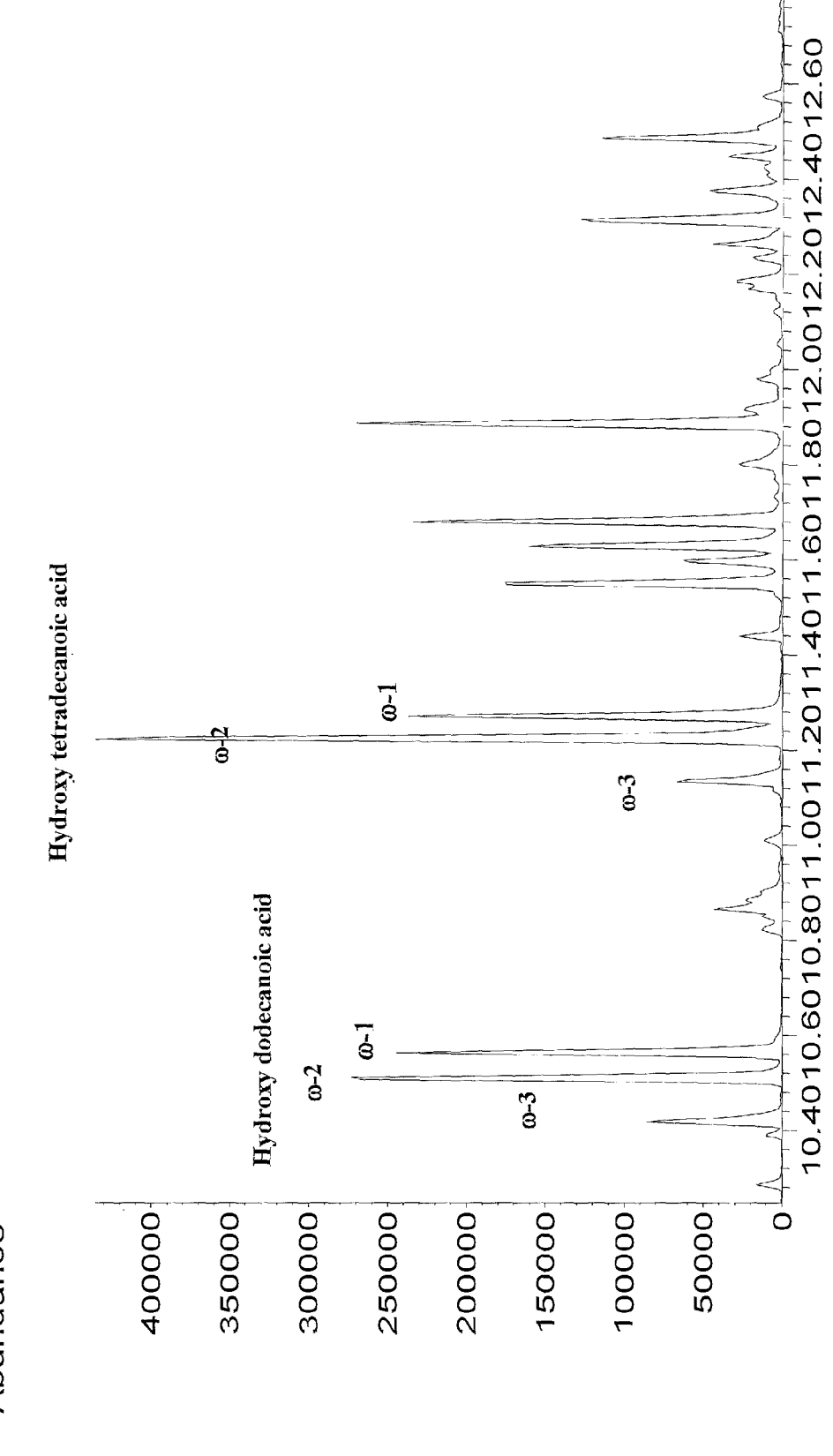
FIGS. 22A through 22B show GC/MS chromatographs of extracts from recombinant *E. coli* strains expressing cyp102A7-proteins producing ω-1, ω-2, and ω-3 hydroxy fatty acids (FIG. 22A), or ω-1, ω-2, and ω-3 hydroxy fatty alcohols (FIG. 22B) from glucose. All samples were derivatized with BSTFA+1% TMCS.

The yrhJ gene encoding P450-BM3-type oxygenase CYP102A7 from *Bacillus licheniformis* (Dietrich et al. (2008) *Appl. Microbiol. Biotechnol.* 79: 931) was amplified from *Bacillus licheniformis* ATCC14580 genomic DNA (Accession Number AAU41718; SEQ ID NO: 63). The gene was cloned into a pCL1920-derivative (SC101 replicon, spectinomycin resistance marker) such that an inducible Ptrc promoter controls its transcription. In addition, the gene was cloned into a pCL1920-derivative such that an inducible Ptrc promoter controls an operon made of (and in this order) yrhJ, a variant of thioesterae (tesA), alcohol dehydrogenase (AlrA), a variant of 3-keto-acyl-ACP synthase (fabB) and the transcriptional regulator fadR. The plasmids were named pHM105 and pSL170.02, respectively, and were transformed into *E. coli* strains LC972 and XL959 (see Table 14, supra). These strains are briefly described here (see also Table 14). The genome of strain LC972 was engineered as follows: the acyl-CoA dehydrogenase (fadE) gene was deleted. Phosphopantetheinyl transferase, two copies of a variant of thioesterae (tesA) and a synthetic fatty acid biosynthesis operon (consisting of several genes described in table 1) were overexpressed. Strain XL959 was LC972 with a pACYC derivative plasmid expressing a variant of carboxylic acid reductase carB. The four new recombinant *E. coli* strains XL960-XL963 (see Table 18, supra) were analyzed for their ability to produce hydroxylated fatty acid derivatives from glucose as described in Examples 1 and 2, except that 35° C. was used as incubation temperature. Neither of the strains produced any ω-hydroxylated fatty acids or fatty acid derivatives. However, all strains produced the subterminally hydroxylated fatty acid derivatives as described in Example 8. FIG. 22A shows a chromatograph after BFTSA derivatization from strain XL961. The peaks were identified as described in Example 8 as the following ω-1, ω-2 and ω-3-hydroxy fatty acids: 11-hydroxy dodecanoic acid (RT=10.563), 10-hydroxy dodecanoic acid (RT=10.512), 9-hydroxy dodecanoic acid (RT=10.412), 13-hydroxy tetradecanoic acid (RT=11.279), 12-hydroxy tetradecanoic acid (RT=11.233), 11-hydroxy tetradecanoic acid (RT=11.133), 15-hydroxy hexadecanoic acid (RT=11.679), 14-hydroxy hexadecanoic acid (RT=11.623) and 13-hydroxy hexadecanoic acid (RT=11.439). Small peaks that most likely corresponded to unsaturated subterminally hydroxylated fatty acids were also detected.

Figure 22B:
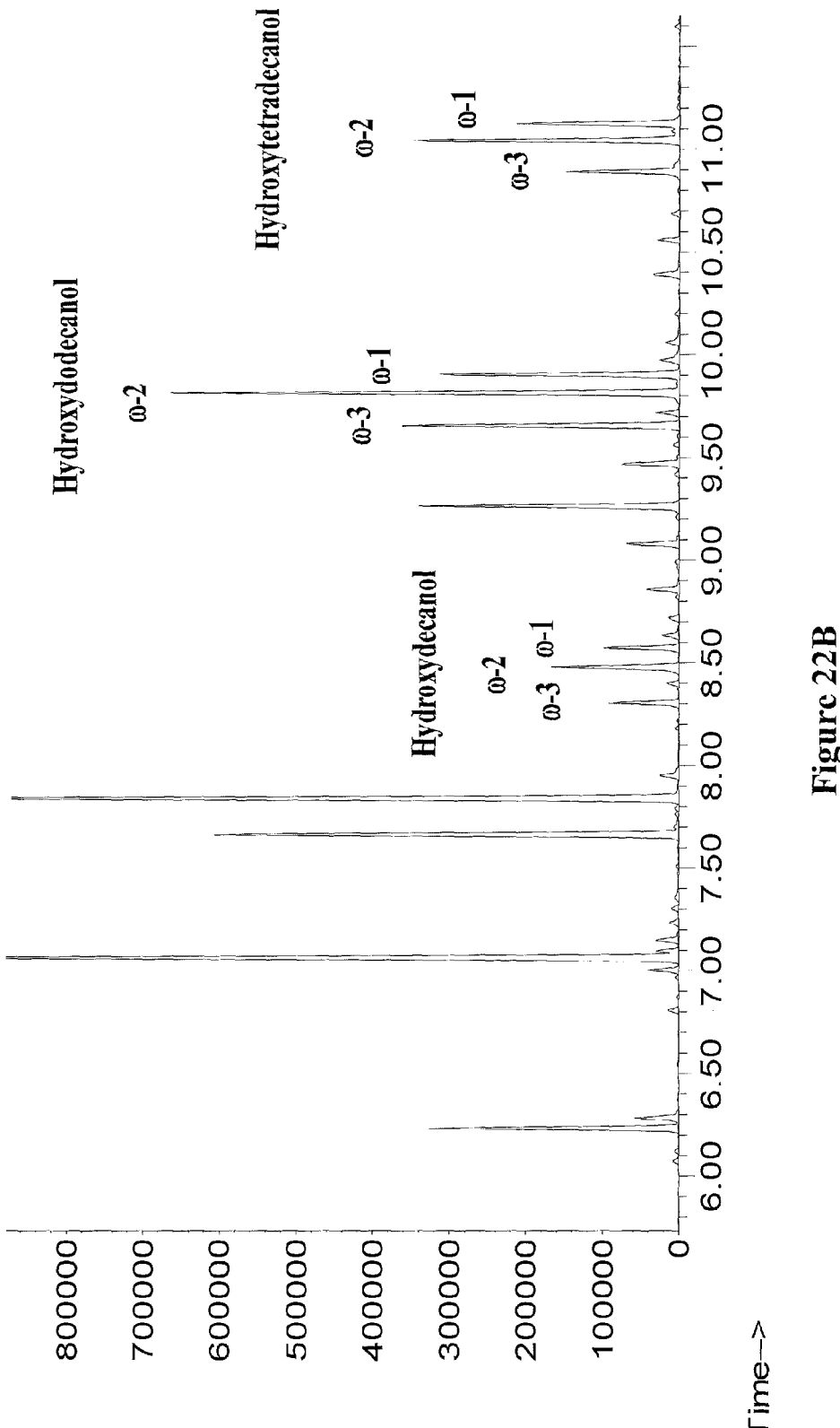
Figure 23A:
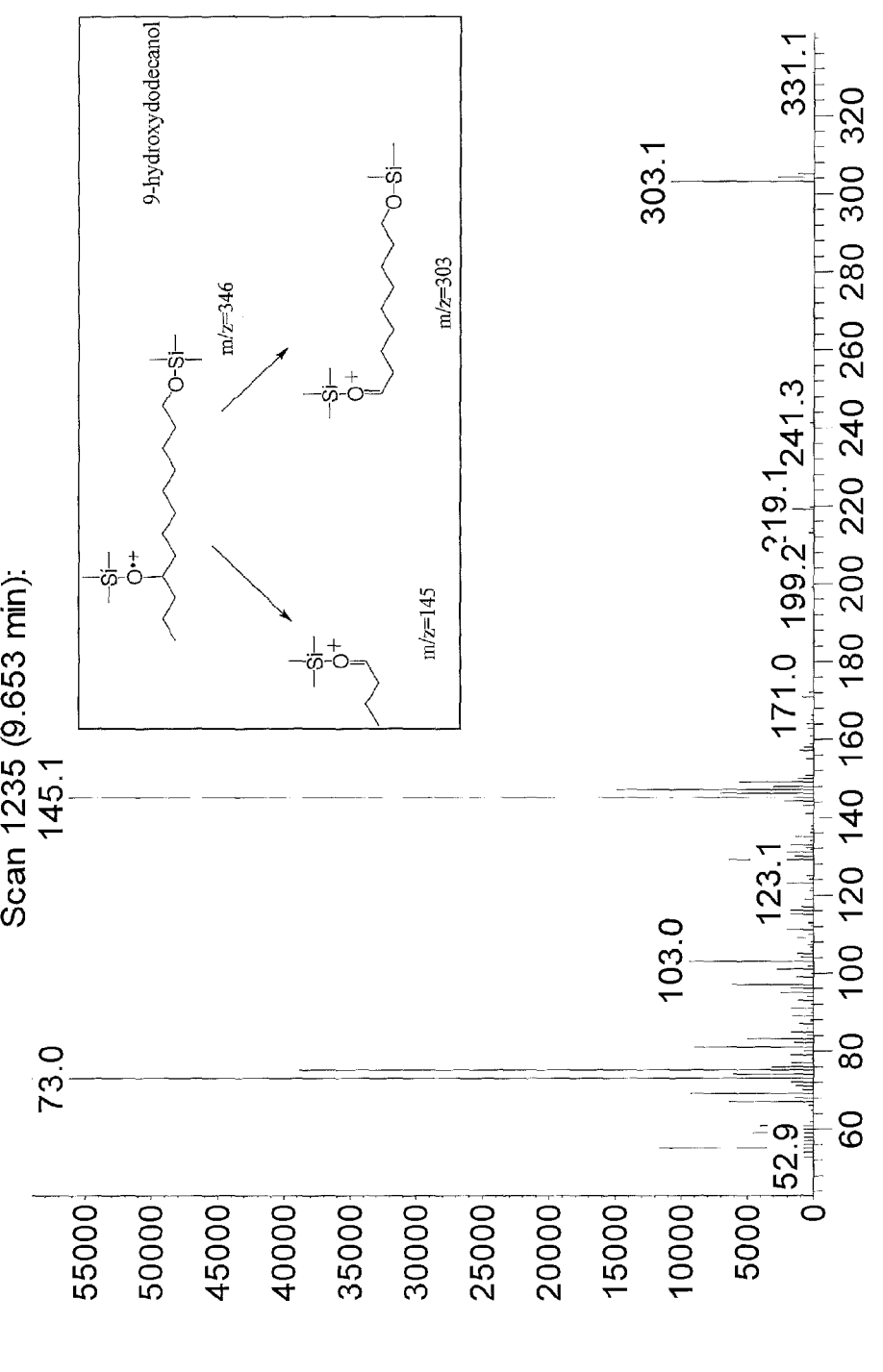
FIGS. 23A through 23C illustrate the mass spectra and ion fragmentation patterns of derivatized 9-hydroxy dodecanol (peak at 9.653 minutes) (FIG. 23A), derivatized 10-hydroxy dodecanol (peak at 9.808 minutes) (FIG. 23B), and derivatized 11-hydroxy dodecanol (peak at 9.905 minutes) (FIG. 23C). Derivatizing agent was BSTFA+1% TMCS. The samples are from extracts of *E. coli* strain XL963.
Figure 23B:
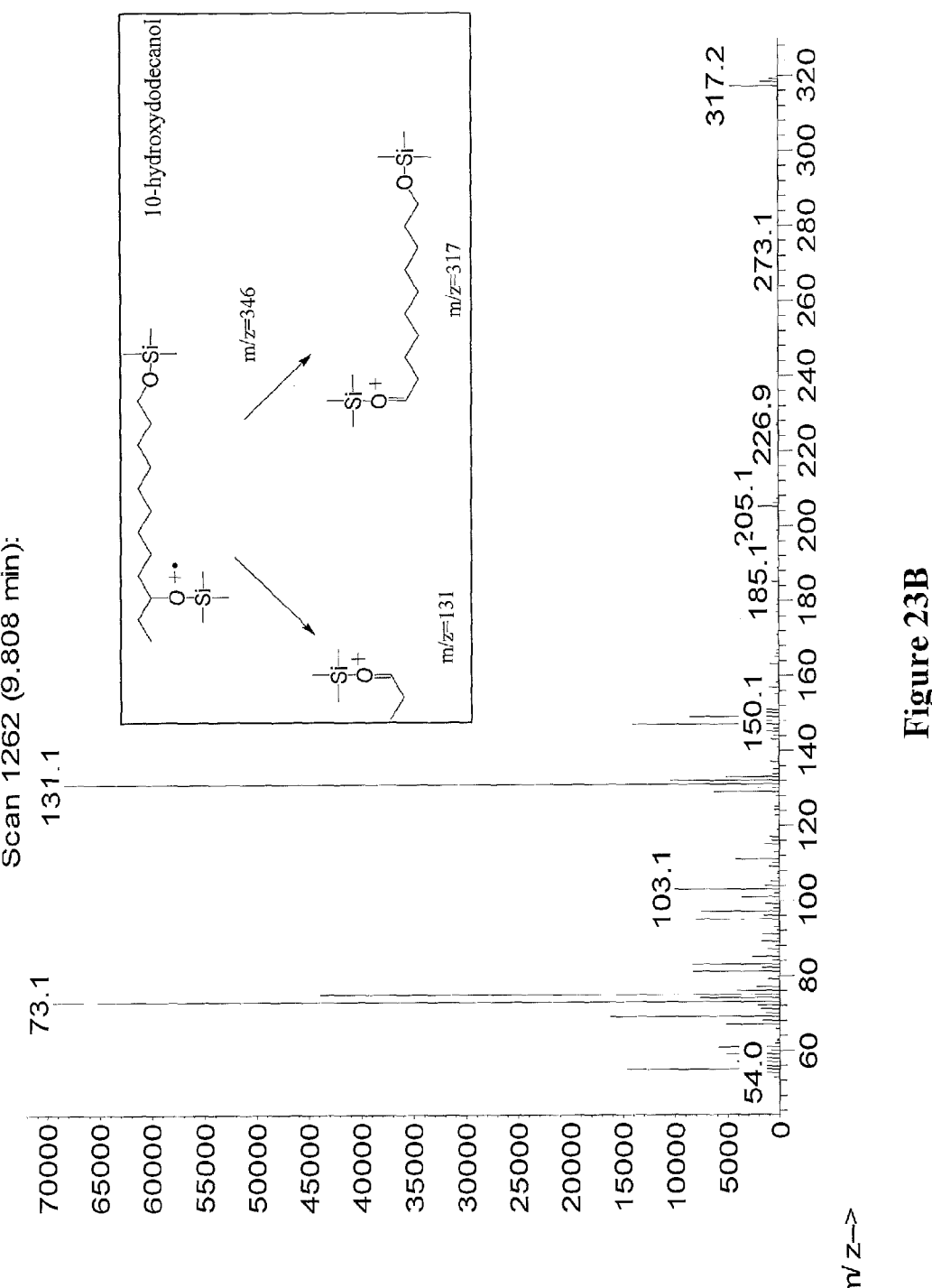
Figure 23C:
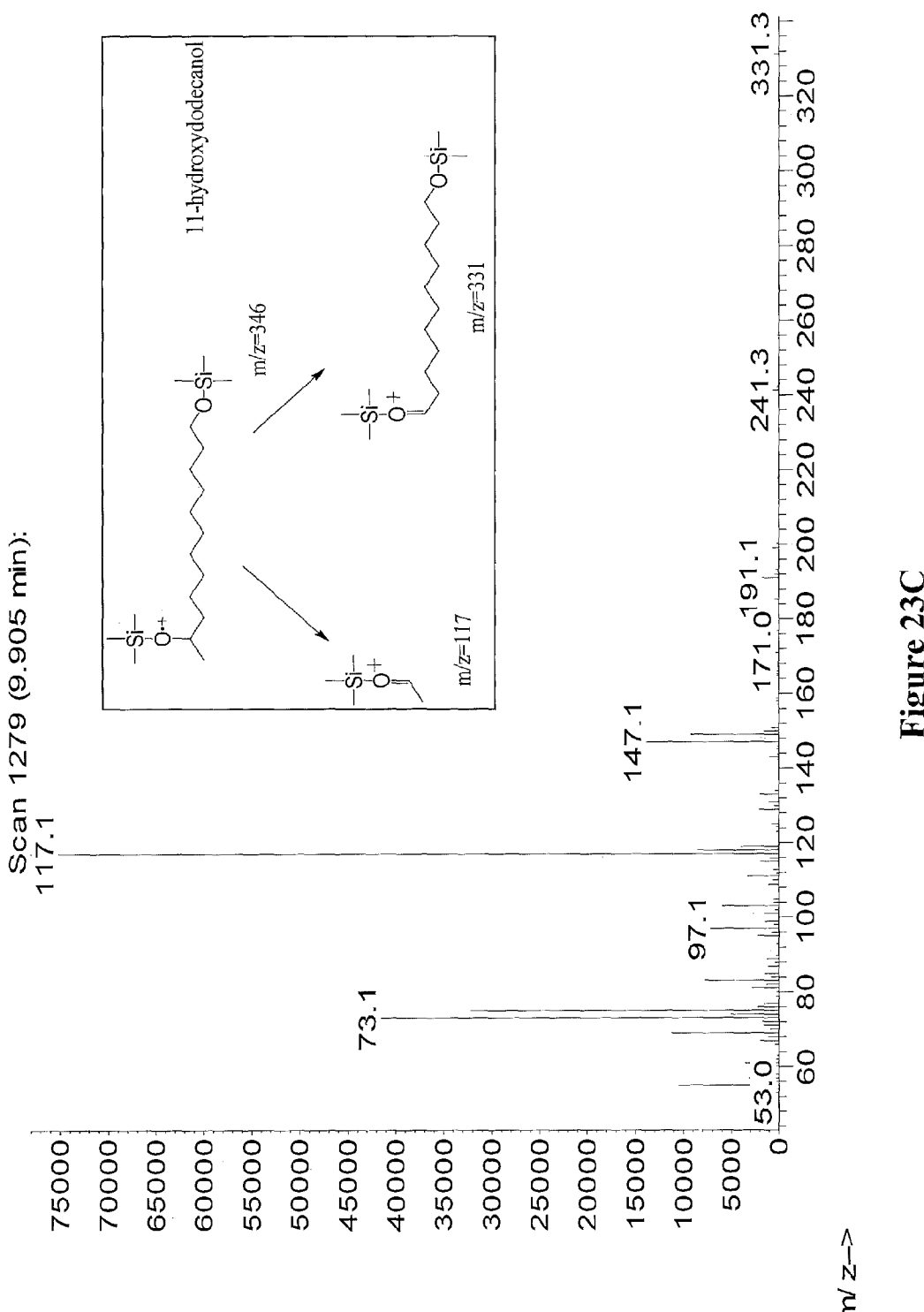
Figure 24A:
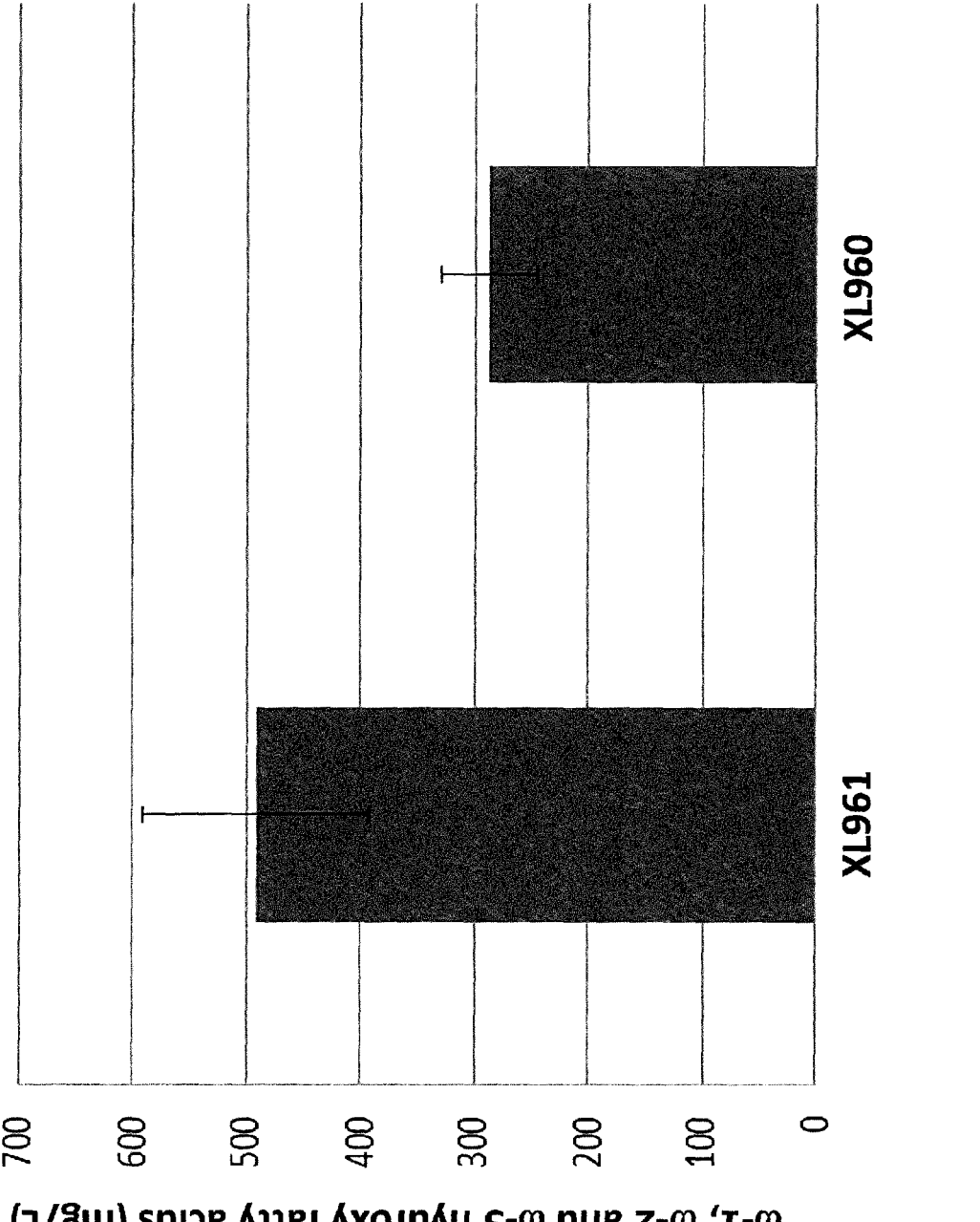
FIGS. 24A through 24B show the amount of subterminally (e.g., ω-1, ω-2 and/or ω-3) hydroxylated fatty acids (FIG. 24A) and subterminally hydroxylated fatty alcohols (FIG. 24B) produced from glucose by recombinant *E. coli* strains expressing cyp102A7.
Figure 24B:
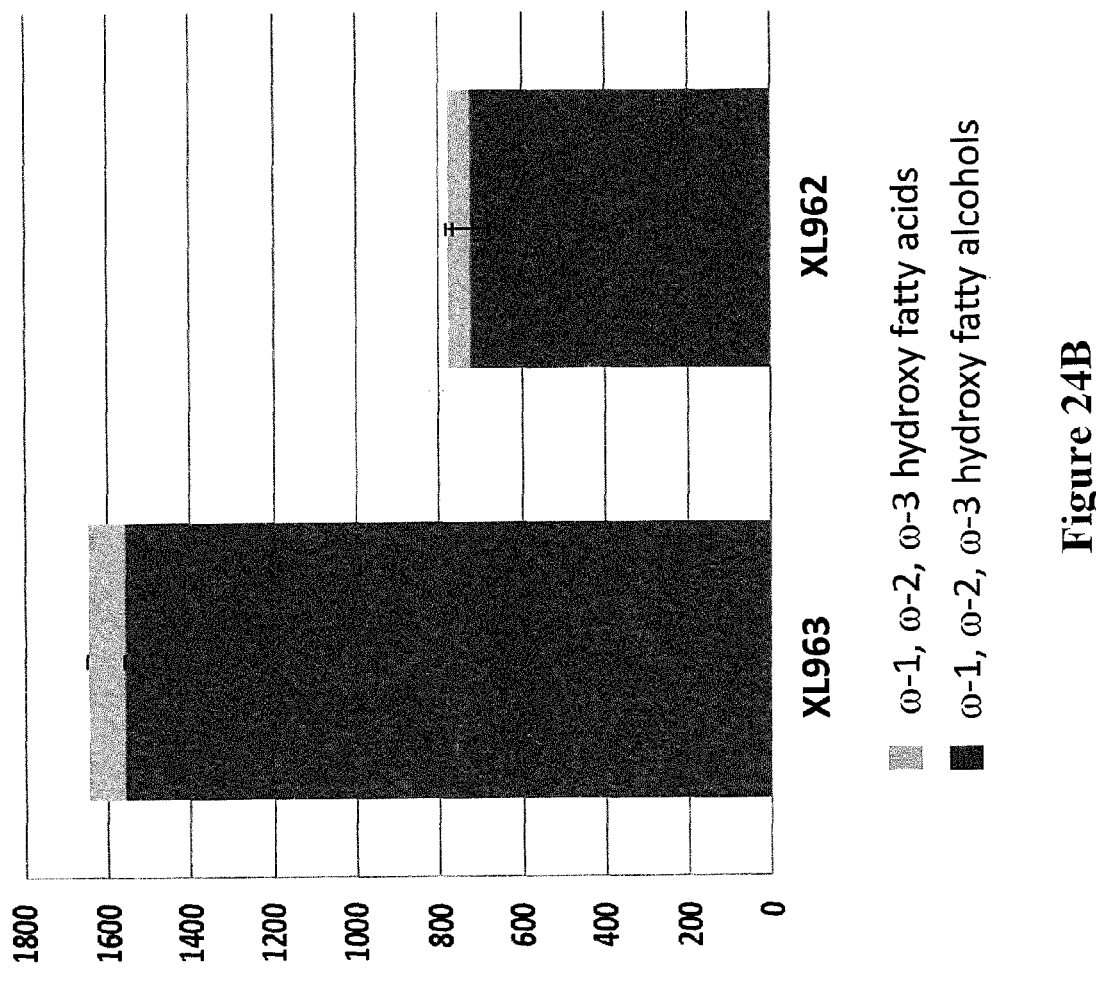

FIG. 22B shows a chromatograph after BFTSA derivatization from strain XL963. The peaks were identified as the following ω-1, ω-2 and ω-3-hydroxy fatty alcohols: The peaks at RT 8.303, 8.480, and 8.572 minutes were 7, 8 and 9-hydroxydecanol, respectively, the peaks at RT 9.264, 9.653 and 9.905 were 9, 10 and 11-hydroxydodecanol, respectively, and the peaks at RT 10.889, 11.044 and 11.124 were 11, 12 and 13-tetradecanol, respectively. The detailed mass spectra and ion fragmentation pattern used to identify 9, 10 and 11-hydroxydodecanol are shown in FIGS. 23A, 23B and 23C. Given that similar strains in Example 8 produced only trace amounts of subterminally hydroxylated fatty acids, it was surprising and unexpected that all four strains produced substantial amounts of these products (up to −1.6 g/L). FIG. 24A shows the amounts of ω-1, ω-2 and ω-3-hydroxyl fatty acids produced by strains XL960 and XL961 and FIG. 24B shows the amounts of ω-1, ω-2 and ω-3-hydroxyl fatty alcohols produced by strains XL962 and XL963. Thus, this example shows that *E. coli* strains engineered for overproducing fatty acid derivatives when combined with the expression of a cyp102A7 from *B. licheniformis* efficiently produced ω-1, ω-2 and ω-3-hydroxyl fatty acid derivatives from glucose as sole carbon source.

Example 10: Production α,ω-Diesters from Glucose
by Recombinant *E. coli* Strains An acyl-CoA synthetase/ligase or transferase gene is cloned downstream of a gene encoding a cyp153A-RedRhF fusion protein into a pCL derivative vector such that the two genes form an operon and transcription of the operon is controlled by the IPTG-inducible Ptrc promoter. Examples of suitable cyp153A and RedRhF fusion partners are given in Tables 2A and 2D. Examples of suitable acyl-CoA synthetases/ligases or transferases are given in Table 7. The resulting plasmid is transformed into a fatty acid methyl ester producing *E. coli* strain, e.g. KASH286 (see Example 6 and Table 14, supra). The strain is analyzed for its ability to produce ω-hydroxylated fatty acid derivatives from glucose as described in Example 1 and 2. The strain is expected to produce α,ω-diesters.

Example 11: Production ω-Amino Fatty Acid
Derivatives from Glucose by Recombinant *E. coli*
Strains A gene encoding a cyp153A-RedRhF fusion protein, a gene encoding an alcohol oxidase or dehydrogenase and a gene encoding an aminotransferase or transaminase are cloned into a pCL derivative vector such that the three genes form an operon and transcription of the operon is controlled by the IPTG-inducible Ptrc promoter. Examples of suitable cyp153A and RedRhF fusion partners are given in Tables 2A and 2D. Examples of suitable alcohol oxidases or dehydrogenases are given in Table 3A and Examples of suitable aminotransferases or transaminases are given in Table 4. The resulting plasmid is transformed into a fatty acid producing *E. coli* strain, e.g., stNH1293 (see Example 6 and Table 14, supra). The strain is analyzed for its ability to produce ω-hydroxylated fatty acid derivatives from glucose as described in Examples 1 and 2. The strain is expected to produce ω-amino fatty acids. Alternatively, the resulting plasmid is transformed into a fatty acid methyl ester producing *E. coli* strain, e.g., KASH286 (see Example 6 and Table 14, supra). The strain is analyzed for its ability to produce ω-hydroxylated fatty acid derivatives from glucose as described in Examples 1 and 2. The strain is expected to produce ω-amino fatty acid methyl esters.

Example 12: Production of ω-Hydroxylated Fatty Acid Derivatives from Diverse Feedstocks As fatty acid biosynthesis is ubiquitous in nature, the Examples provided herein can be further implemented in other organisms that naturally utilize feedstocks beyond carbohydrates. For example, these pathways could be expressed in a photosynthetic microorganism, allowing for the production of ω-hydroxylated fatty acid derivatives from $CO_2$. In particular, they could be expressed in the cytoplasm of a cyanobacteria, that when grown under suitable conditions, such as in a photobioreactor or an open pond, they would produce ω-hydroxylated fatty acid derivatives that could be isolated from the culture. Alternatively, it will be clear to one skilled in the art that these pathways can be expressed in a carbon monoxide utilizing organism, such as those from the genus Clostridia. For example, when these engineered microorganisms are grown in the appropriate RedRhF-type as well as BM3-type proteins. Genes coding for the chimeric hybrid proteins were assembled and cloned into a pCL1920-derivative vector as described in Example 5 (supra). The resulting plasmids were transformed into strain AlcV334 (see Table 14). These additional six strains engineered to produce ω-hydroxylated fatty acid derivatives were then analyzed for their ability to produce ω-hydroxylated fatty acid derivatives from a renewable feedstock such as glucose as described in Examples 1 and 2. Table 20 below shows the amounts of ω-hydroxylated fatty acids produced by these strain in comparison to StEP675 within 18 h at 32° C. StEP675 is strain AlcV 334 expressing a chimeric protein consisting of CYP153A from *M. aquaeolei* and a reductase domain from *Rhodococcus* sp. NCIMB 9784 (see Example 6). As can be seen in Table 20 below, most strains expressing the CYP153A-Reductase hybrid fusion proteins efficiently produced ω-hydroxylated fatty acid derivatives from glucose as sole carbon source. In conclusion, chimeric CYP153A-Reductase hybrid fusion proteins consisting of proteins from different members of the CYP153A family and different members of the RedRhF-type or BM3-type Reductase families efficiently produced ω-hydroxylated fatty acid derivatives from glucose as sole carbon source when expressed in *E. coli*.

TABLE 19

Additional recombinant *E. coli* Strains Expressing hybrid cyp153A-Reductase fusion proteins for Production of ω-Hydroxylated Fatty Acid Derivatives from Renewable Carbohydrate Feedstocks

| | P450 cyp153A domain | | Reductase domain | | SEQ |
|---|---|---|---|---|---|
| Strain | Source microbe | Accession # | Source microbe | Accession # | ID |
| sIB.012 | *M. aquaeolei* | YP_957888 | *Cupriavidus metallodurans* | YP_587063 | 48 |
| sIB.013 | *M. aquaeolei* | YP_957888 | *Acinetobacter radioresistens* | ZP_06072406 | 50 |
| sIB.027 | *Sphingomonas macrogoltabida* | CAH61448 | *Rhodococcus* sp. NCIMB9784 | AAM67416 | 52 |
| sIB.028 | *M. aquaeolei* | YP_957888 | *Bacillus megaterium* | AAA87602 | 54 |
| sIB.029 | *M. aquaeolei* | YP_957888 | *Bacillus licheniformis* | AAU41718 | 56 |
| sIB.030 | *Alcanovorax borkumensis* | WP_011587498 | *Rhodococcus* sp. NCIMB9784 | AAM67416 | 58 | conditions (e.g., in a reactor supplied with CO from steel mill flu gas or from syn gas derived from the reformation of organic materials such as natural gas or biomass), they will produce ω-hydroxylated fatty acid derivatives that can be recovered from the culture.

Example 13: Production ω-Hydroxylated Fatty Acid Derivatives from Glucose by Recombinant *E. coli* Strains Expressing Various CYP153A-Reductase Hybrid Fusion Proteins This example shows the production of ω-hydroxy fatty acids from a renewable carbohydrate feedstock such as glucose, by recombinant *E. coli* strains expressing additional chimeric hybrid proteins in which various CYP153A P450 oxygenase domains are fused with various reductase domains.

In this experiment, genes coding the CYP153A P450 catalytic proteins from three microbes and reductase domain proteins from four microbes were either amplified from genomic DNA or synthesized as codon-optimized DNA (see Table 19 below). The reductase domain proteins comprised

TABLE 20

ω-Hydroxylated Fatty Acid Derivatives Produced by Additional Recombinant *E. coli* Strains from Glucose

| Strain | ω-hydroxylated fatty acid derivative formed from glucose (mg/L) * | |
|---|---|---|
| stEP675 | ω-hydroxylated fatty acids (C12, C14, C16) | 626 ± 75 |
| sIB.012 | ω-hydroxylated fatty acids (C12, C14, C16) | 751 ± 19 |
| sIB.013 | ω-hydroxylated fatty acids (C12, C14, C16) | 451 ± 31 |
| sIB.027 | ω-hydroxylated fatty acids (C12, C14, C16) | 38 ± 9 |
| sIB.028 | ω-hydroxylated fatty acids (C12, C14, C16) | 802 ± 155 |
| sIB.029 | ω-hydroxylated fatty acids (C12, C14, C16) | 825 ± 11 |
| sIB.030 | ω-hydroxylated fatty acids (C12, C14, C16) | 462 ± 83 |

The following protocols and methods pertain to Examples 14 through 19.

Protocols and Methods
Screening a Library

All protocols described herein rely on a 96 well plate-master block 2 mL system (Greiner Bio-One, Monroe, NC or Corning, Amsterdam, The Netherlands) for growing cultures, and plates (Costar, Inc.) for extracting fatty acid species from the culture broth. The protocols provided below are examples of fermentation conditions. Alternative protocols can be used to evaluate fatty acid species production.

32° C. Plim Culture Protocol:

30 μL LB culture (from an LB culture growing in a 96 well plate) was used to inoculate 290 μL Plim media (Table 21 below), which was then incubated for approximately 16 hours at 32° C. shaking. 40 μL of the overnight seed was used to inoculate 360 μL Plim media. After growing at 32° C. for 2 hours, the cultures were induced with IPTG (final concentration 1 mM) (Table 21 below). The cultures were then incubated at 32° C. with shaking for 20 hours if not noted otherwise, after which they were extracted following the standard extraction protocol detailed below.

35° C. Nlim Culture Protocol:

40 μL LB culture (from an LB culture growing in a 96 well plate) was used to inoculate 360 μL LB media (Table 21 below), which was then incubated for approximately 4 hours at 32° C. shaking. 40 μL of the LB seed was used to inoculate 360 μL Nlim media. After growing at 32° C. for 2 hours at 35° C., the cultures were induced with IPTG (final concentration 1 mM) (Table 21 below). The cultures were then incubated at 35° C. with shaking for 20 hours if not noted otherwise, after which they were extracted following the standard extraction protocol detailed below.

TABLE 21

Media Names and Formulations

| Media Name | | | Formulation |
|---|---|---|---|
| Plim | 1 | × | 5× Plim Salt Soln. with (NH4)$_2$SO$_4$ |
| | 1 | × | 1000× Trace Vitamins |
| | 1 | mg/L | 10 mg/mL Thiamine |
| | 1 | mM | 1M MgSO4 |
| | 0.1 | mM | 1M CaCl2 |
| | 40 | g/L | 500 g/L glucose |
| | 1 | × | 1000× Trace minerals |
| | 10 | mg/L | 10 g/L Fe Citrate |
| | 100 | μg/mL | 100 mg/ml spectinomycin |
| | 100 | mM | 2M BisTris (pH 7.0) |
| | 0.5 | mM | Aminolevulinic acid |
| Nlim | 1 | × | 5× Salt Soln. with NH4Cl |
| | 1 | × | 1000× Trace Vitamins |
| | 1 | mg/L | 10 mg/mL Thiamine |
| | 1 | mM | 1M MgSO4 |
| | 0.1 | mM | 1M CaCl2 |
| | 40 | g/L | 500 g/L glucose |
| | 1 | × | 1000× Trace minerals |
| | 10 | mg/L | 10 g/L Fe Citrate |
| | 100 | μg/mL | 100 mg/ml spectinomycin |
| | 100 | mM | 2M BisTris (pH 7.0) |
| | 0.5 | mM | Aminolevulinic acid |

Fatty Acid Species Standard Extraction Protocol:

To each well to be extracted 80 μL of 1M HCl, followed by 400 μL of butyl acetate (with 500 mg/L pentadecanol as internal standard) was added. The 96 well plates were then heat-sealed using a plate sealer (ALPS-300 heater; Abgene, ThermoScientific, Rockford, IL), and shaken for 15 minutes at 2000 rpm using MIXMATE mixer (Eppendorf, Hamburg, Germany). After shaking, the plates were centrifuged for 10 minutes at 4500 rpm at room temperature (Allegra X-15R, rotor SX4750A, Beckman Coulter, Brea, CA) to separate the aqueous and organic layers. 100 μL of the organic layer was transferred to a 96 well plate (polypropylene, Corning, Amsterdam, The Netherlands) and derivatized with 100 μL of BSTFA. The plate was subsequently heat sealed and stored at −20° C. until evaluated by GC-FID using the ω-OH FFA method was carried out as follows: 1 μL of sample was injected onto an analytical column (DB-1, 10 m×180 μm×0.2 μM film thickness, available from JW 121-101A) in an Agilent 7890A GC Ultra device (Agilent, Santa Clara, CA) with a flame ionization detector (FID) with a 1-20 split. The instrument was set up to detect and quantify $C_{10}$ to $C_{19}$ fatty acids and ω-hydroxy fatty acids. The protocol detailed above represents standard conditions, which may be modified as necessary to optimize the analytical results.

Building Error Prone Libraries

Standard techniques known to those of skill in the art were used to prepare error prone libraries. In one example, the vector backbone was prepared using restriction endonucleases in the vector, while the creation of diversity in the DNA insert was generated by PCR amplification from a DNA template under conditions favoring the incorporation of mismatched nucleotides. In one approach, the cloning of the vector backbone and a DNA insert with diversity was performed using the INFUSION Cloning System (Clontech Laboratories, Inc., Mountain View, CA), according to the manufacturer's protocol.

Building Saturation Libraries

Standard techniques known to those of skill in the art were used to prepare saturation libraries. In one example, the vector backbone was prepared using restriction endonucleases in the vector, while the creation of diversity in the DNA insert was generated using degenerate primers. In one approach, the cloning of the vector backbone and a DNA insert with diversity was performed using INFUSION Cloning System (Clontech Laboratories, Inc., Mountain View, CA) according to the manufacturer's protocol.

Building Combination Libraries

Mutations identified as beneficial were combined to provide CYP153-reductase hybrid fusion polypeptide variants (e.g., CYP153A-RedRhF hybrid protein variants) with further improvements in the production of ω-OH fatty acid derivative species. Standard techniques known to those of skill in the art were used to prepare the combination libraries. In one example, the vector backbone was prepared using restriction endonucleases in the vector, while the creation of diversity in the DNA insert was generated using primers to introduce the desired mutations. As described above, in one approach, the cloning of the vector backbone and a DNA insert with diversity was performed using INFUSION Cloning System (Clontech Laboratories, Inc., Mountain View, CA), according to manufacturer's protocol. Combination libraries can be generated using the transfer PCR (tPCR) protocol (Erijman et al. (2011) *J. Structural Bio.* 175:171-177).

Library Screening

Once the library diversity was generated in an error-prone, saturation library or combination library, it was screened using one of the methods described above. Two types of hits were identified: (1) increased amount of ω-hydroxy fatty acids (ωOH FFA titer); and/or (2) increased conversion of fatty acids to ω-hydroxy fatty acids. The mutations in the hybrid cyp153A-RedRhF protein variants within each hit were identified by sequencing, using standard techniques routinely employed by those of skill in the art. Tables 23, 24 and 25 below list the mutations (hits) identified as beneficial in saturation libraries.

Example 14: Strain and Plasmid Construction for Library Screening

This example describes the strains and plasmids constructed for saturation or combinatorial mutagenesis library screening.

A gene coding for a hybrid-fusion protein made of the CYP153A(G307A) P450 catalytic protein from *Marinobacter aquaeoli* and the c-terminal FMN- and Fe/S-containing reductase domain of P450RhF from *Rhodococcus* sp. NCIMB9784 was created as follows: The cyp165A(G307A)_Maqu gene was amplified from genomic DNA and fused with a codon-optimized synthetic P450RhF reductase domain by cross-over PCR. The resulting fusion gene (SEQ ID NO: 5) was cloned into a pACYC-derivative (i.e., p15A replicon, kanamycin resistance marker) such that its transcription was controlled by the IPTG-inducible Ptrc promoter. The plasmid was named pEP125 (see Table 22, infra). The gene coding for the CYP153A(G307A)-Red450RhF hybrid fusion protein was also amplified from pEP125 and cloned into a pCL1920-derivative vector (SC101 replicon, spectinomycin resistance marker), such that its transcription was controlled by the IPTG-inducible Ptrc promoter and it formed an operon with genes coding for a plant thioesterase (fatB1), a variant of 3-keto-acyl-ACP synthase (fabB) and a transcriptional regulator (fadR). The plasmid was named pLC81 (see Table 22, infra).

Additional plasmids were created as follows: The gene coding a plant thioesterase (fatB1) from *Umbellularia californica* was synthesized as codon-optimized DNA and cloned into a pCL1920-derivative vector (SC101 replicon, spectinomycin resistance marker), such that its transcription was controlled by the IPTG-inducible Ptrc promoter and it formed an operon with genes coding for acetyl-CoA carboxylase (accDACB), biotin ligase (birA) and a acyl-carrier protein. The plasmid was named pNH305 (see Table 22, infra). Plasmid pAS033 was created by replacing fatB1 in pNH305 with a codon-optimized synthetic plant thioesterase (fatA3) from *Arabidopsis thaliana* (see Table 22, infra). Plasmid pEP146 was created by replacing fatB1 in pLC81 with a codon-optimized synthetic plant thioesterase (fatA3) from *Arabidopsis thaliana* (see Table 22, infra). pEP146 also carried a mutation in the plasmid encoded repA protein.

Base strains used for plasmid transformation were GLP077 and BZ128. Briefly, the genome of base strain GLPH077 was manipulated as follows: the acyl-CoA dehydrogenase (fadE) gene was deleted and a transcriptional regulator (fadR) and a synthetic fatty acid biosynthesis operon were overexpressed. Briefly, the genome of base strain BZ128 was manipulated as follows: the fadE (acyl-CoA dehydrogenase) gene was deleted and a synthetic fatty acid biosynthesis operon, a β-hydroxy fatty acyl-ACP dehydratase (fabZ) and a variant of a thioesterase (tesA) were overexpressed. In addition, the strain had previously been subjected to transposon as well as N-methyl-N'-nitro-N-nitrosoguanidine (NTG) mutagenesis and screening.

TABLE 22

| Plasmids used for Library Screening | |
| --- | --- |
| Plasmid | Description |
| pAS033 | pCL-fatA3_Atal-accDCBAbirA_Cglu-acp_Ecol |
| pEP125 | pACYC-cyp153A(G307A)_Maqu-RedRhF_Rhod |
| pNH305 | pCL-fatB1_Ucal-accDCBAbirA_Cglu-acp_Ecol |
| pLC81 | pCL- cyp153A(G307A)_Maqu-RedRhF_Rhod-fatB1_Ucal-fadB_Ecol-fadR_Ecol |
| pEP146 | pCL*- cyp153A(G307A)_Maqu-RedRhF_Rhod-fatA3-Atal-fadB_Ecol-fadR_Ecol |

The hybrid cyp153A(G307A)-Red450RhF fusion protein was tested to see if expression in host cells could produce ω-OH fatty acid derivatives. A microorganism expressing SEQ ID NO: 5 was capable of producing over a 1 g/L of ω-OH fatty acid derivatives from glucose. Thus, this engineered enzyme was selected for further evolution studies.

Example 15: Saturation Libraries of the P50 Catalytic Domain of cyp153A(G307A)-Red450RhF Fusion Protein A full saturation library of the P450 catalytic domain of CYP153A-Red450RhF fusion protein, was built and screened for variants that showed improvements over CYP153A(G307A)-Red450RhF (i.e., the template polypeptide). G307A (a glycine residue replaces an alanine in position 307) is a beneficial mutation that improves ω-hydroxylase activity of CYP153A (see Honda Malca et al. (2012) Chem. Commun. 48:5115). The selection criteria for hits was (1) increased amount of ω-hydroxy fatty acids (ωOH FFA titer); and/or (2) increased conversion of fatty acids to ω-hydroxy fatty acids.

Standard techniques known to those of skill in the art were used to prepare saturation libraries. Plasmids pEP125 and pLC81 (see Table 22, supra) were used to make the full saturation libraries. Three saturation libraries were screened: For the first library pEP125 was transformed together with pNH305 into strain GLPH077, for the second library pLC81 was transformed into BZ128, and for the third library pEP125 was transformed together with pAS.033 into GLPH077Strain. The 1st and 2nd library were screened in particular for improved variants in ω-hydroxy dodecanoic acid formation and the 3rd library was screened in particular for improved variants in ω-hydroxy hexadecenoic acid formation. The libraries were screened using one of the standard protocols described above. The improved variants are shown in Tables 23 through 25 below (infra). In particular, variants of position 141 were identified multiple times and were found to be significantly improved enzymes both for ω-hydroxy dodecanoic acid and ω-hydroxy hexadecenoic acid formation.

TABLE 23

Summary of Improved Variants from 1st Site Saturation Library
of the Catalytic Domain of CYP153A(G307A)-Red450RhF

| ω-OH FFA | Total FAS | % ω-OH FFA | FIOC | % C12:0 ω-OH in C12:0 | FIOC | Amino Acids | Codons |
|---|---|---|---|---|---|---|---|
| 1346.3 | 2236.6 | 60.2 | 1.33 | 83.1 | 1.08 | V141Q | GTG/CAG |
| 1201.1 | 2149.3 | 55.9 | 1.23 | 84.1 | 1.10 | D134G | GAC/GGG |
| 1106.2 | 2006.9 | 55.1 | 1.22 | 82 | 1.07 | R40H | AGG/CAC |
| 1007.9 | 1839.7 | 54.8 | 1.21 | 86.1 | 1.12 | V141I | GTG/ATC |
| 962.5 | 1791.2 | 53.7 | 1.19 | 81.1 | 1.06 | K41V | AAG/GTG |
| 1228.6 | 2298.6 | 53.4 | 1.18 | 80.2 | 1.05 | M419V | ATG/GTC |
| 1046.8 | 1958.5 | 53.4 | 1.18 | 80.1 | 1.05 | V154A | GTG/GCC |
| 990.7 | 1865.4 | 53.1 | 1.17 | 84.9 | 1.11 | D134G | GAC/GGT |
| 1203.1 | 2313.1 | 52 | 1.15 | 81.6 | 1.07 | D134G | GAC/GGG |
| 908.7 | 1773.2 | 51.2 | 1.13 | 80.3 | 1.05 | I11C | ATT/TGC |
| 1020.1 | 2057 | 49.6 | 1.09 | 81.4 | 1.06 | R205L | CGC/TTG |
| 1256 | 2688.4 | 46.7 | 1.03 | 72.6 | 0.95 | L304W | CTC/TGG |
| 883.2 | 1960.8 | 45.3 | 1.00 | 76.6 | 1.00 | | |

FIOC: Fold improvement over control; control is bold

TABLE 24

Summary of Improved Variants from 2nd site Saturation Library
of the Catalytic Domain of CYP153A(G307A)-Red450RhF

| Mutation 1 | Mutation 2 | Total ω-OH FFA | Total FAS | % ω-OH FFA | FIOC | % C12:0 ω-OH in C12:0 FAS | FIOC |
|---|---|---|---|---|---|---|---|
| V415R | 0 | 928.10 | 2880.10 | 32.23 | 1.85 | 33.29 | 1.96 |
| V415R | 0 | 941.13 | 2980.97 | 31.58 | 1.81 | 32.98 | 1.94 |
| V154A | 0 | 694.63 | 2959.63 | 23.47 | 1.35 | 23.06 | 1.36 |
| V154A | 0 | 716.00 | 2963.77 | 24.16 | 1.39 | 23.88 | 1.40 |
| V154A | 0 | 686.93 | 2926.97 | 23.47 | 1.35 | 23.40 | 1.38 |
| V141M | E142Q | 717.80 | 2873.73 | 24.98 | 1.44 | 28.51 | 1.68 |
| V141I | 0 | 749.07 | 2971.23 | 25.21 | 1.45 | 31.96 | 1.88 |
| V141I | 0 | 778.87 | 2886.77 | 26.98 | 1.55 | 34.27 | 2.02 |
| V141I | 0 | 754.67 | 2918.90 | 25.85 | 1.49 | 32.85 | 1.93 |
| V141I | R258Y | 672.13 | 2909.13 | 23.10 | 1.33 | 29.24 | 1.72 |
| V141I | 0 | 810.23 | 2912.67 | 27.83 | 1.60 | 35.86 | 2.11 |
| S233R | 0 | 720.13 | 2838.00 | 25.37 | 1.46 | 30.82 | 1.81 |
| S233R | 0 | 746.20 | 2912.97 | 25.61 | 1.47 | 31.15 | 1.83 |
| S233M | 0 | 735.57 | 2905.40 | 25.33 | 1.46 | 25.77 | 1.52 |
| S233N | 0 | 698.80 | 2915.17 | 23.97 | 1.38 | 24.40 | 1.44 |
| S233N | 0 | 732.47 | 2949.93 | 24.83 | 1.43 | 25.29 | 1.49 |
| S233N | 0 | 725.97 | 3018.60 | 24.05 | 1.38 | 24.76 | 1.46 |
| R82D | E271F | 629.03 | 2914.83 | 21.58 | 1.24 | 20.90 | 1.23 |
| R6F | R178N | 792.33 | 2845.17 | 27.85 | 1.60 | 28.56 | 1.68 |
| R6F | V141I | 833.13 | 2871.87 | 29.01 | 1.67 | 36.28 | 2.13 |
| R27L | 0 | 742.57 | 2857.53 | 25.99 | 1.49 | 26.10 | 1.54 |
| R178N | 0 | 701.17 | 2983.60 | 23.50 | 1.35 | 24.98 | 1.47 |
| Q129R | 0 | 675.07 | 2847.37 | 23.71 | 1.36 | 27.97 | 1.65 |
| Q129R | 0 | 812.23 | 3044.30 | 26.68 | 1.53 | 31.29 | 1.84 |
| Q129R | 0 | 660.53 | 2967.23 | 22.26 | 1.28 | 26.24 | 1.54 |
| P149R | S157V | 684.03 | 3011.80 | 22.71 | 1.31 | 23.04 | 1.36 |
| P149R | 0 | 771.40 | 2959.70 | 26.06 | 1.50 | 26.12 | 1.54 |
| P149R | 0 | 731.10 | 2966.13 | 24.65 | 1.42 | 24.75 | 1.46 |
| P149R | 0 | 757.97 | 3014.93 | 25.14 | 1.45 | 25.49 | 1.50 |
| P149R | 0 | 765.90 | 2963.50 | 25.84 | 1.49 | 26.16 | 1.54 |
| P149R | 0 | 734.30 | 2923.70 | 25.12 | 1.44 | 25.50 | 1.50 |
| P149R | 0 | 745.00 | 2993.83 | 24.88 | 1.43 | 25.47 | 1.50 |
| P136T | 0 | 724.53 | 2980.20 | 24.31 | 1.40 | 24.97 | 1.47 |
| P136T | 0 | 729.37 | 3017.67 | 24.17 | 1.39 | 24.90 | 1.46 |
| P136T | 0 | 678.33 | 2850.87 | 23.79 | 1.37 | 24.39 | 1.43 |
| P136C | 0 | 702.27 | 2947.23 | 23.83 | 1.37 | 25.36 | 1.49 |
| P136C | 0 | 689.77 | 3069.63 | 22.47 | 1.29 | 24.01 | 1.41 |
| N407A | 0 | 731.50 | 3042.77 | 24.04 | 1.38 | 24.56 | 1.44 |
| N407A | 0 | 704.47 | 3015.93 | 23.36 | 1.34 | 23.75 | 1.40 |
| M228R | 0 | 344.60 | 2992.27 | 11.52 | 0.66 | 18.33 | 1.08 |
| L168V | 0 | 793.20 | 2938.23 | 27.00 | 1.55 | 27.84 | 1.64 |
| G161P | 0 | 718.33 | 2938.47 | 24.45 | 1.41 | 24.28 | 1.43 |
| G161A | 0 | 639.93 | 2943.40 | 21.74 | 1.25 | 21.65 | 1.27 |
| G138F | N407A | 667.93 | 2825.43 | 23.64 | 1.36 | 26.09 | 1.53 |
| F116R | V415R | 678.77 | 2854.97 | 23.78 | 1.37 | 24.14 | 1.42 |
| E142R | 0 | 663.67 | 2925.83 | 22.68 | 1.30 | 22.86 | 1.34 |
| E142R | 0 | 628.03 | 2930.57 | 21.43 | 1.23 | 21.62 | 1.27 |

TABLE 24-continued

Summary of Improved Variants from $2^{nd}$ site Saturation Library
of the Catalytic Domain of CYP153A(G307A)-Red450RhF

| Mutation 1 | Mutation 2 | Total ω-OH FFA | Total FAS | % ω-OH FFA | FIOC | % C12:0 ω-OH in C12:0 FAS | FIOC |
|---|---|---|---|---|---|---|---|
| E142R | 0 | 639.23 | 2972.03 | 21.51 | 1.24 | 21.86 | 1.29 |
| D153G | 0 | 787.87 | 3018.90 | 25.13 | 1.50 | 26.94 | 1.58 |
| D153G | 0 | 746.20 | 3039.10 | 24.55 | 1.41 | 25.31 | 1.49 |
| 0 | 0 | 543.65 | 3117.75 | 17.44 | 1.00 | 17.04 | 1.00 |

FIOC: Fold improvement over control; control is bold

TABLE 25

Summary of Improved Variants from $3^{rd}$ Site Saturation Library of the Catalytic Domain of CYP153A(G307A)-Red450RhF

| ω-OH FFA | Total FAS | % ω-OH FFA | FIOC | % C16:0 ω-OH in C16:0 | FIOC | % C16:1 ω-OH in C16:1 | FIOC | Amino Acids | Codons |
|---|---|---|---|---|---|---|---|---|---|
| 1298.5 | 2342.5 | 55.43 | 1.53 | 64.61 | 1.33 | 49.02 | 2.00 | N309R | AAC/CGG |
| 1095.9 | 2374.3 | 46.16 | 1.28 | 58.36 | 1.20 | 34.41 | 1.40 | V141G | GTG/GGG |
| 1564 | 3448.1 | 45.36 | 1.25 | 62.78 | 1.29 | 32.88 | 1.34 | L132T | CTC/ACT |
| 1092.9 | 2391.4 | 45.70 | 1.26 | 60.82 | 1.25 | 32.96 | 1.34 | F144R | TTC/AGG |
| 1170.5 | 2529.6 | 46.27 | 1.28 | 62.41 | 1.28 | 31.91 | 1.30 | I131L | ATT/TTG |
| 1232.9 | 2685.8 | 45.90 | 1.27 | 55.17 | 1.13 | 37.63 | 1.53 | G308W | GGC/TGG |
| 931.1 | 2570.1 | 36.2 | 1.00 | 48.70 | 1.00 | 24.53 | 1.00 | | |

FIOC: Fold improvement over control; control is bold

Example 16: Partial Site Saturation Libraries of the Reductase Domain of CYP153A(G307A)-Red450RhF Fusion Protein A partial saturation library (every $10^{th}$ amino acid was mutated) of the reductase domains of hybrid CYP153A-Red450RhF fusion protein, was built and screened for variants that showed improvements over CYP153A(V141I, A231T, G307A)-Red450RhF (SEQ ID NO: 32), a variant identified in the site saturation mutagenesis library of the catalytic P450 CYP153A domain. The selection criteria for hits was (1) increased amount of ω-hydroxy dodecanoic acid (ωOH FFA titer); and/or (2) increased conversion of dodecanoic acid to ω-hydroxy dodecanoic acid. Standard techniques known to those of skill in the art were used to prepare saturation libraries. For the library, pLC81 harboring CYP153A(V141I, A231T, G307A)-Red450RhF was transformed into BZ128. The library was screened using one of the standard protocols described above. The improved variants are shown in Table 26 below. In particular the variants A796V (SEQ ID: 42) and P666A were significantly improved enzymes.

TABLE 26

Summary of Improved Variants from a Partial
Saturation Library of the Reductase Domain of
CYP153A(V141I A231T G307A)-Red450RhF

| RhF Mutation | ω-OH FFA | FAS | % ω-OH FFA | FIOC | C12:0 ω-OH in C12:0 FAS | FIOC |
|---|---|---|---|---|---|---|
| P666K | 1012.1 | 2945.5 | 34.36 | 1.09 | 44.08 | 1.07 |
| P666A | 1575.9 | 2918.7 | 53.99 | 1.71 | 68.35 | 1.66 |
| T516E | 1150.4 | 2966.2 | 38.78 | 1.23 | 49.01 | 1.19 |

TABLE 26-continued

Summary of Improved Variants from a Partial
Saturation Library of the Reductase Domain of
CYP153A(V141I A231T G307A)-Red450RhF

| RhF Mutation | ω-OH FFA | FAS | % ω-OH FFA | FIOC | C12:0 ω-OH in C12:0 FAS | FIOC |
|---|---|---|---|---|---|---|
| V696K | 983.4 | 2955.4 | 33.27 | 1.05 | 43.02 | 1.05 |
| 0 | 950.3 | 3004.6 | 31.63 | 1.00 | 41.13 | 1.00 |
| A796V | 2458.0 | 3884.7 | 63.27 | 1.81 | 76.58 | 1.70 |
| 0 | 1363.7 | 3905.2 | 34.92 | 1.00 | 44.96 | 1.00 |

FIOC: Fold improvement over control; control is bold

Example 17: Combinatorial Library of the Reductase Domain of CYP153A(G307A)-Red450RhF Fusion Protein Beneficial mutations identified in the partial saturation library of the reductase domain (Example 17) were the basis of a combination library to further improve CYP153A (G307A)-Red450RhF fusion protein. The selection criteria was (1) increased amount of ω-hydroxy dodecanoic acid (ωOH FFA titer); and/or (2) increased conversion of dodecanoic acid to ω-hydroxy dodecanoic acid.

The combination library was constructed in pLC81 harboring CYP153A(V141I, A231T, G307A)-Red450RhF (SEQ ID: 32) and transformed into BZ128. Standard techniques known to those of skill in the art were used to prepare combination libraries. The library was screened using one of the standard protocols described above. The improved variants are shown in Table 27 below.

TABLE 27

| Summary of Improved Variants from a Combination Library of the Reductase Domain of CYP153A(V141I, A231T, G307A)-Red450RhF | | | | | | | |
|---|---|---|---|---|---|---|---|
| P450 Mutation | RhF Mutation | ω-OH FFA | FAS | % ω-OH FFA | FIOC | % C12:0 ω-OH in C12:0 FAS | FIOC |
| 141I, 231T | T516G, P666M, A769V | 851 | 983 | 86.8 | 1.29 | 88.3 | 1.23 |
| 141I, 231T | T516G, P666H, A769V | 1557 | 2214 | 69.2 | 1.03 | 73.1 | 1.02 |
| 141I, 231T | T516V, P666D, A769V | 1491 | 1999 | 74.5 | 1.11 | 76.9 | 1.07 |
| 141I, 231T | P665M, V696T | 916.88 | 1125 | 81.4 | 1.21 | 82.9 | 1.15 |
| 141I, 231T | A769V | 1528.33 | 2280 | 67.1 | 1.00 | 71.8 | 1.00 |

FIOC: Fold improvement over control; control is bold

Example 18: Combinatorial Library of the Catalytic and Reductase Domain of CYP153A(G307A)-Red450RhF Fusion Protein Beneficial mutations identified in the saturation libraries (Example 16 and 17) were the basis of a combination library to further improve CYP153A(G307A)-Red450RhF fusion protein. The selection criteria was (1) increased amount of ω-hydroxy dodecanoic acid (ωOH FFA titer); and/or (2) increased conversion of dodecanoic acid to ω-hydroxy dodecanoic acid. The combination library was constructed in pLC81 and transformed into BZ128. Standard techniques known to those of skill in the art were used to prepare combination libraries. The library was screened using one of the standard protocols described above. The best two improved variants are shown in Table 28.

TABLE 28

| Best Improved Variants from a Combinatorial Library of CYP153A(G307A)-Red450RhF | | | | |
|---|---|---|---|---|
| Mutations | SEQ ID | ω-OH FFA* | FAS* | ω-OH FFA | C12:0 ω-OH in C12:0 FAS |
| R271, R82D, V141M, R178N, N407A | 34 | 2290.3 | 3665.1 | 62.4% | 74.1% |
| R271, R82D, V141M, R178N, N407A, A796V | 44 | 3499.5 | 4154.9 | 84.5% | 93.1% |

*Titer (mg/L) after 48 h

Example 19: Site Saturation Mutagenesis of the Position 141 and 309 of CYP153A(G307A, A796V)-Red450RhF It was noticed that changes in position 141 influenced substrate specificity. Therefore, a site saturation mutagenesis of these two positions were carried out in CYP153A (G307A, A796V)-Red450RhF. The selection criteria for the hits was (1) increased amount of ω-hydroxy hexadecenoic acid; and/or (2) increased conversion of hexadecenoic acid to ω-hydroxy hexadecenoic acid.

Figure 27:
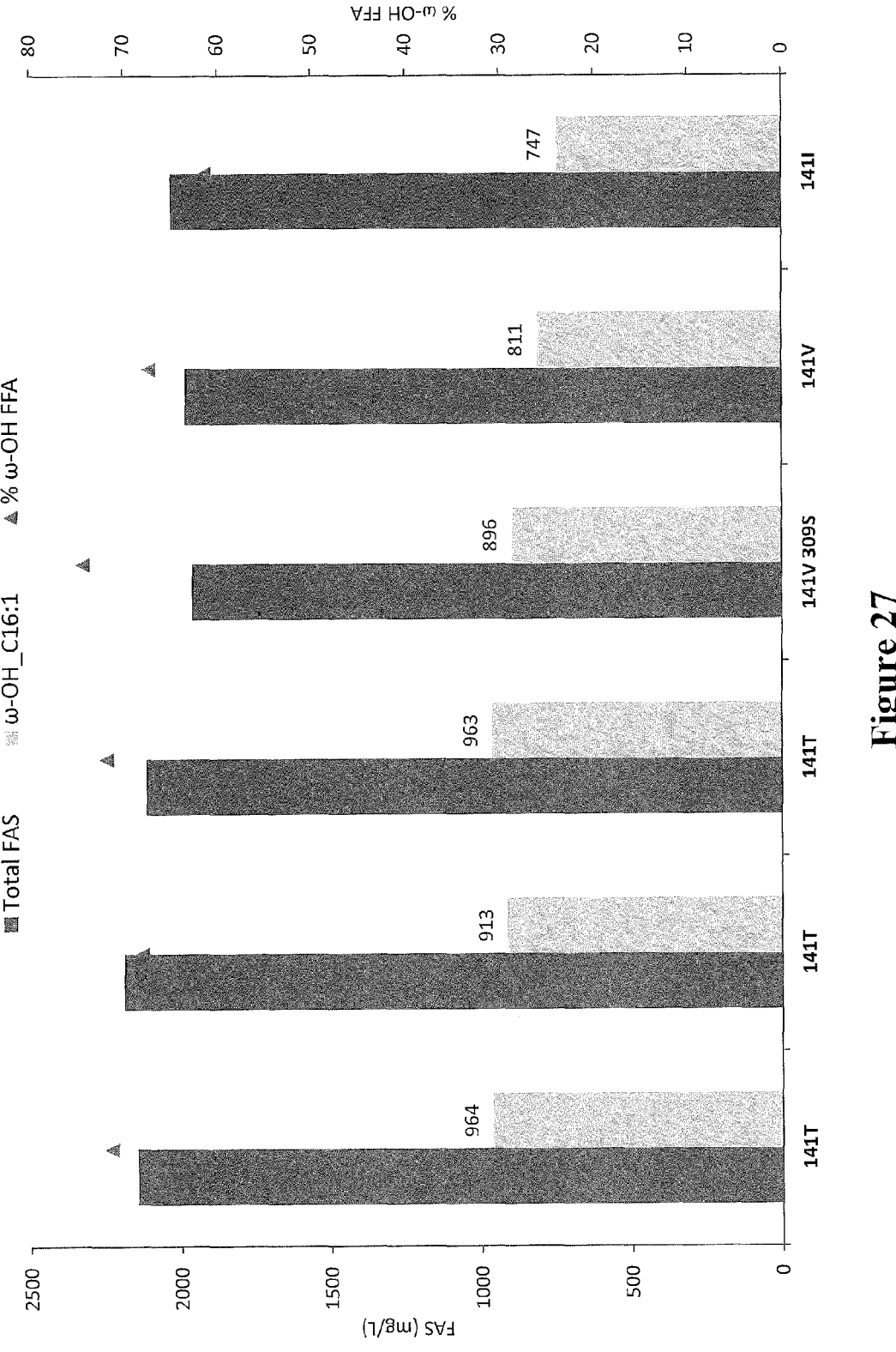
FIG. 27 shows the results of culturing microorganisms that express CYP153A-reductase hybrid fusion protein variants. As shown, the variants with V141T (SEQ ID: 46) produced the highest ω-hydroxy hexadecenoic acid titer and highest conversion from hexadecenoic acid.

For the library, pEP146 harboring CYP153A(G307A A796V)-Red450RhF (SEQ ID: 38) was transformed into BZ128. Standard techniques known to those of skill in the art were used to prepare site saturation libraries. The library was screened using one of the standard protocols described above. In particular, the variants with V141T (SEQ ID: 46) showed highest ω-hydroxy hexadecenoic acid titer and highest conversion from hexadecenoic acid (FIG. 27).

Example 20: High Titer Production of ω-Hydroxylated Fatty Acids from Glucose by Recombinant E. coli Strains Expressing an Improved Hybrid CYP153A-Red450RhF Fusion Protein This example shows high-yielding production of ω-hydroxy fatty acids from a renewable carbohydrate feedstock such as glucose, by recombinant E. coli strains expressing an improved hybrid CYP153A-Red450RhF fusion protein.

The gene coding for a variant hybrid CYP153A-Red450RhF fusion protein (SEQ ID No: 46) was cloned into a pCL1920-derivative vector (modified SC101 replicon, spectinomycin resistance marker), such that its transcription was controlled by the IPTG-inducible Ptrc promoter and it formed an operon with a plant thioesterase (fatA3), a variant of 3-keto-acyl-ACP synthase (fabB) and a transcriptional regulator (fadR). The plasmid was transformed into strain L439 resulting in strain stEP.798. Briefly, the genome of base strain L439 contained the following manipulations: the fadE (acyl-CoA dehydrogenase) gene was deleted and a synthetic fatty acid biosynthesis operon and a variant of a thioesterase (tesA) were overexpressed. In addition, the strain had previously been subjected to transposon as well as N-methyl-N'-nitro-N-nitrosoguanidine (NTG) mutagenesis and screening.

The strain was run in a bioreactor as follows: A cell bank vial of the strain was cultivated in a LB shake flask containing spectinomycin (115 mg/L) at 32° C. until the OD reading of the culture >1. A 5% v/v transfer of this culture is made into FA seed media (2 g/L ammonium chloride, 0.5 g/L sodium chloride, 0.3 g/L potassium phosphate monobasic, 1 mM magnesium sulfate, 0.1 mM calcium chloride, 20 g/L glucose, 1 mL/L of a trace elements solution, 10 mg/L of ferric citrate tribasic monohydrate, 100 mM of bis tris buffer, and 115 mg spectinomycin), and cultivated overnight at 32° C. This seed culture was then used to inoculate a prepared bioreactor for production. The initial bioreactor media for this process contained: 0.5 g/L ammonium chloride, 1 g/L sodium chloride, 4 g/L potassium phosphate monobasic, 2.2 g/L magnesium sulfate heptahydrate, 140 mg/L calcium chloride dihydrate, 10 mL/L of a trace elements solution, 80 mg/L of ferric citrate tribasic monohydrate, 0.6 mL/L of a trace vitamins solution, and 5 g/L of corn steep powder. Post-sterile additions to the bioreactor included: 0.2 mM aminolevulinic acid, 30 g/L of glucose, and 115 mg/L spectinomycin.

Prior to inoculation, the bioreactor parameters were stabilized and control loops turned on—dissolved oxygen setpoint: 30%; temperature setpoint: 29° C.; aeration setpoint: 0.5 vvm; pH setpoint: 6.9. Bioreactor was inoculated with 5% v/v of a seed culture and induced with 1 mM IPTG when the density of the culture was greater than OD 30. A complex glucose feed solution (586 g/L glucose, 2.2 g/L magnesium sulfate heptahydrate, 0.4 g/L potassium phosphate monobasic, 80 mg/L ferric citrate tribasic monohydrate, and 10 mL/L of a trace element solution) was fed to the culture at a maximal rate of 10 g/L glucose (based on the nominal culture volume), using a DO trigger to indicate to the controller when the media was exhausted of glucose. The bioreactor was sampled throughout the run and harvested after 72 hours of cultivation.

Figure 25:
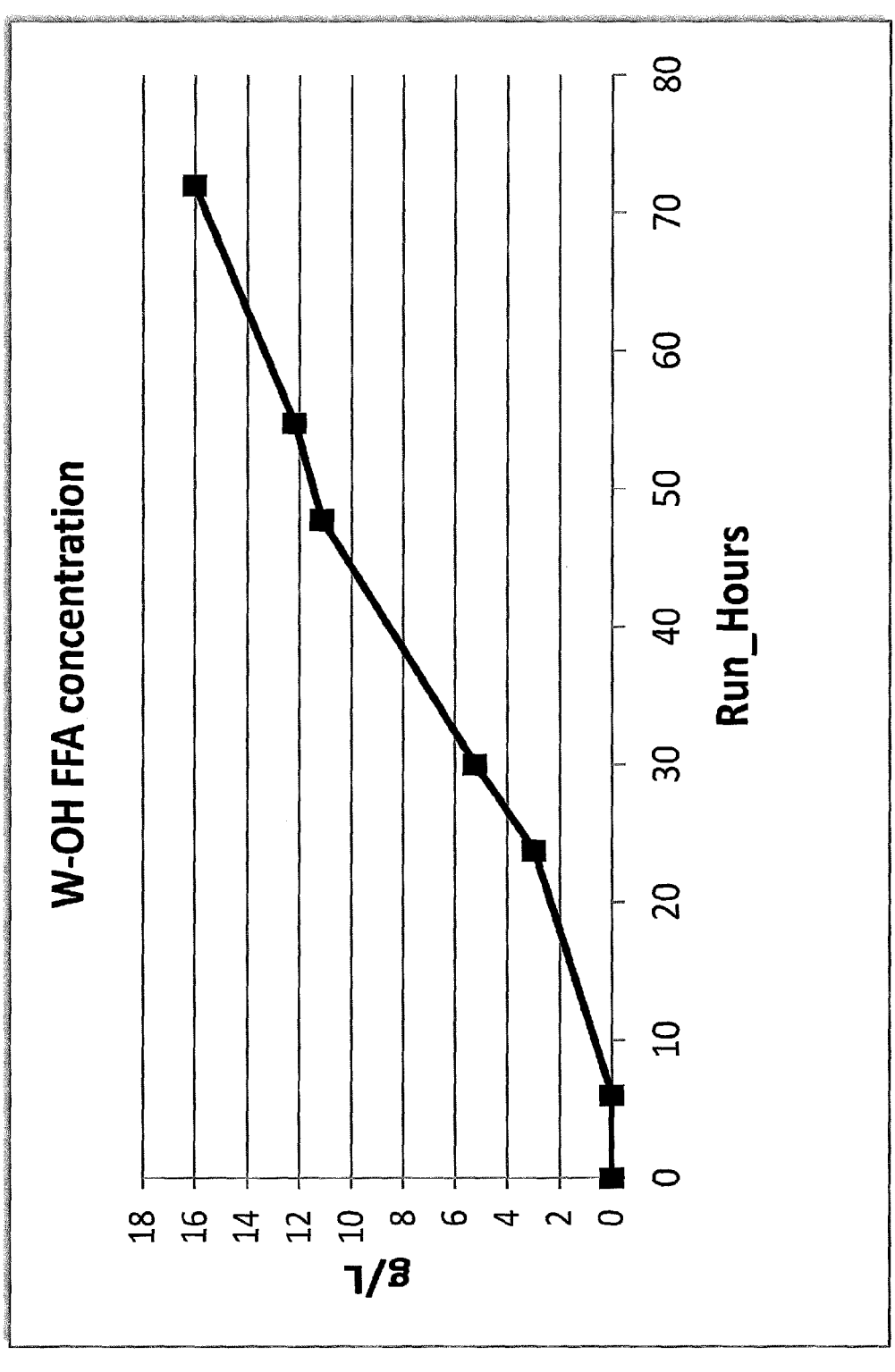
FIG. 25 shows ω-hydroxylated fatty acids produced by *E. coli* strain stEP.798.

FIG. 25 shows the amounts of ω-hydroxylated fatty acid produced by strain stEP.798 over the course of 72h at 30.5° C., which reached a high titer of 16.0 g/L after 72 h. The produced ω-hydroxylated fatty acids consisted of 63:1% ω-hydroxy hexadecenoic acid (C16:1), 26.4% ω-hydroxy hexadecanoic acid (C16:0), 7.6% ω-hydroxy tetradecanoic acid (C14:0), 1.9% ω-hydroxy tetradecenoic acid (C14:1) and small amounts of ω-hydroxy dodecenoic acid (C12:0) and ω-hydroxy dodecenoic acid (C12:1) (C12 less than 1%). In addition, stEP.798 produced 3.0 g/L fatty acids at 72h. In conclusion, expression of an improved hybrid CYP153A-Red450RhF fusion protein in a fatty acid-overproducing *E. coli* strain enabled high-titer ω-hydroxylated fatty acid production from a renewable carbohydrate feedstock.

Example 21: High Titer Production of α,ω-Dicacids from Glucose by Recombinant *E. coli* Strains Expressing an Improved Hybrid CYP153A-Red450RhF Fusion Protein This example shows high-yielding production of α,ω-dicacids from a renewable carbohydrate feedstock such as glucose, by recombinant *E. coli* strains expressing an improved hybrid CYP153A-Red450RhF fusion protein and heterologous alcohol oxidase (alkJ) and aldehyde dehydrogenase (alkH).

The gene coding for a variant hybrid CYP153A-Red450RhF fusion protein (SEQ ID NO: 42) was cloned into a pCL1920-derivative vector (modified SC101 replicon, spectinomycin resistance marker), such that its transcription was controlled by the IPTG-inducible Ptrc promoter and it formed an operon with a plant thioesterase (fatB1), an alcohol oxidase (alkJ), an aldehyde dehydrogenase (alkH), a variant of 3-keto-acyl-ACP synthase (fabB) and a transcriptional regulator (fadR). The plasmid was transformed into strain L1012 resulting in strain L1017. Briefly, the genome of base strain L1012 contained the following manipulations: the fadE (acyl-CoA dehydrogenase) and adhE (alcohol dehydrogenase) genes were deleted and a synthetic fatty acid biosynthesis operon, a β-hydroxy fatty acyl-ACP dehydratase (fabZ) and a variant of a thioesterase (tesA) were overexpressed. In addition, the strain had previously been subjected to transposon as well as of N-methyl-N'-nitro-N-nitrosoguanidine (NTG) mutagenesis and screening.

The strain was run in a bioreactor as follows: A cell bank vial of the strain was cultivated in a LB shake flask containing spectinomycin (115 mg/L) at 32° C. until the OD reading of the culture >1. A 2% v/v transfer of this culture is made into FA seed media (2 g/L ammonium chloride, 0.5 g/L sodium chloride, 0.3 g/L potassium phosphate monobasic, 1 mM magnesium sulfate, 0.1 mM calcium chloride, 20 g/L glucose, 1 mL/L of a trace elements solution, 10 mg/L of ferric citrate tribasic monohydrate, 100 mM of bis tris buffer, and 115 mg spectinomycin), and cultivated overnight at 32° C. This seed culture was then used to inoculate a prepared bioreactor for production. The initial bioreactor media for this process contained: 0.5 g/L ammonium chloride, 1 g/L sodium chloride, 4 g/L potassium phosphate monobasic, 2.2 g/L magnesium sulfate heptahydrate, 140 mg/L calcium chloride dihydrate, 10 mL/L of a trace elements solution, 80 mg/L of ferric citrate tribasic monohydrate, 0.6 mL/L of a trace vitamins solution, and 5 g/L of corn steep powder. Post-sterile additions to the bioreactor included: 0.2 mM aminolevulinic acid, 30 g/L of glucose, and 115 mg/L spectinomycin.

Prior to inoculation, the bioreactor parameters were stabilized and control loops turned on—dissolved oxygen setpoint: 30%; temperature setpoint: 31° C.; aeration setpoint: 0.5 vvm; pH setpoint: 6.9. The bioreactor was inoculated with 5% v/v of a seed culture and induced with 1 mM IPTG when the density of the culture is greater than OD 30. A complex glucose feed solution (586 g/L glucose, 2.2 g/L magnesium sulfate heptahydrate, 0.4 g/L potassium phosphate monobasic, 80 mg/L ferric citrate tribasic monohydrate, and 10 mL/L of a trace element solution) was fed to the culture as a 10 g/L bolus (based on the nominal culture volume), using a pH trigger to indicate to the controller when the media was exhausted of glucose. The bioreactor was sampled throughout the run and harvested after 48 hours of cultivation.

Figure 26:
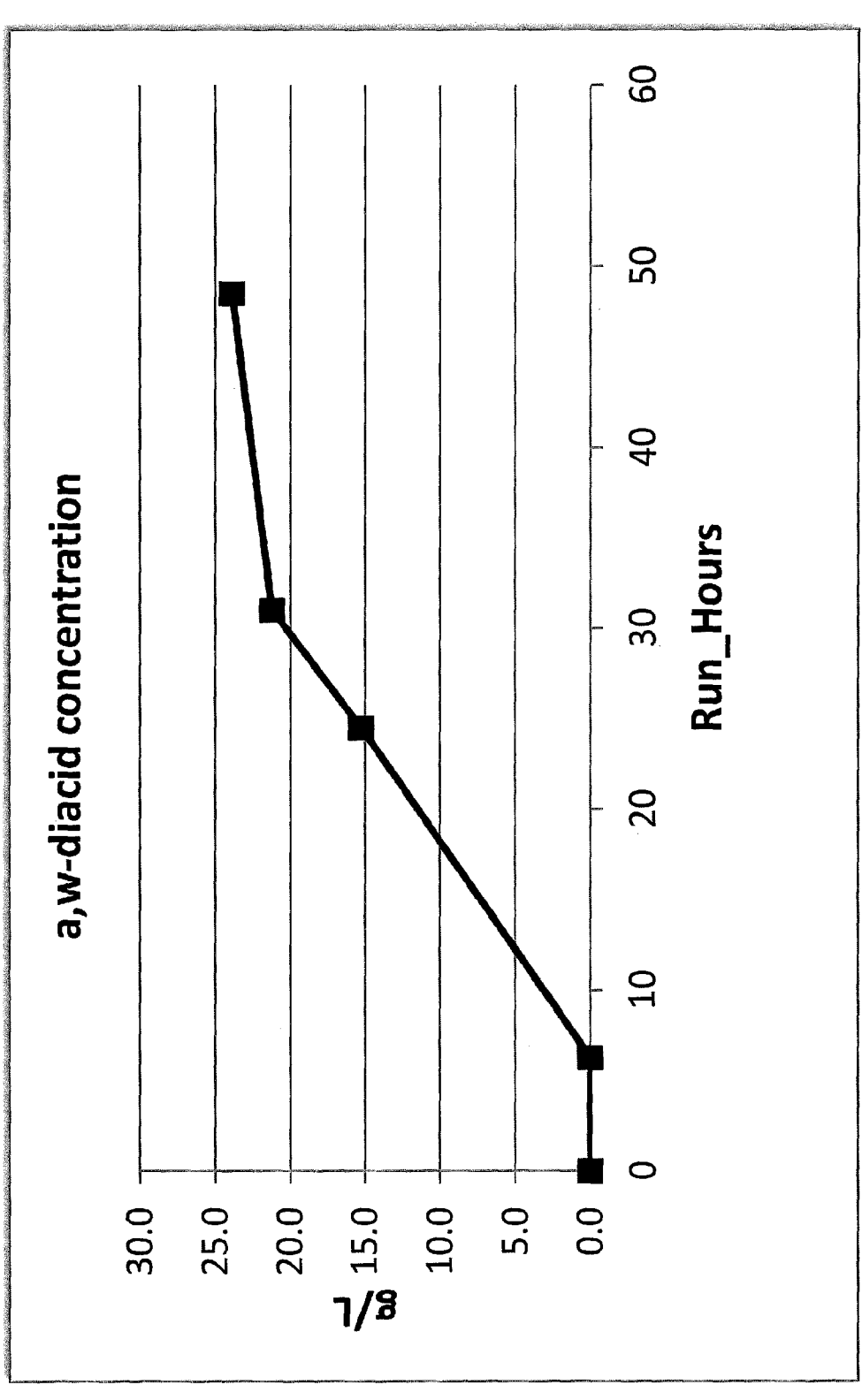
FIG. 26 shows α,ω-diacids produced by *E. coli* strain L1017.

FIG. 26 shows the amounts of α,ω-diacids produced by strain L1017 over the course of 48h at 30.5° C. The strain produced 21.2 g/L α,ω-diacids at 31h and reached a high titer of 23.9 g/L after 48 h. The produced α,ω-diacids consisted of 85.9% α,ω-dodecanoic acid (C12:0), 4.7% α,ω-dodecenoic acid (C12:1), 5.7% α,ω-tetradecanoic acid (C14:0), 2.9% α,ω-tetradecenoic acid (C14:1) and small amounts of α,ω-hexadecenoic acid (C16:1) (C16 less than 1%). In addition, stEP.798 produced 9.3 g/L fatty acids at 48h. Only trace amounts of ω-hydroxy fatty acids were detected. In conclusion, expression of an improved hybrid CYP153A-Red450RhF fusion protein in a fatty acid-overproducing *E. coli* strain with coexpression of alcohol oxidase (alkJ) and aldehyde dehydrogenase (alkH) enabled high-titer α,ω-diacids production from a renewable carbohydrate feedstock.

As is apparent to one with skill in the art, various modifications and variations of the above aspects and embodiments can be made without departing from the spirit and scope of this disclosure. Such modifications and variations are within the scope of this disclosure.

SEQUENCE LISTING

```
Sequence total quantity: 69
SEQ ID NO: 1              moltype = DNA   length = 1413
FEATURE                  Location/Qualifiers
source                   1..1413
                         mol_type = genomic DNA
                         organism = Marinobacter aquaeolei
SEQUENCE: 1
atgccaacac tgcccagaac atttgacgac attcagtccc gactgattaa cgccacctcc   60
```

-continued

```
agggtggtgc cgatgcagag gcaaattcag ggactgaaat tcttaatgag cgccaagagg   120
aagaccttcg gcccacgccg accgatgccc gaattcgttg aaacacccat cccggacgtt   180
aacacgctgg cccttgagga catcgatgtc agcaatccgt ttttataccg gcagggtcag   240
tggcgcgcct atttcaaacg gttgcgtgat gaggcgccgg tccattacca gaagaacagc   300
cctttcggcc ccttctggtc ggtaactcgg tttgaagaca tcctgttcgt ggataagagt   360
cacgacctgt tttccgccga gccgcaaatc attctcggtg accctccgga ggggctgtcg   420
gtggaaatgt tcatagcgat ggatccgccg aaacacgatg tgcagcgcag ctcggtgcag   480
ggagtagtgg caccgaaaaa cctgaaggag atggaggggc tgatccgatc acgcaccggc   540
gatgtgcttg acagcctgcc tacagacaaa ccctttaact gggtacctgc tgtttccaag   600
gaactcacag gccgcatgct ggcgacgctt ctggattttc cttacgagga acgccacaag   660
ctggttgagt ggtcggacag aatggcaggt gcagcatcgg ccaccggcgg ggagtttgcc   720
gatgaaaatg ccatgtttga cgacgcggca gacatggccc ggtctttctc caggctttgg   780
cgggacaagg aggcgcgccg cgcagcaggc gaggagcccg gtttcgattt gatcagcctg   840
ttgcagagca acaaagaaac gaaagacctg atcaatcggc cgatggagtt tatcggtaat   900
ttgacgctgc tcatagtcgg cggcaacgat acgacgcgca actcgatgag tggtggcctg   960
gtggccatga acgaatccc cagggaattt gaaaaattga aggcaaaacc ggagttgatt   1020
ccgaacatgg tgtcggaaat catccgctgg caaacgccgc tggcctatat cgccgaatc   1080
gccaagcagg atgtcgaact gggcgggcag accatcaaga agggtgatcg agttgtcatg   1140
tggtacgcgt cgggtaaccg ggacgagcgc aaatttgaca accccgatca gttcatcatt   1200
gatcgcaagg acgcacgaaa ccacatgtcg ttcggctatg gggttcaccg ttgcatgggc   1260
aaccgtctgc ctgaactgca actgcgcatc ctctgggaag aaatactcaa gcgttttgac   1320
aacatcgaag tcgtcgaaga gcccgagcgg gtgcagtcca acttcgtgcg gggctattcc   1380
aggttgatgg tcaaactgac accgaacagt taa                                1413
```

```
SEQ ID NO: 2              moltype = AA   length = 470
FEATURE                   Location/Qualifiers
source                    1..470
                          mol_type = protein
                          organism = Marinobacter aquaeolei
SEQUENCE: 2
MPTLPRTFDD IQSRLINATS RVVPMQRQIQ GLKFLMSAKR KTFGPRRPMP EFVETPIPDV   60
NTLALEDIDV SNPFLYRQGQ WRAYFKRLRD EAPVHYQKNS PFGPFWSVTR FEDILFVDKS   120
HDLFSAEPQI ILGDPPEGLS VEMFIAMDPP KHDVQRSSVQ GVVAPKNLKE MEGLIRSRTG   180
DVLDSLPTDK PFNWVPAVSK ELTGRMLATL LDFPYEERHK LVEWSDRMAG AASATGGEFA   240
DENAMFDDAA DMARSFSRLW RDKEARRAAG EEPGFDLISL LQSNKETKDL INRPMEFIGN   300
LTLLIVGGND TTRNSMSGGL VAMNEFPREF EKLKAKPELI PNMVSEIIRW QTPLAYMRRI   360
AKQDVELGGQ TIKKGDRVVM WYASGNRDER KFDNPDQFII DRKDARNHMS FGYGVHRCMG   420
NRLAELQLRI LWEEILKRFD NIEVVEEPER VQSNFVRGYS RLMVKLTPNS               470
```

```
SEQ ID NO: 3              moltype = DNA   length = 1413
FEATURE                   Location/Qualifiers
source                    1..1413
                          mol_type = genomic DNA
                          organism = Marinobacter aquaeolei
SEQUENCE: 3
atgccaacac tgcccagaac atttgacgac attcagtccc gactgattaa cgccacctcc   60
agggtggtgc cgatgcagag gcaaattcag ggactgaaat tcttaatgag cgccaagagg   120
aagaccttcg gcccacgccg accgatgccc gaattcgttg aaacacccat cccggacgtt   180
aacacgctgg cccttgagga catcgatgtc agcaatccgt ttttataccg gcagggtcag   240
tggcgcgcct atttcaaacg gttgcgtgat gaggcgccgg tccattacca gaagaacagc   300
cctttcggcc ccttctggtc ggtaactcgg tttgaagaca tcctgttcgt ggataagagt   360
cacgacctgt tttccgccga gccgcaaatc attctcggtg accctccgga ggggctgtcg   420
gtggaaatgt tcatagcgat ggatccgccg aaacacgatg tgcagcgcag ctcggtgcag   480
ggagtagtgg caccgaaaaa cctgaaggag atggaggggc tgatccgatc acgcaccggc   540
gatgtgcttg acagcctgcc tacagacaaa ccctttaact gggtacctgc tgtttccaag   600
gaactcacag gccgcatgct ggcgacgctt ctggattttc cttacgagga acgccacaag   660
ctggttgagt ggtcggacag aatggcaggt gcagcatcgg ccaccggcgg ggagtttgcc   720
gatgaaaatg ccatgtttga cgacgcggca gacatggccc ggtctttctc caggctttgg   780
cgggacaagg aggcgcgccg cgcagcaggc gaggagcccg gtttcgattt gatcagcctg   840
ttgcagagca acaaagaaac gaaagacctg atcaatcggc cgatggagtt tatcggtaat   900
ttgacgctgc tcatagtcgg cggcaacgat acgacgcgca actcgatgag tggtggcctg   960
gtggccatga acgaatccc cagggaattt gaaaaattga aggcaaaacc ggagttgatt   1020
ccgaacatgg tgtcggaaat catccgctgg caaacgccgc tggcctatat cgccgaatc   1080
gccaagcagg atgtcgaact gggcgggcag accatcaaga agggtgatcg agttgtcatg   1140
tggtacgcgt cgggtaaccg ggacgagcgc aaatttgaca accccgatca gttcatcatt   1200
gatcgcaagg acgcacgaaa ccacatgtcg ttcggctatg gggttcaccg ttgcatgggc   1260
aaccgtctgc ctgaactgca actgcgcatc ctctgggaag aaatactcaa gcgttttgac   1320
aacatcgaag tcgtcgaaga gcccgagcgg gtgcagtcca acttcgtgcg gggctattcc   1380
aggttgatgg tcaaactgac accgaacagt taa                                1413
```

```
SEQ ID NO: 4              moltype = AA   length = 470
FEATURE                   Location/Qualifiers
source                    1..470
                          mol_type = protein
                          organism = Marinobacter aquaeolei
SEQUENCE: 4
MPTLPRTFDD IQSRLINATS RVVPMQRQIQ GLKFLMSAKR KTFGPRRPMP EFVETPIPDV   60
NTLALEDIDV SNPFLYRQGQ WRAYFKRLRD EAPVHYQKNS PFGPFWSVTR FEDILFVDKS   120
HDLFSAEPQI ILGDPPEGLS VEMFIAMDPP KHDVQRSSVQ GVVAPKNLKE MEGLIRSRTG   180
```

```
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS             470

SEQ ID NO: 5              moltype = DNA  length = 2400
FEATURE                   Location/Qualifiers
misc_feature              1..2400
                          note = source = /note="Description of Artificial Sequence:
                          Synthetic polynucleotide"
source                    1..2400
                          mol_type = other DNA
                          organism = synthetic construct
SEQUENCE: 5
atgccaacac tgcccagaac atttgacgac attcagtccc gactgattaa cgccacctcc   60
agggtggtgc cgatgcagag gcaaattcag ggactgaaat tcttaatgag cgccaagagg  120
aagaccttcg gcccacgccg accgatgccc gaattcgttg aaacacccat ccgcgacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctgggtg accctccgga ggggctgtcg  420
gtggaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcgac cgatggagtt tatcggtaat  900
ttgacgctgc tcatagtcgc cggcaacgat acgacgcgca actcgatgag tggtggcctg  960
gtggccatga cgaattccc  cagggaattt gaaaaattga aggcaaaacc ggagttgatt 1020
ccgaacatgg tgtcggaaat catccgctgg caaacgccgc tggcctatat gcgccgaatc 1080
gccaagcagg atgtcgaact gggcggccag accatcaaga agggtgatcg agttgtcatg 1140
tggtacgcgt cgggtaaccg ggacgagcgc aaatttgaca accccgatca gttcatcatt 1200
gatcgcaagg acgcacgaaa ccacatgtcg ttcggctatg gggttcaccg ttgcatgggc 1260
aaccgtctgg ctgaactgca actgcgcatc ctctgggaag aaatactcaa gcgttttgac 1320
aacatcgaag tcgtcgaaga gcccgagcgg gtgcagtcca acttcgtgcg gggctattcc 1380
aggttgatgg tcaaactgac accgaacagt gtactccatc gtcatcaacc tgtcaccatc 1440
ggcgagccgg ccgctcgtgc tgtgagccgc acggtgaccg ttgagcgtct tgatcgcatt 1500
gccgacgatg tccttcgcct ggtccttcgc gatgctggag gtaaaaccct cccgacgtgg 1560
acgcctggcg ctcacatcga cctggatctg ggtgctctga gccgtcagta ttcgctctgc 1620
ggcgctccgg atgctccgtc gtacgaaatc gccgtgcact tagatccgga aagccgtggt 1680
ggaagccgct atattcatga acagctggaa gttggaagtc cgctgcgtat gcgtggccca 1740
cgcaaccatt tcgccctgga tccgggtgcg gaacattacg tgtttgttgc cggggggtatc 1800
ggcatcacgc cggtgctggc aatggcggat catgcccgtg cgcgtggttg gtcgtacgaa 1860
ctgcattatt gtggtcgtaa tcgtagcggt atggcttacc tggaacgcgt cgcgggacat 1920
ggtgaccgcg ctgccttgca cgtatctgaa gaaggcaccc gcattgatct ggcggcatta 1980
cttgctgaac cggcgccggg cgtgcaaatc tacgcctgcg gtccgggccg tttattagcg 2040
ggtcttgaag acgcgtctcg taattggccg gatggcgcgc ttcatgtgga gcatttcact 2100
tcgagtttag ccgcttttgga tccggatgtc gaacatgcct ttgatttgga gctgcgtgac 2160
tctggcctta ccgttcgcgt cgagccaact cagaccgttt tagacgcttt gcgtgcgaac 2220
aatatcgacg tcccgtcgga ttgcgaagag gggctgtgtg gttcttgcga gtagccgtt 2280
ctggatggcg aggttgatca ccgtgatacc gttctgacta aggccgagcg cgccgcgaat 2340
cgtcagatga tgacttgctg cagtcgtgca tgcggtgatc gtctggcgct gcgcctctaa 2400

SEQ ID NO: 6              moltype = AA  length = 799
FEATURE                   Location/Qualifiers
REGION                    1..799
                          note = source = /note="Description of Artificial Sequence:
                          Synthetic polypeptide"
source                    1..799
                          mol_type = protein
                          organism = synthetic construct
SEQUENCE: 6
MPTLPRTFDD IQSRLINATS RVVPMQRQIQ GLKFLMSAKR KTFGPRRPMP EFVETPIPDV   60
NTLALEDIDV SNPFLYRQGQ WRAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                             799
```

```
SEQ ID NO: 7            moltype = DNA  length = 2400
FEATURE                 Location/Qualifiers
misc_feature            1..2400
                        note = source = /note="Description of Artificial Sequence:
                        Synthetic polynucleotide"
source                  1..2400
                        mol_type = other DNA
                        organism = synthetic construct
SEQUENCE: 7
atgccaacac tgcccagaac atttgacgac attcagtccc gactgattaa cgccacctcc  60
agggtggtgc cgatgcagct gcaaattcag ggactgaaat tcttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
gtggaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga acgaattccc cagggaattt gaaaaattga aggcaaaacc ggagttgatt  1020
ccgaacatgg tgtcggaaat catccgctgg caaacgccgc tggcctatat cgcgccgaatc  1080
gccaagcagg atgtcgaact gggcggccag accatcaaga agggtgatcg agttgtcatg  1140
tggtacgcgt cgggtaaccg ggacgagcgc aaatttgaca accccgatca gttcatcatt  1200
gatcgcaagg acgacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaaaccct cccgacgtgg  1560
acgcctggcg ctcacatcga cctggatctg ggtgctctga gccgtcagta ttcgctctgc  1620
ggcgctccgg atgctccgtc gtacgaaatc gccgtgcact tagatccgga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cggggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt ggcgtgcaac  2220
aatatcgacg tcccgtcgga ttgcgaagag gggctgtgtg gttcttgcga gtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggcgct gcgcctctaa  2400

SEQ ID NO: 8            moltype = AA  length = 799
FEATURE                 Location/Qualifiers
REGION                  1..799
                        note = source = /note="Description of Artificial Sequence:
                        Synthetic polypeptide"
source                  1..799
                        mol_type = protein
                        organism = synthetic construct
SEQUENCE: 8
MPTLPRTFDD IQSRLINATS RVVPMQLQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                                799

SEQ ID NO: 9            moltype = DNA  length = 2400
FEATURE                 Location/Qualifiers
misc_feature            1..2400
                        note = source = /note="Description of Artificial Sequence:
```

```
                        Synthetic polynucleotide"
source                  1..2400
                        mol_type = other DNA
                        organism = synthetic construct
SEQUENCE: 9
atgccaacac tgcccagaac atttgacgac attcagtccc gactgattaa cgccacctcc  60
agggtggtgc cgatgcagag gcaaattcag ggactgaaat tcttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tgggacgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
gtggaaatgt tcatagcgat ggatccgccg aaacacgatg tgcagcgcag ctcggtgcag  480
ggagtagtgg caccgaaaaa cctgaaggag atggagggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga acgaattccc cagggaattt gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cgggtaaccg ggacgagcgc aaatttgaca acccgatca gttcatcatt  1200
gatcgcaagg acgcacgaaa ccacatgtcg ttcggctagg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgtcc ggtccttcgc gatgctggag gtaaaaccct cccgacgtgg  1560
acgcctggcg ctcacatcga cctggatctg ggtgctctga gccgtcagta ttcgctctgc  1620
ggcgctccgg atgctccgtc gtacgaaatc gccgtgcact tagatccgga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cgggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattacg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggcgct gcgcctctaa  2400
```

```
SEQ ID NO: 10          moltype = AA  length = 799
FEATURE                Location/Qualifiers
REGION                 1..799
                       note = source = /note="Description of Artificial Sequence:
                       Synthetic polypeptide"
source                 1..799
                       mol_type = protein
                       organism = synthetic construct
SEQUENCE: 10
MPTLPRTFDD IQSRLINATS RVVPMQRQIQ GLKFLMSAKR KTFGPRRPMP EFVETPIPDV  60
NTLALEDIDV SNPFLYRQGQ WDAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                                799
```

```
SEQ ID NO: 11          moltype = DNA  length = 2400
FEATURE                Location/Qualifiers
misc_feature           1..2400
                       note = source = /note="Description of Artificial Sequence:
                       Synthetic polynucleotide"
source                 1..2400
                       mol_type = other DNA
                       organism = synthetic construct
SEQUENCE: 11
```

```
atgccaacac tgcccagaac atttgacgac attcagtccc gactgattaa cgccacctcc   60
agggtggtgc cgatgcagag gcaaattcag ggactgaaat tcttaatgag cgccaagagg  120
aagaccttcg gcccacgccg accgatgccc gaattcgttg aaacacccat cccgacgtt   180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
atcgaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga acgaattccc cagggaattt gaaaaattga aggcaaaacc ggagttgatt 1020
ccgaacatgg tgtcggaaat catccgctgg caaacgcccg tggcctatat gcgccgaatc 1080
gccaagcagg atgtcgaact gggcggccag accatcaaga agggtgatcg agttgtcatg 1140
tggtacgcgt cgggtaaccg ggacgagcgc aaatttgaca accccgatca gttcatcatt 1200
gatcgcaagg acgcacgaaa ccacatgtcg ttcggctatg gggttcaccg ttgcatgggc 1260
aaccgtctgg ctgaactgca actgcgcatc ctctgggaag aaatactcaa gcgtttttgac 1320
aacatcgaag tcgtcgaaga gccccgagcgg gtgcagtcca acttcgtgcg gggctattcc 1380
aggttgatgg tcaaactgac accgaacagt gtactccatc gtcatcaacc tgtcaccatc 1440
ggcgagccgg ccgctcgtgc tgtgagccgc acggtgaccg ttgagcgtct tgatcgcatt 1500
gccgacgatg tccttcgcct ggtccttcgc gatgctgagg gtaaaaccct cccgacgtgg 1560
acgcctggcg ctcacatcga cctggatctg ggtgctctga gccgtcagta ttcgctctgc 1620
ggcgctccgg atgctccgtc gtacgaaatc gccgtgcact tagatccgga aagccgtggt 1680
ggaagccgct atattcatga acagctggaa gttggaagtc cgctgcgtat gcgtggccca 1740
cgcaaccatt tcgccctgga tccggggtgcg gaacattacg tgtttgttgc cggggggtatc 1800
ggcatcacgc cggtgctggc aatggcggat catgcccgtg cgcgtggttg gtcgtacgaa 1860
ctgcattatt gtggtcgtaa tcgtagcggt atggcttacc tggaacgcgt cgcgggacat 1920
ggtgaccgcg ctgccttgca cgtatctgaa gaaggcaccc gcattgatct ggcggcatta 1980
cttgctgaac cggcgccggg cgtgcaaatc tacggcctgc ggtccgggccg tttattagcg 2040
ggtcttgaag acgcgtctcg taattggccg gatggcgcgc ttcatgtgga gcatttcact 2100
tcgagtttag ccgctttgga tccggatgtc gaacatgcct ttgatttgga gctgcgtgac 2160
tctgccctta ccgttcgcgt cgagccaact cagaccgttt tagacgcttt gcgtgcgaac 2220
aatatcgacg tcccgtcgga ttgcgaagag gggctgtgtg gttcttgcga agtagccgtt 2280
ctggatggcg aggttgatca ccgtgatacc gttctgacta aggccgagcg cgccgcgaat 2340
cgtcagatga tgacttgctg cagtcgtgca tgcggtgatc gtctggcgct gcgcctctaa 2400
```

SEQ ID NO: 12          moltype = AA  length = 799
FEATURE                Location/Qualifiers
REGION                 1..799
                       note = source = /note="Description of Artificial Sequence:
                       Synthetic polypeptide"
source                 1..799
                       mol_type = protein
                       organism = synthetic construct SEQUENCE: 12
```
MPTLPRTFDD IQSRLINATS RVVPMQRQIQ GLKFLMSAKR KTFGPRRPMP EFVETPIPDV   60
NTLALEDIDV SNPFLYRQGQ WRAYFKRLRD EAPVHYQKNS PFGPFWSVTR FEDILFVDKS  120
HDLFSAEPQI ILGDPPEGLS IEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                                799
```

SEQ ID NO: 13          moltype = DNA  length = 2400
FEATURE                Location/Qualifiers
misc_feature           1..2400
                       note = source = /note="Description of Artificial Sequence:
                       Synthetic polynucleotide"
source                 1..2400
                       mol_type = other DNA
                       organism = synthetic construct SEQUENCE: 13
```
atgccaacac tgcccagaac atttgacgac attcagtccc gactgattaa cgccacctcc   60
agggtggtgc cgatgcagag gcaaattcag ggactgaaat tcttaatgag cgccaagagg  120
aagaccttcg gcccacgccg accgatgccc gaattcgttg aaacacccat cccgacgtt   180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
```

-continued

```
cctttcggcc ccttctggtc ggtaactcgg tttgaagaca tcctgttcgt ggataagagt   360
cacgacctgt tttccgccga gccgcaaatc attctcggtg accctccgga ggggctgtcg   420
caggaaatgt tcatagcgat ggatccgccg aaacacgatg tgcagcgcag ctcggtgcag   480
ggagtagtgg caccgaaaaa cctgaaggag atggaggggc tgatccgatc acgcaccggc   540
gatgtgcttg acagcctgcc tacagacaaa ccctttaact gggtacctgc tgtttccaag   600
gaactcacag gccgcatgct ggcgacgctt ctggattttc cttacgagga acgccacaag   660
ctggttgagt ggtcggacag aatggcaggt gcagcatcgg ccaccggcgg ggagtttgcc   720
gatgaaaatg ccatgtttga cgacgcggca gacatggccc ggtctttctc caggctttgg   780
cgggacaagg aggcgcgccg cgcagcaggc gaggagcccg gtttcgattt gatcagcctg   840
ttgcagagca acaaagaaac gaaagacctg atcaatccgc cgatggagtt tatcggtaat   900
ttgacgctgc tcatagtcgc cggcaacgat acgacgcgca actcgatgag tggtggcctg   960
gtggccatga acgaattccc cagggaattt gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga aggttgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgacggg gtgcagtcca acttcgtgcg gggctattcc  1380
aggttgatgg tcaaactgac accgaacagt gtactccatc gtcatcaacc tgtcaccatc  1440
ggcgagccgc ccgctcgtgc tgtgagccgc acggtgaccg ttgagcgtct tgatcgcatt  1500
gccgacgatg tccttcgcct ggtccttcgc gatgctggag gtaaaaccct cccgacgtgg  1560
acgcctggcg ctcacatcga cctggatctg ggtgctctga gccgtcagta ttcgctctgc  1620
ggcgctccgg atgctccgtc gtacgaaatc gccgtgcact agatccgga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cggggggtatc  1800
ggcatcacgc cggtgctggc aatggcggat catgcccgtg gcgctggttg gtcgtacgaa  1860
ctgcattatt gtggtcgtaa tcgtagcggt atggcttacc tggaacgcgt gcgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acggcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggca aggttgatca ccgtgatacc gttctgacta aggccgagcg cgccgcgaat  2340
cgtcagatga tgacttgctg cagtcgtgca tgcggtgatc gtctggcgct cgcgcctctaa  2400
```

SEQ ID NO: 14                    moltype = AA   length = 799
FEATURE                          Location/Qualifiers
REGION                           1..799
                                 note = source = /note="Description of Artificial Sequence:
                                 Synthetic polypeptide"
source                           1..799
                                 mol_type = protein
                                 organism = synthetic construct
SEQUENCE: 14
MPTLPRTFDD IQSRLINATS RVVPMQRQIQ GLKFLMSAKR KTFGPRRPMP EFVETPIPDV   60
NTLALEDIDV SNPFLYRQGQ WRAYFKRLRD EAPVHYQKNS PFGPFWSVTR FEDILFVDKS  120
HDLFSAEPQI ILGDPPEGLS QEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                              799

SEQ ID NO: 15                    moltype = DNA   length = 2400
FEATURE                          Location/Qualifiers
misc_feature                     1..2400
                                 note = source = /note="Description of Artificial Sequence:
                                 Synthetic polynucleotide"
source                           1..2400
                                 mol_type = other DNA
                                 organism = synthetic construct
SEQUENCE: 15
atgccaacac tgcccagaac atttgacgac attcagtccc gactgattaa cgccacctcc   60
agggtggtgc cgatgcagag gcaaattcag ggactgaaat cttaatgag cgccaagagg  120
aagaccttcg gcccacgccg accgatgccc gaattcgttg aaacaccat cccggacgtt  180
aacacgctgg cccttgagga catcgatgtc agcaatccgt ttttataccg gcagggtcag  240
tggcgcgcct atttcaaacg gttcgctgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
gggaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
```

```
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga cgaattccc  cagggaattt gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgc ccgctcgtgc tgtgagccgc acggtgaccg ttgagcgtct tgatcgcatt  1500
gccgacgatg tccttcgcct ggtccttcgc gatgctggag gtaaaaccct cccgacgtgg  1560
acgcctggcg ctcacatcga cctggatctg ggtgctctga gccgtcagta ttcgctctgc  1620
ggcgctccgg atgctccgtc gtacgaaatc gccgtgcact tagatccgga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cggggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggca aggttgatca ccgtgatacc gttctgacta aggccgagcg cgccgcgaat  2340
cgtcagatga tgacttgctg cagtcgtgca tgcggtgatc gtctggcgct gcgcctctaa  2400
```

```
SEQ ID NO: 16               moltype = AA   length = 799
FEATURE                     Location/Qualifiers
REGION                      1..799
                            note = source = /note="Description of Artificial Sequence:
                            Synthetic polypeptide"
source                      1..799
                            mol_type = protein
                            organism = synthetic construct
SEQUENCE: 16
MPTLPRTFDD IQSRLINATS RVVPMQRQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS GEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                               799
```

```
SEQ ID NO: 17               moltype = DNA   length = 2400
FEATURE                     Location/Qualifiers
misc_feature                1..2400
                            note = source = /note="Description of Artificial Sequence:
                            Synthetic polynucleotide"
source                      1..2400
                            mol_type = other DNA
                            organism = synthetic construct
SEQUENCE: 17
atgccaacac tgcccagaac atttgacgac attcagtccc gactgattaa cgccacctcc  60
agggtggtgc cgatgcagag gcaaattcag ggactgaaat cttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
atggaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
```

```
ttgacgctgc  tcatagtcgc  cggcaacgat  acgacgcgca  actcgatgag  tggtggcctg   960
gtggccatga  acgaattccc  cagggaattt  gaaaaattga  aggcaaaacc  ggagttgatt  1020
ccgaacatgg  tgtcggaaat  catccgctgg  caaacgccgc  tggcctatat  gcgccgaatc  1080
gccaagcagg  atgtcgaact  gggcggccag  accatcaaga  agggtgatcg  agttgtcatg  1140
tggtacgcgt  cgggtaaccg  ggacgagcgc  aaatttgaca  accccgatca  gttcatcatt  1200
gatcgcaagg  acgacgaaa   ccacatgtcg  ttcggctatg  gggttcaccg  ttgcatgggc  1260
aaccgtctgg  ctgaactgca  actgcgcatc  ctctgggaag  aaatactcaa  gcgttttgac  1320
aacatcgaag  tcgtcgaaga  gcccgagcgg  gtgcagtcca  acttcgtgcg  gggctattcc  1380
aggttgatgg  tcaaactgac  accgaacagt  gtactccatc  gtcatcaacc  tgtcaccatc  1440
ggcgagccgg  ccgctcgtgc  tgtgagccgc  acggtgaccg  ttgagcgtct  tgatcgcatt  1500
gccgacgatg  tccttcgcct  ggtccttcgc  gatgctggag  gtaaaaccct  cccgacgtgg  1560
acgcctggcg  ctcacatcga  cctggatctg  ggtgctctga  gccgtcagta  ttcgctctgc  1620
ggcgctccgg  atgctccgtc  gtacgaaatc  gccgtgcact  tagatccgga  aagccgtggt  1680
ggaagccgct  atattcatga  acagctggaa  gttggaagtc  cgctgcgtat  gcgtggccca  1740
cgcaaccatt  tcgccctgga  tccgggtgcg  gaacattacg  tgtttgttgc  cgggggtatc  1800
ggcatcacgc  cggtgctggc  aatggcggat  catcccgtg   cgcgtggttg  gtcgtacgaa  1860
ctgcattatt  gtggtcgtaa  tcgtagcggt  atggcttacc  tggaacgcgt  cgcgggacat  1920
ggtgaccgcg  ctgccttgca  cgtatctgaa  gaaggcaccc  gcattgatct  ggcggcatta  1980
cttgctgaac  cggcgccggg  cgtgcaaatc  tacgcctgcg  gtccgggccg  tttattagcg  2040
ggtcttgaag  acgcgtctcg  taattggccg  gatggcgcgc  ttcatgtgga  gcatttcact  2100
tcgagtttag  ccgctttgga  tccggatgtc  gaacatgcct  ttgatttgga  gctgcgtgac  2160
tctggcctta  ccgttcgcgt  cgagccaact  cagaccgttt  tagacgcttt  cgcgtgcgaac  2220
aatatcgacg  tcccgtcgga  ttgcgaagag  gggctgtgtg  gttcttgcga  gtagcccgtt  2280
ctggatggcg  aggttgatca  ccgtgatacc  gttctgacta  aggccgagcg  cgccgcgaat  2340
cgtcagatga  tgacttgctg  cagtcgtgca  tgcggtgatc  gtctggcgct  gcgcctctaa  2400
```

```
SEQ ID NO: 18          moltype = AA  length = 799
FEATURE                Location/Qualifiers
REGION                 1..799
                       note = source = /note="Description of Artificial Sequence:
                       Synthetic polypeptide"
source                 1..799
                       mol_type = protein
                       organism = synthetic construct
SEQUENCE: 18
MPTLPRTFDD  IQSRLINATS  RVVPMQRQIQ  GLKFLMSAKR  KTFGPRRPMP  EFVETPIPDV   60
NTLALEDIDV  SNPFLYRQGQ  WRAYFKRLRD  EAPVHYQKNS  PFGPFWSVTR  FEDILFVDKS  120
HDLFSAEPQI  ILGDPPEGLS  MEMFIAMDPP  KHDVQRSSVQ  GVVAPKNLKE  MEGLIRSRTG  180
DVLDSLPTDK  PFNWVPAVSK  ELTGRMLATL  LDFPYEERHK  LVEWSDRMAG  AASATGGEFA  240
DENAMFDDAA  DMARSFSRLW  RDKEARRAAG  EEPGFDLISL  LQSNKETKDL  INRPMEFIGN  300
LTLLIVAGND  TTRNSMSGGL  VAMNEFPREF  EKLKAKPELI  PNMVSEIIRW  QTPLAYMRRI  360
AKQDVELGGQ  TIKKGDRVVM  WYASGNRDER  KFDNPDQFII  DRKDARNHMS  FGYGVHRCMG  420
NRLAELQLRI  LWEEILKRFD  NIEVVEEPER  VQSNFVRGYS  RLMVKLTPNS  VLHRHQPVTI  480
GEPAARAVSR  TVTVERLDRI  ADDVLRLVLR  DAGGKTLPTW  TPGAHIDLDL  GALSRQYSLC  540
GAPDAPSYEI  AVHLDPESRG  GSRYIHEQLE  VGSPLRMRGP  RNHFALDPGA  EHYVFVAGGI  600
GITPVLAMAD  HARARGWSYE  LHYCGRNRSG  MAYLERVAGH  GDRAALHVSE  EGTRIDLAAL  660
LAEPAPGVQI  YACGPGRLLA  GLEDASRNWP  DGALHVEHFT  SSLAALDPDV  EHAFDLELRD  720
SGLTVRVEPT  QTVLDALRAN  NIDVPSDCEE  GLCGSCEVAV  LDGEVDHRDT  VLTKAERAAN  780
RQMMTCCSRA  CGDRLALRL                                                    799
```

```
SEQ ID NO: 19          moltype = DNA  length = 2400
FEATURE                Location/Qualifiers
misc_feature           1..2400
                       note = source = /note="Description of Artificial Sequence:
                       Synthetic polynucleotide"
source                 1..2400
                       mol_type = other DNA
                       organism = synthetic construct
SEQUENCE: 19
atgccaacac  tgcccagaac  atttgacgac  attcagtccc  gactgattaa  cgccacctcc   60
agggtggtgc  cgatgcagag  gcaaattcag  ggactgaaat  tcttaatgag  cgccaagagg  120
aagaccttcg  gcccacgccg  accgatgccc  gaattcgttg  aaacacccat  cccggacgtt  180
aacacgctgg  cccttgagga  catcgatgtc  agcaatccgt  ttttataccg  gcagggtcag  240
tggcgcgcct  atttcaaacg  gttgcgtgat  gaggcgccgg  tccattacca  gaagaacagc  300
cctttcggcc  ccttctggtc  ggtaactcgg  tttgaagaca  tcctgttcgt  ggataagagt  360
cacgacctgt  tttcgccga   gccgcaaatc  attctcggtg  accctccgga  ggggctgtcg  420
ctggaaatgt  tcatagcgat  ggatccgccc  aaacacgatg  tgcagcgcag  ctcggtgcag  480
ggagtagtgg  caccgaaaaa  cctgaaggag  atggaggggc  tgatccgatc  acgcaccggc  540
gatgtgcttg  acagcctgcc  tacagacaaa  ccctttaact  gggtacctgc  tgtttccaag  600
gaactcacag  gccgcatgct  ggcgacgctt  ctggattttc  cttacgagga  acgccacaag  660
ctggttgagt  ggtcggacag  aatggcaggt  gcagcatcgg  ccaccggcgg  ggagtttgcc  720
gatgaaaatg  ccatgtttga  cgacgcggca  gacatggccc  ggtctttctc  caggctttgg  780
cgggacaagg  aggcgcgccg  cgcagcaggc  gaggagcccg  gtttcgattt  gatcagcctg  840
ttgcagagca  acaaagaaac  gaaagacctg  atcaatcggc  cgatggagtt  tatcggtaat  900
ttgacgctgc  tcatagtcgc  cggcaacgat  acgacgcgca  actcgatgag  tggtggcctg  960
gtggccatga  acgaattccc  cagggaattt  gaaaaattga  aggcaaaacc  ggagttgatt  1020
ccgaacatgg  tgtcggaaat  catccgctgg  caaacgccgc  tggcctatat  gcgccgaatc  1080
gccaagcagg  atgtcgaact  gggcggccag  accatcaaga  agggtgatcg  agttgtcatg  1140
tggtacgcgt  cgggtaaccg  ggacgagcgc  aaatttgaca  accccgatca  gttcatcatt  1200
```

```
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaaaccct cccgacgtgg  1560
acgcctggcg ctcacatcga cctggatctg ggtgctctga gccgtcagta ttcgctctgc  1620
ggcgctccgg atgctccgtc gtacgaaatc gccgtgcact tagatccgga aagccgtggt  1680
ggaagccgct atattcatga acagctggaa gttggaagtc cgctgcgtat gcgtggccta  1740
cgcaaccatt tcgccctgga tccgggtgcg gaacattacg tgtttgttgc cgggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggcgct gcgcctctaa  2400
```

SEQ ID NO: 20              moltype = AA   length = 799
FEATURE                    Location/Qualifiers
REGION                     1..799
                           note = source = /note="Description of Artificial Sequence:
                            Synthetic polypeptide"
source                     1..799
                           mol_type = protein
                           organism = synthetic construct
SEQUENCE: 20
```
MPTLPRTFDD IQSRLINATS RVVPMQRQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS LEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                               799
```

SEQ ID NO: 21              moltype = DNA   length = 2400
FEATURE                    Location/Qualifiers
misc_feature               1..2400
                           note = source = /note="Description of Artificial Sequence:
                            Synthetic polynucleotide"
source                     1..2400
                           mol_type = other DNA
                           organism = synthetic construct
SEQUENCE: 21
```
atgccaacac tgcccagaac atttgacgac attcagtccc gactgattaa cgccacctcc  60
agggtggtgc cgatgcagag gcaaattcag ggactgaaat tcttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
acggaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa cccttaact ggtgacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcgcc cgatggagtt tatcggtaat  900
ttgacgctgc tcatagtcgc cggcaacgat acgacgcgca actcgatgag tggtggcctg  960
gtggccatga cgaattccc cagggaattt gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cggggaaccg ggacgagcgc aaatttgaca acccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
```

-continued

```
gccgacgatg tccttcgcct ggtccttcgc gatgctggag gtaaaaccct cccgacgtgg    1560
acgcctggcg ctcacatcga cctggatctg ggtgctctga gccgtcagta ttcgctctgc    1620
ggcgctccgg atgctccgtc gtacgaaatc gccgtgcact tagatccgga aagccgtggt    1680
ggaagccgct atattcatga acagctggaa gttggaagtc cgctgcgtat gcgtggccca    1740
cgcaaccatt tcgccctgga tccgggtgcg gaacattacg tgtttgttgc cggggggtatc    1800
ggcatcacgc cggtgctggc aatggcggat catgcccgtg cgcgtggttg gtcgtacgaa    1860
ctgcattatt gtggtcgtaa tcgtagcggt atggcttacc tggaacgcgt cgcgggacat    1920
ggtgaccgcg ctgccttgca cgtatctgaa gaaggcaccc gcattgatct ggcggcatta    1980
cttgctgaac cggcgccggg cgtgcaaatc tacgcctgcg gtccgggccg tttattagcg    2040
ggtcttgaag acgcgtctcg taattggccg gatggcgcgc ttcatgtgga gcatttcact    2100
tcgagtttag ccgctttgga tccggatgtc gaacatgcct ttgatttgga gctgcgtgac    2160
tctgccctta ccgttcgcgt cgagccaact cagaccgttt tagacgcttt gcgtgcgaac    2220
aatatcgacg tcccgtcgga ttgcgaagag gggctgtgtg gttcttgcga agtagccgtt    2280
ctggatggcg aggttgatca ccgtgatacc gttctgacta aggccgagcg cgccgcgaat    2340
cgtcagatga tgacttgctg cagtcgtgca tgcggtgatc gtctggcgct gcgcctctaa    2400
```

```
SEQ ID NO: 22          moltype = AA  length = 799
FEATURE                Location/Qualifiers
REGION                 1..799
                       note = source = /note="Description of Artificial Sequence:
                       Synthetic polypeptide"
source                 1..799
                       mol_type = protein
                       organism = synthetic construct
SEQUENCE: 22
MPTLPRTFDD IQSRLINATS RVVPMQRQIQ GLKFLMSAKR KTFGPRRPMP EFVETPIPDV    60
NTLALEDIDV SNPFLYRQGQ WRAYFKRLRD EAPVHYQKNS PFGPFWSVTR FEDILFVDKS    120
HDLFSAEPQI ILGDPPEGLS TEMFIAMDPP KHDVQRSSVQ GVVAPKNLKE MEGLIRSRTG    180
DVLDSLPTDK PFNWVPAVSK ELTGRMLATL LDFPYEERHK LVEWSDRMAG AASATGGEFA    240
DENAMFDDAA DMARSFSRLW RDKEARRAAG EEPGFDLISL LQSNKETKDL INRPMEFIGN    300
LTLLIVAGND TTRNSMSGGL VAMNEFPREF EKLKAKPELI PNMVSEIIRW QTPLAYMRRI    360
AKQDVELGGQ TIKKGDRVVM WYASGNRDER KFDNPDQFII DRKDARNHMS FGYGVHRCMG    420
NRLAELQLRI LWEEILKRFD NIEVVEEPER VQSNFVRGYS RLMVKLTPNS VLHRHQPVTI    480
GEPAARAVSR TVTVERLDRI ADDVLRLVLR DAGGKTLPTW TPGAHIDLDL GALSRQYSLC    540
GAPDAPSYEI AVHLDPESRG GSRYIHEQLE VGSPLRMRGP RNHFALDPGA EHYVFVAGGI    600
GITPVLAMAD HARARGWSYE LHYCGRNRSG MAYLERVAGH GDRAALHVSE EGTRIDLAAL    660
LAEPAPGVQI YACGPGRLLA GLEDASRNWP DGALHVEHFT SSLAALDPDV EHAFDLELRD    720
SGLTVRVEPT QTVLDALRAN NIDVPSDCEE GLCGSCEVAV LDGEVDHRDT VLTKAERAAN    780
RQMMTCCSRA CGDRLALRL                                                 799
```

```
SEQ ID NO: 23          moltype = DNA  length = 2400
FEATURE                Location/Qualifiers
misc_feature           1..2400
                       note = source = /note="Description of Artificial Sequence:
                       Synthetic polynucleotide"
source                 1..2400
                       mol_type = other DNA
                       organism = synthetic construct
SEQUENCE: 23
atgccaacac tgcccagaac atttgacgac attcagtccc gactgattaa cgccacctcc    60
agggtggtgc cgatgcagag gcaaattcag ggactgaaat tcttaatgag cgccaagagg    120
aagaccttcg gcccacgccg accgatgccc gaattcgttg aaacacccat cccgacgtt     180
aacacgctgg cccttgagga catcgatgtc agcaatccgt ttttataccg gcagggtcag    240
tggcgcgcct atttcaaacg gttgcgtgat gaggcgccgg tccattacca gaagaacagc    300
cctttcggcc ccttctggtc ggtaactcgg tttgaagaca tctgttcgt ggataagagt    360
cacgacctgt tttccgccga gccgcaaatc attctcggtg accctccgga ggggctgtcg    420
gtggaaatgt tcatagcgat ggatccgccg aaacacgatg tgcagcgcag ctcggtgcag    480
ggagtagtgg caccgaaaaa cctgaaggag atggagggc tgatccgatc aaacaccggc    540
gatgtgcttg acagcctgcc tacagacaaa ccctttaact gggtacctgc tgtttccaaa    600
gaactcacga gccgcatgct ggcgacgctt ctggattttc cttacgagga acgccacaag    660
ctggttgagt ggtcggacag aatggcaggt gcagcatcgg ccaccggcgg ggagtttgcc    720
gatgaaaatg ccatgtttga cgacgcggca gacatggccc ggtctttctc caggctttgg    780
cgggacaagg aggcgcgccg cgcagcaggc gaggagcccg gtttcgattt gatcagcctg    840
ttgcagagca acaaagaaac gaaagacctg atcaatccgc cgatggagtt tatcggtaat    900
ttgacgctgc tcatagtcgc cggcaacgat acgacgcgca actcgatgag tggtggcctg    960
gtggccatga cgaattccc cagggaattt gaaaaattga aggcaaaacc ggagttgatt    1020
ccgaacatgg tgtcggaaat catccgctgg caaacgccgc tggcctatat gcgccgaatc    1080
gccaagcagg atgtcgaact gggcggccag accatcaaga agggtgatcg agttgtcatg    1140
tggtacgcaa gcgggtaaccg ggacgagcgc aaatttgaca accccgatca gttcatcatt    1200
gatcgcaagg acgcacgaaa ccacatgtcg ttcggctatg gggttcaccg ttgcatgggc    1260
aaccgtctgg ctgaactgca actgcgcatc ctctgggaag aaatactcaa gcgttttgac    1320
aacatcgaag tcgtcgaaga gcccgagcgg gtgcagtcca acttcgtgcg gggctattcc    1380
aggttgatgg tcaaactgac accgaacagt gtactccatg tcatcaacc tgtccaccatc    1440
ggcgagccgg ccgctgtgc tgtgagccgc acggtgaccg ttgagcgtct tgatcgcatt    1500
gccgacgatg tccttcgcct ggtccttcgc gatgctggag gtaaaaccct cccgacgtgg    1560
acgcctggcg ctcacatcga cctggatctg ggtgctctga gccgtcagta ttcgctctgc    1620
ggcgctccgg atgctccgtc gtacgaaatc gccgtgcact tagatccgga aagccgtggt    1680
ggaagccgct atattcatga acagctggaa gttggaagtc cgctgcgtat gcgtggccca    1740
cgcaaccatt tcgccctgga tccgggtgcg gaacattacg tgtttgttgc cggggggtatc    1800
```

```
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggcgct gcgcctctaa  2400
```

SEQ ID NO: 24                moltype = AA   length = 799
FEATURE                      Location/Qualifiers
REGION                       1..799
                             note = source = /note="Description of Artificial Sequence:
                             Synthetic polypeptide"
source                       1..799
                             mol_type = protein
                             organism = synthetic construct
SEQUENCE: 24
```
MPTLPRTFDD IQSRLINATS RVVPMQRQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSNTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                                799
```

SEQ ID NO: 25                moltype = DNA   length = 2400
FEATURE                      Location/Qualifiers
misc_feature                 1..2400
                             note = source = /note="Description of Artificial Sequence:
                             Synthetic polynucleotide"
source                       1..2400
                             mol_type = other DNA
                             organism = synthetic construct
SEQUENCE: 25
```
atgccaacac tgcccagaac atttgacgac attcagtccc gactgattaa cgccacctcc  60
agggtggtgc cgatgcagag gcaaattcag ggactgaaat tcttaatgag cgccaagagg  120
aagaccttcg gcccacgccg accgatgccc gaattcgttg aaacacccat ccccgacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcgtg accctccgga ggggctgtca  420
gtggaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggatttc cttacgagga agccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggccgggat acgacgcgca actcgatgag tggtggcctg  960
gtggccatga cgaattccc cagggaattg gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaaaccct cccgacgtgg  1560
acgcctggcg ctcacatcga cctggatctg ggtgctctga gccgtcagta ttcgctctgc  1620
ggcgctccga tgctccgtc gtacgaaatc gccgtgcact agatccggga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc ggggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgcgc ttcatgtgga gcatttcact  2100
```

```
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggcgct gcgcctctaa  2400
```

```
SEQ ID NO: 26          moltype = AA   length = 799
FEATURE                Location/Qualifiers
REGION                 1..799
                       note = source = /note="Description of Artificial Sequence:
                       Synthetic polypeptide"
source                 1..799
                       mol_type = protein
                       organism = synthetic construct
SEQUENCE: 26
MPTLPRTFDD IQSRLINATS RVVPMQRQIQ GLKFLMSAKR KTFGPRRPMP EFVETPIPDV   60
NTLALEDIDV SNPFLYRQGQ WRAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGRD TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                                799
```

```
SEQ ID NO: 27          moltype = DNA   length = 2400
FEATURE                Location/Qualifiers
misc_feature           1..2400
                       note = source = /note="Description of Artificial Sequence:
                       Synthetic polynucleotide"
source                 1..2400
                       mol_type = other DNA
                       organism = synthetic construct
SEQUENCE: 27
atgccaacac tgcccagaac atttgacgac attcagtccc gactgattaa cgccacctcc   60
agggtggtgc cgatgcagag gcaaattcag ggactgaaat tcttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
gtggaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcggcatcgg ccaccggcgg ggagtttgac  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga acgaattccc cagggaattt gaaaaattga aggcaaaacc ggagttgatt 1020
ccgaacatgg tgtcggaaat catccgctgg caaacgccgc tggcctatat gcgccgaatc 1080
gccaagcagg atgtcgaact gggcggccag accatcaaga agggtgatcg agttgtcatg 1140
tggtacgcgt cgggtaaccg ggacgagcgc aaatttgaca accccgatca gttcatcatt 1200
gatcgcaagg acgcacgaaa ccacatgtcg ttcggctatg gggttcaccg ttgcatgggc 1260
aaccgtctgg ctgaactgca actgcgcatc ctctgggaag aaatactcaa gcgttttgac 1320
aacatcgaag tcgtcgaaga gcccgagcgg gtgcagtcca acttcgtgcg gggctattcc 1380
aggttgatgg tcaaactgac accgaacagt gtactccatc gtcatcaacc tgtcaccatc 1440
ggcgagccga ccgctcgtgc tgtgagccgc acggtgaccg ttgagcgtct tgatcgcatt 1500
gccgacgatg tccttcgcct ggtccttcgc gatgctggag gtaaaaccct cccgacgtgg 1560
acgcctggcg ctcacatcga cctggatctg ggtgctctga gccgtcagta ttcgctctgc 1620
ggcgctccga tgctccgtc gtacgaaatc gccgtgcact agatccgga aagccgtggt 1680
ggaagccgct atattcatga acagctggaa gttggaagtc cgctgcgtat gcgtggccca 1740
cgcaaccatt tcgccctgga tccgggtgcg gaacattacg tgtttgttgc cgggggtatt 1800
ggcatcacgc cggtgctggc aatggcggat catgcccgtg cgcgtggttg gtcgtacgaa 1860
ctgcattatt gtggtcgtaa tcgtagcggt atggcttacc tggaacgcgt cgcgggacat 1920
ggtgaccgcg ctgccttgca cgtatctgaa gaaggcaccc gcattgatct ggcggcatta 1980
cttgctgaac cggcgccggg cgtgcaaatc tacgcctgcg gtccgggccg tttattagcg 2040
gtcttgaag acgcgtctcg taattggccg gatgccgcgc ttcatgtgga gcatttcact 2100
tcgagtttag ccgctttgga tccggatgtc gaacatgcct ttgatttgga gctgcgtgac 2160
tctggcctta ccgttcgcgt cgagccaact cagaccgttt tagacgcttt gcgtgcgaac 2220
aatatcgacg tcccgtcgga ttgcgaagag gggctgtgtg gttcttgcga agtagccgtt 2280
ctggatggcg aggttgatca ccgtgatacc gttctgacta aggccgagcg cgccgcgaat 2340
cgtcagatga tgacttgctg cagtcgtgca tgcggtgatc gtctggcgct gcgcctctaa 2400
```

```
SEQ ID NO: 28          moltype = AA   length = 799
FEATURE                Location/Qualifiers
REGION                 1..799
                       note = source = /note="Description of Artificial Sequence:
                        Synthetic polypeptide"
source                 1..799
                       mol_type = protein
                       organism = synthetic construct
SEQUENCE: 28
MPTLPRTFDD IQSRLINATS RVVPMQRQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                              799

SEQ ID NO: 29          moltype = DNA   length = 2400
FEATURE                Location/Qualifiers
misc_feature           1..2400
                       note = source = /note="Description of Artificial Sequence:
                        Synthetic polynucleotide"
source                 1..2400
                       mol_type = other DNA
                       organism = synthetic construct
SEQUENCE: 29
atgccaacac tgcccagaac atttgacgac attcagtccc gactgattaa cgccacctcc  60
agggtggtgc cgatgcagag gcaaattcag ggactgaaat tcttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
gtggaaatgt tcatagcgat ggatccgccg aaacacgatg tgcagcgcag ctcggtgcag  480
ggagtagtgg caccgaaaaa cctgaaggag atggagggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga acgaattccc cagggaattt gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gcgtcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaaacct cccgacgtgg  1560
acgcctggcg ctcacatcga cctggatctg ggtgctctga gccgtcagta ttcgctctgc  1620
ggcgctccgg atgctccgtc gtacgaaatc gccgtgcact agatccggaa aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cggggggatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgctc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga gtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggcgct cgcgctctaa  2400

SEQ ID NO: 30          moltype = AA   length = 799
FEATURE                Location/Qualifiers
REGION                 1..799
                       note = source = /note="Description of Artificial Sequence:
```

```
                          Synthetic polypeptide"
source                    1..799
                          mol_type = protein
                          organism = synthetic construct
SEQUENCE: 30
MPTLPRTFDD IQSRLINATS RVVPMQRQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGRHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                                799

SEQ ID NO: 31            moltype = DNA  length = 2400
FEATURE                  Location/Qualifiers
misc_feature             1..2400
                         note = source = /note="Description of Artificial Sequence:
                         Synthetic polynucleotide"
source                   1..2400
                         mol_type = other DNA
                         organism = synthetic construct
SEQUENCE: 31
atgccaacac tgcccagaac atttgacgac attcagtccc gactgattaa cgccacctcc  60
agggtggtgc cgatgcagag gcaaattcag ggactgaaat tcttaatgag cgccaagagg  120
aagaccttcg gcccacgccg accgatgccc gaattcgttg aaacacccat cccgacgtt   180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcgggc ccttctggtc ggtaactcgg tttgaagaca tcctgttcgt ggataagagt  360
cacgacctgt tttccgccga gccgcaaatc attctcggtg accctccgga ggggctgtcg  420
atcgaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt acagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga acgaattccc cagggaattt gaaaaattga aggcaaaacc ggagttgatt  1020
ccgaacatgg tgtcggaaat catccgctgg caaacgcccc tggcctatat cgcgccgaatc 1080
gccaagcagg atgtcgaact gggcggccag accatcaaga agggtgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgtttttgac 1320
aacatcgaag tcgtcgaaga gccccagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaaacct cccgacgtgg   1560
acgcctggcg ctcacatcga cctggatctg ggtgctctga gccgtcagta ttcgctctgc  1620
ggcgctccgg atgctccgtc gtacgaaatc gccgtgcact agatccgga aagccgtggt   1680
ggaagccgct atattcatga acagctggaa gttggaagtc cgctgcgtat gcgtggccca  1740
cgcaaccatt tcgccctgga tccgggtgcg gaacattacg tgtttgttgc cgggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggccgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggcgct cgcgctctaa  2400

SEQ ID NO: 32            moltype = AA  length = 799
FEATURE                  Location/Qualifiers
REGION                   1..799
                         note = source = /note="Description of Artificial Sequence:
                         Synthetic polypeptide"
source                   1..799
                         mol_type = protein
                         organism = synthetic construct
SEQUENCE: 32
```

```
MPTLPRTFDD IQSRLINATS RVVPMQRQIQ GLKFLMSAKR KTFGPRRPMP EFVETPIPDV     60
NTLALEDIDV SNPFLYRQGQ WRAYFKRLRD EAPVHYQKNS PFGPFWSVTR FEDILFVDKS    120
HDLFSAEPQI ILGDPPEGLS IEMFIAMDPP KHDVQRSSVQ GVVAPKNLKE MEGLIRSRTG    180
DVLDSLPTDK PFNWVPAVSK ELTGRMLATL LDFPYEERHK LVEWSDRMAG TASATGGEFA    240
DENAMFDDAA DMARSFSRLW RDKEARRAAG EEPGFDLISL LQSNKETKDL INRPMEFIGN    300
LTLLIVAGND TTRNSMSGGL VAMNEFPREF EKLKAKPELI PNMVSEIIRW QTPLAYMRRI    360
AKQDVELGGQ TIKKGDRVVM WYASGNRDER KFDNPDQFII DRKDARNHMS FGYGVHRCMG    420
NRLAELQLRI LWEEILKRFD NIEVVEEPER VQSNFVRGYS RLMVKLTPNS VLHRHQPVTI    480
GEPAARAVSR TVTVERLDRI ADDVLRLVLR DAGGKTLPTW TPGAHIDLDL GALSRQYSLC    540
GAPDAPSYEI AVHLDPESRG GSRYIHEQLE VGSPLRMRGP RNHFALDPGA EHYVFVAGGI    600
GITPVLAMAD HARARGWSYE LHYCGRNRSG MAYLERVAGH GDRAALHVSE EGTRIDLAAL    660
LAEPAPGVQI YACGPGRLLA GLEDASRNWP DGALHVEHFT SSLAALDPDV EHAFDLELRD    720
SGLTVRVEPT QTVLDALRAN NIDVPSDCEE GLCGSCEVAV LDGEVDHRDT VLTKAERAAN    780
RQMMTCCSRA CGDRLALRL                                                 799

SEQ ID NO: 33            moltype = DNA   length = 2400
FEATURE                  Location/Qualifiers
misc_feature             1..2400
                         note = source = /note="Description of Artificial Sequence:
                         Synthetic polynucleotide"
source                   1..2400
                         mol_type = other DNA
                         organism = synthetic construct
SEQUENCE: 33
atgccaacac tgcccagaac atttgacgac attcagtccc gactgattaa cgccacctcc     60
agggtggtgc cgatgcagct gcaaattcag ggactgaaat tcttaatgag cgccaagagg    120
aagaccttcg gcccacgccg accgatgccc gaattcgttg aaacacccat cccggacgtt    180
aacacgctgg cccttgagga catcgatgtc agcaatccgt ttttataccg gcagggtcag    240
tgggacgcct atttcaaacg gttgcgtgat gaggcgccgg tccattacca gaagaacagc    300
cctttcggcc ccttctggtc ggtaactcgg tttgaagaca tcctgttcgt ggataagagt    360
cacgacctgt tttccgccga gccgcaaatc attctcggtg accctccgga ggggctgtcg    420
atggaaatgt tcatagcgat ggatccgccg aaacacgatg tgcagcgcag ctcggtgcag    480
ggagtagtgc caccgaaaaa cctgaaggag atggagggc tgatccgatc aaacaccggc    540
gatgtgcttg acagcctgcc tacagacaaa ccctttaact gggtacctgc tgtttccaag    600
gaactcacag gccgcatgct ggcgacgctt ctggattttc cttacgagga acgccacaag    660
ctggttgagt ggtcggacag aatggcaggt gcagcatcgg ccaccggcgg ggagtttgcc    720
gatgaaaatg ccatgtttga cgacgcggca gacatggccc ggtctttctc caggctttgg    780
cgggacaagg aggcgcgccg cgcagcaggc gaggagcccg gtttcgattt gatcagcctg    840
ttgcagagca caaagaaac gaaagacctg atcaatcgc cgatggagtt tatcggtaat    900
ttgacgctgc tcatagtcgc cggcgcggat acgacgcgca actcgatgag tggtggcctg    960
gtggccatga cgaattccc cagggaattt gaaaaattga aggcaaaacc ggagttgatt   1020
ccgaacatgg tgtcggaaat catccgctgg caaacgccgc tggcctatat gcgccgaatc   1080
gccaagcagg atgtcgaact gggcgggcca accatcaaga agggtgatcg agttgtcatg   1140
tggtacgcgt cgggtaaccg ggacgagcgc aaatttgaca accccgatca gttcatcatt   1200
gatcgcaagg acgcacgaaa ccacatgtcg ttcggctatg gggttcaccg ttgcatgggc   1260
aaccgtctgg ctgaactgca actgcgcatc ctctgggaag aaatactcaa gcgttttgac   1320
aacatcgaag tcgtcgaaga gcccgaacgg gtgcagtcca acttcgtgcg gggctattcc   1380
aggttgatgg tcaaactgac accgaacagt gtactccatc gtcatcaacc tgtcaccatc   1440
ggcgagccgg ccgctcgtgc cgtgagccgc acggtgaccg ttgagcgtct tgatcgcatt   1500
gccgacgatg tccttcgcct ggtccttcgc gatgctggag gtaaaaccct cccgacgtgg   1560
acgcctggcg ctcacatcga cctggatctg ggtgctctga gccgtcagta ttcgctctgc   1620
ggcgctccgg atgctccgtc gtacgaaatc gccgtgcact agatccgga aagccgtggt   1680
ggaagccgct atattcatga acagctggaa gttggaagtc cgctgcgtat gcgtggccca   1740
cgcaaccatt tcgccctgga tccgggtgcg gaacattacg tgtttgttgc cggggggtatc   1800
ggcatcacgc cggtgctggc aatggcggat catgcccgtg cgcgtggttg gtcgtacgaa   1860
ctgcattatt gtggtcgtaa tcgtagcggt atggcttacc tggaacgcgt cgcgggacat   1920
ggtgaccgcg ctgccttgca cgtatctgaa gaaggcaccc gcattgatct ggcggcatta   1980
cttgctgaac cggcgccggg cgtgcaaatc tacgcctgcg gtccgggccg tttattagcg   2040
ggtcttgaag acgcgtctcg taattggccg gatggcgcgc ttcatgtgga gcatttcact   2100
tcgagtttag ccgctttgga tccggatgtc gaacatgcct ttgatttgga gctgcgtgac   2160
tctggcctta ccgttcgcgt cgagccaact cagaccgttt tagacgcttt gcgtgcgaac   2220
aatatcgacg tcccgtcgga ttgcgaagag gggctgtgtg gttcttcgca gtagccgtt   2280
ctggatggca aggttgatca ccgtgatacc gttctgacta aggccgagcg cgccgcgaat   2340
cgtcagatga tgacttgctg cagtcgtgca tgcggtgatc gtctggcgct cgcgcctctaa   2400

SEQ ID NO: 34            moltype = AA   length = 799
FEATURE                  Location/Qualifiers
REGION                   1..799
                         note = source = /note="Description of Artificial Sequence:
                         Synthetic polypeptide"
source                   1..799
                         mol_type = protein
                         organism = synthetic construct
SEQUENCE: 34
MPTLPRTFDD IQSRLINATS RVVPMQLQIQ GLKFLMSAKR KTFGPRRPMP EFVETPIPDV     60
NTLALEDIDV SNPFLYRQGQ WDAYFKRLRD EAPVHYQKNS PFGPFWSVTR FEDILFVDKS    120
HDLFSAEPQI ILGDPPEGLS MEMFIAMDPP KHDVQRSSVQ GVVAPKNLKE MEGLIRSNTG    180
DVLDSLPTDK PFNWVPAVSK ELTGRMLATL LDFPYEERHK LVEWSDRMAG AASATGGEFA    240
DENAMFDDAA DMARSFSRLW RDKEARRAAG EEPGFDLISL LQSNKETKDL INRPMEFIGN    300
```

```
LTLLIVAGAD TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                              799

SEQ ID NO: 35          moltype = DNA  length = 2400
FEATURE                Location/Qualifiers
misc_feature           1..2400
                       note = source = /note="Description of Artificial Sequence:
                       Synthetic polynucleotide"
source                 1..2400
                       mol_type = other DNA
                       organism = synthetic construct
SEQUENCE: 35
atgccaacac tgcccagaac atttgacgac attcagtccc gactgattaa cgccacctcc  60
agggtggtgc cgatgcagag gcaaattcag ggactgaaat tcttaatgag cgccaagagg  120
aagaccttcg gcccacgccg accgatgccc gaattcgttg aaacacccat ccccgacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
gtggaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gttccgattt gatcagcctg  840
ttgcagagca caaagaaac gaaagacctg atcaatcggc cgatggagtt tatcggtaat  900
ttgacgctgc tcatagtcgc cggcaacgat acgacgcgca actcgatgag tggtggcctg  960
gtggccatga cgaattccc cagggaattt gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cggggtaaccg ggacgagcgc aaatttgaca acccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaaaccct cccgacgtgg  1560
acgcctggcg ctcacatcga cctggatctg ggtgctctga gccgtcagta ttcgctctgc  1620
ggcgctccgg atgctccgtc gtacgaaatc gccgtgcact tagatccgga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cggggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcggcggg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggcgct cgcgcctcaa  2400

SEQ ID NO: 36          moltype = AA  length = 799
FEATURE                Location/Qualifiers
REGION                 1..799
                       note = source = /note="Description of Artificial Sequence:
                       Synthetic polypeptide"
source                 1..799
                       mol_type = protein
                       organism = synthetic construct
SEQUENCE: 36
MPTLPRTFDD IQSRLINATS RVVPMQRQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
```

```
GITPVLAMAD HARARGWSYE LHYCGRNRSG MAYLERVAGH GDRAALHVSE EGTRIDLAAL   660
LAEPAAGVQI YACGPGRLLA GLEDASRNWP DGALHVEHFT SSLAALDPDV EHAFDLELRD   720
SGLTVRVEPT QTVLDALRAN NIDVPSDCEE GLCGSCEVAV LDGEVDHRDT VLTKAERAAN   780
RQMMTCCSRA CGDRLALRL                                               799

SEQ ID NO: 37          moltype = DNA  length = 2400
FEATURE                Location/Qualifiers
misc_feature           1..2400
                       note = source = /note="Description of Artificial Sequence:
                       Synthetic polynucleotide"
source                 1..2400
                       mol_type = other DNA
                       organism = synthetic construct
SEQUENCE: 37
atgccaacac tgcccagaac atttgacgac attcagtccc gactgattaa cgccacctcc   60
agggtggtgc cgatgcagag gcaaattcag ggactgaaat tcttaatgag cgccaagagg   120
aagaccttcg gcccacgccg accgatgccc gaattcgttg aaacacccat cccggacgtt   180
aacacgctgg cccttgagga catcgatgtc agcaatccgt ttttataccg gcagggtcag   240
tggcgcgcct atttcaaacg gttgcgtgat gaggcgccgg tccattacca gaagaacagc   300
cctttcggcc ccttctggtc ggtaactcgg tttgaagaca tcctgttcgt ggataagagt   360
cacgacctgt tttccgccga gccgcaaatc attctcggtg accctccgga ggggctgtcg   420
gtggaaatgt tcatagcgat ggatccgccg aaacacgatg tgcagcgcag ctcggtgcag   480
ggagtagtgg caccgaaaaa cctgaaggag atggaggggc tgatccgatc acgcaccggc   540
gatgtgcttg acagcctgcc tacagacaaa ccctttaact gggtacctgc tgtttccaag   600
gaactcacag gccgcatgct ggcgacgctt ctggattttc cttacgagga acgccacaag   660
ctggttgagt ggtcggacag aatggcaggt gcagcatcgg ccaccggcgg ggagtttgcc   720
gatgaaaatg ccatgtttga cgacgcggca gacatggccc ggtctttctc caggctttgg   780
cgggacaagg aggcgcgccg cgcagcaggc gaggagcccg gtttcgattt gatcagcctg   840
ttgcagagca acaaagaaac gaaagacctg atcaatcggc cgatggagtt tatcggtaat   900
ttgacgctgc tcatagtcgc cggcaacgat acgacgcgca actcgatgag tggtggcctg   960
gtggccatga acgaattccc cagggaattt gaaaaattga aggcaaaacc ggagttgatt   1020
ccgaacatgg tgtcggaaat catccgctgg caaacgccgc tggcctatat gcgccgaatc   1080
gccaagcagg atgtcgaact gggcggccag accatcaaga agggtgatcg agttgtcatg   1140
tggtacgcgt cgggtaaccg ggacgagcgc aaatttgaca accccgatca gttcatcatt   1200
gatcgcaagg acgcacgaaa ccacatgtcg ttcggctatg gggttcaccg ttgcatgggc   1260
aaccgtctgg ctgaactgca actgcgcatc ctctgggaag aaatactcaa gcgtttttgac   1320
aacatcgaag tcgtcgaaga gcccgagcgg gtgcagtcca acttcgtgcg gggctattcc   1380
aggttgatgg tcaaactgac accgaacagt gtactccatc gtcatcaacc tgtccaccatc   1440
ggcgagccgc ccgctcgtgc tgtgagccgc acggtgaccg ttgagcgtct tgatcgcatt   1500
gccgacgatg tccttcgcct ggtccttcgc gatgctggag gtaaaaccct cccgacgtgg   1560
acgcctggcg ctcacatcga cctggatctg ggtgctctga gccgtcagta ttcgctctgc   1620
ggcgctccgg atgctccgtc gtacgaaatc gccgtgcact agatccggga aagccgtggt   1680
ggaagccgct atattcatga acagctggaa gttggaagtc cgctgcgtat gcgtggccca   1740
cgcaaccatt tcgccctgga tccgggtgcg gaacattacg tgtttgttgc cggggggtatc   1800
ggcatcacgc cggtgctggc aatggcggat catgcccgtg cgcgtggttg gtcgtacgaa   1860
ctgcattatt gtggtcgtaa tcgtagcggt atggcttacc tggaacgcgt cgcgggacat   1920
ggtgaccgcg ctgccttgca cgtatctgaa gaaggcaccc gcattgatct ggcggcatta   1980
cttgctgaac cggcgccggg cgtgcaaatc tacgcctgcg gtccgggccg tttattagcg   2040
ggtcttgaag acgcgtctcg taattggccg gatggcgcgc ttcatgtgga gcatttcact   2100
tcgagtttag ccgctttgga tccggatgtc gaacatgcct ttgatttgga gctgcgtgac   2160
tctggcctta ccgttcgcgt cgagccaact cagaccgttt tagacgcttt gcgtgcgaac   2220
aatatcgacg tcccgtcgga ttgcgaagag gggctgtgtg gttcttgcga agtagccgtt   2280
ctggatggcg aggttgatca ccgtgatacc gttctgacta aggccgagcg cgccgcgaat   2340
cgtcagatga tgacttgctg cagtcgtgca tgcggtgatc gtctggtcct cgcgcctctaa   2400

SEQ ID NO: 38          moltype = AA  length = 799
FEATURE                Location/Qualifiers
REGION                 1..799
                       note = source = /note="Description of Artificial Sequence:
                       Synthetic polypeptide"
source                 1..799
                       mol_type = protein
                       organism = synthetic construct
SEQUENCE: 38
MPTLPRTFDD IQSRLINATS RVVPMQRQIQ GLKFLMSAKR KTFGPRRPMP EFVETPIPDV   60
NTLALEDIDV SNPFLYRQGQ WRAYFKRLRD EAPVHYQKNS PFGPFWSVTR FEDILFVDKS   120
HDLFSAEPQI ILGDPPEGLS VEMFIAMDPP KHDVQRSSVQ GVVAPKNLKE MEGLIRSRTG   180
DVLDSLPTDK PFNWVPAVSK ELTGRMLATL LDFPYEERHK LVEWSDRMAG AASATGGEFA   240
DENAMFDDAA DMARSFSRLW RDKEARRAAG EEPGFDLISL LQSNKETKDL INRPMEFIGN   300
LTLLIVAGND TTRNSMSGGL VAMNEFPREF EKLKAKPELI PNMVSEIIRW QTPLAYMRRI   360
AKQDVELGGQ TIKKGDRVVM WYASGNRDER KFDNPDQFII DRKDARNHMS FGYGVHRCMG   420
NRLAELQLRI LWEEILKRFD NIEVVEEPER VQSNFVRGYS RLMVKLTPNS VLHRHQPVTI   480
GEPAARAVSR TVTVERLDRI ADDVLRLVLR DAGGKTLPTW TPGAHIDLDL GALSRQYSLC   540
GAPDAPSYEI AVHLDPESRG GSRYIHEQLE VGSPLRMRGP RNHFALDPGA EHYVFVAGGI   600
GITPVLAMAD HARARGWSYE LHYCGRNRSG MAYLERVAGH GDRAALHVSE EGTRIDLAAL   660
LAEPAPGVQI YACGPGRLLA GLEDASRNWP DGALHVEHFT SSLAALDPDV EHAFDLELRD   720
SGLTVRVEPT QTVLDALRAN NIDVPSDCEE GLCGSCEVAV LDGEVDHRDT VLTKAERAAN   780
RQMMTCCSRA CGDRLVLRL                                               799
```

-continued

```
SEQ ID NO: 39            moltype = DNA   length = 2400
FEATURE                  Location/Qualifiers
misc_feature             1..2400
                         note = source = /note="Description of Artificial Sequence:
                         Synthetic polynucleotide"
source                   1..2400
                         mol_type = other DNA
                         organism = synthetic construct
SEQUENCE: 39
atgccaacac tgcccagaac atttgacgac attcagtccc gactgattaa cgccacctcc  60
agggtggtgc cgatgcagag gcaaattcag ggactgaaat tcttaatgag cgccaagagg  120
aagaccttcg gcccacgccg accgatgccc gaattcgttg aaacacccat cccgacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
gtggaaatgt tcatagcgat ggatccgccg aaacacgatg tgcagcgcag ctcggtgcag  480
ggagtagtgg caccgaaaaa cctgaaggag atggagggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggcttttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga acgaattccc cagggaattt gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaagtcct cccgacgtgg  1560
acgcctggcg ctcacatcga cctggatctg ggtgctctga gccgtcagta ttcgctctgc  1620
ggcgctccgg atgctccgtc gtacgaaatc gccgtgcact tagatccgga aagccgtggt  1680
ggaagccgct atattcatga acagctggaa gttggaagtc cgctgcgtat gcgtggccca  1740
cgcaaccatt tcgccctgga tccggatgcg gaacattacg tgtttgttgc cggggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcggacgg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctcgctgac  2160
tctgccctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggtcct gcgcctctaa  2400

SEQ ID NO: 40            moltype = AA   length = 799
FEATURE                  Location/Qualifiers
REGION                   1..799
                         note = source = /note="Description of Artificial Sequence:
                         Synthetic polypeptide"
source                   1..799
                         mol_type = protein
                         organism = synthetic construct
SEQUENCE: 40
MPTLPRTFDD IQSRLINATS RVVPMQRQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKVLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPADGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLVLRL                                              799

SEQ ID NO: 41            moltype = DNA   length = 2400
FEATURE                  Location/Qualifiers
misc_feature             1..2400
                         note = source = /note="Description of Artificial Sequence:
                         Synthetic polynucleotide"
```

```
source                  1..2400
                        mol_type = other DNA
                        organism = synthetic construct
SEQUENCE: 41
atgccaacac tgcccagaac atttgacgac attcagtccc gactgattaa cgccacctcc  60
agggtggtgc cgatgcagag gcaaattcag ggactgaaat tcttaatgag cgccaagagg  120
aagaccttcg gcccacgccg accgatgccc gaattcgttg aaacacccat cccgacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
atcgaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt acagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga cgaattccc cagggaattt gaaaaattga aggcaaaacc ggagttgatt  1020
ccgaacatgg tgtcggaaat catccgctgg caaacgccgc tggcctatat cgccgaatc  1080
gccaagcagg atgtcgaact gggcggccag accatcaaga agggtgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgtttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaaacct cccgacgtgg  1560
acgcctggcg ctcacatcga cctggatctg ggtgctctga gccgtcagta ttcgctctgc  1620
ggcgctccgg atgctccgtc gtacgaaatc gccgtgcact tagatccgga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cgggggggtacc  1800
ggcatcacgc cggtgctggc aatggcggat catgccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctcggtcct gcgcctctaa  2400

SEQ ID NO: 42          moltype = AA  length = 799
FEATURE                Location/Qualifiers
REGION                 1..799
                       note = source = /note="Description of Artificial Sequence:
                        Synthetic polypeptide"
source                 1..799
                       mol_type = protein
                       organism = synthetic construct
SEQUENCE: 42
MPTLPRTFDD IQSRLINATS RVVPMQRQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS IEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG TASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLVLRL                                                799

SEQ ID NO: 43          moltype = DNA  length = 2400
FEATURE                Location/Qualifiers
misc_feature           1..2400
                       note = source = /note="Description of Artificial Sequence:
                        Synthetic polynucleotide"
source                 1..2400
                       mol_type = other DNA
                       organism = synthetic construct
SEQUENCE: 43
atgccaacac tgcccagaac atttgacgac attcagtccc gactgattaa cgccacctcc  60
```

```
agggtggtgc cgatgcagct gcaaattcag ggactgaaat tcttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tgggacgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
atggaaatgt tcatagcgat ggatccgccg aaacacgatg tgcagcgcag ctcggtgcag  480
ggagtagtgg caccgaaaaa cctgaaggag atggaggggc tgatccgatc aaacaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcgcggat acgacgcgca actcgatgag tggtggcctg  960
gtggccatga cgaattccc caggggaattt gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcgggccag accatcaaga agggtgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gggttcaccg ttgcatgggc  1260
aaccgtctgc ctgaactgca actgcgcatc ctctgggaag aaatactcaa gcgttttgac  1320
aacatcgaag tcgtcgaaga gcccgacgg gtgcagtcca acttcgtgcg gggctattcc  1380
aggttgatgg tcaaactgac accgaacagt gtactccatc gtcatcaacc tgtcaccatc  1440
ggcgagccgc ccgctcgtgc tgtgagccgc acggtgaccg ttgagcgtct tgatcgcatt  1500
gccgacgatg tccttcgcct ggtccttcgc gatgctggag gtaaaaccct cccgacgtgg  1560
acgcctggcg ctcacatcga cctggatctg ggtgctctga gccgtcagta ttcgctctgc  1620
ggcgctccgg atgctccgtc gtacgaaatc gccgtgcact agatccgga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cggggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttcgcga agtagccgtt  2280
ctggatggca aggttgatca ccgtgatacc gttctgacta aggccgagcg cgccgcgaat  2340
cgtcagatga tgacttgctg cagtcgtgca tgcggtgatc gtctggtcct gcgcctctaa  2400
```

SEQ ID NO: 44          moltype = AA  length = 799
FEATURE                Location/Qualifiers
REGION                 1..799
                       note = source = /note="Description of Artificial Sequence:
                       Synthetic polypeptide"
source                 1..799
                       mol_type = protein
                       organism = synthetic construct
SEQUENCE: 44
```
MPTLPRTFDD IQSRLINATS RVVPMQLQIQ GLKFLMSAKR KTFGPRRPMP EFVETPIPDV  60
NTLALEDIDV SNPFLYRQGQ WDAYFKRLRD EAPVHYQKNS PFGPFWSVTR FEDILFVDKS  120
HDLFSAEPQI ILGDPPEGLS MEMFIAMDPP KHDVQRSSVQ GVVAPKNLKE MEGLIRSNTG  180
DVLDSLPTDK PFNWVPAVSK ELTGRMLATL LDFPYEERHK LVEWSDRMAG AASATGEFA  240
DENAMFDDAA DMARSFSRLW RDKEARRAAG EEPGFDLISL LQSNKETKDL INRPMEFIGN  300
LTLLIVAGAD TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLVLRL                                                799
```

SEQ ID NO: 45          moltype = DNA  length = 2400
FEATURE                Location/Qualifiers
misc_feature           1..2400
                       note = source = /note="Description of Artificial Sequence:
                       Synthetic polynucleotide"
source                 1..2400
                       mol_type = other DNA
                       organism = synthetic construct
SEQUENCE: 45
```
atgccaacac tgcccagaac atttgacgac attcagtccc gactgattaa cgccacctcc  60
agggtggtgc cgatgcagag gcaaattcag ggactgaaat tcttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
```

```
cacgacctgt tttccgccga gccgcaaatc attctcggtg accctccgga ggggctgtcg   420
acggaaatgt tcatagcgat ggatccgccg aaacacgatg tgcagcgcag ctcggtgcag   480
ggagtagtgg caccgaaaaa cctgaaggag atggaggggc tgatccgatc acgcaccggc   540
gatgtgcttg acagcctgcc tacagacaaa ccctttaact gggtacctgc tgtttccaag   600
gaactcacag gccgcatgct ggcgacgctt ctggattttc cttacgagga acgccacaag   660
ctggttgagt ggtcggacag aatggcaggt acagcatcgg ccaccggcgg ggagtttgcc   720
gatgaaaatg ccatgtttga cgacgcggca gacatggccc ggtctttctc caggctttgg   780
cgggacaagg aggcgcgccg cgcagcaggc gaggagcccg gtttcgattt gatcagcctg   840
ttgcagagca acaaagaaac gaaagacctg atcaatcggc cgatggagtt tatcggtaat   900
ttgacgctgc tcatagtcgc cggcaacgat acgacgcgca actcgatgag tggtggcctg   960
gtggccatga acgaattccc cagggaattt gaaaaattga aggcaaaacc ggagttgatt  1020
ccgaacatgt gtgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cgggtaaccg ggacgacgcgc aaatttgaca accccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaaaccct cccgacgtgg  1560
acgcctggcg ctcacatcga cctggatctg ggtgctctga gccgtcagta ttcgctctgc  1620
ggcgctccgg atgctccgtc gtacgaaatc gccgtgcact tagatccgga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cggggggtatc  1800
ggcatcacgc cggtgctggc aatggcggat catgcccgtg cgcgtggttg gtcgtacgaa  1860
ctgcattatt gtggtcgtaa tcgtagcggt atggctacc atggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggtcct gcgcctctaa  2400
```

SEQ ID NO: 46          moltype = AA   length = 799
FEATURE                Location/Qualifiers
REGION                 1..799
                       note = source = /note="Description of Artificial Sequence:
                        Synthetic polypeptide"
source                 1..799
                       mol_type = protein
                       organism = synthetic construct
SEQUENCE: 46
```
MPTLPRTFDD IQSRLINATS RVVPMQRQIQ GLKFLMSAKR KTFGPRRPMP EFVETPIPDV   60
NTLALEDIDV SNPFLYRQGQ WRAYFKRLRD EAPVHYQKNS PFGPFWSVTR FEDILFVDKS  120
HDLFSAEPQI ILGDPPEGLS TEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG TASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH DRAALHVSE  EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLVLRL                                               799
```

SEQ ID NO: 47          moltype = DNA   length = 2415
FEATURE                Location/Qualifiers
misc_feature           1..2415
                       note = source = /note="Description of Artificial Sequence:
                        Synthetic polynucleotide"
source                 1..2415
                       mol_type = other DNA
                       organism = synthetic construct
SEQUENCE: 47
```
atgccaacac tgcccagaac atttgacgac attcagtccc gactgattaa cgccacctcc   60
agggtggtgc cgatgcagag gcaaattcag ggactgaaat cttaatgag cgccaagagg  120
aagaccttcg gcccacgccg accgatgccc gaattcgttg aaacacccat cccggacgtt  180
aacacgctgc cccttgagga catcgatgtc agcaatccgt ttttataccg gcagggtcag  240
tggcgcgcct atttcaaacg gttgcgtgat gaggcgccgg tccattacca gaagaacagc  300
cctttcggtc ccttctggtc ggtaactcgg tttgaagaca tcctgttcgt ggataagagt  360
cacgacctgt tttccgccga gccgcaaatc attctcggtg accctccgga ggggctgtcg   420
gtggaaatgt tcatagcgat ggatccgccg aaacacgatg tgcagcgcag ctcggtgcag   480
ggagtagtgg caccgaaaaa cctgaaggag atggaggggc tgatccgatc acgcaccggc   540
gatgtgcttg acagcctgcc tacagacaaa ccctttaact gggtacctgc tgtttccaag   600
gaactcacag gccgcatgct ggcgacgctt ctggatttc cttacgagga acgccacaag   660
```

```
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga acgaattccc cagggaattg gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa gcgttttgac  1320
aacatcgaag tcgtcgaaga gcccgagcgg gtgcagtcca acttcgtgcg gggctattcc  1380
aggttgatgg tcaaactgac accgaacagt gtgctggcgc cacgtgacgc ggtccgcatc  1440
ggcgaaccga ctggcggcac caccggtcgc acgctcattg tcgagcgcgt cgagacggcc  1500
gcgcagggtg tgtcgcggat ccgcctggtt tcgcccgatg gtcgcgcact accgcgttgg  1560
tcgcccgggct cgcatatcga catcgaatgc ggccacaccg gcatctcgcg ccagtattcg  1620
ctgtgcggca accccgccga taccagcgcc ttcgagatcg cggtgctgcg cgagcccgaa  1680
agccgtggtg gatcggcgtg gattcatgcc agtctgcgcg caggcgacaa gctcaaggtt  1740
cgcggcccgc gcaatcactt ccggctcgac gagacctgcc gtcgcgcgat cttcatcgcc  1800
ggtggcattg gcgtgactcc ggtcagcgcc atggcaaggc gtcgcgaaga actgggcgtc  1860
gactacacct tccactattg cggccgcagc cgtgcctcca tggcgatgat cgatgaactg  1920
cgcgccctgc atggtgatcg cgtcgcggatt catgccgcgg atgaaggcca gcgcgccgat  1980
ctcgcgcaag tgctcggcgc acccgatgcg aacacgcaga tctacgcttg tggaccggcc  2040
cggatgatcg aggcgctgga agccctgtgc gcgacatggc ccgaggattc gctgcgcgtc  2100
gaacacttca gttcgaaact tggaacgctc gatccctcca gggaacagcc gtttgcggtc  2160
gaactgaagg actcggggct gacgcttgaa gttcctccgg accagacgct gctcgccacc  2220
ctgcgcgccg cgaacatcga cgtgcaaagc gattgcgagg aaggcctgtg tggatcgtgt  2280
gaagtgcgcg tgctggccgg cgagatcgac caccgcgacg tcgtgctgac gcgcggcgag  2340
cgtgatgcga acaaccggat gatggcctgc tgctcgcgag cggcgaaggg cggaaagatc  2400
gtgctggggc tgtaa                                                    2415
```

```
SEQ ID NO: 48         moltype = AA  length = 804
FEATURE               Location/Qualifiers
REGION                1..804
                      note = source = /note="Description of Artificial Sequence:
                      Synthetic polypeptide"
source                1..804
                      mol_type = protein
                      organism = synthetic construct
SEQUENCE: 48
MPTLPRTFDD IQSRLINATS RVVPMQRQIQ GLKFLMSAKR KTFGPRRPMP EFVETPIPDV  60
NTLALEDIDV SNPFLYRQGQ WRAYFKRLRD EAPVHYQKNS PFGPFWSVTR FEDILFVDKS  120
HDLFSAEPQI ILGDPPEGLS VEMFIAMDPP KHDVQRSSVQ GVVAPKNLKE MEGLIRSRTG  180
DVLDSLPTDK PFNWVPAVSK ELTGRMLATL LDFPYEERHK LVEWSDRMAG AASATGGEFA  240
DENAMFDDAA DMARSFSRLW RDKEARRAAG EEPGFDLISL LQSNKETKDL INRPMEFIGN  300
LTLLIVAGND TTRNSMSGGL VAMNEFPREF EKLKAKPELI PNMVSEIIRW QTPLAYMRRI  360
AKQDVELGGQ TIKKGDRVVM WYASGNRDER KFDNPDQFII DRKDARNHMS FGYGVHRCMG  420
NRLAELQLRI LWEEILKRFD NIEVVEEPER VQSNFVRGYS RLMVKLTPNS VLAPRDAVRI  480
GEPTGGTTGR TLIVERVETA AQGVSRIRLV SPDGRALPRW SPGSHIDIEC GHTGISRQYS  540
LCGDPADTSA FEIAVLREPE SRGGSAWIHA SLRAGDKLKV RGPRNHFRLD ETCRRAIFIA  600
GGIGVTPVSA MARRAKELGV DYTFHYCGRS RASMAMIDEL RALHGDRVRI HAADEGQRAD  660
LAQVLGAPDA NTQIYACGPA RMIEALEALC ATWPEDSLRV EHFSSKLGTL DPSREQPFAV  720
ELKDSGLTLE VPPDQTLLAT LRAANIDVQS DCEEGLCGSC EVRVLAGEID HRDVVLTRGE  780
RDANNRMMAC CSRAAKGGKI VLGL                                          804
```

```
SEQ ID NO: 49         moltype = DNA  length = 2400
FEATURE               Location/Qualifiers
misc_feature          1..2400
                      note = source = /note="Description of Artificial Sequence:
                      Synthetic polynucleotide"
source                1..2400
                      mol_type = other DNA
                      organism = synthetic construct
SEQUENCE: 49
atgccaacac tgcccagaac atttgacgac attcagtccc gactgattaa cgccacctcc  60
agggtggtgc cgatgcagag gcaaattcag ggactgaaat cttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tggcgcgcct atttcaaacg gttgcgtgat gaggcgcgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
gtggaaatgt tcatagcgat ggatccgccg aaacacgatg tgcagcgcag ctcggtgcag  480
ggagtagtgg caccgaaaaa cctgaaggag atggagggc tgatccgatc acgcaccggc  540
gatgtgcttg acagcctgcc tacagacaaa ccctttaact ggtacctgc tgtttccaag  600
gaactcacag gccgcatgct ggcgacgctt ctgattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatggccc ggtctttctc caggctttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
```

```
ttgacgctgc tcatagtcgc cggcaacgat acgacgcgca actcgatgag tggtggcctg    960
gtggccatga acgaattccc cagggaattt gaaaaattga aggcaaaacc ggagttgatt   1020
ccgaacatgg tgtcggaaat catccgctgg caaacgccgc tggcctatat gcgccgaatc   1080
gccaagcagg atgtcgaact gggcggccag accatcaaga agggtgatcg agttgtcatg   1140
tggtacgcgt cgggtaaccg ggacgagcgc aaatttgaca accccgatca gttcatcatt   1200
gatcgcaagg acgacgaaa ccacatgtcg ttcggctatg gggttcaccg ttgcatgggc   1260
aaccgtctgg ctgaactgca actgcgcatc ctctgggaag aaatactcaa gcgttttgac   1320
aacatcgaag tcgtcgaaga gcccgagcgg gtgcagtcca acttcgtgcg gggctattcc   1380
aggttgatgg tcaaactgac accgaacagt actgccagac aaattaccag ttttcctatt   1440
ggagcgcctg atctcaaggc catgacccgc ccggtacgtg tccaggcagt ttatcctgaa   1500
gcagaagata ttatacgtat tgagctggct gctatacacg gtgaagaatt accacgctgg   1560
agtgccggtt cacatattga actggtattg cctaatggcc tgagccgtaa gtactctcta   1620
tgcggtttag cgactgatca attttatacg attgctgtaa agagagagca ggaaagccgg   1680
ggtggttcac aatggattca tcagtattta aaagcaggag aacagatcta cattaaggga   1740
cctaaaaact tttttaaatt aaatttacag gcgagccagt atgtgctgat cgcaggtggg   1800
ataggtatta ctcctattct gagcatggcc agcagcttac gtgaacaggg cgcgcccttac  1860
cggctaattt atctttcacg ccagcgggct agtatggcat tacttaagga agttgctgcg   1920
catggtagtg ctgccgaact ctatatttct tctgaaggta aacggataga cctgcaacag   1980
ctcttgtcag cgctgcctgc cggtacacag gtttgtgcct gtggtccgga agcattactt   2040
gataccttga ccaactatac cgaagacttg tcacaggttc agctcacggt cgagcatttt   2100
ggttcaggga agaacctctt tttatatgaa aatgataccg actttgaagt tgaactgctg   2160
gatagcggtt taacgctgac agtagcccgg gatcagacct tattggacgtg tttgctggac  2220
aaaggaattg atgtcagctt tgactgtacc gagggttttat gtggaagctg tcagcttccg   2280
gttgaagaag gtgaaattga tcatcgcgac aaggtgttga cccgagccga gcgtgacgga   2340
atgaaatcgg taatcagttg ctgttcacga ggaaaaggaa aactcaaact caagctttaa   2400
```

```
SEQ ID NO: 50            moltype = AA  length = 799
FEATURE                  Location/Qualifiers
REGION                   1..799
                         note = source = /note="Description of Artificial Sequence:
                         Synthetic polypeptide"
source                   1..799
                         mol_type = protein
                         organism = synthetic construct
SEQUENCE: 50
MPTLPRTFDD IQSRLINATS RVVPMQRQIQ GLKFLMSAKR KTFGPRRPMP EFVETPIPDV    60
NTLALEDIDV SNPFLYRQGQ WRAYFKRLRD EAPVHYQKNS PFGPFWSVTR FEDILFVDKS   120
HDLFSAEPQI ILGDPPEGLS VEMFIAMDPP KHDVQRSSVQ GVVAPKNLKE MEGLIRSRTG   180
DVLDSLPTDK PFNWVPAVSK ELTGRMLATL LDFPYEERHK LVEWSDRMAG AASATGGEFA   240
DENAMFDDAA DMARSFSRLW RDKEARRAAG EEPGFDLISL LQSNKETKDL INRPMEFIGN   300
LTLLIVAGND TTRNSMSGGL VAMNEFPREF EKLKAKPELI PNMVSEIIRW QTPLAYMRRI   360
AKQDVELGGQ TIKKGDRVVM WYASGNRDER KFDNPDQFII DRKDARNHMS FGYGVHRCMG   420
NRLAELQLRI LWEEILKRFD NIEVVEEPER VQSNFVRGYS RLMVKLTPNS TARQITSFPI   480
GAPDLKAMTR PVRVQAVYPE AEDIIRIELA AIHGEELPRW SAGSHIELVL PNGLSRKYSL   540
CGLATDQFYT IAVKREQESR GGSQWIHQYL KAGEQIYIKG PKNFFKLNLQ ASQYVLIAGG   600
IGITPILSMA SSLREQGRPY RLIYLSRQRA SMALLKEVAA HGSAAELYIS SEGKRIDLQQ   660
LLSALPAGTQ VCACGPEALL DTLTNYTEDL SQVQLTVEHF GSGKNLFLYE NDTDFEVELL   720
DSGLTLTVAR DQTLLDCLLD KGIDVSFDCT EGLCGSCQLP VEEGEIDHRD KVLTRAERDG   780
MKSVISCCSR GKGKLKLKL                                               799
```

```
SEQ ID NO: 51            moltype = DNA  length = 2238
FEATURE                  Location/Qualifiers
misc_feature             1..2238
                         note = source = /note="Description of Artificial Sequence:
                         Synthetic polynucleotide"
source                   1..2238
                         mol_type = other DNA
                         organism = synthetic construct
SEQUENCE: 51
atggaacata caggacaaag cgcggcggcg acgatgccgc tcgattcgat cgacgtgagt    60
atcccagaac tcttctacaa cgacagtgtt ggcgaatatt tcaagcggct gcgcaaggat   120
gatccagtcc actattgcgc cgacagcgcg tttgggccct actggtccat cacgaaatat   180
aatgacataa tgcacgtcga cacaaatcat gacatcttct cgtccgatgc aggatatggc   240
ggcatcataa tcgatgacgg cattcaaaaa ggtggcgatg gcggactgga tcttcccaat   300
ttcatcgcga tggatcggcc gcgacacgac gaacaaagaa aagctgtaag cccgattgta   360
gcccccgcca atttggccgc gcttgaaggc accattcgcg aacgagttag caaaacgctc   420
gatggtcttc cggtgggtga ggagttcgat tgggtagatc gcgtgtcgat cgaaatcacc   480
actcaaatgc tcgccaccct gttcgacttt ccgtttgaag agcgccgcaa gcttacccgc   540
tggtcggatg tgacaaccgc agcacccggc ggcggagttg tcgaaagctg ggatcagaga   600
aaaaccgaat tgttggaatg tgccgcttat ttccaggtgc tttggaatga gcgtgtcaac   660
aaggaccccg gcaacgatct catttcgatg ctggcacatt cgccagccac gcggaacatg   720
acgcccgaag agtatctggg caatgtactt ctcctgatcg ttgccgggaa cgataccaca   780
cgcaattcga tgaccggtgg cgtttttagct ctccacaaga atccggacca gtttgccaag   840
ctaaaagcca accctgcgct ggttgaaacg atggtccctg aaatcattcg ctggcaaaca   900
ccgcttgctc atatgcgccg cacggccatt gcagattccg aactgggtgg gaagaccatc   960
cgcaagggcg acaaggtcgt catgtggtat tattcgggta tcgcgatgac gaagtgatt   1020
gaccgtcccg aagaatttat catcgaccgc ccccggcccc gccagcattt gtcattcggc   1080
tttgggcatcc accgttgcgt tggcaatcgg ctagccgaaa tgcagctccg gatattgtgg   1140
gaagaaaattc tcacgcgttt cagtcgtatc gaagtgatgg ccgaaccgga acgggtccgt   1200
```

```
tcaaattttg tgcgcggtta cgccaagatg atggttcgcg tccacgcggt actccatcgt  1260
catcaacctg tcaccatcgg cgagccggcc gctcgtgctg tgagccgcac ggtgaccgtt  1320
gagcgtcttg atcgcattgc cgacgatgtc cttcgcctgg tccttcgcga tgctggaggt  1380
aaaaccctcc cgacgtggac gcctggcgct cacatcgacc tggatctggg tgctctgagc  1440
cgtcagtatt cgctctgcgg cgctccggat gctccgtcgt acgaaatcgc cgtgcactta  1500
gatccggaaa gccgtggtgg aagccgctat attcatgaac agctggaagt tggaagtccg  1560
ctgcgtatgc gtggcccacg caaccatttc gccctggatc cgggtgcgga acattacgtg  1620
tttgttgccg ggggtatcgg catcacgccg gtgctggcaa tggcggatca tgcccgtgcg  1680
cgtggttggt cgtacgaact gcattattgt ggtcgtaatc gtagcggtat ggcttacctg  1740
gaacgcgtcg cgggacatgg tgaccgcgct gccttgcacg tatctgaaga aggcacccgc  1800
attgatctgg cggcattact tgctgaaccg gcgccgggcg tgcaaatcta cgcctgcggt  1860
ccgggccgtt tattagcggg tcttgaagac gcgtctcgta attggccgga tggcgcgctt  1920
catgtggagc atttcacttc gagtttagcc gctttggatc cggatgtcga acatgccttt  1980
gatttggagc tgcgtgactc tggccttacc gttcgcgtcg agccaactca gaccgtttta  2040
gacgctttgc gtgcgaacaa tatcgacgtc ccgtcggatt gcgaagaggg gctgtgtggt  2100
tcttgcgaag tagccgttct ggatggcgag gttgatcacc gtgataccgt tctgactaag  2160
gccgagcgcg ccgcgaatcg tcagatgatg acttgctgca gtcgtgcatg cggtgatcgt  2220
ctggcgctgc gcctctaa                                                 2238
```

```
SEQ ID NO: 52              moltype = AA  length = 745
FEATURE                    Location/Qualifiers
REGION                     1..745
                           note = source = /note="Description of Artificial Sequence:
                           Synthetic polypeptide"
source                     1..745
                           mol_type = protein
                           organism = synthetic construct
SEQUENCE: 52
MEHTGQSAAA TMPLDSIDVS IPELFYNDSV GEYFKRLRKD DPVHYCADSA FGPYWSITKY   60
NDIMHVDTNH DIFSSDAGYG GIIIDDGIQK GGDGGLDLPN FIAMDRPRHD EQRKAVSPIV  120
APANLAALEG TIRERVSKTL DGLPVGEEFD WVDRVSIEIT TQMLATLFDF PFEERRKLTR  180
WSDVTTAAPG GGVVESWDQR KTELLECAAY FQVLWNERVN KDPGNDLISM LAHSPATRNM  240
TPEEYLGNVL LLIVAGNDTT RNSMTGGVLA LHKNPDQFAK LKANPALVET MVPEIIRWQT  300
PLAHMRRTAI ADSELGGKTI RKGDKVVMWY YSGNRDDEVI DRPEEFIIDR PRPRQHLSFG  360
FGIHRCVGNR LAEMQLRILW EEILTRFSRI EVMAEPERVR SNFVRGYAKM MVRVHAVLHR  420
HQPVTIGEPA ARAVSRTVTV ERLDRIADDV LRLVLRDAGG KTLPTWTPGA HIDLDLGALS  480
RQYSLCGAPD APSYEIAVHL DPESRGGSRY IHEQLEVGSP LRMRGPRNHF ALDPGAEHYV  540
FVAGGIGITP VLAMADHARA RGWSYELHYC GRNRSGMAYL ERVAGHGDRA ALHVSEEGTR  600
IDLAALLAEP APGVQIYACG PGRLLAGLED ASRNWPDGAL HVEHFTSSLA ALDPDVEHAF  660
DLELRDSGLT VRVEPTQTVL DALRANNIDV PSDCEEGLCG SCEVAVLDGE VDHRDTVLTK  720
AERAANRQMM TCCSRACGDR LALRL                                        745
```

```
SEQ ID NO: 53              moltype = DNA  length = 3180
FEATURE                    Location/Qualifiers
misc_feature               1..3180
                           note = source = /note="Description of Artificial Sequence:
                           Synthetic polynucleotide"
source                     1..3180
                           mol_type = other DNA
                           organism = synthetic construct
SEQUENCE: 53
atgccaacac tgcccagaac atttgacgac attcagtccc gactgattaa cgccacctcc   60
agggtggtgc cgatgcagag gcaaattcag ggactgaaat tcttaatgag cgccaagagg  120
aagaccttcg gcccacgccg accgatgccc gaattcgttg aaacacccat cccggacgtt  180
aacacgctgg cccttgagga catcgatgtc agcaatccgt ttttataccg gcagggtcag  240
tggcgcgcct atttcaaacg gttgcgtgat gaggcgccgg tccattacca gaagaacagc  300
cctttcggcc ccttctggtc ggtaactcgg tttgaagaca tcctgttcgt ggataagagt  360
cacgacctgt tttccgccga gccgcaaatc attctcggtg accctccgga ggggctgtcg  420
gtggaaatgt tcatagcgat ggatccgccg aaacacgatg tgcagcgcag ctcggtgcag  480
ggagtagtgg caccgaaaaa cctgaaggag atggaggggc tgatccgatc acgcaccggc  540
gatgtgcttg acagcctgcc tacagacaaa ccctttaact gggtacctgc tgtttccaag  600
gaactcacag gccgcatgct ggcgacgctt ctggattttc cttacgagga acgccacaag  660
ctggttgagt ggtcggacag aatggcaggt gcagcatcgg ccaccggcgg ggagtttgcc  720
gatgaaaatg ccatgtttga cgacgcggca gacatgcctg ggtctttctc caggcgtttgg  780
cgggacaagg aggcgcgccg cgcagcaggc gaggagcccg gtttcgattt gatcagcctg  840
ttgcagagca acaaagaaac gaaagacctg atcaatcggc cgatggagtt tatcggtaat  900
ttgacgctgc tcatagtcgc cggcaacgat acgacgcgca actcgatgag tggtggcctg  960
gtggccatga acgaattccc cagggaattt gaaaaattga aggcaaaacc ggagttgatt  1020
ccgaacatgg tgtcggaaat catccgctgg caaacgccgc tggcctatat gcgccgaatc  1080
gccaagcagg atgtcgaact gggcggccag accatcaaga agggtgatcg agttgtcatg  1140
tggtacgcgt cgggtaaccg ggacgagcgc aaatttgaca accccgatca gttcatcatt  1200
gatcgcaagg acgcacgaaa ccacatgtcg ttcggctatg gggttcaccg ttgcatgggc  1260
aaccgtctgg ctgaactgca actgcgcatc ctctgggaag aaatactcaa cgcgttttgac  1320
aacatcgaag tcgtcgaaga gcccgagcgg gtgcagtcca acttcgtgcg gggctattcc  1380
aggttgatgg tcaaactgac accgaacagt tcacctagca ctgaacagtc tgctaaaaaa  1440
gtacgcaaaa aggcagaaaa cgctcataat acgccgctgc ttgtgctata cggttcaaat  1500
atgggaacag ctgaaggaac ggcgcgtgat ttagcagata ttgcaatgag caaaggattt  1560
gcaccgcagg tcgcaacgct tgattcacac gccggaaatc ttccgcgcga aggagctgta  1620
ttaattgtaa cggcgtctta taacggtcat ccgcctgata acgcaaagca atttgtcgac  1680
```

```
tggttagacc aagcgtctgc tgatgaagta aaaggcgttc gctactccgt atttggatgc 1740
ggcgataaaa actgggctac tacgtatcaa aaagtgcctg cttttatcga tgaaacgctt 1800
gccgctaaag gggcagaaaa catcgctgac cgcggtgaag cagatgcaag cgacgacttt 1860
gaaggcacat atgaagaatg gcgtgaacat atgtggagtg acgtagcagc ctactttaac 1920
ctcgacattg aaaacagtga agataataaa tctactcttt cacttcaatt tgtcgacagc 1980
gccgcggata tgccgcttgc gaaaatgcac ggtgcgtttt caacgaacgt cgtagcaagc 2040
aaagaacttc aacagccagg cagtgcacga agcacgcgac atcttgaaat tgaacttcca 2100
aaagaagctt cttatcaaga aggagatcat ttaggtgtta ttcctcgcaa ctatgaagga 2160
atagtaaacc gtgtaacagc aaggttcggc ctagatgcat cacagcaaat ccgtctggaa 2220
gcagaagaag aaaaattagc tcatttgcca ctcgctaaaa cagtatccgt agaagagctt 2280
ctgcaatacg tggagcttca agatcctgtt acgcgcacgc agcttcgcgc aatggctgct 2340
aaaacggtct gcccgccgca taaagtagag cttgaagcct tgcttgaaaa gcaagcctac 2400
aaagaacaag tgctggcaaa acgtttaaca atgcttgaac tgcttgaaaa atacccggcg 2460
tgtgaaatga aattcagcga atttatcgcc cttctgccaa gcatacgccc gcgctattac 2520
tcgatttctt catcacctcg tgtcgatgaa aaacaagcaa gcatcacggt cagcgttgtc 2580
tcaggagaag cgtggagcgg atatggagaa tataaaggaa ttgcgtcgaa ctatcttgcc 2640
gagctgcaag aaggagatac gattacgtgc tttatttcca caccgcagtc agaatttacg 2700
ctgccaaaag accctgaaac gccgcttatc atggtcggac cgggaacagg cgtcgcgccg 2760
tttagaggct ttgtgcaggc gcgcaaacag ctaaaagaac aaggacagtc acttggagaa 2820
gcacatttat acttcggctg ccgttcacct catgaagact atctgtatca agaagagctt 2880
gaaaacgccc aaagcgaagg catcattacg cttcataccg cttttttctcg catgccaaat 2940
cagccgaaaa catacgttca gcacgtaatg gaacaagacg gcaagaaatt gattgaactt 3000
cttgatcaag gagcgcactt ctatatttgc ggagacggaa gccaaatggc acctgccgtt 3060
gaagcaacgc ttatgaaaag ctatgctgac gttcaccaag tgagtgaagc agacgctcgc 3120
ttatggctgc agcagctaga agaaaaaggc cgatacgcaa aagacgtgtg ggctgggtaa 3180
```

```
SEQ ID NO: 54          moltype = AA  length = 1059
FEATURE                Location/Qualifiers
REGION                 1..1059
                       note = source = /note="Description of Artificial Sequence:
                       Synthetic polypeptide"
source                 1..1059
                       mol_type = protein
                       organism = synthetic construct
SEQUENCE: 54
MPTLPRTFDD IQSRLINATS RVVPMQRQIQ GLKFLMSAKR KTFGPRRPMP EFVETPIPDV 60
NTLALEDIDV SNPFLYRQGQ WRAYFKRLRD EAPVHYQKNS PFGPFWSVTR FEDILFVDKS 120
HDLFSAEPQI ILGDPPEGLS VEMFIAMDPP KHDVQRSSVQ GVVAPKNLKE MEGLIRSRTG 180
DVLDSLPTDK PFNWVPAVSK ELTGRMLATL LDFPYEERHK LVEWSDRMAG AASATGGEFA 240
DENAMFDDAA DMARSFSRLW RDKEARRAAG EEPGFDLISL LQSNKETKDL INRPMEFIGN 300
LTLLIVAGND TTRNSMSGGL VAMNEFPREF EKLKAKPELI PNMVSEIIRW QTPLAYMRRI 360
AKQDVELGGQ TIKKGDRVVM WYASGNRDER KFDNPDQFII DRKDARNHMS FGYGVHRCMG 420
NRLAELQLRI LWEEILKRFD NIEVVEEPER VQSNFVRGYS RLMVKLTPNS SPSTEQSAKK 480
VRKKAENAHN TPLLVLYGSN MGTAEGTARD LADIAMSKGF APQVATLDSH AGNLPREGAV 540
LIVTASYNGH PPDNAKQFVD WLDQASADEV KGVRYSVFGC GDKNWATTYQ KVPAFIDETL 600
AAKGAENIAD RGEADASDDF EGTYEEWREH MWSDVAAYFN LDIENSEDNK STLSLQFVDS 660
AADMPLAKMH GAFSTNVVAS KELQQPGSAR STRHLEIELP KEASYQEGDH LGVIPRNYEG 720
IVNRVTARFG LDASQQIRLE AEEEKLAHLP LAKTVSVEEL LQYVELQDPV TRTQLRAMAA 780
KTVCPPHKVE LEALLEKQAY KEQVLAKRLT MLELLEKYPA CEMKFSEFIA LLPSIRPRYY 840
SISSSPRVDE KQASITVSVV SGEAWSGYGE YKGIASNYLA ELQEGDTITC FISTPQSEFT 900
LPKDPETPLI MVGPGTGVAP FRGFVQARKQ LKEQGQSLGE AHLYFGCRSP HEDYLYQEEL 960
ENAQSEGIIT LHTAFSRMPN QPKTYVQHVM EQDGKKLIEL LDQGAHFYIC GDGSQMAPAV 1020
EATLMKSYAD VHQVSEADAR LWLQQLEEKG RYAKDVWAG 1059
```

```
SEQ ID NO: 55          moltype = DNA  length = 3246
FEATURE                Location/Qualifiers
misc_feature           1..3246
                       note = source = /note="Description of Artificial Sequence:
                       Synthetic polynucleotide"
source                 1..3246
                       mol_type = other DNA
                       organism = synthetic construct
SEQUENCE: 55
atgccaacac tgcccagaac atttgacgac attcagtccc gactgattaa cgccacctcc 60
agggtggtgc cgatgcagag gcaaattcag ggactgaaat cttaatgag cgccaagagg 120
aagaccttcg gcccacgccg accgatgccc gaattcgttg aaacacccat cccggacgtt 180
aacacgctgg cccttgagga catcgatgtc agcaatccgt ttttataccg gcagggtcag 240
tggcgcgcct atttcaaacg gttgcgtgat gaggcgccgg tccattacca gaagaacagc 300
cctttcggcc ccttctggtc ggtaactcgg tttgaagaca tcctgttcgt ggataagagt 360
cacgacctgt tttccgccga gccgcaaatc attctcggtg accctccgga ggggctgtcg 420
gtggaaatgt tcatagcgat ggatccgccg aaacacgatg tgcagcgcag ctcggtgcag 480
ggagtagtgg caccgaaaaa cctgaaggag atggagggc tgatccgatc acgcaccggc 540
gatgtgcttg acagcctgcc tacagacaaa ccctttaact gggtacctgc tgtttccaag 600
gaactcacag gccgcatgct ggcgacgctt ctggattttc cttacgagga acgccacaag 660
ctggttgagt ggtcggacag aatggcaggt gcagcatcgg ccaccggcgg ggagtttgcc 720
gatgaaaatg ccatgtttga cgacgcggca gacatggccc ggtctttctc caggctttgg 780
cgggacaagg aggcgcgccg cgcagcaggc gaggagcccg gttcgatttt gatcagcctg 840
ttgcagagca acaaagaaac gaaagacctg atcaatcggc cgatggagtt tatcggtaat 900
ttgacgctgc tcatagtcgc cggcaacgat acgacgcgca actcgatgag tggtggcctg 960
```

```
gtggccatga acgaattccc cagggaattt gaaaaattga aggcaaaacc ggagttgatt   1020
ccgaacatgg tgtcggaaat catccgctgc caaacgccgc tggcctatat gcgccgaatc   1080
gccaagcagg atgtcgaact gggcggccag accatcaaga agggtgatcg agttgtcatg   1140
tggtacgcgt cgggtaaccg ggacgagcgc aaatttgaca accccgatca gttcatcatt   1200
gatcgcaagg acgcacgaaa ccacatgtcg ttcggctatg gggttcaccg ttgcatgggc   1260
aaccgtctgg ctgaactgca actgcgcatc ctctgggaag aaatactcaa gcgttttgac   1320
aacatcgaag tcgtcgaaga gcccgagcgg gtgcagtcca acttcgtgcg gggctattcc   1380
aggttgatgg tcaaactgac accgaacagt ggcgctcagc ctgaagagaa cggacggcag   1440
gaagaacggc cttccgcacc ggcggcggaa aatacgacg gaacccctct tcttgtgctc   1500
tacggttcaa atctcggcac agccgaagag attgcgaagg agcttgctga agaagcgcgt   1560
gagcaagggt ttcacagccg gacggcggag cttgatcaat acgcaggcgc catcccggca   1620
gaaggggctg ttatcattgt gacggcttcc tataacggaa acccgcccga ttgcgcaaag   1680
gaatttgtca attggcttga gcatgatcag acagacgatt tgcgtggtgt caaatatgcg   1740
gtattcggct gcggtaaccg cagctgggcc agcacctacc agcggattcc gcgcctgatt   1800
gacagcgtat tggaaaaaaa aggcgcccaa aggctgcaca agcttggaga aggggatgca   1860
ggcgatgatt ttgaaggaca gtttgagtca tggaaatatg atctgtggcc gcttttaaga   1920
accgaatttt cattggccga acccgagccg aatcaaacag aaacagacag gcaagcctta   1980
tctgtcgagt tcgtaaacgc acctgcggct tcgccgctag ctaaagctta tcaggtgtca   2040
acagcgaaga tatcggcaaa ccgagaactg cagtgtgaaa agagcgggag aagcacaagg   2100
catattgaaa tatcgcttcc tgaaggcgcc gcatatcagg agggagacca tctcggtgtg   2160
ctaccgcaaa acagcgaagt gctgattggc cgcgtttttc agcggtttgg gctgaacgga   2220
aatgaacaaa ttctgattag cggccggaat caagcatcac atttgccttt ggagaggccc   2280
gttcatgtca aagacctttt tcaacattgc gtcgagctcc aggaaccggc cacaagggcc   2340
cagatacgcg agctggcggc tcatactgtt tgtccgcctc atcagcgcga gcttgaagac   2400
ctgctgaaag atgacgtcta taggatcaa gtgttgaata agcggctgac aatgcttgac   2460
ctgcttgagc aataccccggc ctgtgaactg ccgttcgccc gttttctggc gcttcttcct   2520
ccgctaaaac cgaggtacta ttcgatttcc agttcgccgc agcttaaccc gcggcaaaca   2580
agcatcaccg tctctgtcgt aagtggcccg gcgttgagcg gccgcgggca ttataaggga   2640
gttgcatcga actatctcgc cggccttgag ccgggagacg cgatttcgtg tttcatcaga   2700
gagcctcagt caggcttccg gcttcccgaa gatcctgaaa caccggtgat catggtcggg   2760
ccgggcaccg gaatcgcccc ttaccgcgga tttcttcagg cgcgccgcat ccagcgcgat   2820
gccggtgtga agctcggtga agcgcatttg tacttcggct gccgccgtcc gaacgaagat   2880
tttctgtatc gagacgagtt ggagcaagcg gaaaaggacg gaatcgtcca tctgcataca   2940
gcgtttttccc ggcttgaggg ccggccgaaa acatatgtgc aagatttgct cagagaggat   3000
gcagccttgc tgattcactt gttgaacgaa ggcggccgcc tgtatgtgtg cggagacgga   3060
agccgcatgg ctccagctgt tgaacaagct ttgtgcgagg cgtatcgcat agtacagggt   3120
gcgagtcggg aagagtcgca aagctggctg tccgcacttt tagaagaagg gcgctatgca   3180
aaggatgtat gggacggcgg cgtttcccaa cataatgtga aggcggactg cattgcaaga   3240
acgtaa                                                              3246
```

SEQ ID NO: 56                    moltype = AA  length = 1081
FEATURE                          Location/Qualifiers
REGION                           1..1081
                                 note = source = /note="Description of Artificial Sequence:
                                 Synthetic polypeptide"
source                           1..1081
                                 mol_type = protein
                                 organism = synthetic construct
SEQUENCE: 56

```
MPTLPRTFDD IQSRLINATS RVVPMQRQIQ GLKFLMSAKR KTFGPRRPMP EFVETPIPDV   60
NTLALEDIDV SNPFLYRQGQ WRAYFKRLRD EAPVHYQKNS PFGPFWSVTR FEDILFVDKS   120
HDLFSAEPQI ILGDPPEGLS VEMFIAMDPP KHDVQRSSVQ GVVAPKNLKE MEGLIRSRTG   180
DVLDSLPTDK PFNWVPAVSK ELTGRMLATL LDFPYEERHK LVEWSDRMAG AASATGGEFA   240
DENAMFDDAA DMARSFSRLW RDKEARRAAG EEPGFDLISL LQSNKETKDL INRPMEFIGN   300
LTLLIVAGND TTRNSMSGGL VAMNEFPREF EKLKAKPELI PNMVSEIIRW QTPLAYMRRI   360
AKQDVELGGQ TIKKGDRVVM WYASGNRDER KFDNPDQFII DRKDARNHMS FGYGVHRCMG   420
NRLAELQLRI LWEEILKRFD NIEVVEEPER VQSNFVRGYS RLMVKLTPNS GAQPEENGRQ   480
EERPSAPAAE NTHGTPLLVL YGSNLGTAEE IAKELAEEAR EQGFHSRTAE LDQYAGAIPA   540
EGAVIIVTAS YNGNPPDCAK EFVNWLEHDQ TDDLRGVKYA VFGCGNRSWA STYQRIPRLI   600
DSVLEKKGAQ RLHKLGEGDA GDDFEGQFES WKYDLWPLLR TEFSLAEPEP NQTETDRQAL   660
SVEFVNAPAA SPLAKAYQVF TAKISANREL QCEKSGRSTR HIEISLPEGA AYQEGDHLGV   720
LPQNSEVLIG RVFQRFGLNG NEQILISGRN QASHLPLERP VHVKDLFQHC VELQEPATRA   780
QIRLAAHTV CPPHQRELED LLKDDVYKDQ VLNKRLTMLD LLEQYPACEL PFARFLALLP   840
PLKPRYYSIS SSPQLNPRQT SITVSVVSGP ALSGRGHYKG VASNYLAGLE PGDAISCFIR   900
EPQSGFRLPE DPETPVIMVG PGTGIAPYRG FLQARRIQRD AGVKLGEAHL YFGCRRPNED   960
FLYRDELEQA EKDGIVHLHT AFSRLEGRPK TYVQDLLRED AALLIHLLNE GGRLYVCGDG   1020
SRMAPAVEQA LCEAYRIVQG ASREESQSWL SALLEEGRYA KDVWDGGVSQ HNVKADCIAR   1080
T                                                                   1081
```

SEQ ID NO: 57                    moltype = DNA  length = 2400
FEATURE                          Location/Qualifiers
misc_feature                     1..2400
                                 note = source = /note="Description of Artificial Sequence:
                                 Synthetic polynucleotide"
source                           1..2400
                                 mol_type = other DNA
                                 organism = synthetic construct
SEQUENCE: 57

```
atgtcaacga gttcaagtac aagtaatgac atccaggcaa aaataattaa cgccacatcc   60
```

```
aaagtcgtgc caatgcatct acagatcaag gcactaaaaa acttgatgaa ggtgaagcgg  120
aagaccattg gcacttcccg ccctcaggtg cactttgttg aaaccgattt gcctgacgtc  180
aatgatttgg cgatagaaga tatcgatacg agtaaccctt ttttataccg acaaggtaag  240
gcgaatgcgt actttaagcg gttgcgtgat gaagcgccgg tgcactatca gaagaacagt  300
gctttcgggc cgttctggtc ggtaacacgc tacgaagata tcgtcttcgt ggacaagagc  360
catgatttgt tttccgccga accccaaatt atcttgggtg atcctccgga aggcctgtcg  420
gttgaaatgt tcatcgctat ggatcctccc aagcacgacg tacagcgtcg ggcagtccag  480
ggtgttgttg cgcccaagaa cctgaaagaa atggaaggac tgatccgcaa cgcgcaccgg  540
gacgtactgg atagcctgcc gttggacact ccgttcaact gggtgccggt ggtgtcgaaa  600
gagctgaccg ggcgcatgct agcctcactg ttagatttcc cgtatgacga acgcgaaaaa  660
ctggttggct ggtcggatcg attgtccggc gcgtcctcgg caaccggcgg cgagtttacg  720
aatgaagatg tgttttttga tgacgcggca gatatggcgt gggctttctc caagctttgg  780
cgtgataaag aagcccgtca aaaagcaggt gaagagccgg gtttcgattt gatcagcatg  840
cttcagtcca atgaagacac aaaagatctg atcaatcgtc ctttggaatt cattggtaat  900
ctcgcgttgt tgattgttgg cggtaatgac accacgcgta actcaatgag cggggggggtg  960
ctggctttaa atcagttccc agagcaattc gagaagctaa aggcgaaccc aaagcttatc  1020
cccaatatgg tctctgaaat cattcgctgg caaacgccgc ttgcgtatat gcgccgggtt  1080
gccaagcagg atgtggagct gaacggacag accatcaaga aggatgtcg cgtgctgatg  1140
tggtatgcgt cgggcaacca ggatgagaga aaatttgaga atcctgagca attcatcatc  1200
gaccgcaaag atacgcgtaa ccatgtgtcg tttggttatg gggttcaccg ttgtatgggc  1260
aaccgccttg ccgaactgca gctgcgtatt ctgtgggaag agcttctccc tcgctttgaa  1320
aacatcgaag tgatcggtga gccggagcgc gtgcaatcga actttgtgcg gggctattcc  1380
aagatgatgg ttaagttgac ggctaaaaaa gtactccatc gtcatcaacc tgtcaccatc  1440
ggcgagccgg ccgctcgtgc tgtgagccgc acggtgaccg ttgagcgtct tgatcgcatt  1500
gccgacgatg tccttcgcct ggtccttcgc gatgctggag gtaaaaccct cccgacgtgg  1560
acgcctggcg ctcacatcga cctggatctg ggtgctctga ccgtcagta ttcgctctgc  1620
ggcgctccgg atgctccgtc gtacgaaatc gccgtgcact agatccgga aagccgtggt  1680
ggaagccgct atattcatga acagctggaa gttggaagtc cgctgcgtat gcgtggccca  1740
cgcaaccatt tcgccctgga tccgggtgcg gaacattacg tgtttgttgc cggggggtatc  1800
ggcatcacgc cggtgctggc aatggcggat catgcccgtg cgcgtggttg gtcgtacgaa  1860
ctgcattatt gtggtcgtaa tcgtagcggt atggcttacc tggaacgcgt cgcgggacat  1920
ggtgaccgcg ctgccttgca cgtatctgaa gaaggcaccc gcattgatct ggcggcatta  1980
cttgctgaac cggcgccggg cgtgcaaatc tacgcctgcg gtccgggccg tttattagcg  2040
ggtcttgaag acgcgtctcg taattggccg gatggcgcgc ttcatgtgga gcatttcact  2100
tcgagtttag ccgctttgga tccggatgtc gaacatgcct ttgatttgga gctgcgtgac  2160
tctggcctta ccgttcgcgt cgagccaact cagaccgttt tagacgcttt gcgtgcgaac  2220
aatatcgacg tcccgtcgga ttgcgaagag gggctgtgtg gttcttgcga agtagccgtt  2280
ctggatggcg aggttgatca ccgtgatacc gttctgacta aggccgagcg cgccgcgaat  2340
cgtcagatga tgacttgctg cagtcgtgca tgcggtgatc gtctggcgct gcgcctctaa  2400
```

SEQ ID NO: 58                    moltype = AA   length = 799
FEATURE                          Location/Qualifiers
REGION                           1..799
                                 note = source = /note="Description of Artificial Sequence:
                                 Synthetic polypeptide"
source                           1..799
                                 mol_type = protein
                                 organism = synthetic construct
SEQUENCE: 58
MSTSSSTSND IQAKIINATS KVVPMHLQIK ALKNLMKVKR KTIGTSRPQV HFVETDLPDV  60
NDLAIEDIDT SNPFLYRQGK ANAYFKRLRD EAPVHYQKNS AFGPFWSVTR YEDIVFVDKS  120
HDLFSAEPQI ILGDPPEGLS VEMFIAMDPP KHDVQRRAVQ GVVAPKNLKE MEGLIRKRTG  180
DVLDSLPLDT PFNWVPVVSK ELTGRMLASL LDFPYDEREK LVGWSDRLSG ASSATGGEFT  240
NEDVFFDDAA DMAWAFSKLW RDKEARQKAG EEPGFDLISM LQSNEDTKDL INRPLEFIGN  300
LALLIVGGND TTRNSMSGGV LALNQFPEQF EKLKANPKLI PNMVSEIIRW QTPLAYMRRV  360
AKQDVELNGQ TIKKGDRVLM WYASGNQDER KFENPEQFII DRKDTRNHVS FGYGVHRCMG  420
NRLAELQLRI LWEELLPRFE NIEVIGEPER VQSNFVRGYS KMMVKLTAKK VLHRHQPVTI  480
GEPAARAVSR TVTVERLDRI ADDVLRLVLR DAGGKTLPTW TPGAHIDLDL GALSRQYSLC  540
GAPDAPSYEI AVHLDPESRG GSRYIHEQLE VGSPLRMRGP RNHFALDPGA EHYVFVAGGI  600
GITPVLAMAD HARARGWSYE LHYCGRNRSG MAYLERVAGH GDRAALHVSE EGTRIDLAAL  660
LAEPAPGVQI YACGPGRLLA GLEDASRNWP DGALHVEHFT SSLAALDPDV EHAFDLELRD  720
SGLTVRVEPT QTVLDALRAN NIDVPSDCEE GLCGSCEVAV LDGEVDHRDT VLTKAERAAN  780
RQMMTCCSRA CGDRLALRL                                             799

SEQ ID NO: 59                    moltype = DNA   length = 1392
FEATURE                          Location/Qualifiers
source                           1..1392
                                 mol_type = genomic DNA
                                 organism = Mycobacterium marinum
SEQUENCE: 59
atgagcaata ttcgcgaggc agtcactgcc aaggctcagg caacaattcc gatggaccga  60
ataatccagg gcgcccacct ctacgacaga acgcggcgct gggtcaccgg caccaacggt  120
gaaaaaatct tcatcgagcg accgatcccg ccggctgacg aggttgaact gaccgacatc  180
gaccttagca atccttttcct ctatcgtcag ggtcgctcga gtcctatta cgagcgccta  240
cgcaacgagg ctcccgtgca ctatcaggcc cacagcgcgt tcggcccgtt ctggtcggta  300
acgcggcatg ccgacatcgt ggcgtcgac aagaaccacg aggtcttctc ctccgagccg  360
ttcatcgtca tcgggagccc gccgcgcttc ctcgacattg cgatgttcat cgcgatggac  420
cccccaaaac acgaccggca acggcaggct gtccagggtg tggtcgcacc gaagaacctg  480
cgtgagatgg agggcctcat ccgcgagcgg gtggtagacg tgctcgacgc tctgccgctt  540
```

-continued

```
ggcgaaccgt tcaactgggt gcagcacgtc tcgatcgagc taaccgcgcg catgctggcc  600
acgctgctgg acttcccgtt cgagcagcgg cgcaagctcg tccaatggtc cgatctcgcc  660
acctccatgg agcaagccaa cggtgggccc tcggacaacg acgagatatt tcgcggcatg  720
gtcgatatgc ctagaggtct cagcgctcac tggcgggaca aggcagcccg gacagctgcc  780
ggagagctgc ccggcttcga tctgatcacc atgttgcaga gcgacgagag caccaaggac  840
ctgatcgatc gcccgatgga gttcttgggc aacttggtat tgctgatcgt gggtggcaac  900
gatacgaccc gcaattccat gagcggtggt gttctggcgc tgaacgagtt ccctgaccag  960
tttgagaagc tgaaggcgaa ccccgagctg atccccaaca tggtctcgga gatcatccgg  1020
tggcaaaccc cgctcgcgca tatgcgccgg atcgccaagg ccgacactgt gctcaacggg  1080
cagttcatcc gcaagggcga caaggtcctg atgtggtacg cctcgggcaa ccgcgacgag  1140
cgcgtgttcg atcggcccga tgacctgatt atcgatcggg ccaacgcccg taaccacatc  1200
tccttcggtt tcggcgtgca ccgctgtatg ggtaaccggc tggccgagat gcagttgcgg  1260
atcctgtggg aggagctgct tccgcggttc gagaacatcg aggtcgtcgg tgagcccgag  1320
tacgtgcagt ccaacttcgt gagggggatc agtaagctga tggtccgcct caccccgaaa  1380
ggtggcgcat ga                                                       1392
```

```
SEQ ID NO: 60          moltype = AA  length = 463
FEATURE                Location/Qualifiers
source                 1..463
                       mol_type = protein
                       organism = Mycobacterium marinum
SEQUENCE: 60
MSNIREAVTA KAQATIPMDR IIQGAHLYDR TRRWVTGTNG EKIFIERPIP PADEVELTDI   60
DLSNPFLYRQ GRWKSYYERL RNEAPVHYQA HSAFGPFWSV TRHADIVAVD KNHEVFSSEP  120
FIVIGSPPRF LDIAMFIAMD PPKHDRQRQA VQGVVAPKNL REMEGLIRER VVDVLDALPL  180
GEPFNWVQHV SIELTARMLA TLLDPFPFEQR RKLVQWSDLA TSMEQANGGP SDNDEIFRGM  240
VDMARGLSAH WRDKAARTAA GELPGFDLIT MLQSDESTKD LIDRPMEFLG NLVLLIVGGN  300
DTTRNSMSGG VLALNEFPDQ FEKLKANPEL IPNMVSEIIR WQTPLAHMRR IAKADTVLNG  360
QFIRKGDKVL MWYASGNRDE RVFDRPDDLI IDRANARNHI SFGFGVHRCM GNRLAEMQLR  420
ILWEELLPRF ENIEVVGEPE YVQSNFVRGI SKLMVRLTPK GGA                    463
```

```
SEQ ID NO: 61          moltype = DNA  length = 3150
FEATURE                Location/Qualifiers
source                 1..3150
                       mol_type = genomic DNA
                       organism = Bacillus megaterium
SEQUENCE: 61
atgacaatta aagaaatgcc tcagccaaaa acgtttggag agcttaaaaa tttaccgtta   60
ttaaacacag ataaaccggt tcaagctttg atgaaaattg cggatgaatt aggagaaatc  120
tttaaattcg aggcgcctgg tcgtgtaacg cgctacttat caagtcagcg tctaattaaa  180
gaagcatgcg atgaatcacg ctttgataaa aacttaagtc aagcgcttaa atttgtacgt  240
gattttgcag gagacgggtt agctacaagc tggacgcatg aaaaaaattg gaaaaaagcg  300
cataatatct tacttccaag cttcagtcag caggcaatga aaggctatca tgcgatgatg  360
gtcgatatcg ccgtgcagct tgttcaaaag tgggagcgtc taaatgcaga tgagcatatt  420
gaagtaccgg aagacatgac acgtttaacg cttgatacaa ttggtctttg cggctttaac  480
tatcgcttta acagctttta ccgagatcag cctcatccat ttattacaag tatggtccgt  540
gcactggatg aagcaatgaa caagctgcag cgagcaaatc cagacgaccc acgttatgat  600
gaaaacaagc gccagtttca agaagatatc aaggtgatga acgacctagt agataaaatt  660
attgcagatc gcaaagcaag cggtgaacaa agcgatgatt tattaacgca tatgctaaac  720
ggaaaagatc cagaaacggg tgagccgctt gatgacgaga cattcgcta tcaaattatt  780
acattcttaa ttgcgggaca cgaaacaaca agtggtcttt tatcatttgc gctgtatttc  840
ttagtgaaaa atccacatgt attacaaaaa gcagcagaag aagcagcacg agttctagta  900
gatcctgttc caagctacaa acaagtcaaa cagcttaaat atgtcggcat ggtcttaaac  960
gaagcgctgc gcttatggcc aactgctcct gcgtttttccc tatatgcaaa agaagatacg 1020
gtgcttggag gagaatatcc tttagaaaaa ggcgacgaac taatggttct gattcctcag 1080
cttcaccgtg ataaaacaat ttggggagac gatgtggaag agttccgtcc agagcgtttt 1140
gaaaatccaa gtgcgattcc gcagcatgcg tttaaaccgt ttggaaacgg tcagcgtgcg 1200
tgtatcggtc agcagttcgc tcttcatgaa gcaacgctgg tacttggtat gatgctaaaa 1260
cactttgact ttgaagatca tacaaactac gagctggata ttaaagaaac tttaacgtta 1320
aaacctgaag gctttgtggt aaaagcaaaa tcgaaaaaaa ttccgcttgg cggtattcct 1380
tcacctagca ctgaacagtc tgctaaaaaa gtacgcaaaa aggcagaaaa cgctcataat 1440
acgccgctgc ttgtgctata cggttcaaat atgggaacag ctgaaggaac ggcgcgtgat 1500
ttagcagata ttgcaatgag caaaggattt gcaccgcagg tcgcaacgct tgattccac 1560
gccggaaatc ttccgcgcga aggagctgta ttaattgtaa cggcgtctta taacggtcat 1620
ccgcctgata acgcaaagca atttgtcgac tggttagacc aagcgtctgc tgatgaagta 1680
aaaggcgttc gctactccgt atttggatgc ggcgataaaa actgggctac tacgtatcaa 1740
aaagtgcctg cttttatcga tgaaacgctt gccgctaaag gggcagaaaa catcgctgac 1800
cgcggtgaag cagatgcaag cgacgacttt gaaggcacat atgaagaatg gcgtgaacat 1860
atgtggagtg acgtagcagc ctactttaac ctcgacattg aaaacagtga agataataaa 1920
tctactcttt cacttcaatt tgtcgacagc gccgcggata tgccgcttgc gaaaatgcac 1980
ggtgcgtttt caacgaacgt cgtagcaagc aaagaacttc aacagccagg cagtgcacga 2040
agcacgcgac atcttgaaat tgaacttcca aaagaagctt cttatcaaga aggagatcat 2100
ttaggtgtta ttcctcgcaa ctatgaagga atagtaaacc gtgtaacagc aaggttcggc 2160
ctagatgcat cacagcaaat ccgtctggaa gcagaagaag aaaaattagc tcatttgcca 2220
ctcgctaaaa cagtatccgt agaagagctt ctgcaatacg tggagcttca agatcctgtt 2280
acgcgcacgc agcttcgcgc aatggctgct aaaacggtct gcccgccgca taaagtagag 2340
cttgaagcct tgcttgaaaa gcaagcctac aaagaacaag tgctggcaaa acgtttaaca 2400
atgcttgaac tgcttgaaaa ataccccggcg tgtgaaatga aattcagcga atttatcgcc 2460
cttctgccaa gcatacgccc gcgctattac tcgatttctt catcacctcg tgtcgatgaa 2520
```

```
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
atggtcggac cgggaacagg cgtcgcgccg tttagaggct ttgtgcaggc gcgcaaacag   2760
ctaaaagaac aaggacagtc acttggagaa gcacatttat acttcggctg ccgttcacct   2820
catgaagact atctgtatca agaagagctt gaaaacgccc aaagcggaag catcattacg   2880
cttcataccg cttttctcg catgccaaat cagccgaaaa catacgttca gcacgtaatg    2940
gaacaagacg gcaagaaatt gattgaactt cttgatcaag gagcgcactt ctatatttgc   3000
ggagacggaa gccaaatggc acctgccgtt gaagcaacgc ttatgaaaag ctatgctgac   3060
gttcaccaag tgagtgaagc agacgctcgc ttatggctgc agcagctaga agaaaaaggc   3120
cgatacgcaa aagacgtgtg ggctgggtaa                                     3150

SEQ ID NO: 62            moltype = AA   length = 1049
FEATURE                  Location/Qualifiers
source                   1..1049
                         mol_type = protein
                         organism = Bacillus megaterium
SEQUENCE: 62
MTIKEMPQPK TFGELKNLPL LNTDKPVQAL MKIADELGEI FKFEAPGRVT RYLSSQRLIK   60
EACDESRFDK NLSQALKFVR DFAGDGLATS WTHEKNWKKA HNILLPSFSQ QAMKGYHAMM   120
VDIAVQLVQK WERLNADEHI EVPEDMTRLT LDTIGLCGFN YRFNSFYRDQ PHPFITSMVR   180
ALDEAMNKLQ RANPDDPAYD ENKRQFQEDI KVMNDLVDKI IADRKASGEQ SDDLLTHMLN   240
GKDPETGEPL DDENIRYQII TFLIAGHETT SGLLSFALYF LVKNPHVLQK AAEEEAARVLV  300
DPVPSYKQVK QLKYVGMVLN EALRLWPTAP AFSLYAKEDT VLGGEYPLEK GDELMVLIPQ   360
LHRDKTIWGD DVEEFRPERF ENPSAIPQHA FKPFGNGQRA CIGQQFALHE ATLVLGMMLK   420
HFDFEDHTNY ELDIKETLTL KPEGFVVKAK SKKIPLGGIP SPSTEQSAKK VRKKAENAHN   480
TPLLVLYGSN MGTAEGTARD LADIAMSKGF APQVATLDSH AGNLPREGAV LIVTASYNGH   540
PPDNAKQFVD WLDQASADEV KGVRYSVFGC GDKNWATTYQ KVPAFIDETL AAKGAENIAD   600
RGEADASDDF EGTYEEWREH MWSDVAAYFN LDIENSEDNK STLSLQFVDS AADMPLAKMH   660
GAFSTNVVAS KELQQPGSAR STRHLEIELP KEASYQEGDH LGVIPRNYEG IVNRVTARFG   720
LDASQQIRLE AEEEKLAHLP LAKTVSVEEL LQYVELQDPV TRTQLRAMAA KTVCPPHKVE   780
LEALLEKQAY KEQVLAKRLT MLELLEKYPA CEMKFSEFIA LLPSIRPRYY SISSSPRVDE   840
KQASITVSVV SGEAWSGYGE YKGIASNYLA ELQEGDTITC FISTPQSEFT LPKDPETPLI   900
MVGPGTGVAP FRGFVQARKQ LKEQGQSLGE AHLYFGCRSP HEDYLYQEEL ENAQSEGIIT   960
LHTAFSRMPN QPKTYVQHVM EQDGKKLIEL LDQGAHFYIC GDGSQMAPAV EATLMKSYAD   1020
VHQVSEADAR LWLQQLEEKG RYAKDVWAG                                      1049

SEQ ID NO: 63            moltype = DNA   length = 3225
FEATURE                  Location/Qualifiers
source                   1..3225
                         mol_type = genomic DNA
                         organism = Bacillus licheniformis
SEQUENCE: 63
atgaacaagt tagatggaat tccaatccct aaaacttacg ggccgctcgg caacctgcct   60
ttgcttgaca aaaacagggt ctcccagtca ctttggaaaa tcgcggatga gatggggcct   120
atctttcaat ttaagtttgc ggatgcgatt ggggttttg tgtccagcca tgaactggtt    180
aaagaagtct ctgaagaatc ccgttttgac aaaaacaggt ggaagggct attgaaagtt    240
cgcgagttca gcggagacgg gctctttaca agctggacgg aagaacccaa ttggcggaaa   300
gcccacaaca tccttctgcc gagcttcagc cagaaagcga tgaagggata ccatcccatg   360
atgcaggata tcgccgtcca gctcattcaa aagtggtccc gtctcaatca ggatgaaagc   420
attgatgtgc cggacgatat gacgcggctg acgctggaca cgatcgggct atgcgggttt   480
aactaccgct ttaacagctt ctaccgtgaa gggcagcatc cgtttattga gagcatggtc   540
cggggtttga gcgaagcgat gagacagacg aagcgcttcc cgctgcagga taagctgatg   600
attcaaacga agcgccggtt taacagcgat gtcgagtcga tgtttctct tgttgaccgg    660
atcatcgctg accggaagca ggccgagagt gaaagcggaa atgacctctt gtcgcttatg   720
cttcatgcga aagaccctga gaccggcgaa aaactggatg atgagaatat ccgctatcaa   780
attattacat ttttgattgc cggacacgag acgacgagcg gttattatc gtttgcaatc     840
tatctgctcc tgaagcatcc ggataagctt aagaaagcgt atgaagaagc agaccgcgtg   900
ctgaccgatc ccgtcccatc ctacaaacag gttcagcagc tgaaatacat ccgaatgatt   960
ttgaatgaat cgataaggct ttggccgacg gcaccggctt tctctcttta tgcaaaagaa   1020
gaaacggtta tcgggggaaa atatttgatt ccaaaaggac agagcgttac agtgctcatc   1080
ccaaaactgc acagagatca aagcgtctgg ggagaagatg ccgaggcatt ccggcctgaa   1140
cggttcgagc agatggacag cattccggcg cacgcataca aaccgtttgg caacggccaa   1200
agggcatgca tcggccatgca gttcgccctt catgaagcga gcttgtgct cggcatgatt    1260
cttcagtact ttgatcttga agatcatgca aactaccaat tgaagatcaa agaatcgctg   1320
acattaaaac cggatggttt cacaatccgg gtgaggccga ggaaaaaaga agcaatgacg   1380
gcgatgccgg cgctcagcc tgaagagaac ggacggcagg aagaacggcc ttccgcaccg    1440
gcggcggaaa atacgcacgg aaccctctt cttgtgctct acggttcaaa tctcggcaca    1500
gccgaagaga ttgcgaagga gcttgctgaa gaagcgcgtg agcaagggtt tcacagccgg   1560
acggcggagc ttgatcaata cgcaggcgcc atcccggcag aagggctgt tatcattgtg     1620
acggcttcct ataacggaaa cccgcccgat tgcgcaaagg aatttgtcaa ttggcttgag   1680
catgatcaga cagacgattt gcgtggtgtc aaatatgcgg tattcggctg cggtaaccgc   1740
agctgggcca gcacctacca gcggattccg cgcctgattg acagcgtatt ggaaaaaaaa   1800
ggcgcccaaa ggctgcacaa gcttggagaa ggggatgcag gcgatgattt tgaaggacag   1860
tttgagtcat ggaaatatga tctgtggccg cttttaagaa ccgaatttc attggccgaa    1920
cccgagccga atcaaacaga aacagacagg caagccttat ctgtcgagtt cgtaaacgca   1980
cctgcggctt cgccgctggc taaagcttat caggtgttca cagcgaagat atcggcaaac   2040
cgagaactgc agtgtgaaaa gagcgggaga agcacaaggc atattgaaat atcgcttcct   2100
gaaggcgccg catatcagga gggagaccat ctcggtgtgc taccgcaaaa cagcgaagtg   2160
```

```
ctgattggcc gcgttttttca gcggtttggg ctgaacggaa atgaacaaat tctgattagc   2220
ggccggaatc aagcatcaca tttgcctttg gagaggcccg ttcatgtcaa agaccttttt   2280
caacattgcg tcgagctcca ggaaccggcc acaagggccc agatacgcga gctggcggct   2340
catactgttt gtccgcctca tcagcgcgag cttgaagacc tgctgaaaga tgacgtctat   2400
aaggatcaag tgttgaataa gcggctgaca atgcttgacc tgcttgagca ataccggcc    2460
tgtgaactgc cgttcgcccg ttttctggcg cttcttcctc cgctaaaacc gaggtactat   2520
tcgatttcca gttcgccgca gcttaacccg cggcaaacaa gcatcaccgt ctctgtcgta   2580
agtggcccgg cgttgagcgg ccgcgggcat tataagggag ttgcatcgaa ctatctcgcc   2640
ggccttgagc cgggagacgc gatttcgtgt ttcatcagag agcctcagtc aggcttccgg   2700
cttcccgaag atcctgaaac accggtgatc atggtcggac cgggcaccgg aatcgcccct   2760
taccgcggat ttcttcaggc gcgccgcatc cagcgcgatg ccggtgtgaa gctcggtgaa   2820
gcgcatttgt acttcggctg ccgccgtccg aacgaagatt ttctgtatcg agacgagttg   2880
gagcaagcgg aaaaggacgg aatcgtccat ctgcatacag cgttttcccg gcttgagggc   2940
cggccgaaaa catatgtgca agatttgctc agagagatg cagccttgct gattcacttg   3000
ttgaacgaag gcggccgcct gtatgtgtgc ggagacggaa gccgcatggc tccagctgtt   3060
gaacaagctt tgtgcgaggc gtatcgcata gtacagggtg cgagtcggga agagtcgcaa   3120
agctggctgt ccgcactttt agaagaaggg cgctatgcaa aggatgtatg ggacggcggc   3180
gtttcccaac ataatgtgaa ggcggactgc attgcaagaa cgtaa                    3225
```

```
SEQ ID NO: 64          moltype = AA  length = 1074
FEATURE                Location/Qualifiers
source                 1..1074
                       mol_type = protein
                       organism = Bacillus licheniformis
SEQUENCE: 64
MNKLDGIPIP KTYGPLGNLP LLDKNRVSQS LWKIADEMGP IFQFKFADAI GVFVSSHELV   60
KEVSEESRFD KNMGKGLLKV REFSGDGLFT SWTEEPNWRK AHNILLPSFS QKAMKGYHPM   120
MQDIAVQLIQ KWSRLNQDES IDVPDDMTRL TLDTIGLCGF NYRFNSFYRE GQHPFIESMV   180
RGLSEAMRQT KRFPLQDKLM IQTKRRFNSD VESMFSLVDR IIADRKQAES ESGNDLLSLM   240
LHAKDPETGE KLDDENIRYQ IITFLIAGHE TTSGLLSFAI YLLLKHPDKL KKAYEEADRV   300
LTDPVPSYKQ VQQLKYIRMI LNESIRLWPT APAFSLYAKE ETVIGGKYLI PKGQSVTVLI   360
PKLHRDQSVW GEDAEAFRPE RFEQMDSIPA HAYKPFGNGQ RACIGMQFAL HEATLVLGMI   420
LQYFDLEDHA NYQLKIKESL TLKPDGFTIR VRPRKKEAMT AMPGAQPEEN GRQEERPSAP   480
AAENTHGTPL LVLYGSNLGT AEEIAKELAE EAREQGFHSR TAELDQYAGA IPAEGAVIIV   540
TASYNGNPPD CAKEFVNWLE HDQTDDLRGV KYAVFGCGNR SWASTYQRIP RLIDSVLEKK   600
GAQRLHKLGE GDAGDDFEGQ FESWKYDLWP LLRTEFSLAE PEPNQTETDR QALSVEFVNA   660
PAASPLAKAY QVFTAKISAN RELQCEKSGR STRHIEISLP EGAAYQEGDH LGVLPQNSEV   720
LIGRVFQRFG LNGNEQILIS GRNQASHLPL ERPVHVKDLF QHCVELQEPA TRAQIRELAA   780
HTVCPPHQRE LEDLLKDDVY KDQVLNKRLT MLDLLEQYPA CELPFARFLA LLPPLKPRYY   840
SISSSPQLNP RQTSITVSVV SGPALSGRGH YKGVASNYLA GLEPGDAISC FIREPQSGFR   900
LPEDPETPVI MVGPGTGIAP YRGFLQARRI QRDAGVKLGE AHLYFGCRRP NEDFLYRDEL   960
EQAEKDGIVH LHTAFSRLEG RPKTYVQDLL REDAALLIHL LNEGGRLYVC GDGSRMAPAV   1020
EQALCEAYRI VQGASREESQ SWLSALLEEG RYAKDVWDGG VSQHNVKADC IART          1074
```

```
SEQ ID NO: 65          moltype = DNA  length = 16
FEATURE                Location/Qualifiers
misc_feature           1..16
                       note = source = /note="Description of Artificial Sequence:
                       Synthetic oligonucleotide"
source                 1..16
                       mol_type = other DNA
                       organism = synthetic construct
SEQUENCE: 65
taaggaggaa aacaaa                                                    16
```

```
SEQ ID NO: 66          moltype = DNA  length = 1677
FEATURE                Location/Qualifiers
source                 1..1677
                       mol_type = genomic DNA
                       organism = Pseudomonas putida
SEQUENCE: 66
atgtacgact atataatcgt tggtgctgga tctgcaggat gtgtgcttgc taatcgtctt   60
tcggccgacc cctctaaaag agtttgttta cttgaagctg ggccgcgaga tacgaatccg   120
ctaattcata tgccgttagg tattgctttg cttcaaata gtaaaaagtt gaattgggct   180
tttcaaactg cgccacagca aaatctcaac ggccggagcc ttttctggcc acgaggaaaa   240
acgttaggtg gttcaagctc aatcaacgca atggtctata tccgagggca tgaagacgat   300
taccacgcat gggagcaggc ggccggccgc tactgggggtt ggtaccgggc tcttgagttg   360
ttcaaaaggc ttgaatgcaa ccagcgattc gataagtccg agcaccatgg ggttgacgga   420
gaattagctg ttagtgattt aaaatatatc aatccgctta gcaaagcatt cgtgcaagcc   480
ggcatggagg ccaatattaa tttcaacgga gatttcaacg gcgagtacca ggacggcgta   540
gggttctatc aagtaaccca aaaaaatgga caacgctgga gctcggcgcg tgcattcttg   600
cacggtgtac tttccagacc aaatctagac atcattactg atgcgcatgc atcaaaaatt   660
cttttttgaag accgtaaggc ggttggtgtt tcttatataa agaaaaatat gcaccatcaa   720
gtcaagacaa cgagtggtgg tgaagtactt cttagtcttg gcgcagtcgg cacgcctcac   780
cttctaatgc tttctggtgt tggggctgca gccgagctta aggaacatgg tgtttctcta   840
gtccatgatc ttcctgaggt ggggaaaaat cttcaagatc atttggacat cacattgatg   900
tgcgcagcaa attcgagaga gccgataggt gttgctcttt cttttcatccc tcgtggtgtc   960
tcgggtttgt tttcatatgt gtttaagcgc gagggggttc tcactagtaa cgtggcagag   1020
tcgggtggtt ttgtaaaaag ttctcctgat cgtgatcggc caatttgca gtttcatttc   1080
```

-continued

```
cttccaactt atcttaaaga tcacggtcga aaaatagcgg gtggttatgg ttatacgcta   1140
catatatgtg atcttttgcc taagagccga ggcagaattg gcctaaaaag cgccaatcca   1200
ttacagccgc ctttaattga cccgaactat cttagcgatc atgaagatat taaaaccatg   1260
attgcgggta ttaagatagg gcgcgctatt ttgcaggccc catcgatggc gaagcatttt   1320
aagcatgaag tagtaccggg ccaggctgtt aaaactgatg agaaataat cgaagatatt   1380
cgtaggcgag ctgagactat ataccatccg gtaggtactt gtaggatggg taaagatcca   1440
gcgtcagttg ttgatccgtg cctgaagatc cgtgggttgg caaatattag agtcgttgat   1500
gcgtcaatta tgccgcactt ggtcgcgggt aacacaaacg ctccaactat tatgattgca   1560
gaaaatgcgg cagaaataat tatgcggaat cttgatgtgg aagcattaga ggctagcgct   1620
gagtttgctc gcgagggtgc agagctagag ttggccatga tagctgtctg catgtaa      1677
```

SEQ ID NO: 67                    moltype = AA   length = 558
FEATURE                          Location/Qualifiers
source                           1..558
                                 mol_type = protein
                                 organism = Pseudomonas putida
SEQUENCE: 67

```
MYDYIIVGAG SAGCVLANRL SADPSKRVCL LEAGPRDTNP LIHMPLGIAL LSNSKKLNWA   60
FQTAPQQNLN GRSLFWPRGK TLGGSSSINA MVYIRGHEDD YHAWEQAAGR YWGWYRALEL   120
FKRLECNQRF DKSEHHGVDG ELAVSDLKYI NPLSKAFVQA GMEANINFNG DFNGEYQDGV   180
GFYQVTQKNG QRWSSARAFL HGVLSRPNLD IITDAHASKI LFEDRKAVGV SYIKKNMHHQ   240
VKTTSGGEVL LSLGAVGTPH LLMLSGVGAA AELKEHGVSL VHDLPEVGKN LQDHLDITLM   300
CAANSREPIG VALSFIPRGV SGLFSYVFKR EGFLTSNVAE SGGFVKSSPD RDRPNLQFHF   360
LPTYLKDHGR KIAGGYGYTL HICDLLPKSR GRIGLKSANP LQPPLIDPNY LSDHEDIKTM   420
IAGIKIGRAI LQAPSMAKHF KHEVVPGQAV KTDDEIIEDI RRRAETIYHP VGTCRMGKDP   480
ASVVDPCLKI RGLANIRVVD ASIMPHLVAG NTNAPTIMIA ENAAEIIMRN LDVEALEASA   540
EFAREGAELE LAMIAVCM                                                 558
```

SEQ ID NO: 68                    moltype = DNA   length = 1452
FEATURE                          Location/Qualifiers
source                           1..1452
                                 mol_type = genomic DNA
                                 organism = Pseudomonas putida
SEQUENCE: 68

```
atgaccatac caattagcct agccaagtta aactctagtg ccgatacca ttcagcgctt   60
gaagtatta atttgcagaa agttgcaagt agtgcgcgtc gtggtaaatt tggcatagca   120
gagcgcatcg ctgctcttaa tttacttaag gaaactattc agcgtcgtga gcctgaaatt   180
attgctgcac ttgcagcgga ctttcgcaag ccggcaagcg aggtgaagct aacagaaatc   240
tttccggtat tgcaagaaat taatcatgcc aaacggaacc ttaaagattg gatgaagcca   300
cggcgagtga gggcggcact tagtgtagcg ggcacgcggg caggacttcg ttacgagcct   360
aagggtgtct gtttgataat tgcgccgtgg aactatccat tcaaccttag tttcggtcct   420
cttgtatctg cgttagcggc aggaaatagc gttgttataa agccgtctga attgacacca   480
cacactgcaa cactgatcgg atctatagtc agggaggcat tctctgtcga cctagtcgct   540
gtggtggagg gtgatgccgc agtttcccag gagctgttgg ctctgccatt tgaccatatt   600
tttttactg gtagtcctag ggtcggcaag ttagtgatgg aagcggcgtc aaaaacactc   660
gcttcggtta ctttggagtt aggcggaaaa tctccaacca ttattggacc aacagcaaat   720
ttgccgaaag ctgcgcgcaa catagtgtgg ggaaagtttt caaacaacgg ccagacgtgc   780
atagcgcctg atcacgtatt tgttcatcgg tgtatagccc agaaattcaa tgaaattctt   840
gtgaaagaga ttgtgcgagt ttatggaag gattttgctg cgcagcgtag atcggcagac   900
tattgcagga tcgtcaatga tcaacatttc aatcgaatta ataaactcct gactgacgcg   960
aaagctaaag gtgcaaaaat tctgcaaggg ggtcaagttg acgcgactga gaggcttgtg   1020
gtgccaacgg ttttatctaa cgtcactgct gctatggata ttaaccatga ggaaatattc   1080
gggccgctac ttcctataat tgaatacgat gatatagatt ctgtaattaa gcgtgtgaat   1140
gacggtgaca gcccctggc gctgtatgtc ttttctgaag ataaacaatt tgtaaataac   1200
atcgtggctc gtacaagctc tggttcggtc ggagttaatc tgagtgtcgt gcactttttg   1260
caccctaatc tcccatttgg cggtgtcaat aatagtggta tcggcagtgc tcatggagtt   1320
tacgggttca gggcgttttc tcacgaaaaa ccagttctta tagataagtt ctcaatcacg   1380
cattggttgt ttccgcctta taccaagaag gtgaagcagt tgattggtat cacagttaag   1440
tatttgagct ga                                                       1452
```

SEQ ID NO: 69                    moltype = AA   length = 483
FEATURE                          Location/Qualifiers
source                           1..483
                                 mol_type = protein
                                 organism = Pseudomonas putida
SEQUENCE: 69

```
MTIPISLAKL NSSADTHSAL EVFNLQKVAS SARRGKFGIA ERIAALNLLK ETIQRREPEI   60
IAALAADFRK PASEVKLTEI FPVLQEINHA KRNLKDWMKP RRVRAALSVA GTRAGLRYEP   120
KGVCLIIAPW NYPFNLSFGP LVSALAAGNS VVIKPSELTP HTATLIGSIV REAFSVDLVA   180
VVEGDAAVSQ ELLALPFDHI FFTGSPRVGK LVMEAASKTL ASVTLELGGK SPTIIGPTAN   240
LPKAARNIVW GKFSNNGQTC IAPDHVFVHR CIAQKFNEIL VKEIRVYGK DFAAQRRSAD   300
YCRIVNDQHF NRINKLLTDA KAKGAKILQG GQVDATERLV VPTVLSNVTA AMDINHEEIF   360
GPLLPIIEYD DIDSVIKRVN DGDKPLALYV FSEDKQFVNN IVARTSSGSV GVNLSVVHFL   420
HPNLPFGGVN NSGIGSAHGV YGFRAFSHEK PVLIDKFSIT HWLFPPYTKK VKQLIGITVK   480
YLS                                                                 483
```

We claim:

1. A modified ω-hydroxylase of EC 1.14.15.3, comprising a modified CYP153A polypeptide having at least 90% sequence identity to SEQ ID NO:4, wherein the modified ω-hydroxylase comprises at least one mutation at an amino acid position corresponding to one or more of positions 6, 11, 27, 40, 41, 82, 116, 129, 131, 132, 134, 136, 138, 141, 142, 144, 149, 153, 154, 157, 161, 168, 178, 205, 228, 231, 233, 258, 271, 304, 308, 309, 407, 415, and 419 of SEQ ID NO:4.

2. The modified ω-hydroxylase of claim 1, wherein the at least one mutation corresponds to one or more of R6F, I11C, R27L, R40H, K41V, R82D, F116R, Q129R, I131L, L132T, D134G, P136T, P136C, G138F, V141Q, V141G, V141I, V141T, V141M, V141L, E142Q, E142R, F144R, P149R, D153G, V154A, S157V, G161P, G161A, L168V, R178N, R205L, M228R, A231T, S233R, S233N, R258Y, E271F, L304W, G308W, N309R, N309S, N407A, V415R, and M419V.

3. A modified CYP153A-reductase hybrid fusion polypeptide comprising the modified CYP153A polypeptide of claim 1 fused to a reductase domain.

4. The modified ω-hydroxylase of claim 3, wherein the modified CYP153A-reductase hybrid fusion polypeptide has at least 90% sequence identity to SEQ ID NO: 6.

5. The modified ω-hydroxylase of claim 4, wherein the modified CYP153A-reductase hybrid fusion polypeptide has a mutation at an amino acid position corresponding to one or more of positions 516, 666, 696, and 796 of SEQ ID NO:6.

6. The modified ω-hydroxylase of claim 5, wherein the modified CYP153A-reductase hybrid fusion polypeptide has a mutation corresponding to one or more of T516G, T516V, T516E, P666A, P666H, P666D, P666M, P666K, V696K, V696T, and A796V.

7. A recombinant microorganism, comprising the modified CYP153A-reductase hybrid fusion polypeptide of claim 3.

8. A method of producing an ω-hydroxy fatty acid or derivative thereof, the method comprising culturing the recombinant microorganism of claim 7 in a carbon source, and optionally isolating the ω-hydroxy fatty acid or derivative thereof.

9. A recombinant microorganism, comprising the modified ω-hydroxylase of claim 1.

10. A cell culture, comprising the recombinant microorganism of claim 9.

11. A method of producing an ω-hydroxy fatty acid or derivative thereof, the method comprising culturing the recombinant microorganism of claim 9 in a carbon source, and optionally isolating the ω-hydroxy fatty acid or derivative thereof.

12. A CYP153A-reductase hybrid fusion polypeptide variant, comprising at least 90% sequence identity to SEQ ID NO:6 and comprising at least one mutation at an amino acid position corresponding to one or more of positions 6, 11, 27, 40, 41, 82, 116, 129, 131, 132, 134, 136, 138, 141, 142, 144, 149, 153, 154, 157, 161, 168, 178, 205, 228, 231, 233, 258, 271, 304, 308, 309, 407, 415, 419, 516, 666, 696, and 796, wherein the CYP153A-reductase hybrid fusion polypeptide variant catalyzes the conversion of a fatty acid or derivative thereof to an ω-hydroxy fatty acid or derivative thereof.

13. The CYP153A-reductase hybrid fusion polypeptide variant of claim 12, comprising at least one mutation corresponding to R6F, I11C, R27L, R40H, K41V, R82D, F116R, Q129R, I131L, L132T, D134G, P136T, P136C, G138F, V141I, V141T, V141Q, V141G, V141M, V141L, E142R, E142Q, F144R, P149R, D153G, V154A, S157V, G161P, G161A, L168V, R178N, R205L, M228R, A231T, S233R, S233N, R258Y, E271F, L304W, G308W, N309R, N309S, N407A, V415R, M419V, T516E, T516G, T516V, P666A, P666D, P666K, P666H, P666M, V696K, V696T, or A796V, with reference to SEQ ID NO: 6.

14. A recombinant microorganism, comprising the CYP153A-reductase hybrid fusion polypeptide variant of claim 13.

15. A method of producing an ω-hydroxy fatty acid or derivative thereof, the method comprising culturing the recombinant microorganism of claim 14, and optionally isolating the ω-hydroxy fatty acid or derivative thereof.

16. A recombinant microorganism, comprising the CYP153A-reductase hybrid fusion polypeptide variant of claim 12.

17. The recombinant microorganism of claim 16, wherein:

the recombinant microorganism produces an ω-hydroxy fatty acid or a derivative thereof;

the ω-hydroxy fatty acid or derivative thereof is an ω-hydroxy free fatty acid; an ω-hydroxy fatty acid ester; an ω-oxo fatty acid; an ω-oxo fatty acid ester; an α,ω-diacid; an ω-carboxy fatty acid ester; an α,ω-diester; an α,ω-diol; an ω-amino fatty acid; an ω-amino fatty acid ester; or a combination thereof; and the ω-hydroxy fatty acid or derivative thereof is one or more of a saturated or unsaturated C6, C7, C8, C9, C10, C11, C12, C13, C14, C15, C16, C17, C18, C19, or C20 ω-hydroxy fatty acid or derivative thereof; and wherein the recombinant microorganism optionally further expresses a thioesterase, or an ester synthase, or a combination thereof.

18. The recombinant microorganism of claim 16, wherein the recombinant microorganism optionally further expresses a thioesterase, or an ester synthase, or a combination thereof, and wherein the recombinant microorganism further expresses:

(a) an alcohol dehydrogenase or an alcohol oxidase, wherein the recombinant microorganism produces an ω-hydroxy fatty acid derivative that is an ω-oxo fatty acid, an ω-oxo fatty acid ester, or a combination thereof;

(b) an alcohol dehydrogenase or an alcohol oxidase, and an aldehyde dehydrogenase or an aldehyde oxidase, wherein the recombinant microorganism produces an ω-hydroxy fatty acid derivative that is an α,ω-diacid, an ω-carboxy fatty acid ester, or a combination thereof;

(c) an alcohol dehydrogenase or an alcohol oxidase, an aldehyde dehydrogenase or an aldehyde oxidase, and an acyl-CoA ligase or an acyl-CoA transferase, wherein the recombinant microorganism produces an ω-hydroxy fatty acid derivative that is an α,ω-diester;

(d) an alcohol dehydrogenase or an alcohol oxidase, and an aminotransferase or an amine dehydrogenase, wherein the recombinant microorganism produces an ω-hydroxy fatty acid derivative that is an ω-amino fatty acid, an ω-amino fatty acid ester, or a combination thereof;

(e) an alcohol dehydrogenase and a carboxylic acid reductase, wherein the recombinant microorganism produces an ω-hydroxy fatty acid derivative that is an α,ω-diol; or (f) an acyl-ACP reductase and an alcohol dehydrogenase, wherein the recombinant microorganism produces an ω-hydroxy fatty acid derivative that is an α,ω-diol.

19. A cell culture, comprising the recombinant microorganism of claim 16.

20. A method of producing an ω-hydroxy fatty acid or derivative thereof, the method comprising culturing the recombinant microorganism of claim 16 in a carbon source, and optionally isolating the ω-hydroxy fatty acid or derivative thereof.

21. The method of claim 20, wherein:

the ω-hydroxy fatty acid or derivative thereof is one or more of a C7, C8, C9, C10, C11, C12, C13, C14, C15, C16, C17, C18, or C19 ω-hydroxy fatty acid or derivative thereof; and the ω-hydroxy fatty acid or derivative thereof is an ω-hydroxy free fatty acid; an ω-hydroxy fatty acid ester; an ω-oxo fatty acid; an ω-oxo fatty acid ester; an α,ω-diacid; an ω-carboxy fatty acid ester; an α,ω-diester; an α,ω-diol; an ω-amino fatty acid; an ω-amino fatty acid ester; or a combination thereof.

* * * * *